(12) United States Patent
Dong et al.

(10) Patent No.: US 8,709,998 B2
(45) Date of Patent: *Apr. 29, 2014

(54) PEPTIDE VECTORS

(75) Inventors: Zheng Xin Dong, Holliston, MA (US);
Yeelena Shen, Franklin, MA (US);
Jeanne Mary Comstock, West Boylston, MA (US); Sun H. Kim, Needham, MA (US)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 2015 days.

This patent is subject to a terminal disclaimer.

(21) Appl. No.: 10/554,240

(22) PCT Filed: Apr. 21, 2004

(86) PCT No.: PCT/US2004/012200
§ 371 (c)(1),
(2), (4) Date: Oct. 21, 2005

(87) PCT Pub. No.: WO2004/093807
PCT Pub. Date: Nov. 4, 2004

(65) Prior Publication Data
US 2007/0093645 A1    Apr. 26, 2007

Related U.S. Application Data

(60) Provisional application No. 60/464,528, filed on Apr. 22, 2003.

(51) Int. Cl.
| | | |
|---|---|---|
| A61K 38/00 | (2006.01) | |
| A61K 47/00 | (2006.01) | |
| A61P 9/10 | (2006.01) | |
| C07K 14/47 | (2006.01) | |
| A61K 38/31 | (2006.01) | |
| A61P 3/10 | (2006.01) | |
| A61P 7/12 | (2006.01) | |
| A61K 38/24 | (2006.01) | |
| A61P 5/06 | (2006.01) | |
| C07K 14/59 | (2006.01) | |
| A61K 38/10 | (2006.01) | |
| A61P 5/02 | (2006.01) | |
| C07K 14/655 | (2006.01) | |
| A61P 35/00 | (2006.01) | |
| C07K 14/515 | (2006.01) | |
| A61P 35/02 | (2006.01) | |
| A61P 35/04 | (2006.01) | |
| A61K 38/12 | (2006.01) | |
| A61K 38/08 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 38/04 | (2006.01) | |

(52) U.S. Cl.
USPC ............ 514/1.3; 514/1.1; 514/1.9; 514/7.1;
514/10.1; 514/11.1; 514/13.3; 514/19.2;
514/19.4; 514/19.5; 514/19.6; 514/19.7;
514/19.8; 514/19.9; 514/21.1; 514/21.6;
514/21.7; 530/311; 530/313; 530/328; 530/329;
530/332

(58) Field of Classification Search
None
See application file for complete search history.

(56) References Cited

U.S. PATENT DOCUMENTS

| | | | |
|---|---|---|---|
| 4,943,579 A | 7/1990 | Vishnuvajjala et al. | |
| 5,482,698 A | 1/1996 | Griffiths | |
| 5,525,338 A | 6/1996 | Goldenberg | |
| 5,795,909 A | 8/1998 | Shashoua et al. | |
| 5,843,903 A | 12/1998 | Schally et al. | |
| 5,948,750 A | 9/1999 | Garsky et al. | |
| 6,077,499 A | 6/2000 | Griffiths et al. | |
| 6,191,290 B1 | 2/2001 | Safavy | |
| 6,207,660 B1 | 3/2001 | Sessler et al. | |
| 6,472,507 B1 * | 10/2002 | Fischer et al. | 530/326 |
| 7,109,167 B2 * | 9/2006 | Von Wronski et al. | 514/12 |
| 7,135,547 B2 * | 11/2006 | Gengrinovitch | 530/300 |
| 7,211,240 B2 * | 5/2007 | Arbogast et al. | 424/9.1 |
| 7,238,665 B2 * | 7/2007 | Wu et al. | 514/12 |
| 7,420,030 B2 * | 9/2008 | Arap et al. | 530/300 |
| 8,236,762 B2 * | 8/2012 | Dong et al. | 514/11.1 |
| 2002/0094964 A1 | 7/2002 | Chen et al. | |
| 2002/0115596 A1 | 8/2002 | Garsky et al. | |
| 2002/0147136 A1 * | 10/2002 | Von Wronski et al. | 514/8 |
| 2003/0064053 A1 | 4/2003 | Liu et al. | |
| 2003/0064984 A1 | 4/2003 | Ng et al. | |
| 2004/0018974 A1 * | 1/2004 | Arbogast et al. | 514/12 |

(Continued)

FOREIGN PATENT DOCUMENTS

| | | |
|---|---|---|
| EP | 0 450 461 A2 | 10/1991 |
| EP | 0 450 461 A3 | 10/1991 |

(Continued)

OTHER PUBLICATIONS

Slama, J. et al., "The synthesis of glycolipids containing a hydrophilic spacer-group", Carbohydrate Research, 1981, 88:213-222.

Fuselier, et al., "An adjustable release rate linking strategy for cytotoxin-peptide conjugates," Bioor. Med. Chem. Lett., 2003, 10:799-803.

Huang, et al., "Targeting delivery of paclitaxel into tumor cells via somatostatin receptor endocytosis," Chem. Biol., 2000, 7:453-461.

Kovacs, et al., "Recovery of pituitary function after treatment with a targeted cytotoxic analog of lutenizing hormone-releasing hormone," PNAS, 1997, 94:1420-1425.

(Continued)

*Primary Examiner* — Marcela M Cordero Garcia
*Assistant Examiner* — Thea D'Ambrosio
(74) *Attorney, Agent, or Firm* — Janice M. Klunder; Tony K. Uhm

(57) ABSTRACT

The invention features targeted cytotoxic compounds and methods relating to their therapeutic use for the treatment of neoplasia and other conditions.

21 Claims, No Drawings

(56) References Cited

U.S. PATENT DOCUMENTS

| | | |
|---|---|---|
| 2005/0070470 A1 | 3/2005 | Coy et al. |
| 2006/0009622 A1 | 1/2006 | Fuselier et al. |
| 2006/0034773 A1* | 2/2006 | Giovenzana et al. ...... 424/9.361 |
| 2006/0153775 A1* | 7/2006 | Von Wronski et al. ...... 424/9.34 |

FOREIGN PATENT DOCUMENTS

| | | |
|---|---|---|
| EP | 0 450 461 B1 | 10/1991 |
| EP | 0 450 480 A2 | 10/1991 |
| EP | 0 450 480 A3 | 10/1991 |
| EP | 0 450 480 B1 | 10/1991 |
| EP | 0 398 305 B1 | 3/1997 |
| EP | 1 118 336 | 7/2001 |
| EP | 0 624 377 | 11/2004 |
| JP | 2002-47298 | 7/2000 |
| WO | 96/40210 | 12/1996 |
| WO | 97/19954 | 6/1997 |
| WO | WO 0001417 A1 * | 1/2000 |
| WO | 01/26693 | 4/2001 |
| WO | WO 0220722 A2 * | 3/2002 |
| WO | 02/34237 | 5/2002 |
| WO | 02/087497 | 11/2002 |
| WO | WO 02/087631 | 11/2002 |
| WO | WO 02/096367 | 12/2002 |
| WO | WO 02/100888 | 12/2002 |
| WO | WO 03/026577 | 4/2003 |
| WO | WO 03/028527 | 4/2003 |
| WO | WO 03/072754 | 9/2003 |
| WO | WO 03074005 A2 * | 9/2003 |

OTHER PUBLICATIONS

Nagy, et al., "Synthesis and biological evaluation of cytotoxic analogs of somatostatin containing doxorubicin or its intensely potent derivative, 2-pyrrolinodoxorubicin," PNAS, 95:1794-1799.

Safavy, et al., "Synthesis and biological evaluation of paclitaxel-C225 conjugate as a model for targeted drug delivery," Bioconjug. Chem., 2003, 14:302-310.

* cited by examiner

PEPTIDE VECTORS

This application is a United States national stage filing under 35 U.S.C. §371 of international (PCT) application No. PCT/US2004/012200 filed Apr. 21, 2004 and designating the U.S. and claiming priority to U.S. provisional application 60/464,528 filed Apr. 22, 2003.

FIELD OF THE INVENTION

The present invention relates to therapeutic compositions and their use in the treatment of disease states. More particularly, the present invention provides compounds, compositions and methods for treating disease states associated with aberrant or undesirable cellular proliferation, migration, and/or physiological activity.

BACKGROUND OF THE INVENTION

Most cytotoxic drugs exhibit undesirable toxic side effects due to their lack of selective action toward the tissues or cells requiring therapeutic effect. Various approaches have been pursued to achieve the selective delivery of cytotoxic agents to a target cell type.

Using biological receptor ligands as carriers of drugs to target these drugs to the cells of interest can reduce toxic side-effects and greatly improve the efficiency of drug delivery. For example, International Patent Publication No. WO97/19954 discloses conjugates of an anthracycline cytotoxic agent such as doxorubicin with a peptide hormone such as LHRH, bombesin or somatostatin. The cytotoxic agent is covalently attached to the peptide via a linker of formula —C(O)—(CH$_2$)$_n$—C(O)—, n=0-7.

Similarly, European Patent Application No. EP1118336 discloses conjugates of somatostatin analogs, e.g., octreotide, lanreotide, and vapreotide, and a cytotoxic drug, such as paclitaxel, doxorubicin, or camptothecin, through a spacer, wherein the spacer is also indicated to have the structure: —C(O)—(CH$_2$), —C(O)—, n=0-7.

U.S. Patent Application Publication No. 2002/0115596 discloses conjugates of cytotoxic agents and oligopeptides in which the amino acid sequences of the peptides are indicated to be cleaved preferentially by free prostate specific antigen. Such conjugates are said to be useful for the treatment of prostate cancer and benign prostatic hyperplasia.

U.S. Patent Application Publication No. 2003/0064984 discloses conjugates of cytotoxic analogs of CC-1065 and the duocarmycins with cleavable linker arms and a targeting agent such as an antibody or a peptide. The cytotoxic analogs are indicated to be released upon cleavage of the linker.

International Patent Application No. WO02/34237 discloses conjugates of active agents covalently attached directly to a polypeptide. The polypeptide is said to stabilize the active agent, e.g., in the stomach, through conformational protection.

There remains, however, a significant need for targeted cytotoxic drugs with improved properties in respect of targeting specificity, systemic toxicity, and pharmacokinetics.

SUMMARY OF THE INVENTION

The instant invention provides targeted cytotoxic compounds comprising a cytotoxic moiety bound to a targeting moiety, such as, for example, a ligand of a biological receptor. The two moieties are bound via a linker, e.g., as described by formula I:

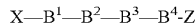

(I)

wherein:

X is a cytotoxic or cytostatic agent;

each of $B^1$, $B^2$, $B^3$, and $B^4$ is, independently for each occurrence, (Doc)$_m$, (Aepa)$_n$, —(C(O)-A1-A2-A3-A4-A5-C(O))$_s$— or (amino acid)$_p$, each of A1 and A5 is, independently for each occurrence, CR$^1$R$^2$;

each of R$^1$ and R$^2$ is, independently for each occurrence, H, F, Br, Cl, I, C$_{(1-30)}$alkyl, C$_{(2-30)}$alkenyl, substituted C$_{(1-30)}$alkyl, substituted C$_{(2-30)}$alkenyl, SR$^3$, S(O)R$^4$, or S(O)$_2$R$^5$, or R$^1$ and R$^2$ together can form a C$_{(3-30)}$cycloalkyl, C$_{(3-30)}$heterocycle, or C$_{(5-30)}$aryl ring;

each of R$^3$, R$^4$, and R$^5$ is, independently for each occurrence, C$_{(1-30)}$alkyl, C$_{(2-30)}$alkenyl, substituted C$_{(1-30)}$alkyl, or substituted C$_{(2-30)}$alkenyl;

each of A$^2$, A$^3$, and A$^4$ is, independently for each occurrence, CR$^6$R$^7$, O, S, (CH$_2$)$_t$ or absent;

each of R$^6$ and R$^7$, independently for each occurrence, H, F, Br, Cl, I, C$_{(1-30)}$alkyl, C$_{(2-30)}$alkenyl, substituted C$_{(1-30)}$alkyl, substituted C$_{(2-30)}$alkenyl, SR$^3$, S(O)R$^4$, or S(O)$_2$R$^5$; or R$^6$ and R$^7$ together may form a ring system;

m is, independently for each occurrence, 0, 1, 2, 3, 4, 5, 6, 7, 8, 9, or 10;

n is, independently for each occurrence, 0, 1, 2, 3, 4, 5, 6, 7, 8, 9, or 10;

p is, independently for each occurrence, 0, 1, or 2;

s is, independently for each occurrence, 1, 2, 3, 4, or 5;

t is, independently for each occurrence, 0, 1, 2, or 3;

Z is a ligand of a biological receptor, an analog thereof, or a derivative of said ligand or of said analog; provided that:

when X is doxorubicin or a doxorubicin derivative, at least one of m and n is not 0; and when X is paclitaxel or a paclitaxel derivative, then B$^1$ is (amino acid)$_p$ and p is 1 or 2;

A first preferred embodiment features a compound according to formula (I) wherein X is a cytotoxic moiety. More preferably X is an anthracycline. More preferably still X is camptothecin, a camptothecin derivative, paclitaxel, a paclitaxel derivative, doxorubicin, or a doxorubicin derivative; provided that: when X is doxorubicin or a doxorubicin derivative, at least one of m and n is not 0, and when X is paclitaxel or a paclitaxel derivative, then B$^1$ is (amino acid)$_p$ and p is 1 or 2;

In a further preferred embodiment of said first preferred embodiment said the invention features compounds of formula (I) wherein:

X is camptothecin or a camptothecin derivative, wherein said camptothecin derivative is:

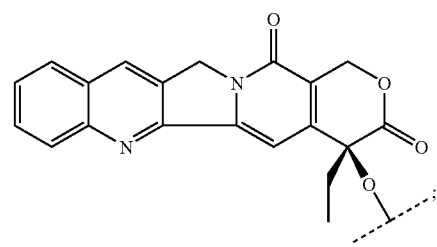

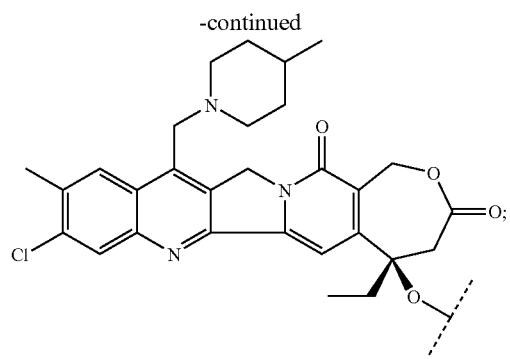

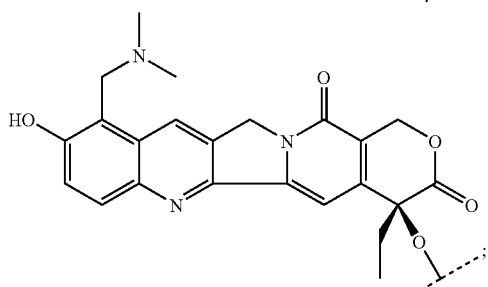

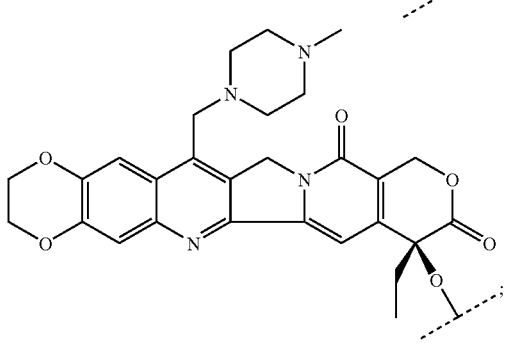

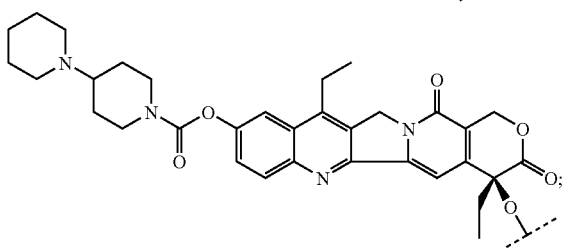

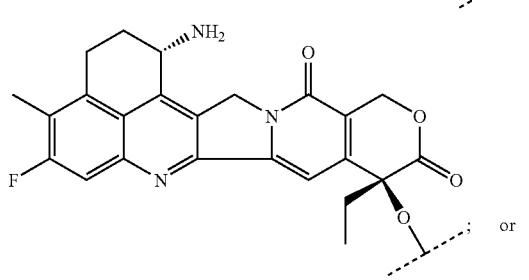

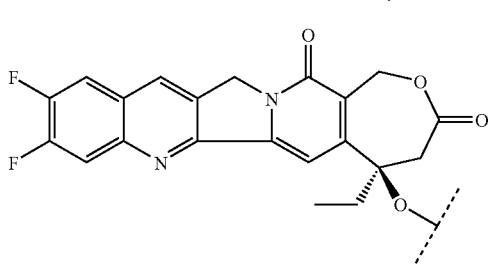

or X is paclitaxel or a paclitaxel derivative, wherein said paclitaxel derivative is:

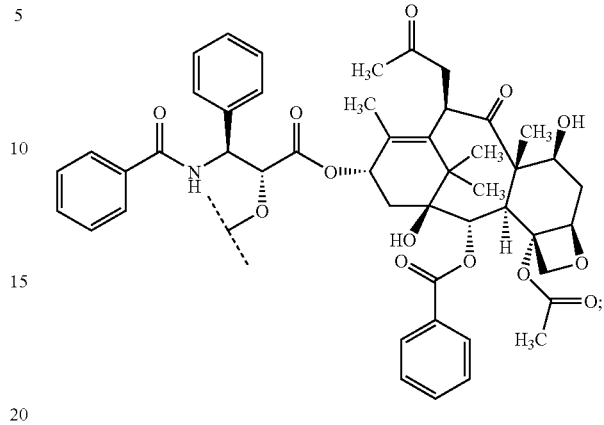

or X is doxorubicin or a doxorubicin derivative, wherein said doxorubicin derivative is:

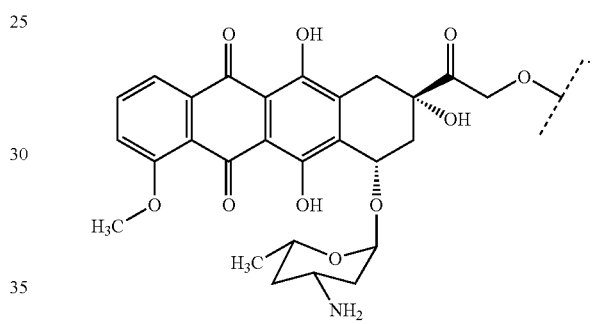

A second preferred embodiment features a compound according to formula (I) wherein the ligand of Z is a somatostatin, a bombesin, or an LHRH, or an analog thereof, or a derivative of said ligand or of said analog.

In a further preferred embodiment of said second preferred embodiment, the invention features compounds of formula (I) wherein Z is:

a somatostatin analog according to the formula:
-DPhe-cyclo(Cys-Tyr-DTrp-Lys-Abu-Cys)-Thr-NH$_2$;
-DPhe-cyclo(Cys-3ITyr-DTrp-Lys-Val-Cys)-Thr-NH$_2$;
-DPhe-cyclo(Cys-3ITyr-DTrp-Lys-Abu-Cys)-Thr-NH$_2$;
-DPhe-cyclo(Cys-3ITyr-DTrp-Lys-Thr-Cys)-Thr-NH$_2$;
-Lys-DTyr-DTyr-cyclo(Cys-Tyr-DTrp-Lys-Abu-Cys)-Thr-NH$_2$;
-Caeg-cyclo(DCys-3Pal-DTrp-Lys-DCys)-Thr(Bzl)-Tyr-NH$_2$;
-D2Nal-cyclo[Cys-Tyr-DTrp-Lys-Val-Cys]-Thr-NH$_2$;
-DPhe-cyclo[Cys-Phe-DTrp-Lys-Thr-Cys]-Thr-ol;
-cyclo({4-(-NH-C2H4-NH-CO-0)Pro}-Phg-DTrp-Lys-Tyr(4-Bzl)-Phe); or
-DPhe-cyclo[Cys-Tyr-DTrp-Lys-Val-Cys]-Trp-NH$_2$; or
a pharmaceutically acceptable salt thereof;
or an LHRH analog according to the formula:
Glp-His-Trp-Ser-Tyr-DLys(-)-Leu-Arg-Pro-Gly-NH$_2$;
Glp-His-Trp-Ser-Tyr-DOrn(-)-Leu-Arg-Pro-Gly-NH$_2$;
Glp-His-Trp-Ser-Tyr-DDab(-)-Leu-Arg-Pro-Gly-NH$_2$;
Glp-His-Trp-Ser-Tyr-DDap(-)-Leu-Arg-Pro-Gly-NH$_2$;
Glp-His-Trp-Ser-Tyr-DApa(-)-Leu-Arg-Pro-Gly-NH$_2$;
Glp-His-Trp-Ser-Tyr-DLys(-)-Leu-Arg-Pro-NHEt;

Glp-His-Trp-Ser-Tyr-DOrn(-)-Leu-Arg-Pro-NHEt;
Glp-His-Trp-Ser-Tyr-DDab(-)-Leu-Arg-Pro-NHEt;
Glp-His-Trp-Ser-Tyr-DDap(-)-Leu-Arg-Pro-NHEt;
Glp-His-Trp-Ser-His-DLys(-)-Trp-Tyr-Pro-Gly-NH$_2$;
Glp-His-Trp-Ser-His-DOrn(-)-Trp-Tyr-Pro-Gly-NH$_2$;
Glp-His-Trp-Ser-His-DDab(-)-Trp-Tyr-Pro-Gly-NH$_2$; or
Glp-His-Trp-Ser-His-DDap(-)-Trp-Tyr-Pro-Gly-NH$_2$; or
a pharmaceutically acceptable salt thereof;
or a bombesin analog according to the formula:

| | |
|---|---|
| -Gln-Trp-Ala-Ala-βAla-His-Phe-Nle-NH$_2$; | (SEQ ID NO: 8) |
| -Gln-Trp-Ala-Val-Gly-His-Leu-Ψ(CH$_2$-NH)-Leu-NH$_2$; | (SEQ ID NO: 9) |
| -Gln-Trp-Ala-Val-Gly-His-Leu-Ψ(CH$_2$-NH)-Phe-NH$_2$; | (SEQ ID NO: 10) |
| -Gln-Trp-Ala-Val-βAla-His-Leu-Leu-NH$_2$; | (SEQ ID NO: 11) |
| -Gln-Trp-Ala-Val-βAla-His-Leu-Nle-NH$_2$; | (SEQ ID NO: 12) |
| -Gln-Trp-Ala-Val-βAla-His-Phe-Nle-NH$_2$; | (SEQ ID NO: 13) |
| -Gln-Trp-Ala-Val-βAla-His-Ala-Nle-NH$_2$; | (SEQ ID NO: 14) |
| -Gln-Trp-Ala-Val-βAla-Ala-Phe-Nle-NH$_2$; | (SEQ ID NO: 15) |
| -Gln-Trp-Ala-Val-Gly-His-Leu-Leu-NH$_2$; | (SEQ ID NO: 1) |
| -Gln-Trp-Ala-Val-Gly-His-Leu-Met-NH$_2$; | (SEQ ID NO: 2) |
| -Gln-Trp-Ala-Val-Gly-His-Phe-Met-NH$_2$; | (SEQ ID NO: 3) |

-DAla-Gln-Trp-Ala-Val-βAla-His-Phe-Nle-NH$_2$;

-DPhe-Gln-Trp-Ala-Ala-βAla-His-Phe-Nle-NH$_2$;

-DPhe-Gln-Trp-Ala-Val-βAla-Ala-Phe-Nle-NH$_2$;

-DPhe-Gln-Trp-Ala-Val-βAla-His-Phe-Nle-NH$_2$;

-DPhe-Gln-Trp-Ala-Val-βAla-His-Phe-Nle-NH$_2$;

-DPhe-Gln-Trp-Ala-Val-βAla-His-Ala-Nle-NH$_2$;

-DPhe-Gln-Trp-Ala-Val-βAla-His-Leu-Leu-NH$_2$;

-DPhe-Gln-Trp-Ala-Val-βAla-His-Leu-Nle-NH$_2$;

-DPhe-Gln-Trp-Ala-Val-Gly-His-Leu-Ψ(CH$_2$-NH)-Leu-NH$_2$;

-DPhe-Gln-Trp-Ala-Val-Gly-His-Leu-Ψ(CH$_2$-NH)-Phe-NH$_2$;

-DPhe-Gln-Trp-Ala-Val-Gly-His-Leu-Met-NH$_2$;

-DPhe-Gln-Trp-Ala-Val-Gly-His-Phe-Met-NH$_2$;

-DPhe-Gln-Trp-Ala-Val-Gly-His-Leu-Leu-NH$_2$;
or
or a pharmaceutically acceptable salt thereof.

A third preferred embodiment features a compound according to formula (I) wherein at least one of m and n is not 0.

A fourth preferred embodiment features a compound the structure of which is specifically disclosed herein. More preferred are compounds and intermediates described in examples 1-79 herein. More preferred still are compounds of examples 19-25, 28-32, 4042, 45-65, and 74-79.

In a fifth preferred embodiment is featured a compound according to the formula:

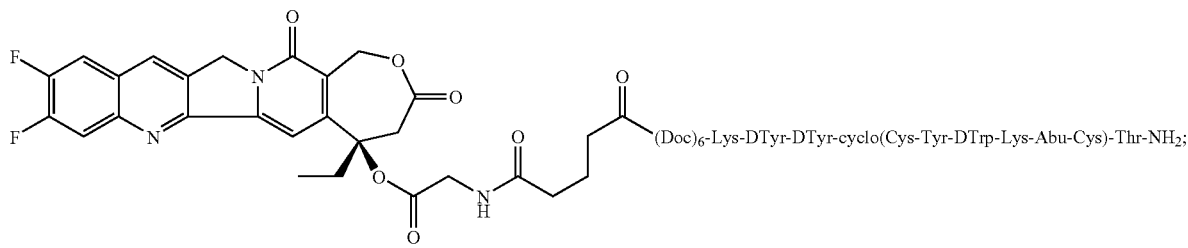
(Doc)$_6$-Lys-DTyr-DTyr-cyclo(Cys-Tyr-DTrp-Lys-Abu-Cys)-Thr-NH$_2$;

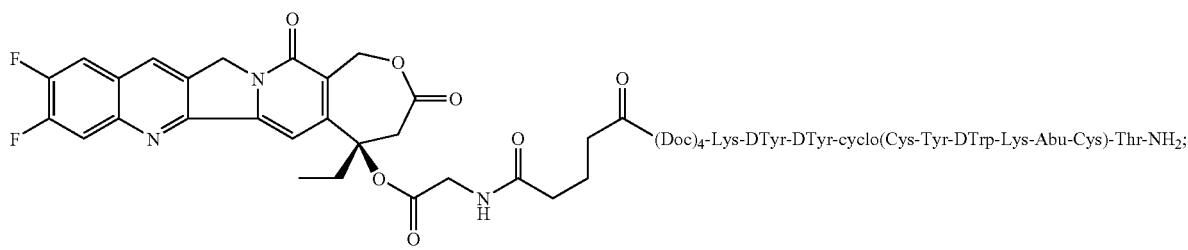
(Doc)$_4$-Lys-DTyr-DTyr-cyclo(Cys-Tyr-DTrp-Lys-Abu-Cys)-Thr-NH$_2$;

-continued
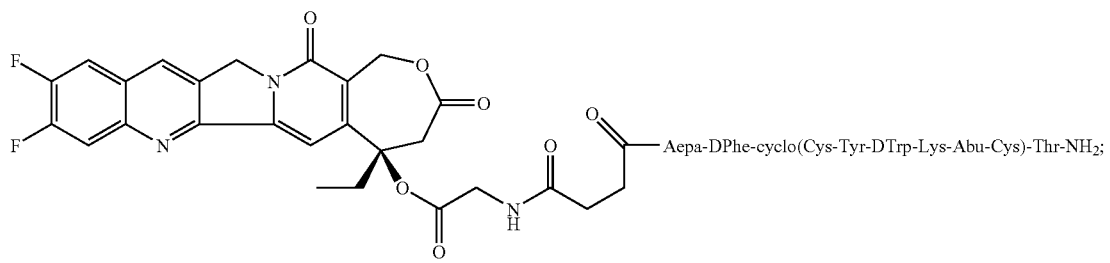
Aepa-DPhe-cyclo(Cys-Tyr-DTrp-Lys-Abu-Cys)-Thr-NH₂;
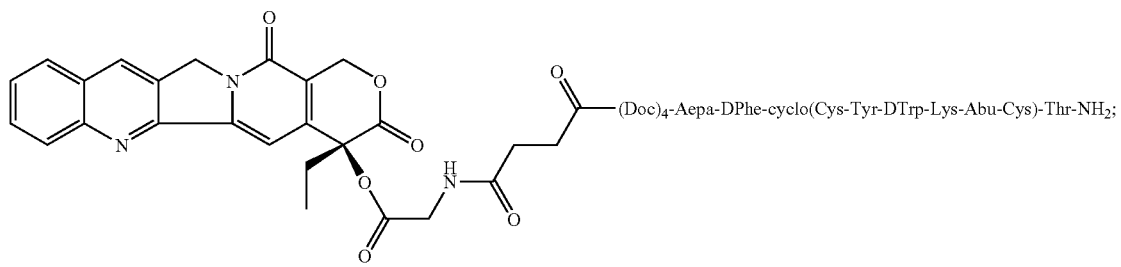
(Doc)₄-Aepa-DPhe-cyclo(Cys-Tyr-DTrp-Lys-Abu-Cys)-Thr-NH₂;
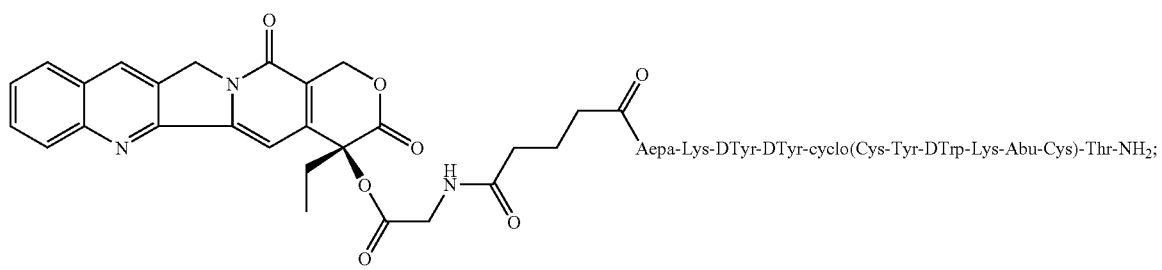
Aepa-Lys-DTyr-DTyr-cyclo(Cys-Tyr-DTrp-Lys-Abu-Cys)-Thr-NH₂;
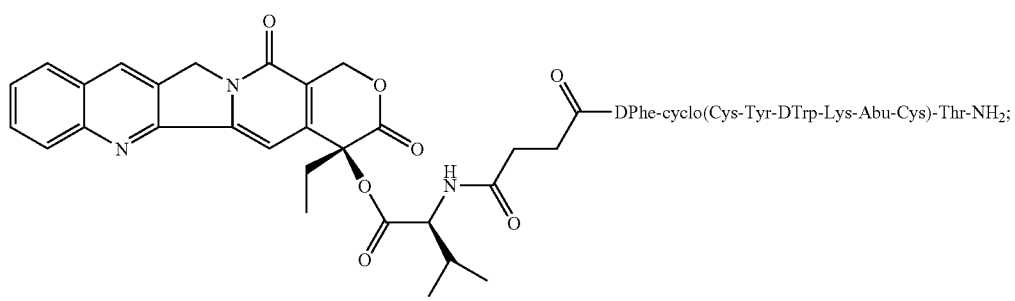
DPhe-cyclo(Cys-Tyr-DTrp-Lys-Abu-Cys)-Thr-NH₂;
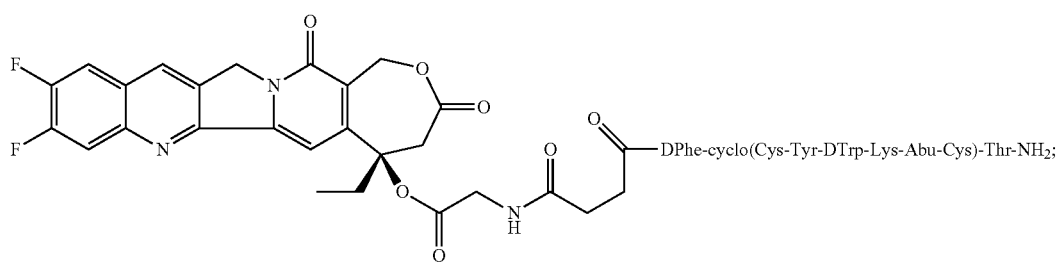
DPhe-cyclo(Cys-Tyr-DTrp-Lys-Abu-Cys)-Thr-NH₂;
(SEQ ID NO: 16)
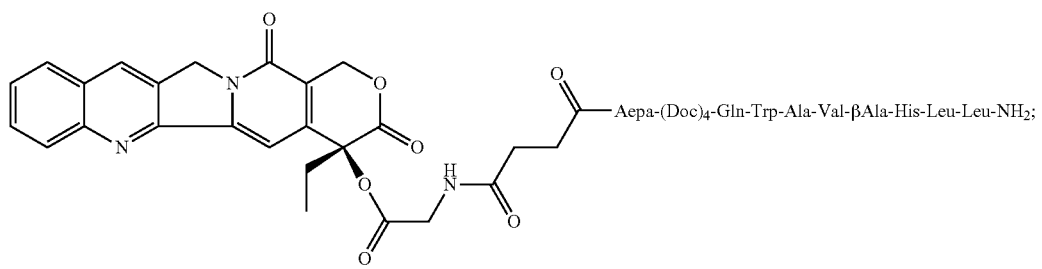
Aepa-(Doc)₄-Gln-Trp-Ala-Val-βAla-His-Leu-Leu-NH₂;

-continued
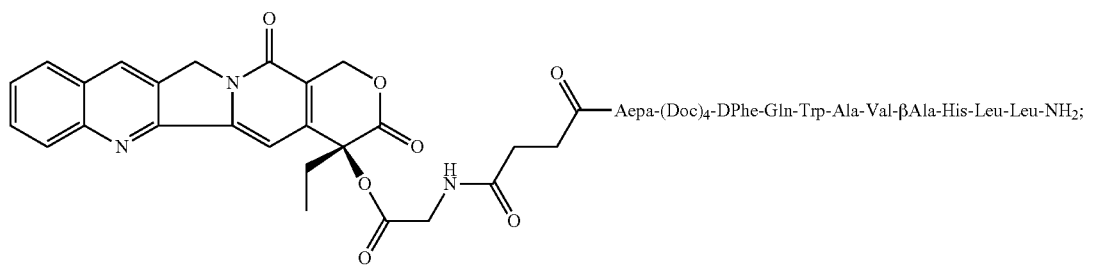
(SEQ ID NO: 16)
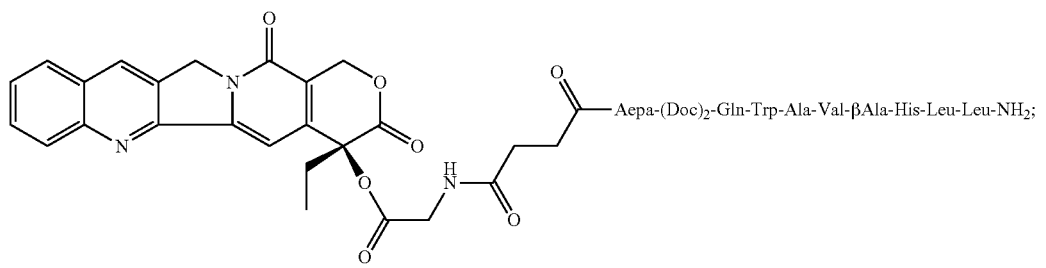
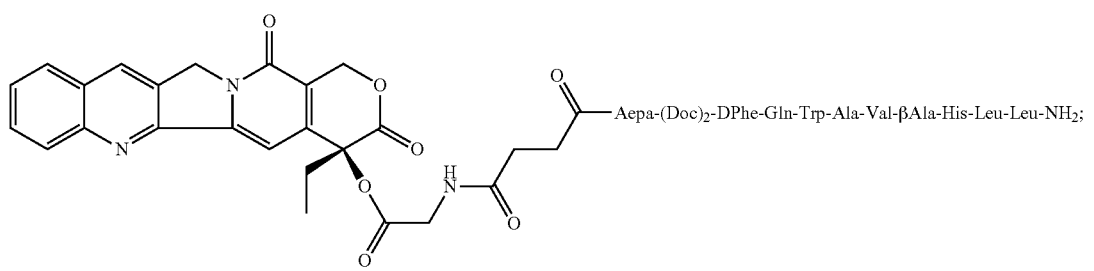
(SEQ ID NO: 19)
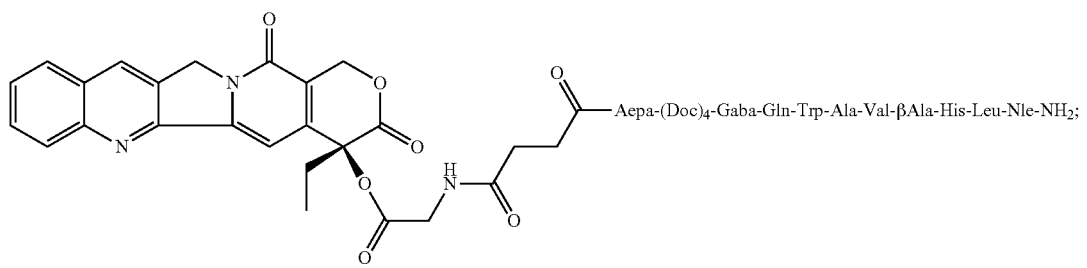
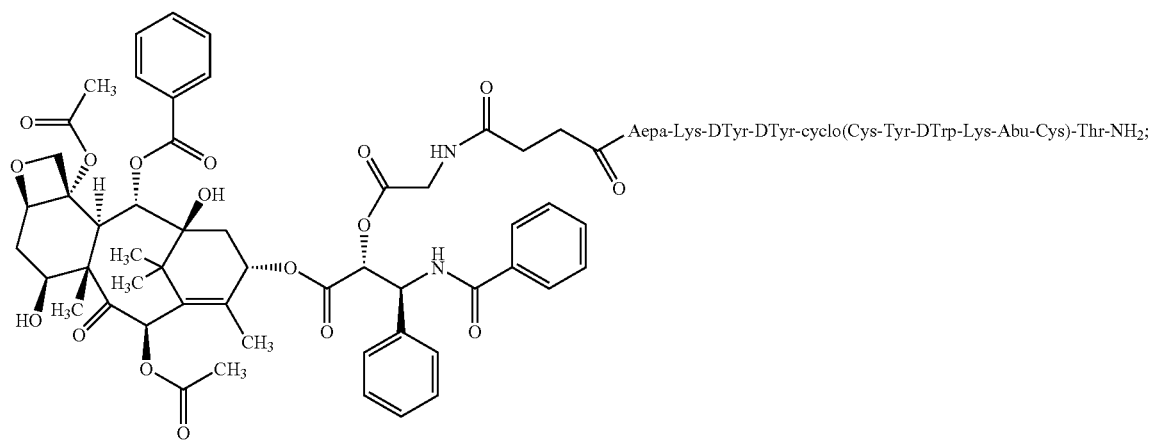

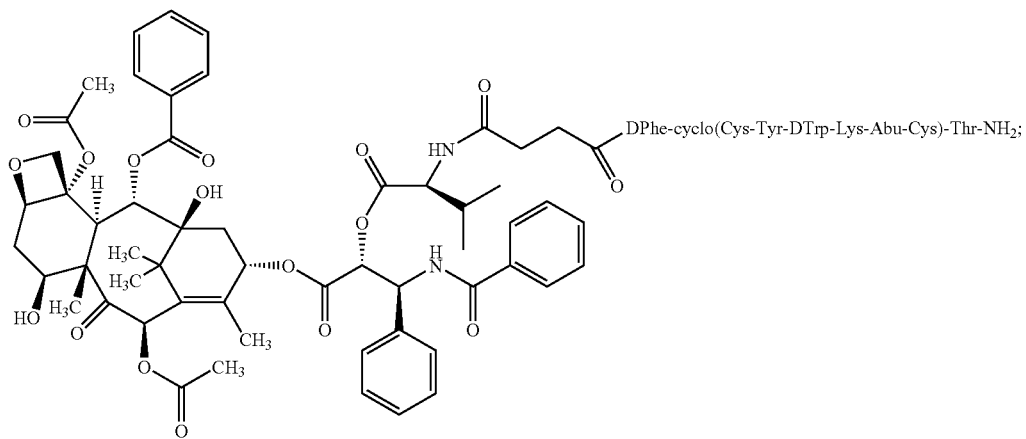
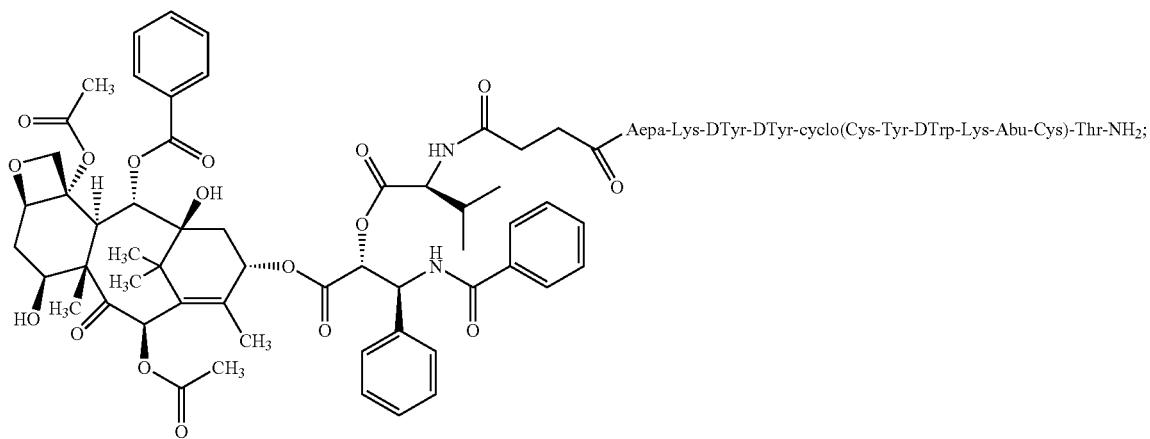
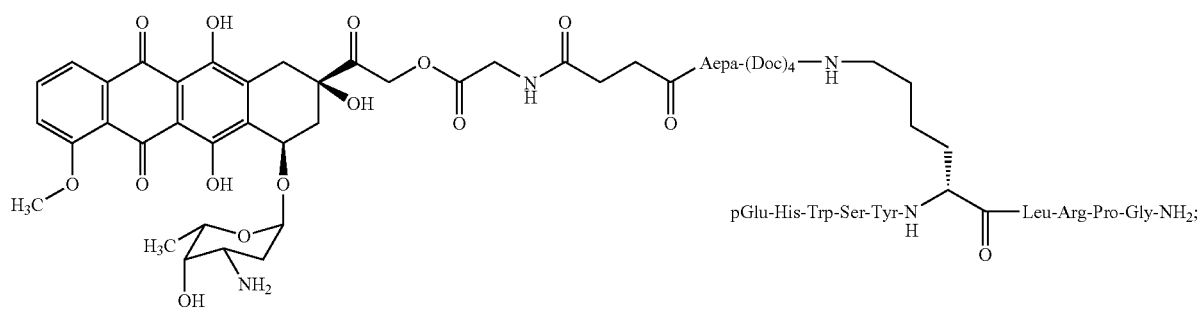
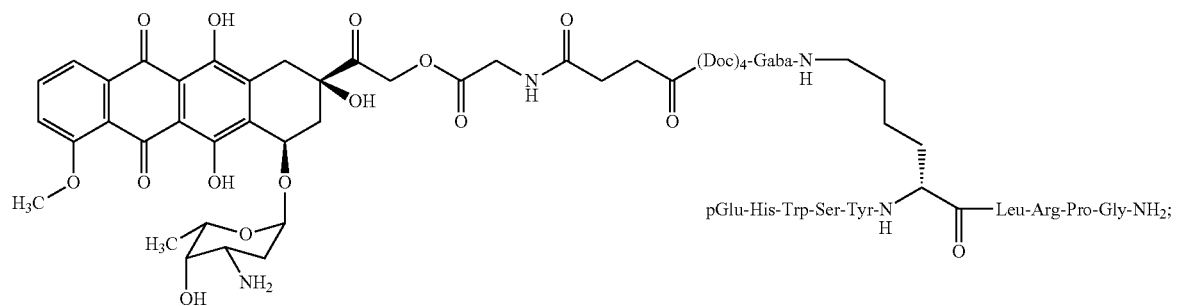

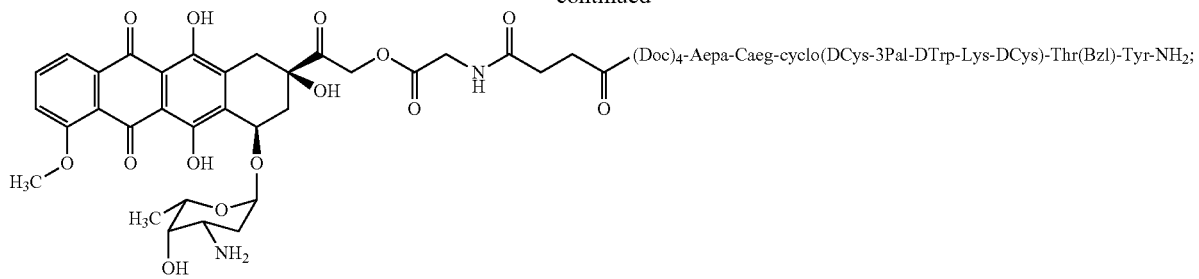
(Doc)₄-Aepa-Caeg-cyclo(DCys-3Pal-DTrp-Lys-DCys)-Thr(Bzl)-Tyr-NH₂;
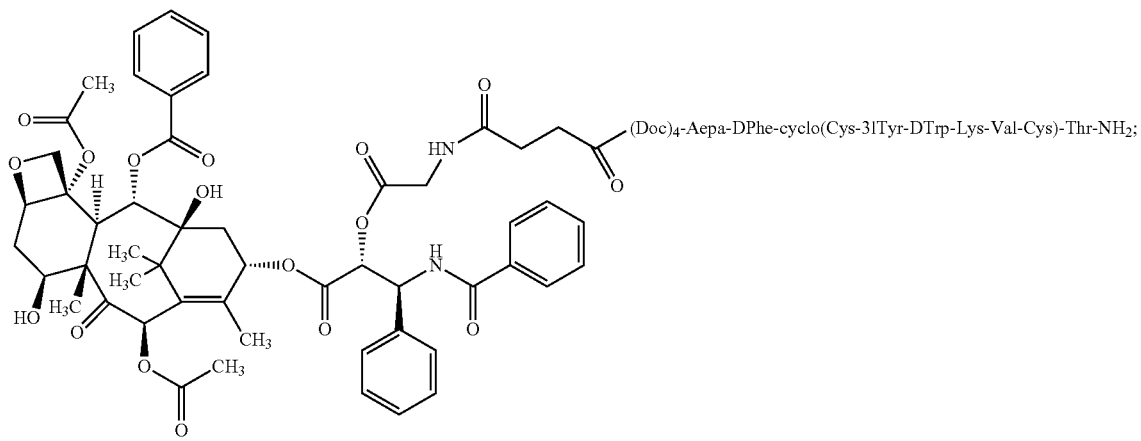
(Doc)₄-Aepa-DPhe-cyclo(Cys-3ITyr-DTrp-Lys-Val-Cys)-Thr-NH₂;
(SEQ ID NO: 18)
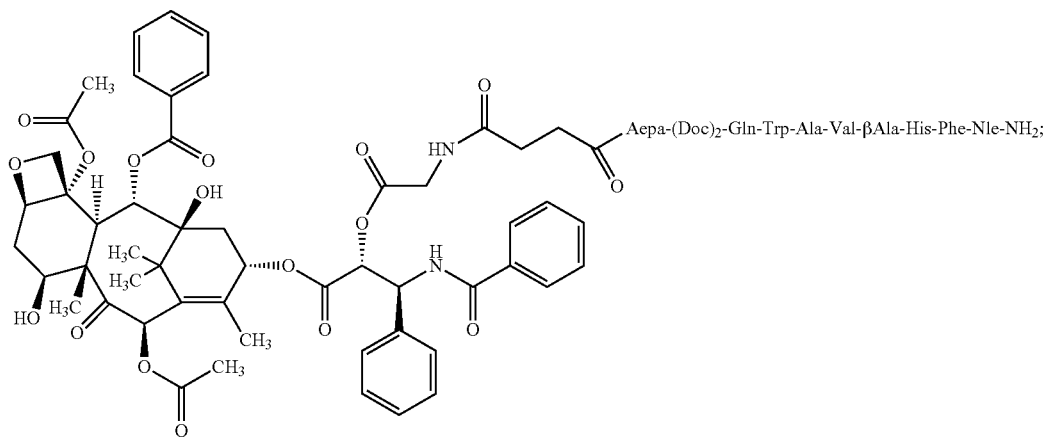
Aepa-(Doc)₂-Gln-Trp-Ala-Val-βAla-His-Phe-Nle-NH₂;
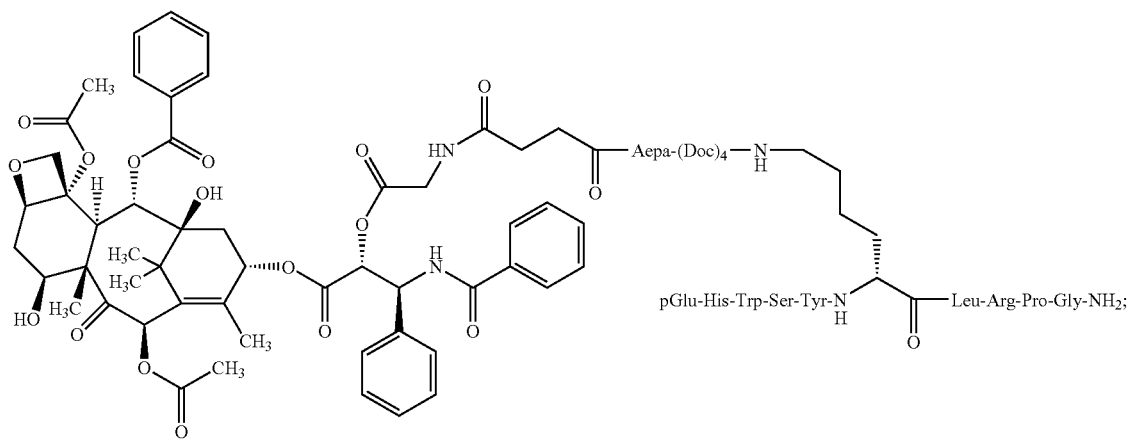

-continued
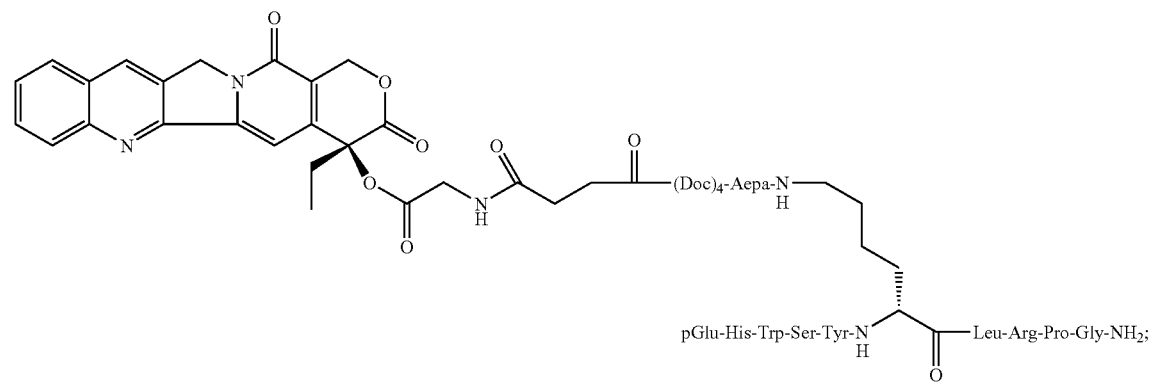
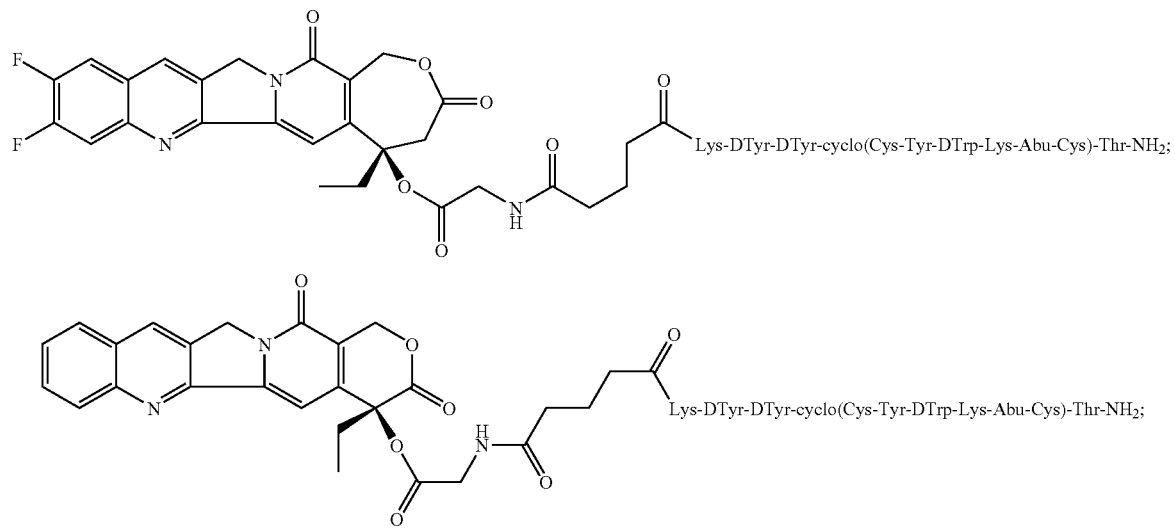
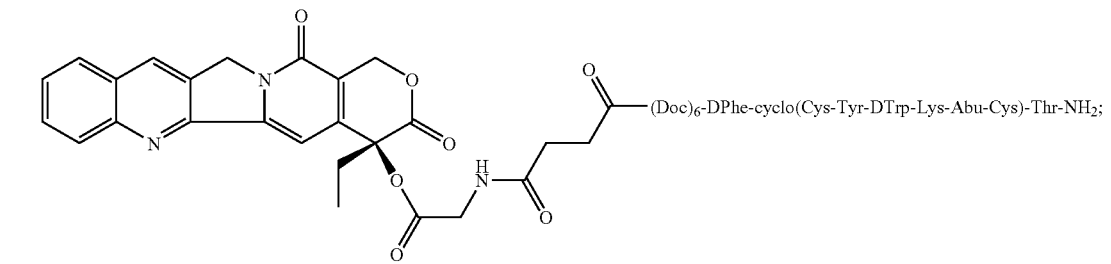
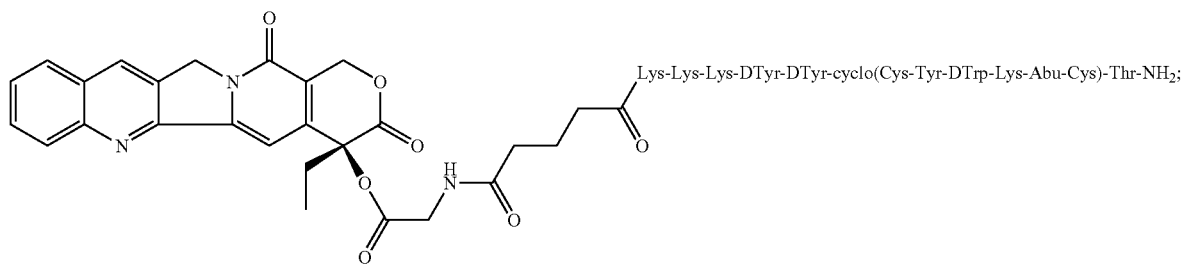
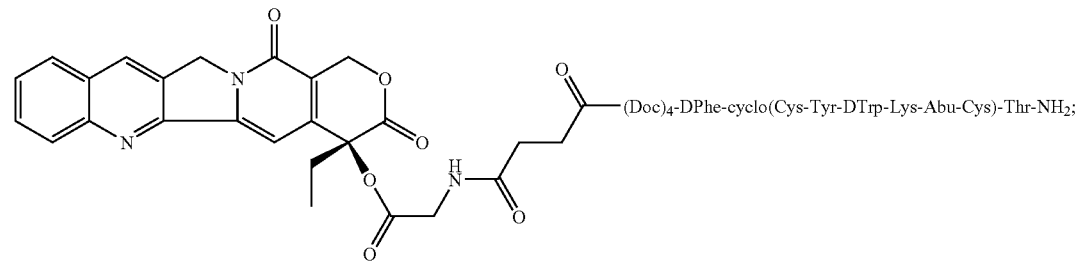

-continued
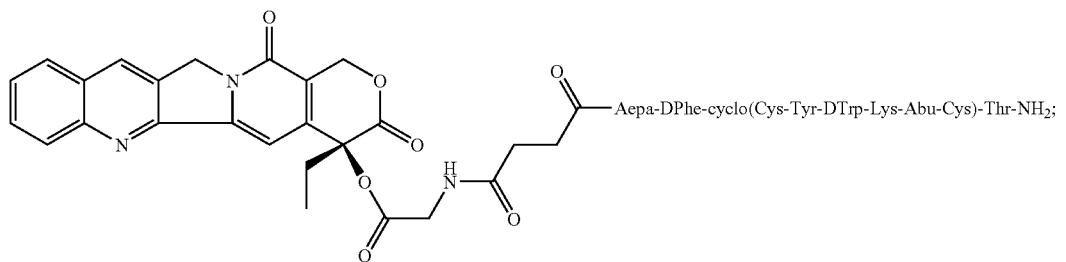
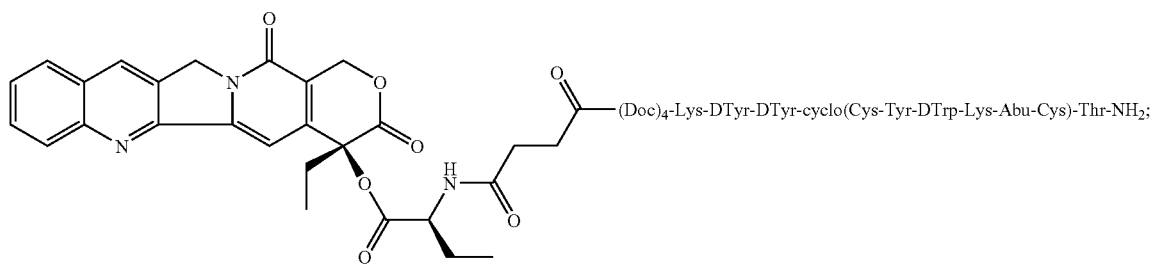
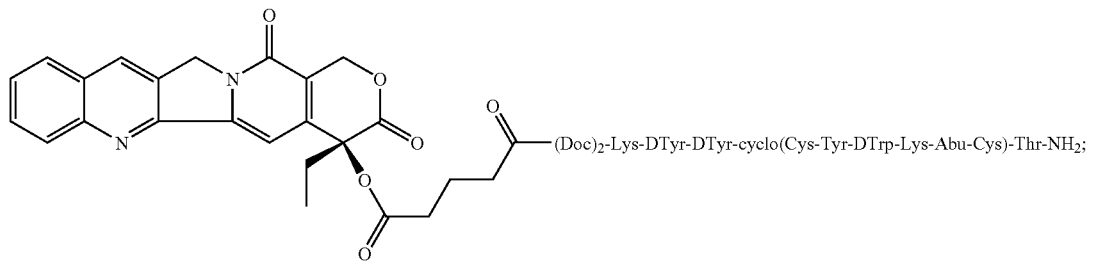
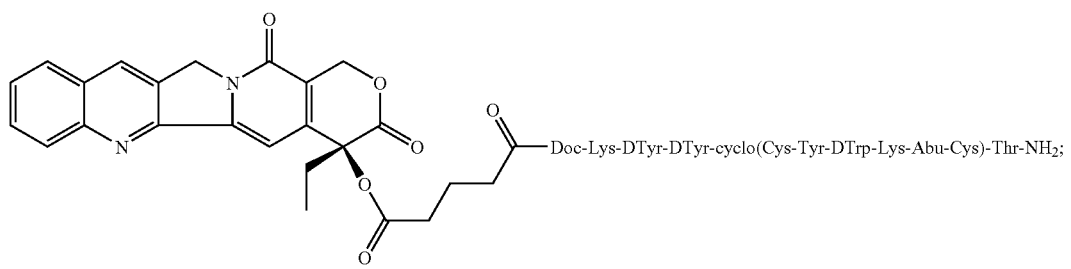
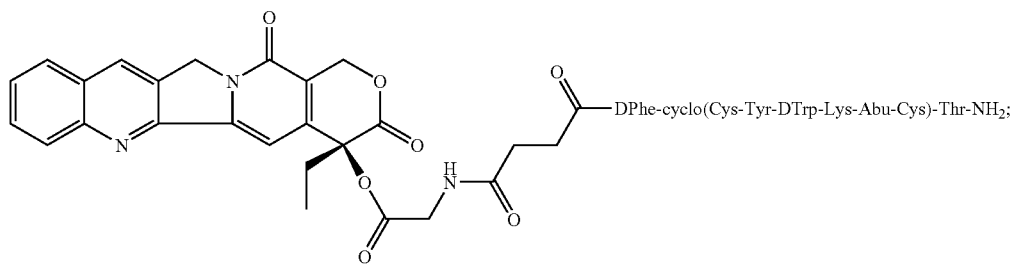
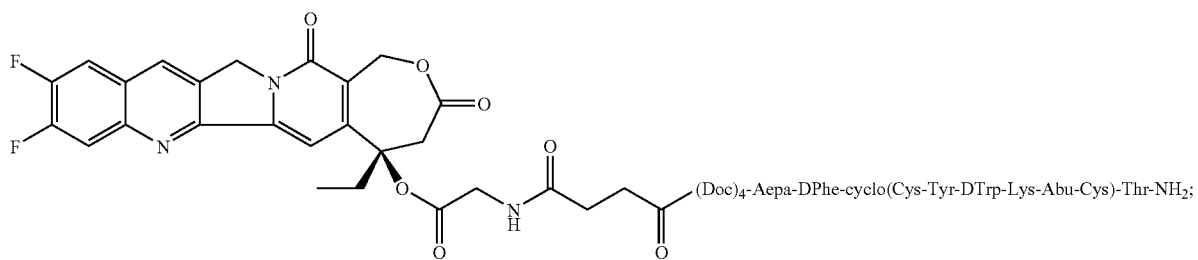

-continued
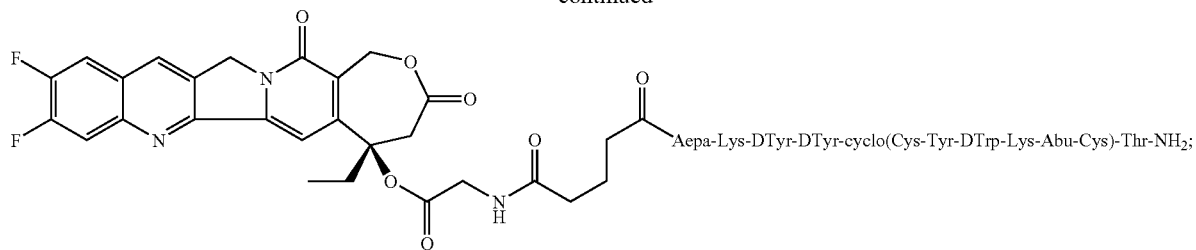
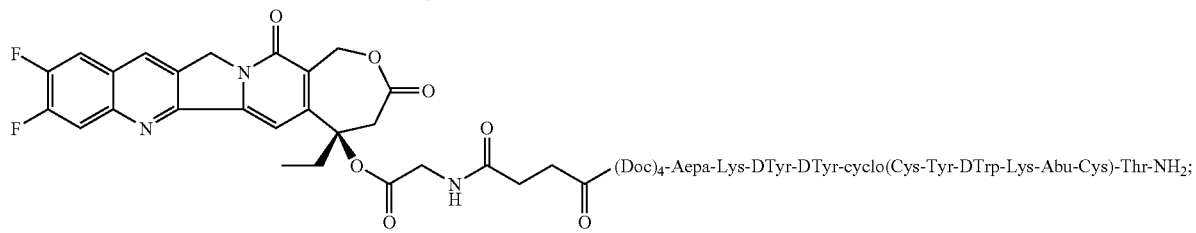
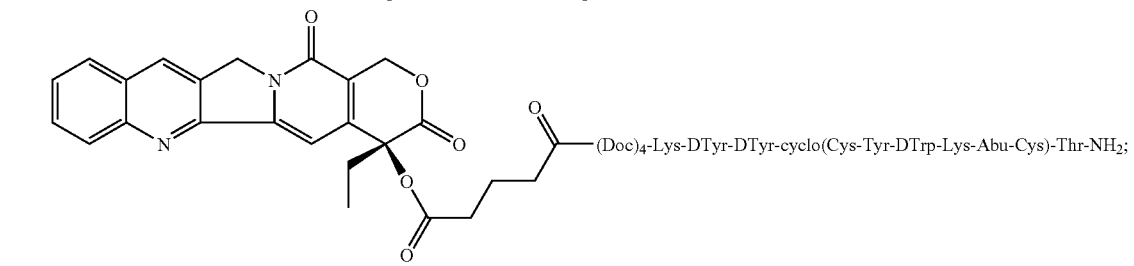
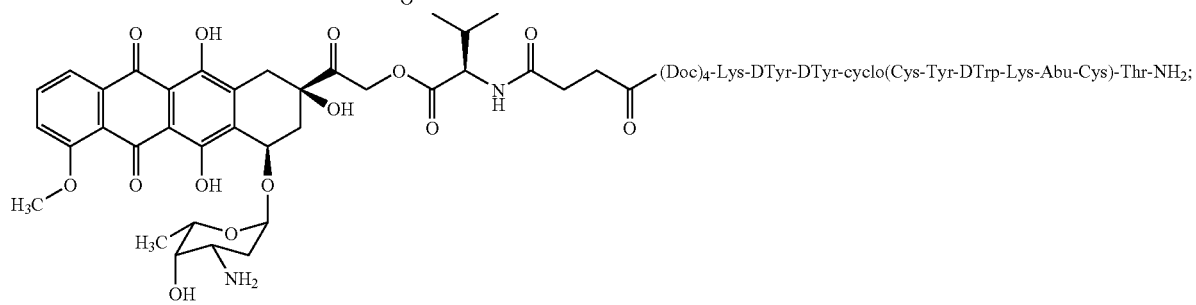
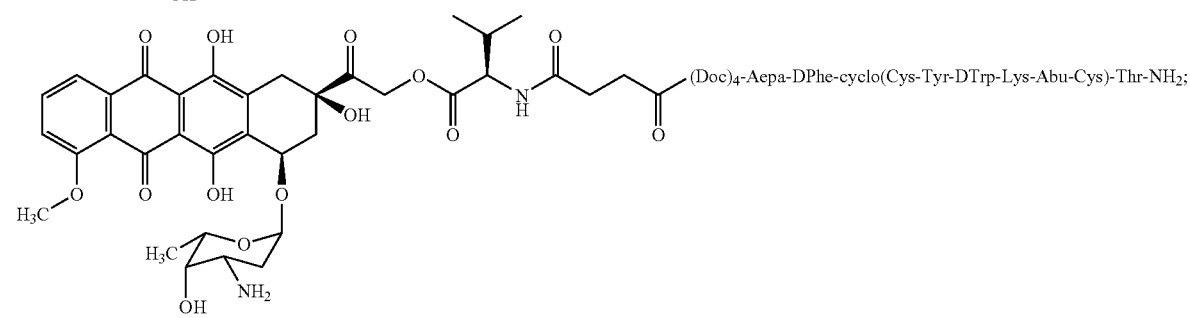
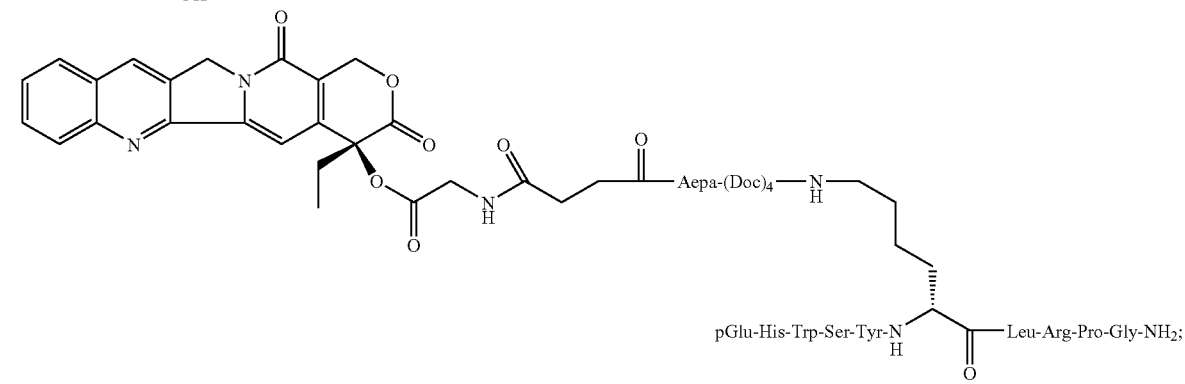

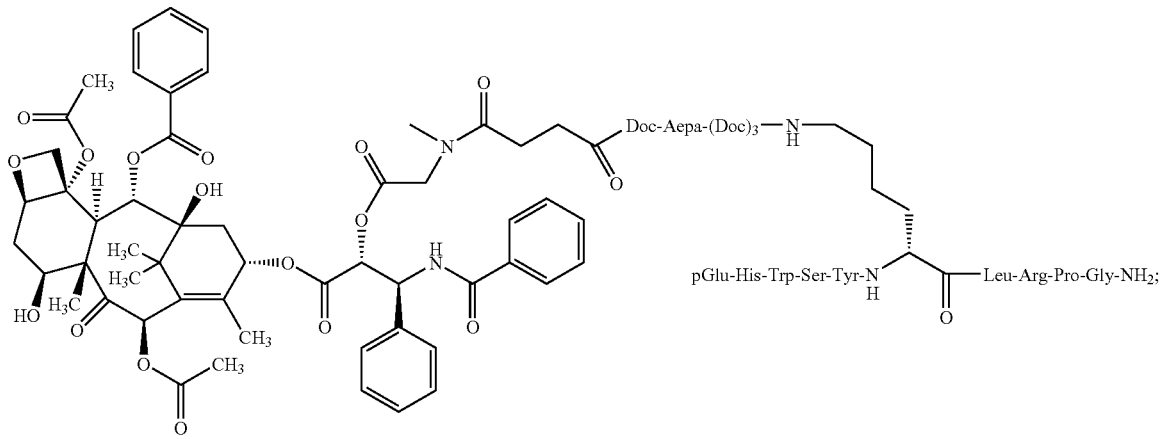
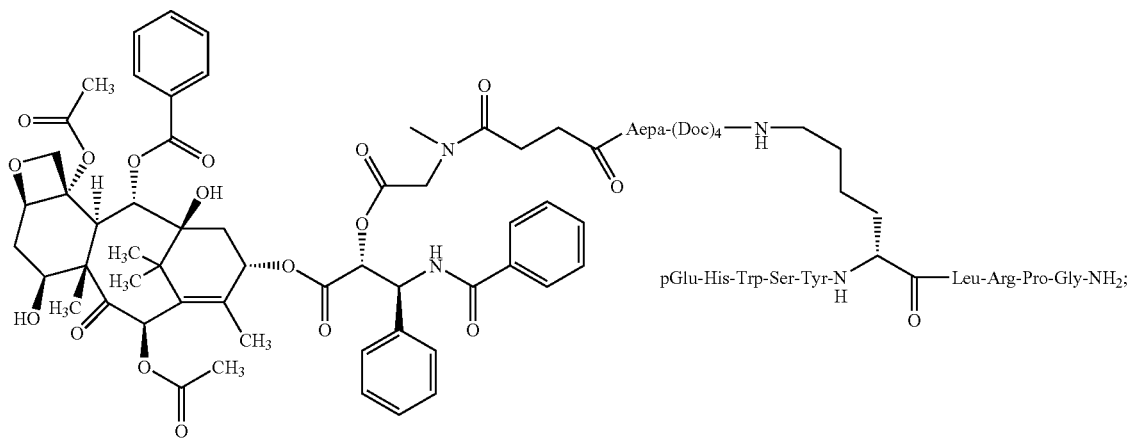
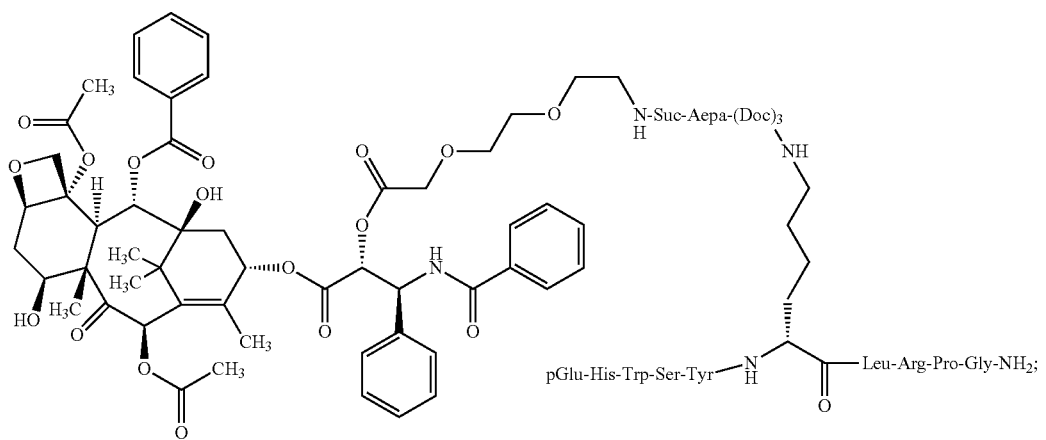

-continued
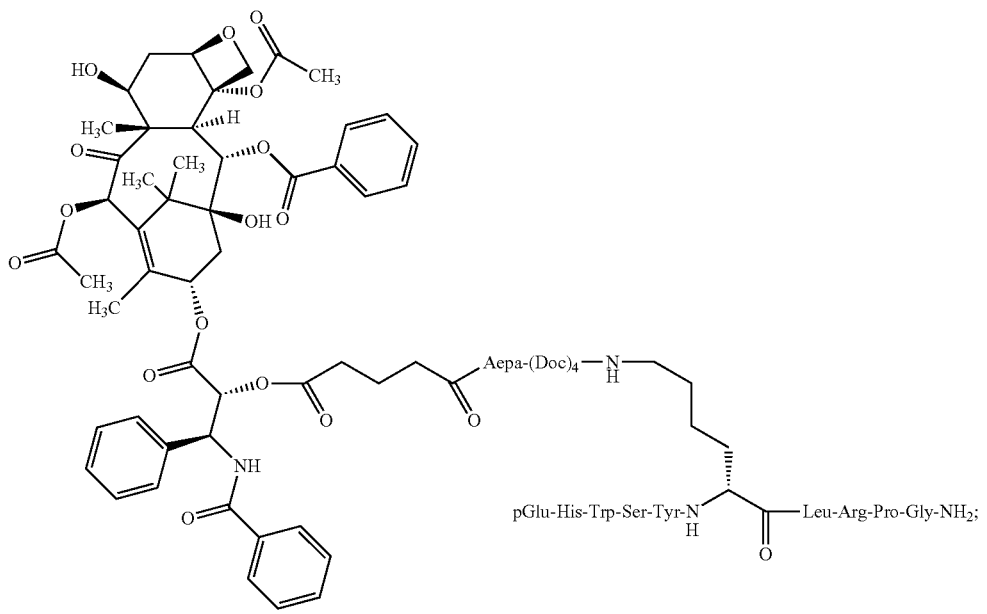
(SEQ ID NO: 19)
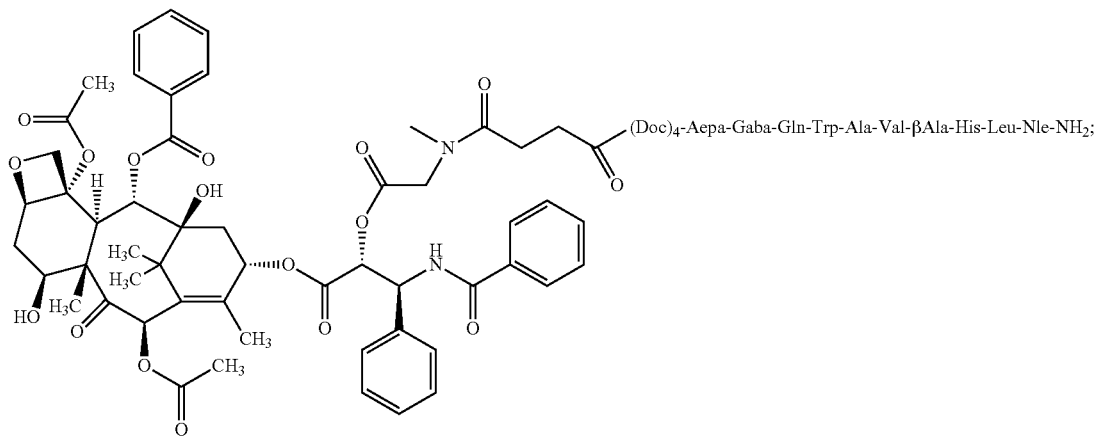
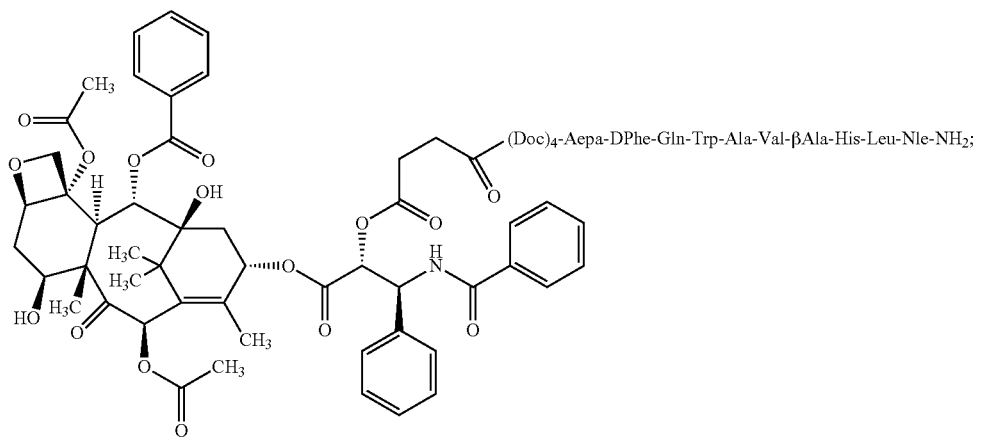

-continued
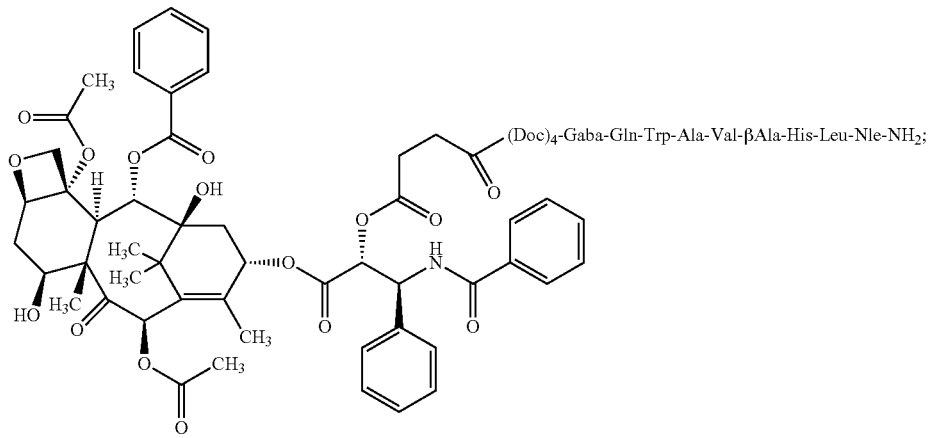
(SEQ ID NO: 19)
(Doc)₄-Gaba-Gln-Trp-Ala-Val-βAla-His-Leu-Nle-NH₂;
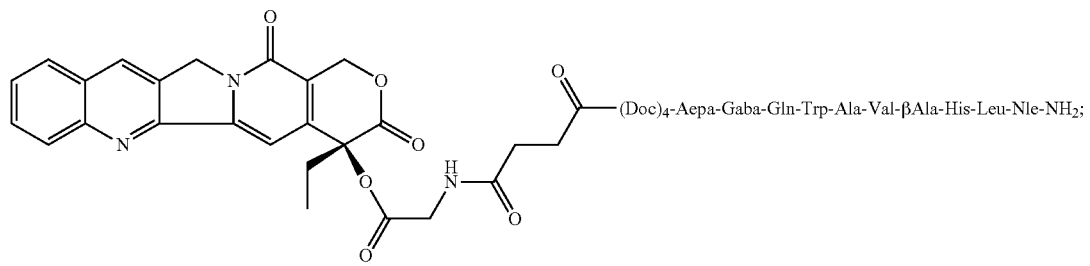
(SEQ ID NO: 19)
(Doc)₄-Aepa-Gaba-Gln-Trp-Ala-Val-βAla-His-Leu-Nle-NH₂;
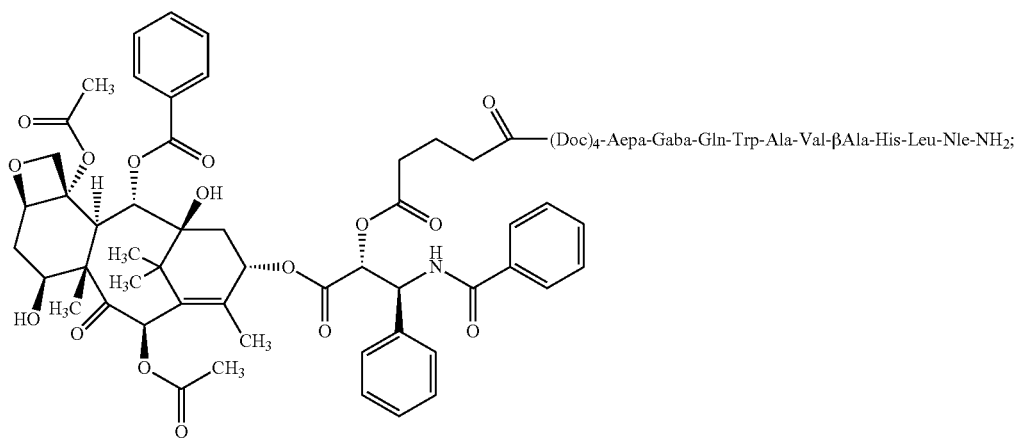
(SEQ ID NO: 19)
(Doc)₄-Aepa-Gaba-Gln-Trp-Ala-Val-βAla-His-Leu-Nle-NH₂;
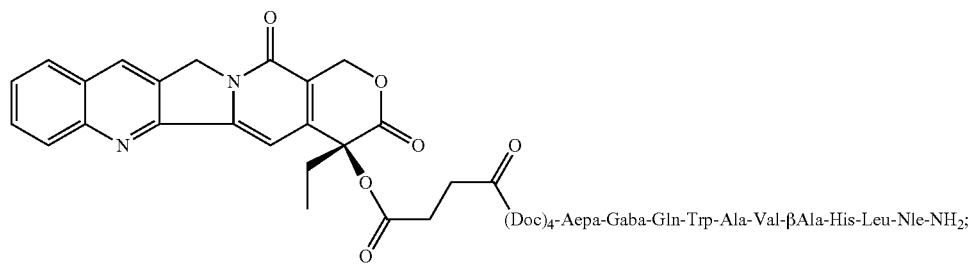
(SEQ ID NO: 19)
(Doc)₄-Aepa-Gaba-Gln-Trp-Ala-Val-βAla-His-Leu-Nle-NH₂;

(SEQ ID NO: 19)
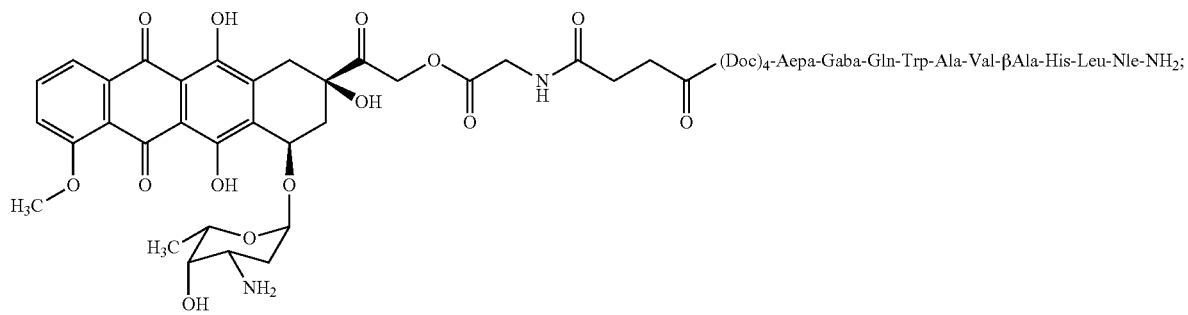
(Doc)₄-Aepa-Gaba-Gln-Trp-Ala-Val-βAla-His-Leu-Nle-NH₂;
(SEQ ID NO: 19)
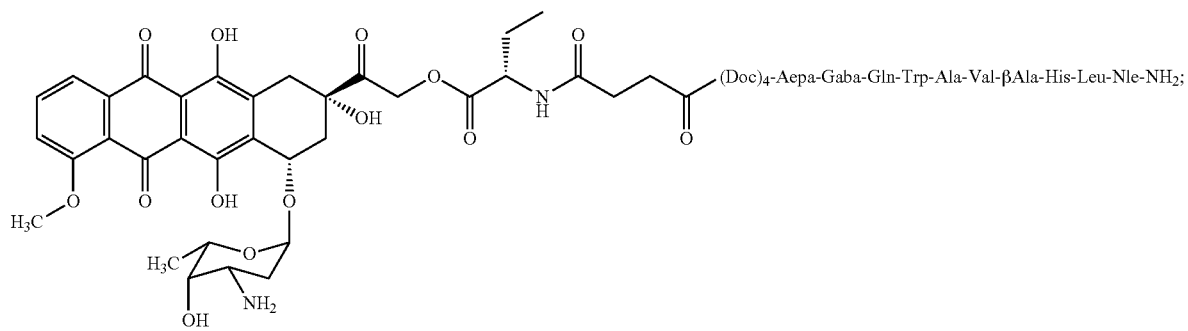
(Doc)₄-Aepa-Gaba-Gln-Trp-Ala-Val-βAla-His-Leu-Nle-NH₂;
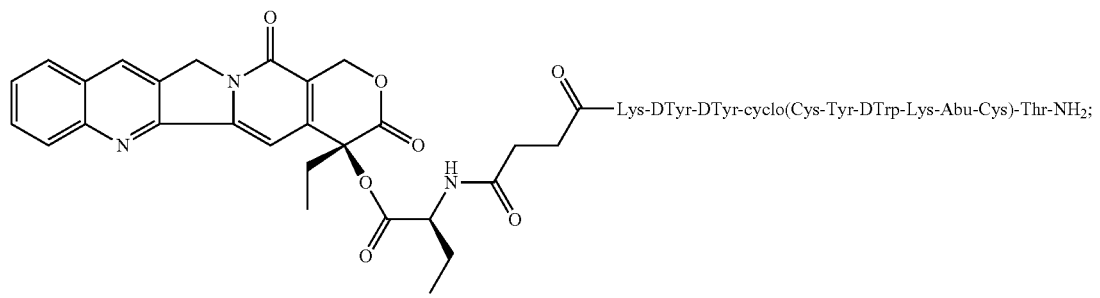
-Lys-DTyr-DTyr-cyclo(Cys-Tyr-DTrp-Lys-Abu-Cys)-Thr-NH₂;
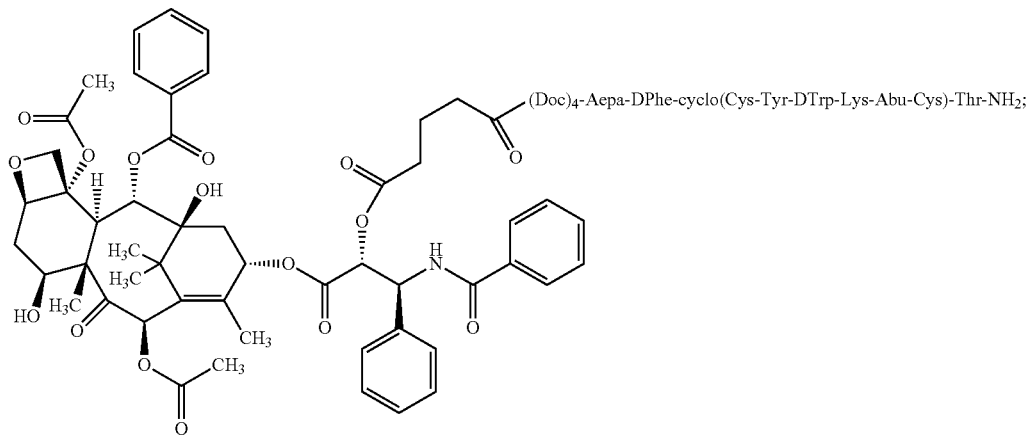
(Doc)₄-Aepa-DPhe-cyclo(Cys-Tyr-DTrp-Lys-Abu-Cys)-Thr-NH₂;

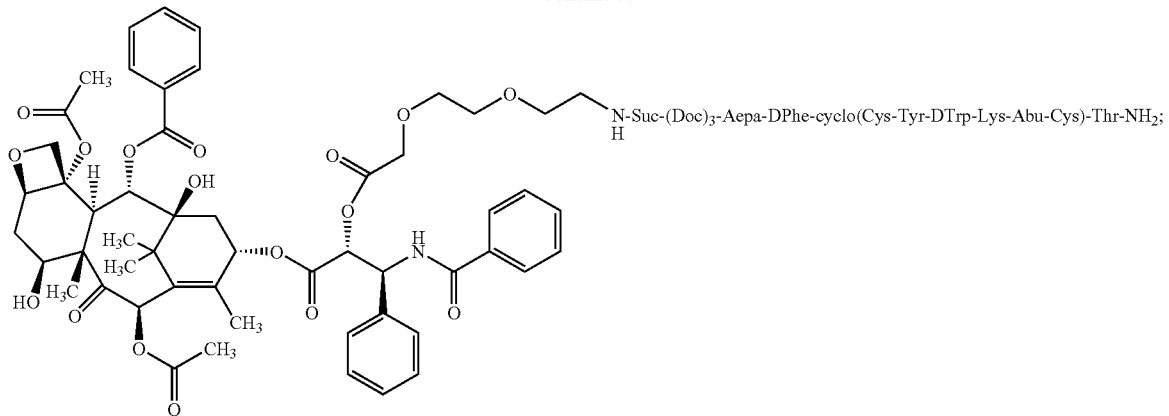
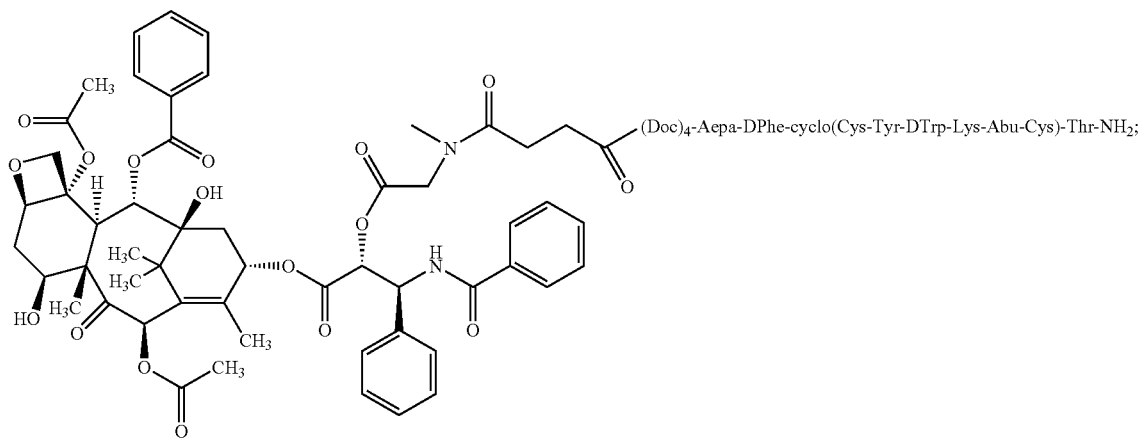
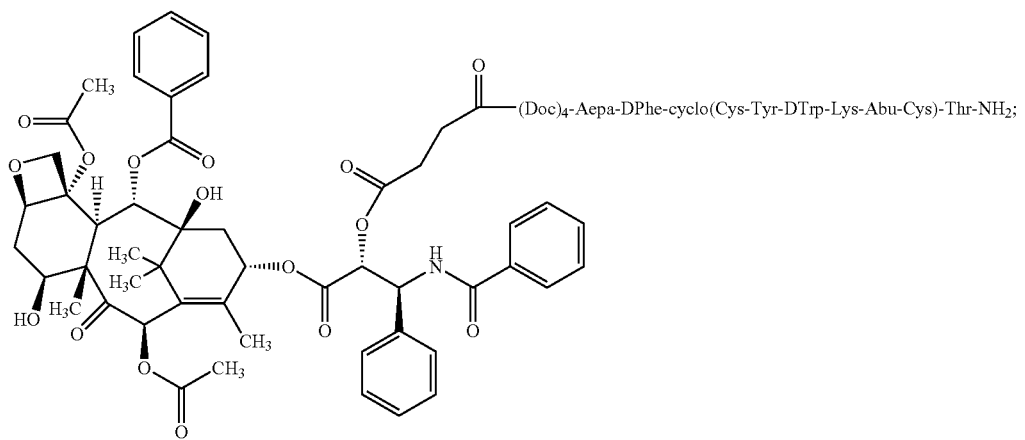
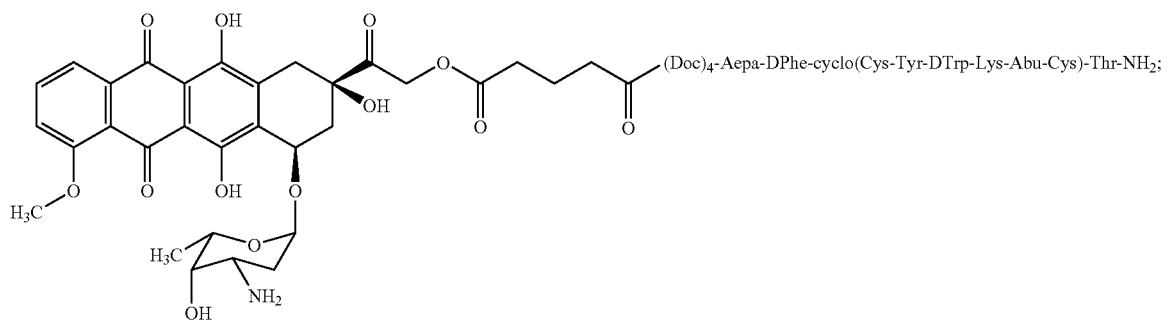

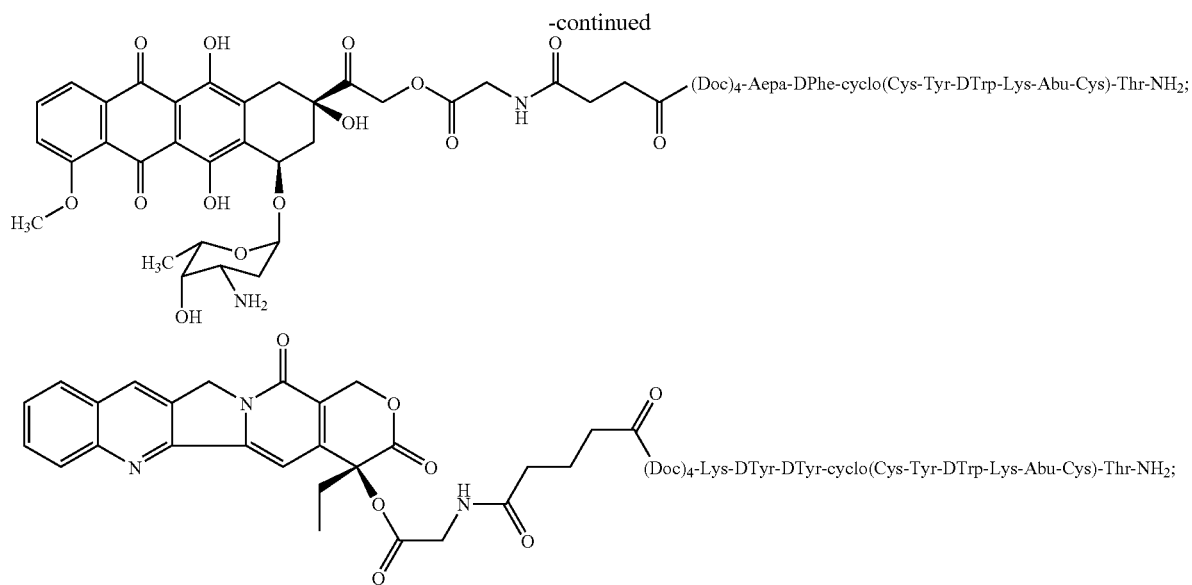
or a pharmaceutically acceptable salt thereof. More preferred are compounds according to the formula:
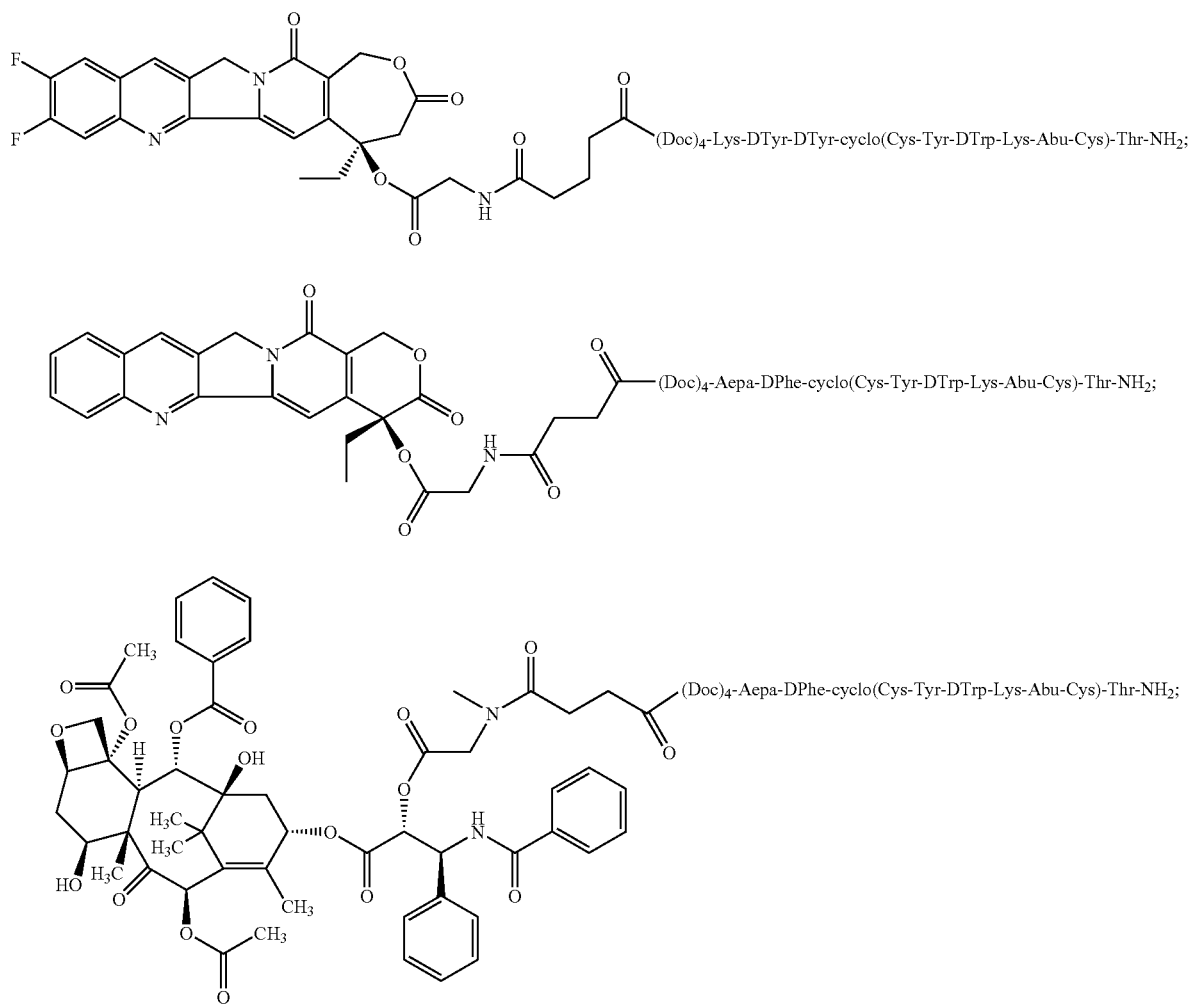

-continued
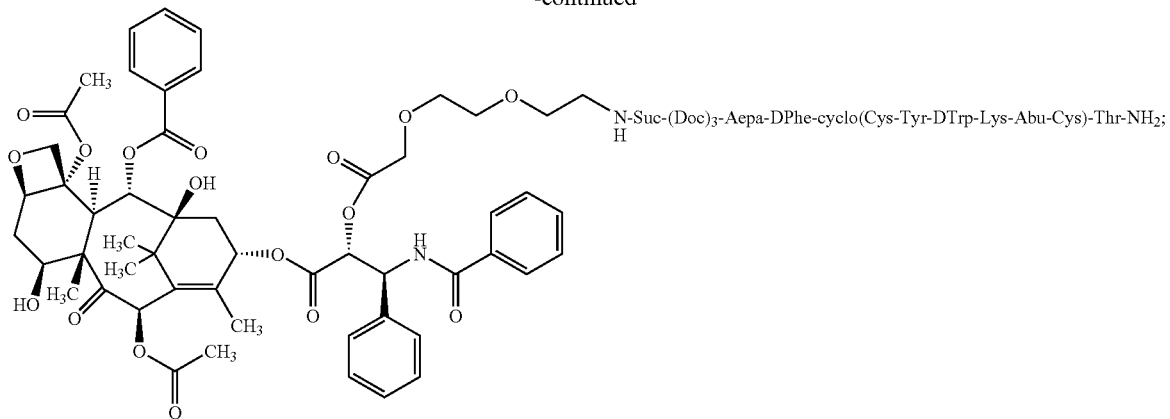
(SEQ ID NO: 19)
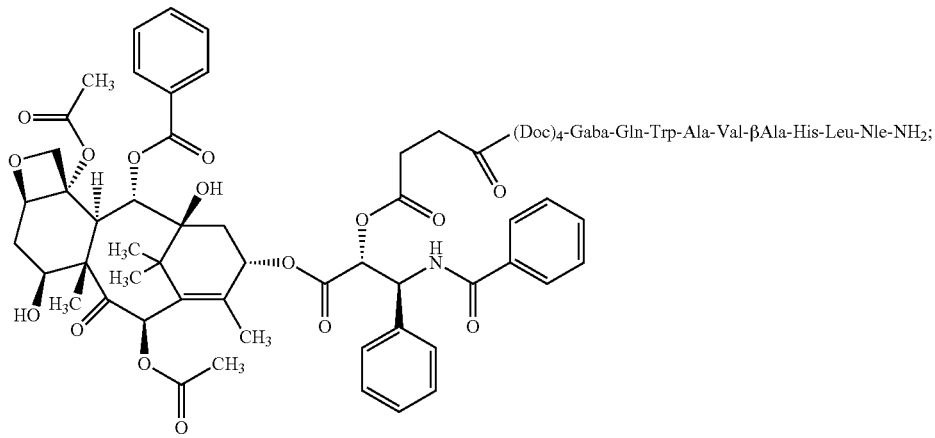
(SEQ ID NO: 19)
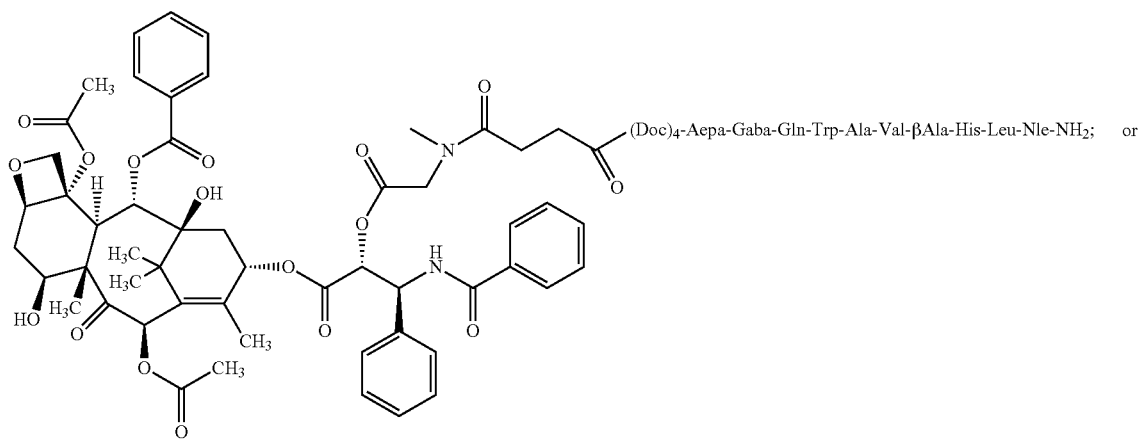
(SEQ ID NO: 19)
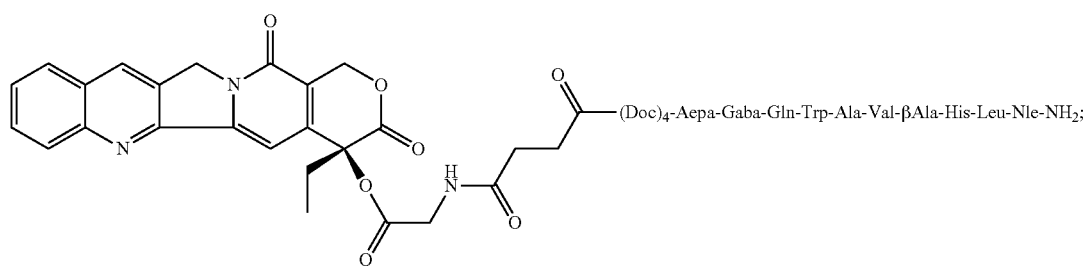

or a pharmaceutically acceptable salt thereof. Even more preferred are compounds comprising the formula:

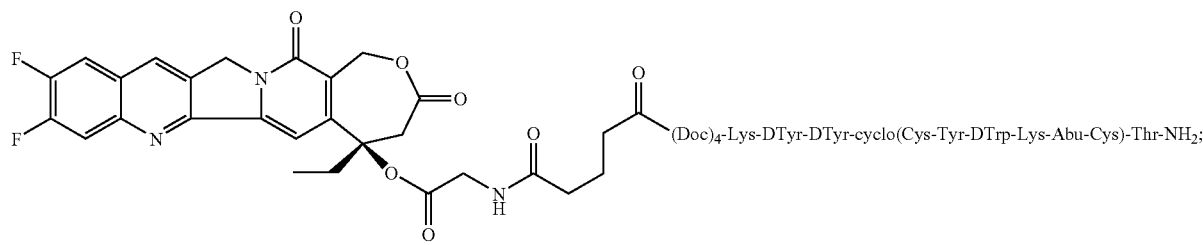

or

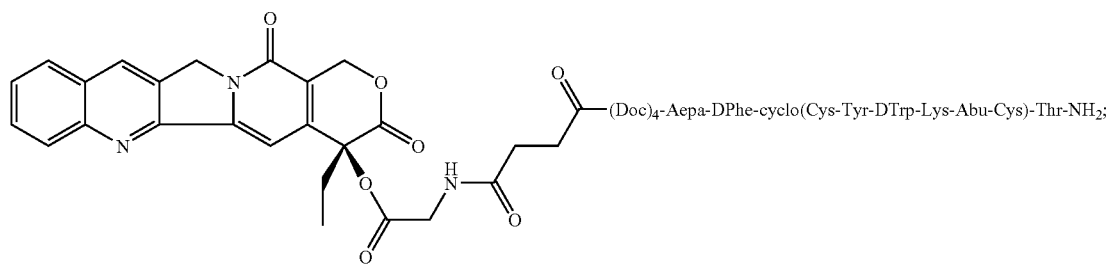

or a pharmaceutically acceptable salt thereof.

In a sixth preferred embodiment is featured a compound selected from the compounds listed in Table A.

In a seventh preferred embodiment is featured a compound selected from the compounds listed in Table B.

In an eighth preferred embodiment is featured a compound selected from the compounds listed in Table C.

In a ninth preferred embodiment is featured a compound selected from the compounds listed in Table D.

In a tenth preferred embodiment is featured a compound selected from the compounds listed in Table E.

In an eleventh preferred embodiment is featured a compound selected from the compounds listed in Table F.

In a twelfth preferred embodiment is featured a compound selected from the compounds listed in Table G.

In a thirteenth preferred embodiment is featured a compound selected from the compounds listed in Table H.

In a fourteenth preferred embodiment is featured a compound selected from the compounds listed in Table I.

In second aspect, the invention features a pharmaceutical composition comprising an effective amount of a targeted cytotoxic compound comprising a cytotoxic moiety bound to a targeting moiety, such as, for example, a ligand of a biological receptor, or a pharmaceutically acceptable salt thereof and a pharmaceutically acceptable carrier. The two moieties are bound via a linker, e.g., as described by formula I defined herein.

In a third aspect, the invention features a method of treating a disease in a subject in need thereof, said method comprising administering to said subject a therapeutically effective amount of a targeted cytotoxic compound according to formula I defined herein, or a pharmaceutically acceptable salt thereof, wherein said disease is selected from the group consisting of fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, and hematopoietic cancer.

In a fourth aspect, the invention features a method of treating a disease in a subject in need thereof, said method comprising administering to said subject a therapeutically effective amount of a targeted cytotoxic compound according to formula I defined herein, or a pharmaceutically acceptable salt thereof, wherein said disease is selected from the group consisting of benign prostatic hyperplasia, restenosis, breast cancer, colon cancer, pancreas cancer, prostate cancer, lung cancer, small cell lung carcinoma, ovarian cancer, epidermal cancer, and hematopoietic cancer.

In a fifth aspect, the invention features a method of treating a disease in a subject in need thereof, said method comprising administering to said subject a therapeutically effective amount of a targeted cytotoxic compound according to formula I defined herein, or a pharmaceutically acceptable salt thereof, wherein said disease is characterized by undesired proliferation of cells that express one or more somatostatin-type receptors.

In a sixth aspect, the invention features a method of treating a disease in a subject in need thereof, said method comprising administering to said subject a therapeutically effective amount of a targeted cytotoxic compound according to formula I defined herein, or a pharmaceutically acceptable salt thereof, wherein said disease is characterized by undesired proliferation of cells that express one or more of bombesin-type receptors.

In a seventh aspect, the invention features a method of treating a disease in a subject in need thereof, said method comprising administering to said subject a therapeutically effective amount of a targeted cytotoxic compound according to formula I defined herein, or a pharmaceutically acceptable salt thereof, wherein said disease is characterized by undesired proliferation of cells that express one or more LHRH-type receptors.

As used herein the term "amino acid" refers to any naturally occurring and unnatural amino acids, including but not limited to α-amino acids, β-amino acids, γ-amino acids, and may be either D-amino acids or L-amino acids unless otherwise indicated. With the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., R=$CH_3$ and R'=H for Ala), or R and R' may be joined to form a ring system. For the N-terminal amino acid, the abbreviation stands for the structure of $(R^2R^3)$—N—C(R)(R')—CO—, wherein $R^2$ and $R^3$ are as defined in formula (I).

An exemplary list of preferred amino acids includes, but is not limited to, Ala, Arg, Asp, Asn, Cys, Glu, pGlu, Gln, Gly, His, Ile, Leu, Lys, Met, Phe, Pro, Ser, Thr, Trp, Tyr, Val, β-Ala, Act, Apc, Gaba, Apn, Ahx, Ahp, Aoc, Anc, Adc, Aun, Ado, Acc, A3c, A4c, A5c, A6c, Aib, Orn, Dab, Dap, hArg, 4Pal, 3Pal, 2Pal, Abu, Cha, Cit, Nle, Nva, Taz, 2Thi, 3Thi, Dhp, Dmt, 2Fua, 3Hyp, 4Hyp, Inc, Inp, Ktp, hLeu. Oic, hPhe, Pip, Sar, Thz, Tic, Tle, Phg and Caeg.

The peptide portion of compounds of the invention may also be denoted herein by another format, e.g., (Tyr[11])Somatostatin(1-14)-NH$_2$, with the substituted amino acid(s) from the natural sequence placed between the first set of parentheses (e.g., Tyr[11] for Phe[11] in somatostatin). The numbers between the second set of parentheses refer to the number of amino acids present in the peptide (e.g., somatostatin(1-11) refers to amino acids 1 through 11 of the peptide sequence for somatostatin). The designation "NH$_2$" in e.g., (Tyr[11])Somatostatin(1-14)-NH$_2$, indicates that the C-terminus of the peptide is amidated. (Tyr[11])Somatostatin(1-14), or alternatively (Tyr[11])Somatostatin(1-14)-OH, indicates that the C-terminus is the free acid.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —C$_{1-4}$ alkyl, —C$_{1-4}$ alkoxy, halogen (i.e., fluorine, chlorine, bromine, and iodine), —OH, —CN, —SH, —NH$_2$, —NO$_2$, —C$_{1-2}$ alkyl substituted with 1 to 5 halogens, —CF$_3$, —OCF$_3$, and —(CH$_2$)$_{0-4}$—COOH. In different embodiments the aryl contains 0, 1, 2, 3, or 4 substituents.

"Alkylaryl" refers to an "alkyl" joined to an "aryl".

The term cycloalkyl is intended to include a mono-cycloalkyl group or a bi-cycloalkyl group of the indicated carbon number known to those of skill in the art.

The term heterocycle includes mono-cyclic and bi-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems also may be non-aromatic, for example pyrrolidine, piperidine, morpholine and the like.

The chemist of ordinary skill will recognize that certain combinations of heteroatom-containing substituents listed in this invention define compounds which will be less stable under physiological conditions. Accordingly, such compounds are less preferred.

Doc is 8-amino-3,6-dioxaoctanoic acid, represented by the structure:

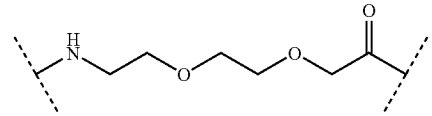

Aepa is 4-(2-aminoethyl)-1-carboxy methyl-piperazine, represented by the structure:

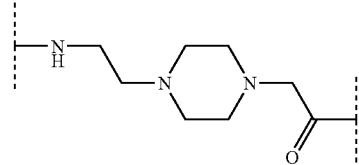

Suc or succ is succinyl, represented by the structure:

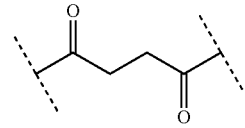

Glut or glutaryl has the structure of:

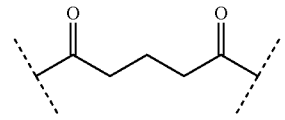

A camptothecin moiety has the structure of:

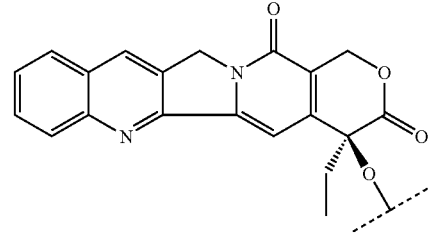

Camptothecin derivative moieties include but are not limited to:
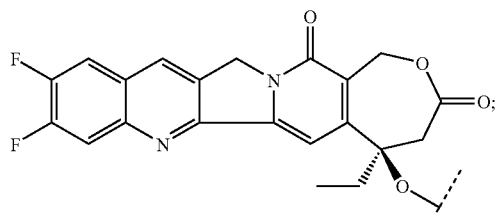
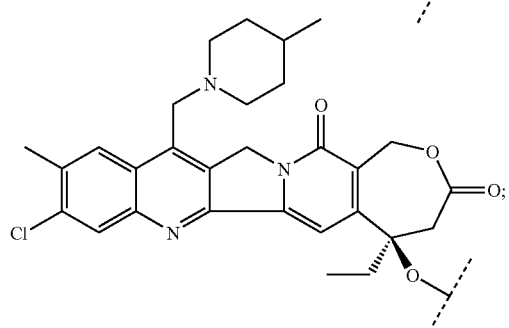
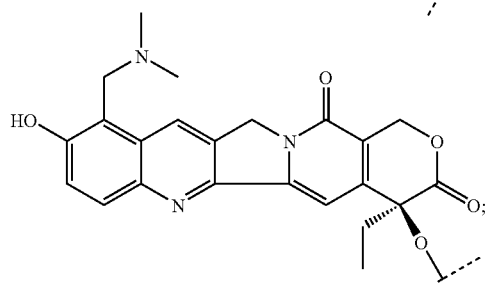
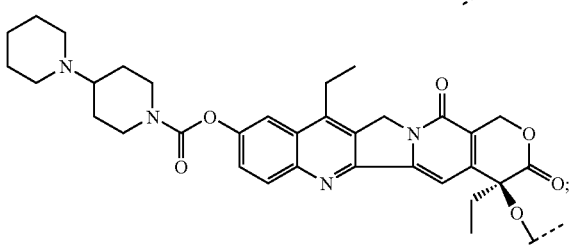
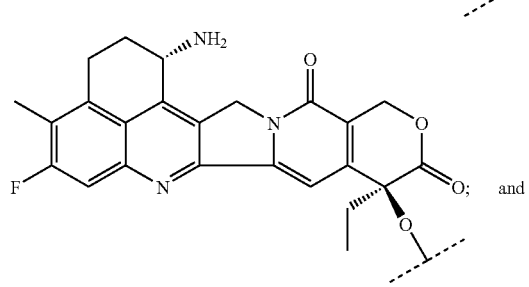 and
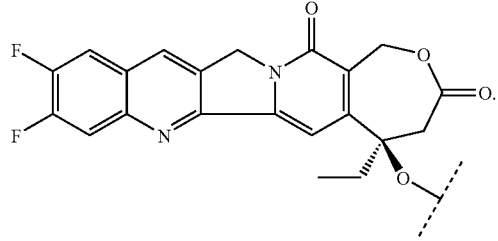
A paclitaxel moiety has the structure of:
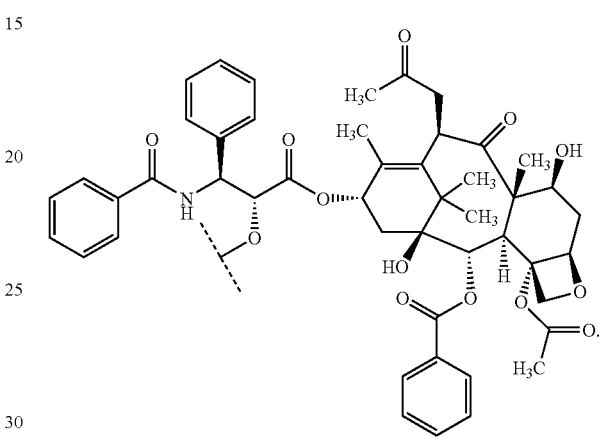
A doxorubicin moiety has the structure of:
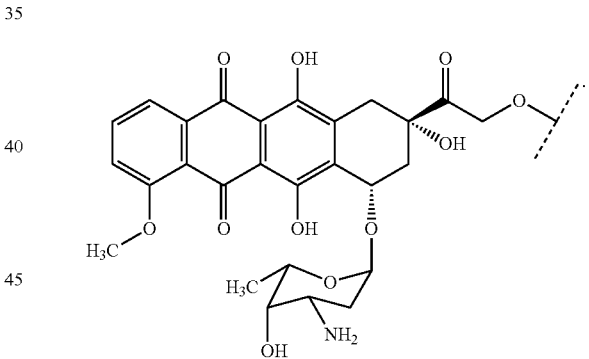
A doxorubicin derivative moiety includes but is not limited to:
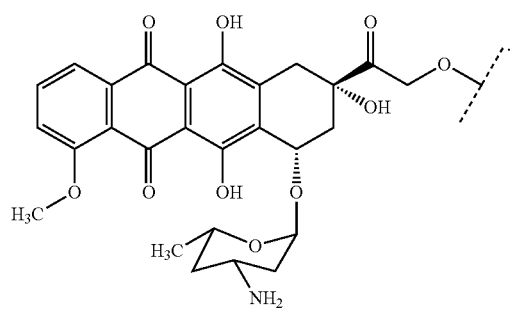

DLys(-) is represented by the structure:

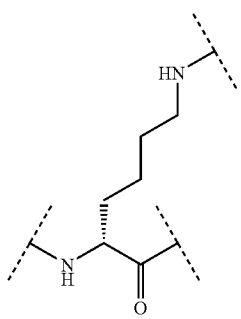

DOrn(-) is represented by the structure:

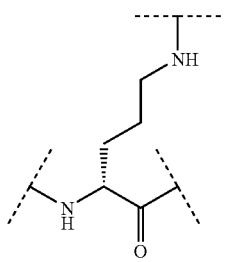

DDab(-) is represented by the structure:

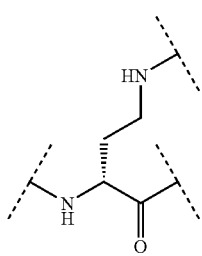

DDap(-) is represented by the structure:

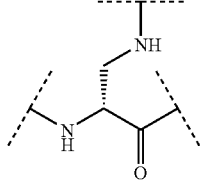

DApa(-) is represented by the structure:

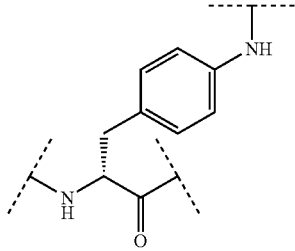

Certain abbreviations used herein are defined as follows:
Abu α-aminobutyric acid
Acc 1-amino-1-cyclo($C_3$-$C_9$)alkyl carboxylic acid
A3c 1-amino-1-cyclopropanecarboxylic acid
A4c 1-amino-1-cyclobutanecarboxylic acid
A5c 1-amino-1-cyclopentanecarboxylic acid
A6c 1-amino-1-cyclohexanecarboxylic acid
Act 4-amino-4-carboxytetrahydropyran, represented by the structure:

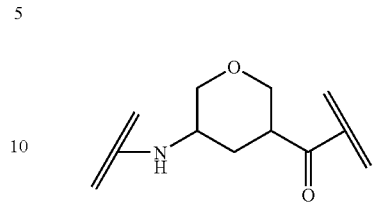

Aib α-aminoisobutyric acid
Ala or A alanine
β-Ala beta-alanine
Apc denotes the structure:

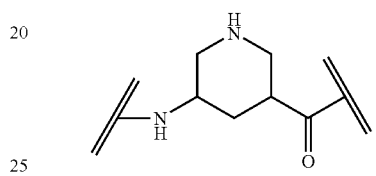

Arg or R arginine
hArg homoarginine
Asn or N asparagine
Asp or D aspartic acid
Ava 5-aminovaleric acid;
Cha β-cyclohexylalanine
Cys or C cysteine
Dab 2,4-diaminobutyric acid
Dap 2,3-diaminopropionic acid
Dhp 3,4-dehydroproline
Dmt 5,5-dimethylthiazolidine-4-carboxylic acid
Doc 8-amino-3,6-dioxaoctanoic acid, denoted by the structure:

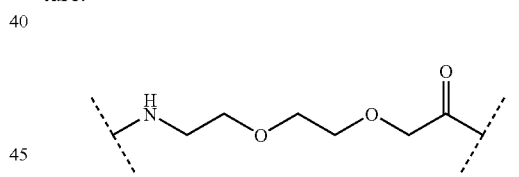

2Fua 1-(2-furyl)-alanine
Gln or Q glutamine
Glu or E glutamic acid
pGlu or Glp pyroglutamic acid
Gly or G glycine
His or H histidine
3Hyp trans-3-hydroxy-L-proline, i.e., (2S,3S)-3-hydroxypyrrolidine-2-carboxylic acid
4Hyp 4-hydroxyproline, i.e., (2S,4R)-4-hydroxypyrrolidine-2-carboxylic acid
Ile or I isoleucine
Inc indoline-2-carboxylic acid
Inp isonipecotic acid
Ktp 4-ketoproline
Leu or L leucine
hLeu homoleucine
Lys or K lysine
Met or M methionine
Nle norleucine
Nva norvaline
Oic octahydroindole-2-carboxylic acid Orn ornithine
2Pal β-(2-pyridinyl)alanine
3Pal β-(3-pyridinyl)alanine
4Pal β-(4-pyridinyl)alanine
Phe or F phenylalanine
hPhe homophenylalanine
Pip pipecolic acid
Pro or P proline
Sar Sarcosine or N-methyl glycine
Ser or S serine
Taz 1-(4-thiazolyl)alanine, denoted by the structure:

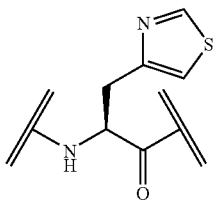

2Thi β-(2-thienyl)alanine
3Thi β-(3-thienyl)alanine
Thr or T threonine
Thz thiazolidine-4-carboxylic acid
Tic 1,2,3,4-tetrahydroisoquinoline-3-carboxylic acid
Tle tert-leucine
Trp or W tryptophan
Tyr or Y tyrosine
Val or V valine
Gaba 4-Aminobutyric acid
Apn 5-Aminopentanoic acid
Ahx 6-Aminohexanoic acid
Ahp 7-Aminoheptanoic acid
Aoc 8-Aminooctanoic acid
Anc 9-Aminononanoic acid
Adc 10-Aminodecanoic acid
Aun 11-Aminoundecanoic acid
Ado 12-Aminododecanoic acid
Phg Phenylglycine
Caeg N-(2-aminoethyl)-N-(2-cytosinyl-1-oxo-ethyl)-glycine, denoted by the structure:

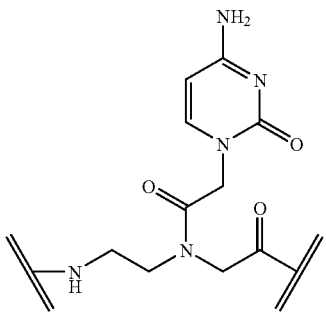

Certain other abbreviations used herein are defined as follows:
Aloc: Allyloxycarbonyl
Boc: tert-butyloxycarbonyl
Bhoc benzhydryloxycarbonyl
Bzl: benzyl
DCM: dichloromethane
Dde: 1-(4,4-dimethyl-2,6-dioxocyclohex-1-ylidine)ethyl]
DIC: N,N-diisopropylcarbodiimide
DIEA: diisopropylethyl amine
Dmab: 4-{N-(1-(4,4-dimethyl-2,6-dioxocyclohexy-lidene)-3-methylbutyl)-amino}benzyl
DMAP: 4-(dimethylamino)pyridine
DMF: dimethylformamide
DNP: 2,4-dinitrophenyl
Et: ethyl
Fmoc: Fluorenylmethyloxycarbonyl
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
Mmt: 4-methoxytrityl
NMP: N-methylpyrrolidone
Pbf: 2,2,4,6,7-pentamethyldihydrobenzofuran-5-sulfonyl
tBu: tert-butyl
TIS: triisopropylsilane
TOS: tosyl
trt trityl
TFA: trifluoro acetic acid
TFFH: tetramethylfluoroforamidinium hexafluorophosphate
Z: benzyloxycarbonyl

DETAILED DESCRIPTION

The invention features targeted cytotoxic compounds comprising a cytotoxic moiety bound to a targeting moiety, such as, for example, a ligand of a biological receptor, and methods relating to their therapeutic use for the treatment of neoplasia, hyperplasia, and other conditions associated with undesired proliferation of cells.

Examples of somatostatin peptides useful in the present invention are described herein. Further examples are those covered by formulae or those specifically recited in the publications set forth below, each of which is hereby incorporated by reference in its entirety:
PCT Application No. WO 03/057214 (2003)
U.S. Application Publication No. 20030191134 (2003)
U.S. Application Publication No. 20030083241 (2003)
U.S. Pat. No. 6,316,414 (2001)
PCT Application No. WO 02/10215 (2002)
PCT Application No. WO 99/22735 (1999)
PCT Application No. WO 98/08100 (1998)
PCT Application No. WO 98/44921 (1998)
PCT Application No. WO 98/45285 (1998)
PCT Application No. WO 98/44922 (1998)
EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);

U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Examples of LHRH (leutinizing hormone releasing hormone) peptides useful in the present invention are described herein. Further examples are those covered by formulae or those specifically recited in the publications set forth below, each of which is hereby incorporated by reference in its entirety:
EP Application No. 0 081 877 (1983)
EP Application No. 0 328 089 (1989)
EP Application No. 0 417 454 (1991)
EP Application No. 0 626 170 (1994)
EP Application No. 0 832 107 (1998)
EP Application No. 1 340 768 (2003)
U.S. Application Publication No. 2003040482 (2003)
U.S. Pat. No. 4,317,815 (1982)
U.S. Pat. No. 4,431,635 (1984)
U.S. Pat. No. 4,581,169 (1986)
U.S. Pat. No. 4,628,044 (1986)
U.S. Pat. No. 4,642,332 (1987)
U.S. Pat. No. 4,656,247 (1987)
U.S. Pat. No. 4,721,775 (1988)
U.S. Pat. No. 5,075,224 (1991)
U.S. Pat. No. 5,140,009 (1992)
U.S. Pat. No. 5,484,592 (1996)
U.S. Pat. No. 5,885,966 (1999)
U.S. Pat. No. 6,284,733 (2001)
U.S. Pat. No. 6,559,282 (2003)
PCT Application No. WO 00/24764 (2000)
PCT Application No. WO 90/11298 (1990)
PCT Application No. WO 92/15330 (1992)
PCT Application No. WO 94/14841 (1994)
PCT Application No. WO 94/25060 (1994)
PCT Application No. WO 96/40757 (1996)

Examples of bombesin peptides useful in the present invention are described herein. Further examples are those covered by formulae or those specifically recited in the publications set forth below, each of which is hereby incorporated by reference in its entirety:
EP Application No. 0 309 297 (1989)
EP Application No. 0 339 193 (1989)
EP Application No. 0402 852 (1990)
EP Application No. 0434 979 (1991)
EP Application No. 0 468 497 (1992)
EP Application No. 0 835 662 (1998)
U.S. Application Publication No. 2003050436 (2003)
U.S. Application Publication No. 2003166539 (2003)
U.S. Pat. No. 5,084,555 (1992)
U.S. Pat. No. 5,100,873 (1992)
U.S. Pat. No. 5,217,955 (1993)
U.S. Pat. No. 5,369,094 (1994)
U.S. Pat. No. 5,410,018 (1995)
U.S. Pat. No. 5,620,955 (1997)
U.S. Pat. No. 5,723,578 (1998)
U.S. Pat. No. 5,843,903 (1998)
U.S. Pat. No. 5,877,277 (1999)
U.S. Pat. No. 6,156,725 (2000)
U.S. Pat. No. 6,307,017 (2001)
PCT Application No. WO 90/03980 (1990)
PCT Application No. WO 91/06563 (1991)
PCT Application No. WO 91/17181 (1991)
PCT Application No. WO 94/02018 (1994)
PCT Application No. WO 94/21674 (1994)

The methods for synthesizing somatostatin, LHRH, and bombesin peptides are well documented and are within the ability of a person of ordinary skill in the art. Further synthetic procedures are provided in the following examples. The following examples also illustrate methods for synthesizing the targeted cytotoxic compounds of the present invention.

Example 1

H-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The titled protected peptide-resin was automatically synthesized on an Applied Biosystems (ABI) (Foster City, Calif.) model 433A peptide synthesizer by using Fluorenylmethyloxycarbonyl (Fmoc) chemistry. A Rink Amide MBHA (4-methylbenzylhydrylamine) resin (Novabiochem, San Diego, Calif.) with substitution of 0.72 mmol/g was used. The following Fmoc amino acids (AnaSpec, San Jose, Calif.) were used: Fmoc-Thr(tBu)-OH, Fmoc-Cys(Trt)-OH, Fmoc-Lys(Boc)-OH, Fmoc-DTrp(Boc)-OH, Fmoc-Tyr(tBu)-OH, Fmoc-DTyr(tBu)-OH Fmoc-Phe-OH, Fmoc-Cys(Trt)-OH, Fmoc-Thr(tBu)-OH, and Fmoc-Abu-OH. The synthesis was carried out on a 0.25 mmol scale. The Fmoc groups were removed by treatment with 20% piperidine in N-methylpyrrolidone (NMP) for 30 min. In each coupling step, the Fmoc amino acid (4 eq, 1 mmol) was first pre-activated in 2 mL of a solution containing 0.45M 2-(1-H-benzotriazole-1-yl)-1,1,2,3-tetramethyluronium hexafluorophosphate (HBTU) and 0.45M 1-hydroxy-benzotriazole (HOBT) in N,N-dimethylformamide (DMF). The resulting activated amino acid ester, 1 mL of diisopropylethylamine (DIEA) and 1 mL of NMP were added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h. The resin was coupled successively according to the sequence. After peptide chain was assembled, the Fmoc was removed and the resin was washed completely by using DMF and dichloromethane (DCM).

Example 2

H-Doc-Doc-Doc-Doc-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 1. Fmoc-8-amino-3,6-dioxaoctanoic acid (Fmoc-Doc-OH) was purchased from Chem-Impex International, Wood Dale, Ill. After the assembly of H-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin (0.45 mmol scale), the protected peptide-resin was transferred into a reaction vessel on a shaker for manual synthesis. The resin was shaken with a DMF solution of Fmoc-Doc-OH (1.5 eq, 0.75 mmol), N,N-diisopropylcarbodiimide (DIC, 1.5 eq, 0.75 mmol) and HOBT (1.5 eq, 0.75 mmol) for 2 h. The resin was washed with DMF and treated with 20% piperidine in DMF to remove Fmoc protecting group. The rest of the three Doc residues were sequentially coupled to the resin using the same manual operation procedure. After removing Fmoc protecting group with 20% piperidine in DMF, the protected peptide-resin was washed with DMF and DCM.

Example 3

H-Doc-Doc-Doc-Doc-Doc-Doc-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 2.

Example 4

H-Aepa-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 1. Fmoc-4-(2-aminoethyl)-1-carboxymethyl-piperazine (Fmoc-Aepa-OH) was purchased from Neosystem, Strasbourg, France. After the assembly of H-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin, the protected peptide-resin was transferred into a reaction vessel on a shaker for manual synthesis. The Fmoc-Aepa-OH (1.5 eq, 0.75 mmol) was pre-activated with O-(7-azabenzotriazol-1-yl)-1,1,3,3-tetramethyluronium hexafluorophosphate (HATU, 1.4 eq, 0.7 mmol) and 1-hydroxy-7-azabenzotriazole (HOAT, 1.4 eq., 0.7 mmol) in 2 mL of DMF for 2 min. The resulting activated ester of Fmoc-Aepa-OH and 1 mL of DIEA were added into the reaction vessel and the mixture was shaken for 2 h. The resin was washed with DMF and treated with 20% piperidine in DMF to remove Fmoc protecting group. The protected peptide-resin was washed with DMF and DCM.

Example 5

H-Doc-Doc-Doc-Doc-Aepa-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 4. The couplings of Fmoc-Doc-OH were performed according to the corresponding procedure described in Example 2.

Example 6

H-DPhe-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 1. Fmoc-DPhe-OH was purchased from AnaSpec, San Jose, Calif.

Example 7

H-Aepa-DPhe-Cys(Trt)-Tyr(tBu)-DTrp(Boc)-Lys(Boc)-Abu-Cys(Trt)-Thr(tBu)-Rink Amide MBHA Resin The titled protected peptide-resin was synthesized substantially according to the procedure described in Example 4.

Example 8

5-O-tBoc-glycyl-5-(R)-ethyl-9,10-difluoro-1,4,5,13-tetrahydro-3H,15H-oxepino[3',4':6'7]indolizino[1,2-b]quinoline-3,15-dione

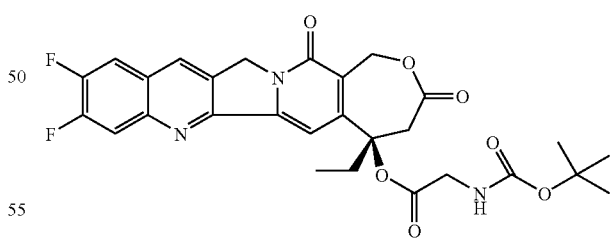

5-(R)-Ethyl-9,10-difluoro-1,4,5,13-tetrahydro-5-hydroxy-3H,15H-oxepino[3',4':6,7]indolizino[1,2-b]quinoline-3,15-dione (300 mg), Boc-Gly-OH (923 mg, 7 eq.) and 4-(dimethylamino)pyridine (DMAP) (560.4 mg, 6 eq.) were dissolved in a mixed solvent system of DCM and DMF (30 mL, v/v, 30/0.5). To the solution was added 1-(3-dimethylaminopropyl)-3-ethylcarbodiimide hydrochloride (EDC) (1.08 g, 7.5 eq.). The mixture was stirred overnight at room temperature and the solvents were removed under reduced pressure. The residue was dissolved in 100 mL of DCM and washed successively with 10% citric acid aqueous solution (20 mL×2), saturated NaHCO₃ (20 mL×2) and brine (10 mL×3). The organic layer was dried over MgSO₄, filtered and evaporated under reduced pressure. The crude product was purified by a flash chromatography on a silica gel column using 10% methanol in DCM as the eluent to give a pure product of 5-O-tBoc-glycyl-5-(R)-ethyl-9,10-difluoro-1,4,5,13-tetrahydro-3H,15H-oxepino[3',4':6,7]indolizino[1,2-b]quinoline-3,15-dione. 330 mg, TLC (silica gel, DCM/MeOH: 9/1): $R_f$=0.43. Electro-spray ionization mass spectrometry (ESI MS) analysis gave the molecular weight at 556.4 (in agreement with the calculated molecular weight of 555.5).

Example 9

5-O-glycyl-5-(R)-Ethyl-9,10-difluoro-1,4,5,13-tetrahydro-3H,15H-oxepino[3',4':6,7]indolizino[1,2-b]quinoline-3,15-dione TFA salt

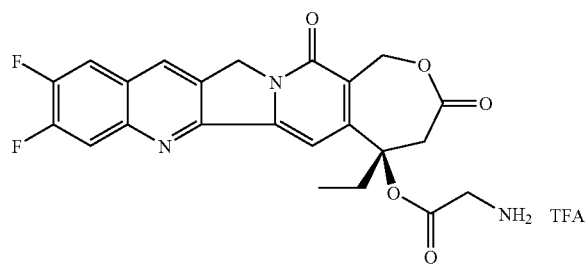 [SMILES: CC[C@@]1(OC(=O)CN)CC(=O)OCc2c1cc1n(c2=O)Cc2cc3cc(F)c(F)cc3nc2-1 ; "TFA"]

5-O-tBoc-glycyl-5-(R)-ethyl-9,10-difluoro-1,4,5,13-tetrahydro-3H,15H-oxepino[3',4':6,7]indolizino[1,2-b]quinoline-3,15-dione (330 mg) was treated with 30% trifluoroacetic acid (TFA) solution in DCM under nitrogen for 1 h. TFA and solvent were removed under reduced pressure. The residue was triturated with cold ether to give a light yellow powder. TLC (silica gel, DCM/MeOH: 9/1): $R_f$=0.13. ESI MS analysis gave the molecular weight at 456.0 (in agreement with the calculated molecular weight of 455.4).

Example 10

5-O-(N-glutaryl-glycyl)-5-(R)-Ethyl-9,10-difluoro-1,4,5,13-tetrahydro-3H,15H-oxepino[3',4':6,7]indolizino[1,2-b]quinoline-3,15-dione

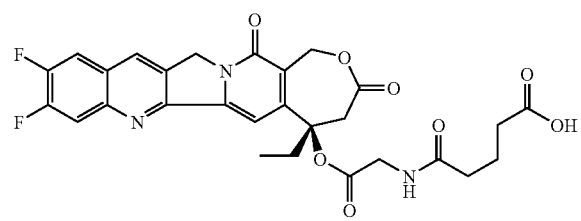 [SMILES: CC[C@@]1(OC(=O)CNC(=O)CCCC(=O)O)CC(=O)OCc2c1cc1n(c2=O)Cc2cc3cc(F)c(F)cc3nc2-1]

A mixture of 5-O-glycyl-5-(R)-ethyl-9,10-difluoro-1,4,5,13-tetrahydro-3H,15H-oxepino[3',4':6,7]indolizino[1,2-b]quinoline-3,15-dione (208 mg, 0.37 mmol), glutaric anhydride (66 mg, 0.58 mmol, 1.5 eq.) and triethylamine (243 mL) in DMF (7 mL) was stirred at room temperature for 3 h. The solvent was removed under reduced pressure. The residue was dissolved in water (10 mL) and the pH of the solution was adjusted to 3 by adding 0.5N HCl solution at 0° C. The precipitate formed was collected by filtration and washed with cold water and ether. After drying under reduced pressure, a solid was obtained (160 mg). Yield was 77%. ESI MS analysis gave the molecular weight at 570.0 (in agreement with the calculated molecular weight of 569.5). Purity was 98% based on analytical HPLC analysis.

Example 11

5-O-(N-succinyl-glycyl)-5-(R)-Ethyl-9,10-difluoro-1,4,5,13-tetrahydro-3H,15H-oxepino[3',4':6,7]indolizino[1,2-b]quinoline-3,15-dione

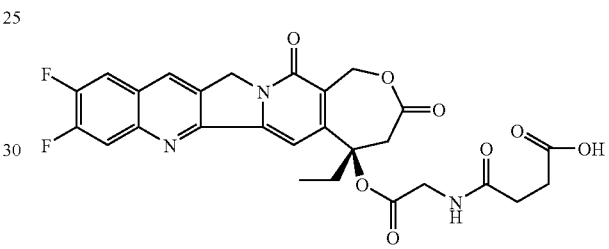

The titled compound was synthesized substantially according to the procedure described in Example 10 by using succinic anhydride. The yield was 86%. ESI MS analysis gave the molecular weight at 556.2 (in agreement with the calculated molecular weight of 555.50). Purity was 96% based on the analytical HPLC analysis.

Example 12

Camptothecin-20-(S)-[O-(tBoc-glycyl)]

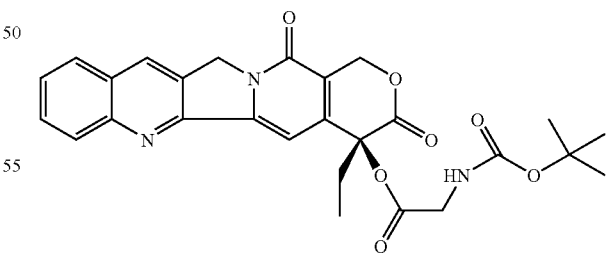

Camptothecin (0.79 g, 2.2 mmol), Boc-Gly-OH (1.2 g, 6.8 mmol, 3 eq.) and DMAP (0.83 g, 6.8 mmol, 3 eq.) were dissolved in a mixed solvent system of DCM and THF (18 mL, v/v, 5/1). The mixture was cooled in an ice-water bath. To it was added 1,3-diisopropylcarbodiimide (DIC) (1.1 mL, 6.8 mmol, 3.1 eq.). After stirring at 0° C. for 0.5 h, the mixture was warmed to room temperature and stirred overnight. The solution was diluted with 50 mL of DCM and washed successively with 10% citric acid aqueous solution (20 mL×2), saturated NaHCO$_3$ (20 mL×2) and brine (10 mL×3). The organic layer was dried over MgSO$_4$, filtered and evaporated under reduced pressure to dryness. The crude product was purified by a flash chromatography on a silica gel column using 4% methanol in DCM as the eluent to give a pure product of camptothecin-20-(S)—(O-tBoc-glycyl) (1.07 g, white solid). TLC (silica, DCM/MeOH: 9/1): R$_f$=0.6. MS ESI analysis gave the molecular weight at 506.3 (in agreement with the calculated molecular weight of 505.53).

Example 13

Camptothecin-20-(S)—(O-glycyl) TFA salt

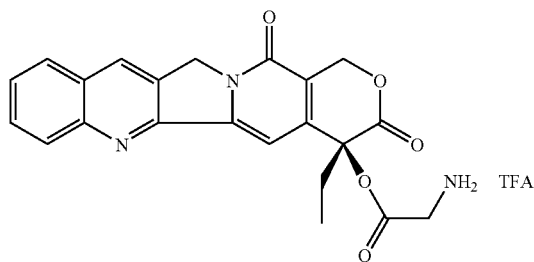 [SMILES: "TFA" ; CC[C@]1(OC(=O)CN)C(=O)OCc2c1cc1n(c2=O)Cc2cc3ccccc3nc2-1]

Camptothecin-20-(S)-[O-(Boc-glycyl)] (1.07 g, 2.1 mmol) was treated with 50% TFA in DCM under N$_2$ for 1 h. TFA and the solvent were removed under reduced pressure. The residue was triturated with cold ether. The precipitate formed was collected by filtration and washed with cold ether, yielding a light yellow powder (0.9 g, 1.78 mmol). Yield=83%, TLC (silica gel, DCM/MeOH: 9/1): R$_f$=0.23. ESI MS analysis gave the molecular weight at 406.2 (in agreement with the calculated molecular weight of 405.41).

Example 14

Camptothecin-20-(S)-[O—(N-succinyl-glycyl)]

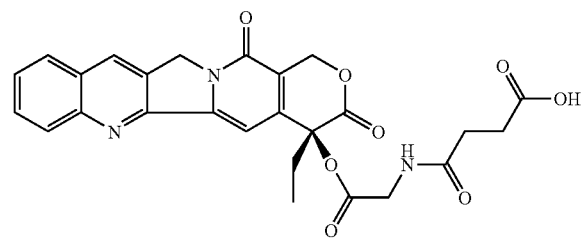 [SMILES: CC[C@]1(OC(=O)CNC(=O)CCC(=O)O)C(=O)OCc2c1cc1n(c2=O)Cc2cc3ccccc3nc2-1]

A mixture of camptothecin-20-(S)—(O-glycyl) TFA (0.9 g, 1.7 mmol), succinic anhydride (0.35 g, 3.5 mmol, 2 eq.), and triethylamine (0.72 mL, 3 eq.) in DMF (10 mL) was stirred at room temperature for 5 min. The precipitate formed was collected by filtration. The solid collected was suspended in cold water (10 mL). The pH of the water suspension was adjusted to 2 by adding 5% aqueous citric acid solution. After stirring at 0° C. for 0.5 h, the precipitate was filtered, washed with cold water and ether, and dried under reduced pressure. 0.88 g (1.58 mmol) of a solid was obtained. The yield was 99%. ESI MS analysis gave the molecular weight at 505.7 (in agreement with the calculated molecular weight of 505.49). Purity was 99% based on analytical HPLC analysis.

Example 15

Camptothecin-20-(S)-[O—(N-glutaryl-glycyl)]

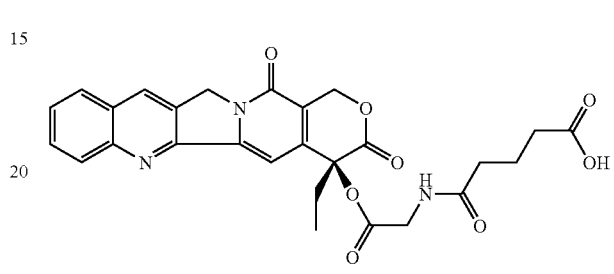

The titled compound was synthesized substantially according to the procedure described in Example 14 by using glutaric anhydride. The yield was 75%. ESI MS analysis gave the molecular weight at 520.5 (in agreement with the calculated molecular weight of 519.52). Purity was 98% based on analytical HPLC analysis.

Example 16

Camptothecin-20-(S)-[O-(Boc-Valyl)]

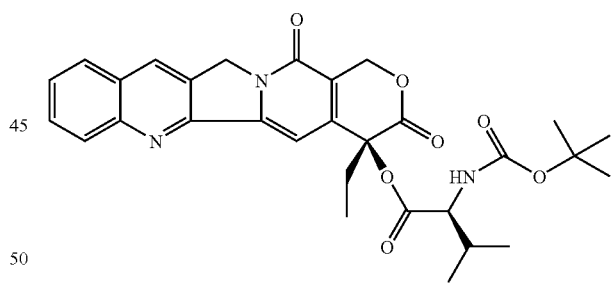

To a suspension of camptothecin (350 mg) and DMAP (180 mg) in DCM (10 mL) at 0° C. was added a DCM solution of Boc-Val-F (2 eq.), which was prepared by using a literature method (Carpino et al., J. Org. Chem., 56, 2611, 1991). After stirring at 0-5° C. for 30 minutes, the mixture was warmed to room temperature and the stirring continued overnight. The mixture was diluted with chloroform (30 mL), washed with water, 10% citric acid aqueous solution and saturated NaHCO$_3$, dried over MgSO$_4$, and filtered. After removing the solvents under reduced pressure, the residue was purified by a chromatography on a silica gel column eluting with chloroform/acetone (9:1). The fractions containing the desired product were pooled and concentrated under reduced pressure, resulting in a solid.

Example 17

Camptothecin-20-(S)—(O-Valyl) TFA salt

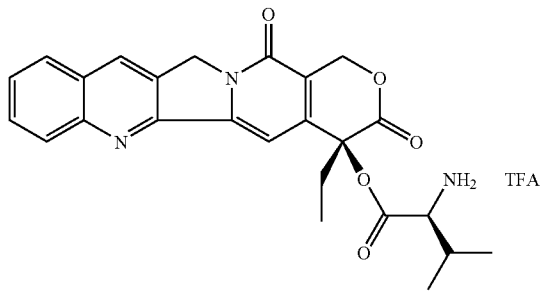 [SMILES: CC[C@]1(OC(=O)[C@@H](N)C(C)C)C(=O)OCc2c1cc1n(c2=O)Cc2cc3ccccc3nc2-1]

Camptothecin-20-(S)-[O-(Boc-Valinyl)] obtained in Example 16 was treated with 35% TFA in chloroform (10 mL) for 30 min. TFA and solvent were removed in vacuo, yielding a solid. ESI MS analysis gave the molecular weight at 448.4 (in agreement with the calculated molecular weight of 447.50).

Example 18

Camptothecin-20-(S)-[O—(N-succinyl-Valyl)]

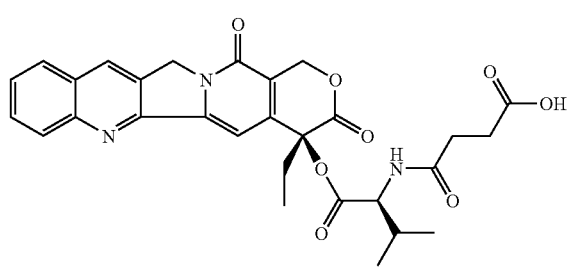 [SMILES: CC[C@]1(OC(=O)[C@@H](NC(=O)CCC(=O)O)C(C)C)C(=O)OCc2c1cc1n(c2=O)Cc2cc3ccccc3nc2-1]

To a mixture of camptothecin-20-(S)—(O-Valyl) TFA salt (150 mg), succinic anhydride (4 eq.), and DMAP (2 eq.) in chloroform (10 mL) was added triethylamine (6 eq.). After stirring at room temperature overnight, the mixture was diluted with chloroform (20 mL). The resulting solution was washed with water and aqueous citric acid solution, dried over $MgSO_4$, and filtered. Solvent was removed in vacuo and the residue was triturated with acetone. 120 mg of the titled compound was obtained. TLC (silca gel, chloroform/methanol=9:1): $R_f$=0.22. ESI MS analysis gave the molecular weight at 548.2 (in agreement with the calculated molecular weight of 547.57).

Example 19

{5-(R)-Ethyl-9,10-difluoro-1,4,5,13-tetrahydro-3H, 15H-oxepino[3',4':6,7]indolizino[1,2-b]quinoline-3, 15-dione-5-O-glycyl-glutaryl}-(Doc)₆-Lys-DTyr-DTyr-cyclo(Cys-Tyr-DTrp-Lys-Abu-Cys-)-Thr-NH₂

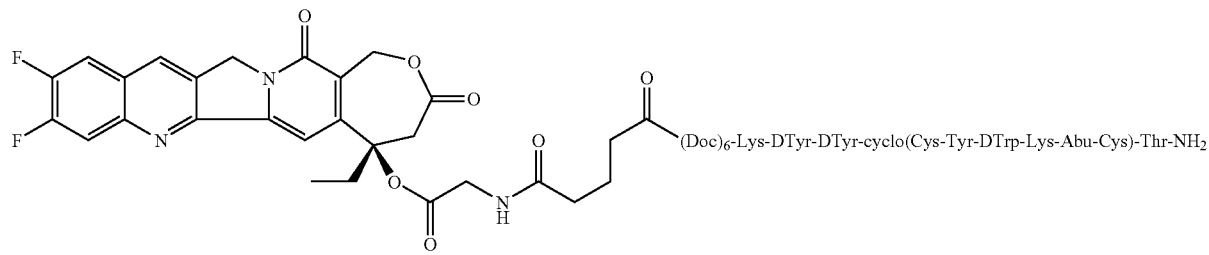

H-(Doc)₆-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin (0.196 mmol) of Example 3 was mixed with 5-O-(N-glutaryl-glycyl)-5-(R)-ethyl-9,10-difluoro-1,4,5,13-tetrahydro-3H,15H-oxepino[3',4':6,7]indolizino[1,2-b]quinoline-3,15-dione (0.123 g, 0.22 mmol, 1.1 eq.) (Example 10), DIC (136 μL, 0.88 mmol, 4.4 eq.) and 1-hydroxy-7-azabenzotriazol (HOAT) (30 mg, 0.22 mmol, 1.1 eq.) in 5 mL of DCM. The mixture was shaken for 2 days. The resin was washed successively with DMF, methanol and DCM. After drying in the air, the resin was treated with a mixture of TFA, $H_2O$ and triisopropylsilane (TIS) (9.5 mL/0.85 mL/0.8 mL) for 2 h. The resin was filtered off and the filtrate was poured into 100 mL of cold ether. The precipitate was collected after centrifuge. The crude product was dissolved in 100 mL of 5% AcOH aqueous solution, to which iodine methanol solution was added dropwise until yellow color maintained. The reaction solution was stirred for additional 1 h. 10% $Na_2S_2O_3$ water solution was added to quench the excess iodine. The crude product in the solution was purified on preparative HPLC system with a column (4×43 cm) of $C_{18}$ DYNAMAX-100A° (Varian, Walnut Creek, Calif.). The column was eluted with a linear gradient from 80% A and 20% B to 55% A and 45% B in 50 min., where A was 0.1% TFA in water and B was 0.1% TFA in acetonitrile. The fractions were checked by an analytical HPLC. Those containing pure product were pooled and lyophilized to dryness. Yield: 25%. The purity was 99.9% based on analytical HPLC analysis. ESI MS analysis gave the molecular weight at 2761.1 (in agreement with the calculated molecular weight of 2761.04).

Example 20

{5-(R)-Ethyl-9,10-difluoro-1,4,5,13-tetrahydro-3H, 15H-oxepino[3',4':6,7]indolizino[1,2-b]quinoline-3, 15-dione-5-O-glycyl-glutaryl}-(Doc)₄-Lys-DTyr-DTyr-cyclo(Cys-Tyr-DTrp-Lys-Abu-Cys)-Thr-NH₂

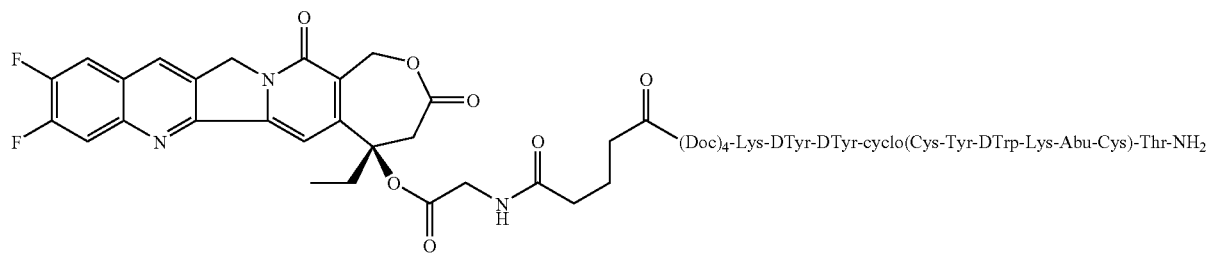

The titled compound was synthesized substantially according to the procedure described in Example 19 by using H-Doc-Doc-Doc-Doc-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin of Example 2. Yield was 21.4%. Purity: 99% based on analytical HPLC analysis. ESI MS analysis gave the molecular weight at 2471.2 (in agreement with the calculated molecular weight of 2471.727).

Example 21

{5-(R)-Ethyl-9,10-difluoro-1,4,5,13-tetrahydro-3H, 15H-oxepino[3',4':6,7]indolizino[1,2-b]quinoline-3, 15-dione-5-O-glycyl-succinyl}-Aepa-DPhe-cyclo(Cys-Tyr-DTrp-Lys-Abu-Cys)-Thr-NH₂

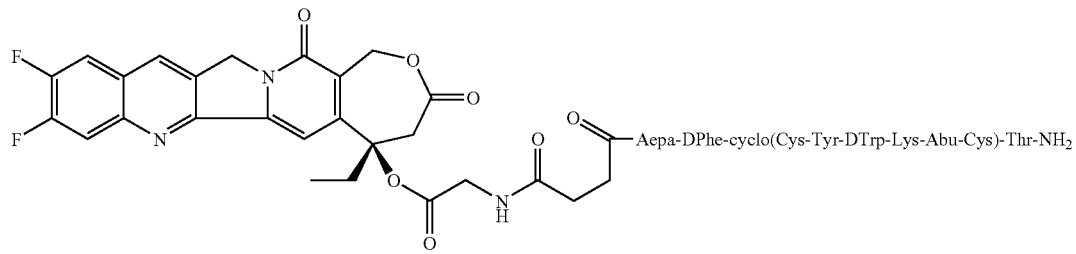

The titled compound was synthesized substantially according to the procedure for Example 19 by using 5-O-(N-succinyl-glycyl)-5-(R)-ethyl-9,10-difluoro-1,4,5,13-tetrahydro-3H,15H-oxepino[3',4':6,7]indolizino[1,2-b]quinoline-3,15-dione (Example 11) and H-Aepa-DPhe-Cys(Trt)-Tyr(tBu)-DTrp(Boc)-Lys(Boc)-Abu-Cys(Trt)-Thr(tBu)-Rink Amide MBHA Resin (Example 7). Yield was 48%, Purity: 99.9% based on analytical HPLC analysis. ESI MS analysis gave the molecular weight at 1739.8 (in agreement with the calculated molecular weight of 1740.14).

Example 22

Camptothecin-20-(S)—O-glycyl-succinyl-Doc-Doc-Doc-Doe-Aepa-DPhe-cyclo(Cys-Tyr-DTrp-Lys-Abu-Cys)-Thr-NH₂

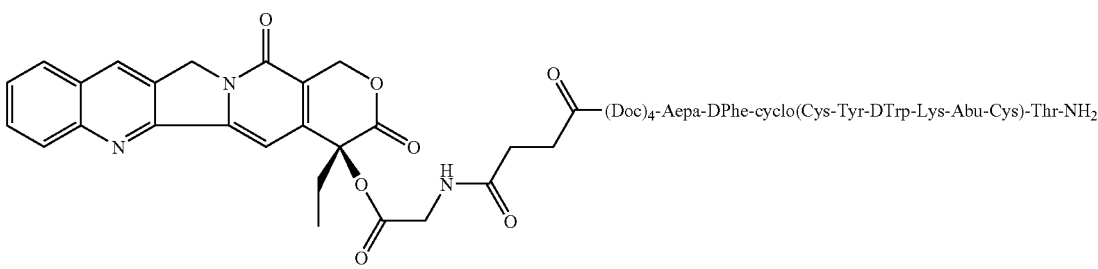

The titled compound was synthesized substantially according to the procedure for Example 19 by using camptothecin-20-(S)-[O—(N-succinyl-glycyl)] (Example 14) and H-Doc-Doc-Doc-Doc-Aepa-DPhe-Cys(Trt)-Tyr(tBu)-DTrp(Boc)-Lys(Boc)-Abu-Cys(Trt)-Thr(tBu)-Rink Amide MBHA Resin. Yield was 32%. Purity was 99% based on analytical HPLC analysis. ESI MS analysis gave the molecular weight at 2269.0. (in agreement with the calculated molecular weight of 2269.8).

20-(S)-[O—(N-succinyl-Valyl)] (Example 18) and H-DPhe-Cys(Trt)-Tyr(tBu)-DTrp(Boc)-Lys(Boc)-Abu-Cys(Trt)-Thr(tBu)-Rink Amide MBHA Resin (Example 6). 145 mg of a pale yellow solid was obtained. ESI MS analysis gave the molecular weight at 1562.4 (in agreement with the calculated molecular weight of 1561.8).

Example 23

Camptothecin-20-(S)—O-glycyl-glutaryl-Aepa-Lys-DTyr-DTyr-cyclo(Cys-Tyr-DTrp-Lys-Abu-Cys)-Thr-NH$_2$ Example 25

{5-(R)-Ethyl-9,10-difluoro-1,4,5,13-tetrahydro-3H,15H-oxepino[3',4':6,7]indolizino[1,2-b]quinoline-3,15-dione-5-O-glycinyl-succinyl}-DPhe-cyclo(Cys-Tyr-DTrp-Lys-Abu-Cys)-Thr-NH$_2$

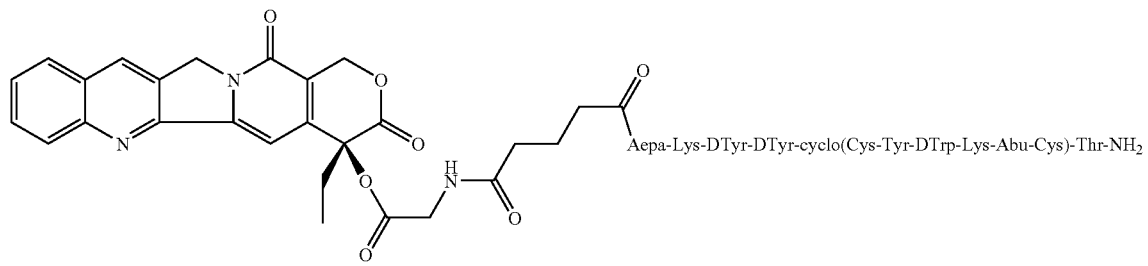

The titled compound was synthesized substantially according to the procedure in Example 19 by using camptothecin-20-(S)-[O-(glutaryl-glycyl)] (Example 15) and H-Aepa-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin (Example 4). Yield was 11%. Purity was 95% based on analytical HPLC analysis. ESI MS analysis gave the molecular weight at 2008.9 (in agreement with the calculated molecular weight of 2009.2).

Example 24

Camptothecin-20-(S)—O-Valyl-succinyl-DPhe-cyclo(Cys-Tyr-DTrp-Lys-Abu-Cys)-Thr-NH$_2$

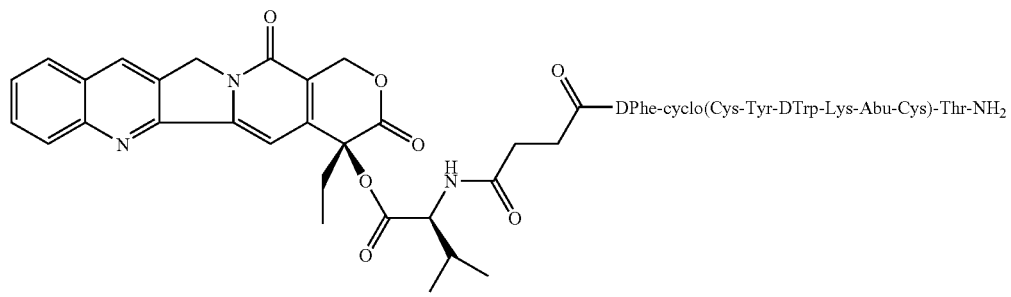

The titled compound was synthesized substantially according to the procedure in Example 19 by using camptothecin-

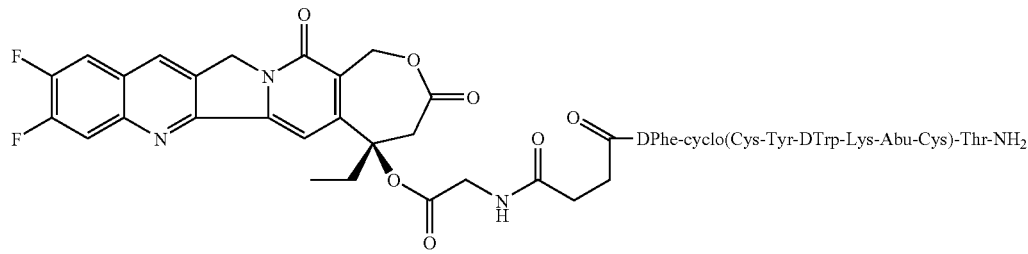

The titled compound was synthesized substantially according to the procedure for Example 19 by using 5-(R)-ethyl-9,10-difluoro-1,4,5,13-tetrahydro-3H,15H-oxepino[3',4':6,7]indolizino[1,2-b]quinoline-3,15-dione-5-O-(N-succinylglycyl) (Example 11) and H-DPhe-Cys(Trt)-Tyr(tBu)-DTrp(Boc)-Lys(Boc)-Abu-Cys(Trt)-Thr(tBu)-Rink Amide MBHA Resin (Example 6). A yellow solid was obtained. ESI MS analysis gave the molecular weight at 1570.2 (in agreement with the calculated molecular weight of 1569.72).

Example 26

H-Aepa-(Doc)$_4$-Gln(Trt)-Trp(Boc)-Ala-Val-βAla-His(Trt)-Leu-Leu-Rink Amide MBHA resin The titled protected peptide-resin was synthesized substantially according to the procedure described for Example 5. Fmoc-His(Trt)-OH, Fmoc-Gln(Trt)-OH, Fmoc-Leu-OH, Fmoc-Ala-OH, and Fmoc-βAla-OH were purchased from AnaSpec (San Jose, Calif.).

Example 27

H-Aepa-(Doc)$_4$-DPhe-Gln(Trt)-Trp(Boc)-Ala-Val-βAla-His(Trt)-Leu-Leu-Rink Amide MBHA resin The titled protected peptide-resin was synthesized substantially according to the procedure described for Example 26.

Example 28

Camptothecin-20-(S)—O-glycinyl-succinyl-Aepa-(Doc)$_4$-Gln-Trp-Ala-Val-βAla-His-Leu-Leu-NH$_2$ mmol, 4.4 eq.), and HOBt (0.275 mmol, 2.2 eq.) in DCM (7 mL) and DMF (7 mL) was shaken at room temperature for 5 days. The peptide was cleaved off from the resin using a solution of TFA, H$_2$O and TIS (9.5 mL/0.85 mL/0.8 mL) for 2 hours. The resin was filtered off and the peptide was precipitated using diethyl ether. After centrifuging the suspension, a pellet of crude peptide was obtained. The crude product was purified on a preparative HPLC system with a Microsorb C$_{18}$ column, eluting with a linear gradient from 100% A and 0% B to 20% A and 80% B in 80 min. A was 0.1% TFA in water and B was 0.1% TFA in acetonitrile. The fractions were checked by an analytical HPLC. The fractions containing the desired product were pooled and lyophilized to dryness. Purity was 96.1% based on analytical HPLC analysis. ESI MS analysis gave the molecular weight at 2172.9 (in agreement with the calculated molecular weight of 2173.44).

Example 29

Camptothecin-20-(S)—O-glycinyl-succinyl-Aepa-(Doc)$_4$-DPhe-Gln-Trp-Ala-Val-βAla-His-Leu-Leu-NH$_2$

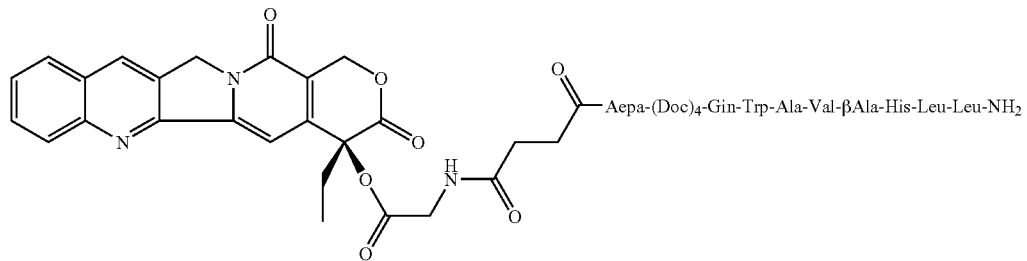

A mixture of H-Aepa-(Doc)$_4$-Gln(Trt)-Trp(Boc)-Ala-Val-βAla-His(Trt)-Leu-Leu-Rink Amide MBHA resin (0.125 mmol) of Example 26, camptothecin-20-(S)-[O—(N-glycyl-succinyl)] (Example 14) (0.138 mmol, 1.1 eq.), DIC (0.55

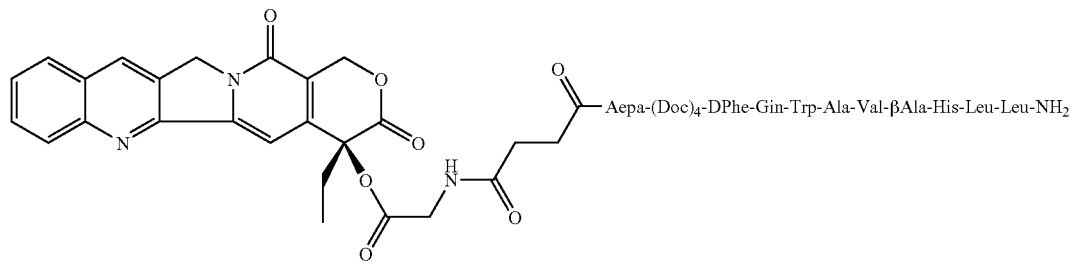

The titled peptide was synthesized substantially according to the procedure described for Example 28. Purity was 99.9% based on analytical HPLC analysis. ESI MS analysis gave the molecular weight at 2321.1 (in agreement with the calculated molecular weight of 2320.62).

Example 30

Camptothecin-20-(S)—O-glycinyl-succinyl-Aepa-(Doc)$_2$-Gln-Trp-Ala-Val-βAla-His-Leu-Leu-NH$_2$

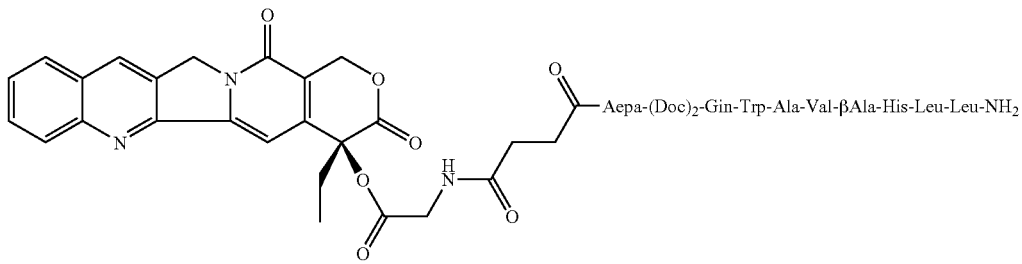

The titled peptide was synthesized substantially according to the procedure described for Example 28. Purity was 99.9% based on analytical HPLC analysis. ESI MS analysis gave the molecular weight at 1882.8 (in agreement with the calculated molecular weight of 1883.13).

Example 31

Camptothecin-20-(S)—O-glycinyl-succinyl-Aepa-(Doc)$_2$-DPhe-Gln-Trp-Ala-Val-βAla-His-Leu-Leu-NH$_2$

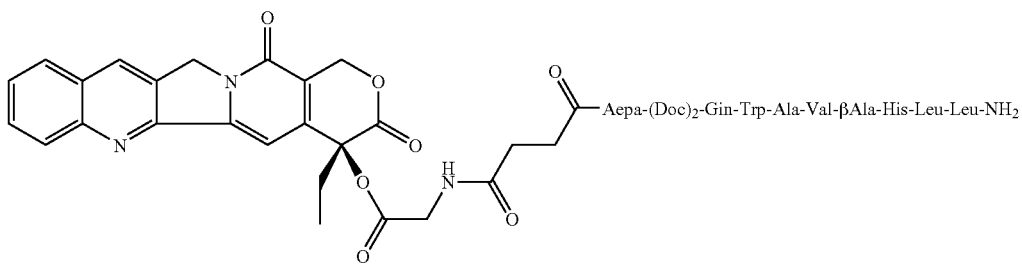

The titled peptide was synthesized substantially according to the procedure described for Example 28. Purity was 99.9% based on analytical HPLC analysis. ESI MS analysis gave the molecular weight at 2030.7 (in agreement with the calculated molecular weight of 2030.30).

Example 32

Camptothecin-20-(S)—O-glycinyl-succinyl-Aepa-(Doc)$_4$-Gaba-Gln-Trp-Ala-Val-βAla-His-Leu-Nle-NH$_2$

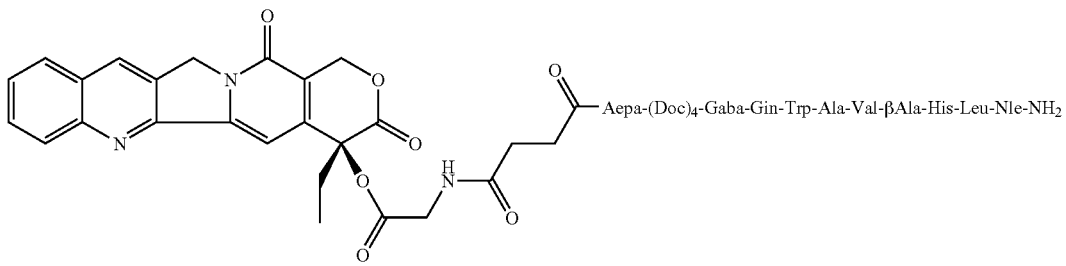

The titled peptide is synthesized substantially according to the procedure described for Example 28 by using Aepa-(Doc)₄-Gaba-Gln(Trt)-Trp(Boc)-Ala-Val-βAla-His(Trt)-Leu-Nle-Rink Amide MBHA resin.

Example 33 pGlu-His(Trt)-Trp(Boc)-Ser(tBu)-Tyr(tBu)-DLys [Nᵉ-Aepa]-Leu-Arg(Pbf)-Pro-Gly-Rink Amide MBHA resin The titled peptide resin was synthesized substantially according to the procedure described in Example 1. Fmoc-Arg(Pbf)-OH, Fmoc-Ser(tBu)-OH, Fmoc-His(Trt)-OH, Fmoc-Pro-OH, Fmoc-Gly-OH, Fmoc-Leu-OH, Fmoc-DLys(Dde)-OH were purchased from Novabiochem, San Diego, Calif. pGlu-OH was from Chem-Impex International, Wood Dale, Ill. The synthesis was carried out on a 0.25 mmol scale. The Fmoc groups are removed by treatment with 20% piperidine in N-methylpyrrolidone (NMP) for 30 min. After finishing the assembly of pGlu-His(Trt)-Trp(Boc)-Ser(tBu)-Tyr(tBu)-DLys(Dde)-Leu-Arg(Pbf)-Pro-Gly-Rink Amide MBHA resin, the protected peptide-resin was transferred into a reaction vessel on a shaker for manual synthesis. The Dde protecting group on DLys residue was removed by using 2% hydrazine in DMF for 0.5 h. The resin was washed completely with DMF, MeOH and DCM and shaken for 2 h with the pre-activated Fmoc-Aepa-OH ester solution (described in Example 4) in DMF containing 0.5 mL of DIEA. The resin was washed with DMF and treated with 20% piperidine in DMF to remove Fmoc protecting group on Aepa residue. The protected peptide-resin was washed completely by using DMF and DCM.

Example 34 pGlu-His(Trt)-Trp(Boc)-Ser(tBu)-Tyr(tBu)-DLys [Nᵉ-(Aepa-(Doc)₄-)]-Leu-Arg(Pbf)-Pro-Gly-Rink Amide MBHA resin The titled protected peptide resin was synthesized substantially according to the procedure in Example 2 by using pGlu-His(Trt)-Trp(Boc)-Ser(tBu)-Tyr(tBu)-DLys[Nᵉ-Aepa]-Leu-Arg(Pbf)-Pro-Gly-Rink Amide MBHA resin (Example 33).

Example 35

H-(Doc)₄-Aepa-Caeg-DCys(Trt)-3Pal-DTrp(Boc)-Lys(Boc)-DCys(Trt)-Thr(Bzl)-Tyr(tBu)-Rink Amide MBHA resin The titled protected peptide resin is synthesized substantially according to the procedure for Example 5. Fmoc-Thr(Bzl)-OH, Fmoc-DCys(Trt)-OH, and Fmoc-3Pal-OH are from Chem-Impex International, Wood Dale, Ill. Fmoc-DTrp(Boc)-OH, Fmoc-Lys(Boc)-OH and Fmoc-Tyr(tBu)-OH are from AnaSpec, San Jose, Calif. Fmoc-Caeg(Bhoc)-OH is from PepSeptive Biosystems, Framingham, Mass.

Example 36

H-(Doc)₄-Aepa-DPhe-Cys(Trt)-3ITyr-DTrp(Boc)-Lys(Boc)-Val-Cys(Trt)-Thr(tBu)-Rink Amide MBHA resin The titled protected peptide resin is synthesized substantially according to the procedure for Example 5. Fmoc-3ITyr-OH and Fmoc-DPhe-OH are from Chem-Impex International, Wood Dale, Ill.

Example 37

Paclitaxel-2'-O-glycyl

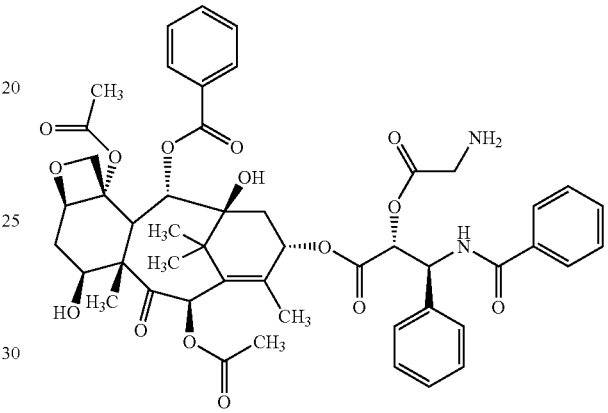

To a solution of Boc-Gly-OH (53 mg) and paclitaxel (215 mg) in 10 mL of dichloromethane was added 4-dimethylaminopyridine (DMAP, 10 mg) followed by EDC (58 mg). After stirring at room temperature overnight, the reaction mixture was diluted with 20 mL of dichloromethane and the mixture was washed with 10% aqueous citric acid, saturated NaHCO₃ and water, dried over MgSO₄, and filtered. The solvent was removed in vacuo. The crude product was treated with 30% TFA in dichloromethane for 45 min at room temperature. TFA and the solvent were removed in vacuo, yielding a solid. 0.256 g, ESI MS analysis gave the molecular weight at 911.0 (in agreement with the calculated molecular weight of 911.1).

Example 38

Paclitaxel-2'-O-(N-glycyl-succinyl)

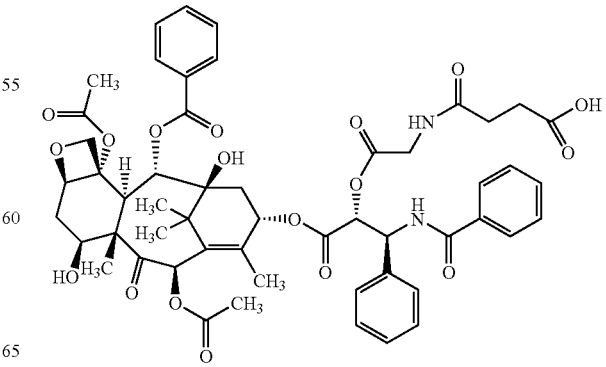

A mixture of paclitaxel-2'-O-glycyl TFA salt (127 mg, 1 eq.) and succinic anhydride (150 mg, 12 eq) in 5 mL of pyridine was stirred overnight at room temperature. The solvent was removed in vacuo. The residue was triturated with water for 1 hour and the precipitate was collected by filtration, washed with water and dried, yielding a solid (94.8 mg). ESI MS analysis gave the molecular weight at 1010.9 (in agreement with the calculated molecular weight of 1011.06).

Example 39

Paclitaxel-2'-O-(N-valyl-succinyl)

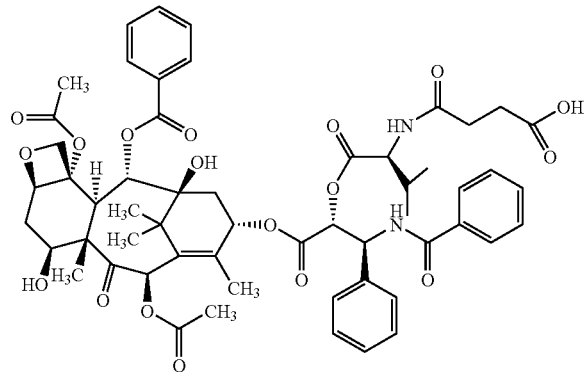 [SMILES: CC(=O)O[C@H]1C(=O)[C@@]2(C)[C@H]([C@H](OC(=O)c3ccccc3)[C@]3(O)C[C@H](OC(=O)[C@H](OC(=O)[C@@H](NC(=O)CCC(=O)O)C(C)C)[C@@H](NC(=O)c4ccccc4)c4ccccc4)C(C)=C1C3(C)C)[C@]1(OC(C)=O)CO[C@@H]1C[C@@H]2O]

The titled compound was synthesized substantially according to the procedures described in Examples 37 and 38 by using Boc-Val-OH. ESI MS analysis gave the molecular weight at 1052.5 (in agreement with the calculated molecular weight of 1053.27).

Example 40

Paclitaxel-2'-O-Gly-Succinyl-Aepa-Lys-DTyr-DTyr-cyclo(Cys-Tyr-DTrp-Lys-Abu-Cys)-Thr-NH$_2$ A mixture of H-Aepa-Lys(Boc)-DTyr(tBu)-DTyr(tBu)-Cys(Trt)-Tyr(tBu)-DTrp(Boc)-Lys(Boc)-Abu-Cys(Trt)-Rink Amide MBHA resin (0.1 mmol) (Example 4), paclitaxel-2'-O-(N-glycyl-succinyl) (Example 39) (1.1 eq.), DIC (136 μL, 4.4 eq.), and HOAT (30 mg, 1.1 eq.) in 5 mL of DCM was shaken for 2 days. The resin was washed successively with DMF, methanol and DCM. After drying in the air, the resin was treated with a mixture of TFA, H$_2$O and triisopropylsilane (TIS) (9.5 mL/0.85 mL/0.8 mL) for 2 h. The resin was filtered off and the filtrate was poured into 100 mL of cold ether. The precipitate was collected after centrifuge. The crude product was dissolved in a mixed solution system (100 mL of 5% acetic acid aqueous solution and 30 mL of acetonitrile). To the solution was added dropwise iodine methanol solution until the yellow color maintained. The reaction solution was stirred for additional 45 min. 10% Na$_2$S$_2$O$_3$ water solution was added to quench excess iodine. The crude product in the solution was purified on a preparative HPLC system with a column (4×43 cm) of C$_{18}$ DYNAMAX-100A$^0$ (Varian, Walnut Creek, Calif.). The column was eluted with a linear gradient from 80% A and 20% B to 55% A and 45% B in 50 min., where A was 0.1% TFA in water and B was 0.1% TFA in acetonitrile. The fractions were checked by an analytical HPLC. Those containing pure product were pooled and lyophilized to dryness. The purity was 98% based on analytical HPLC analysis. ESI MS analysis gave the molecular weight at 2500.9 (in agreement with the calculated molecular weight of 2501.0).

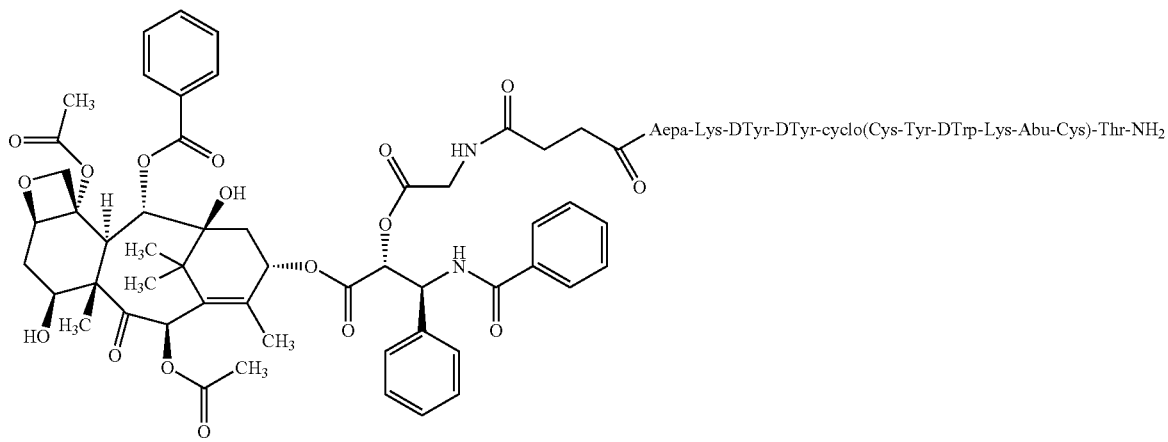

Example 41

Paclitaxel-2'-O-Val-Succinyl-DPhe-cyclo(Cys-Tyr-DTrp-Lys-Abu-Cys)-Thr-NH$_2$

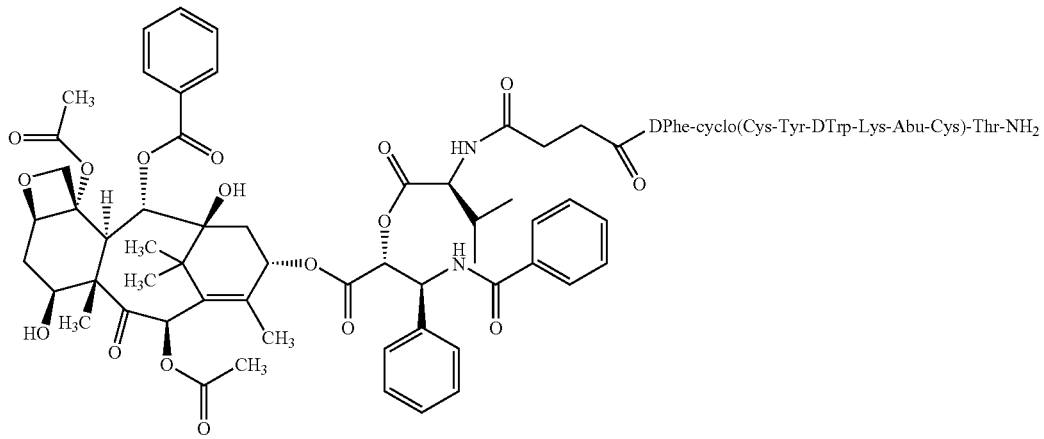

The titled peptide was synthesized substantially according to the procedure described in Example 40. The purity was 99% based on analytical HPLC analysis. ESI MS analysis gave the molecular weight at 2066.2 (in agreement with the calculated molecular weight of 2067.4).

Example 42

Paclitaxel-2'-O-Val-Succinyl-Aepa-Lys-DTyr-DTyr-cyclo(Cys-Tyr-DTrp-Lys-Abu-Cys)-Thr-NH$_2$ The titled peptide was synthesized substantially according to the procedure described in Example 40. The purity was 95% based on analytical HPLC analysis. ESI MS analysis gave the molecular weight at 2544.3 (in agreement with the calculated molecular weight of 2543.9).

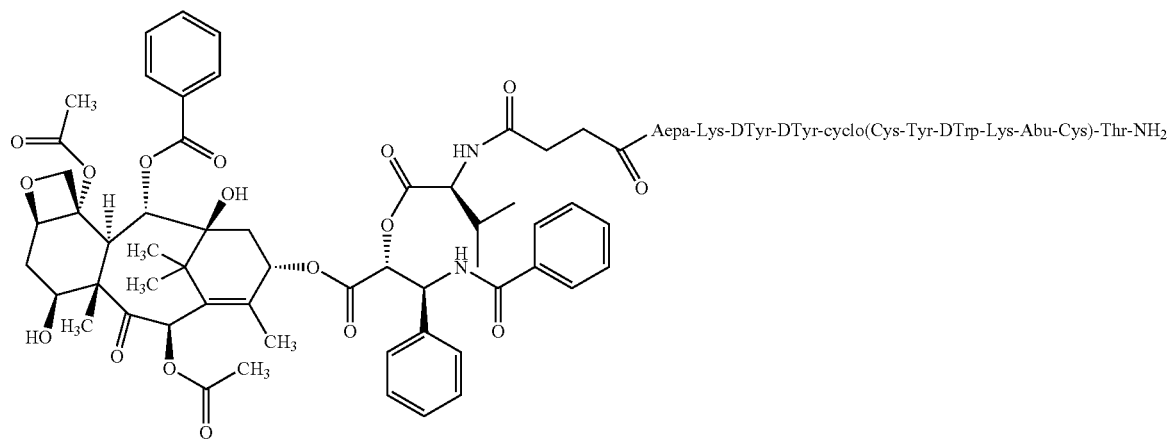

Example 43

N-Boc-Doxorubicin-14-O-(Fmoc-glycine) ester

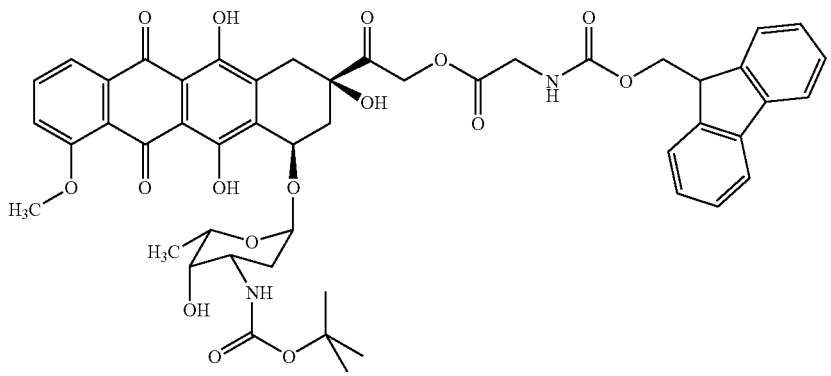 [SMILES: COc1cccc2c1C(=O)c1c(O)c3c(c(O)c1C2=O)C[C@@](O)(C(=O)COC(=O)CNC(=O)OCC1c2ccccc2-c2ccccc21)C[C@H]3OC1CC(NC(=O)OC(C)(C)C)C(O)C(C)O1]

To a solution of doxorubicin-HCl (190 mg) in DMF (5 mL) is added (BOC)$_2$O (1.2 eq), followed by diisopropylethylamine (2.5 eq.). After stirring for 3 hours, volatile substances are removed in vacuo and the residue is treated with water. The solid is collected by filtration, washed with water and dried. The resulting product is dissolved in DMF (10 mL). To it are added Fmoc-Gly-OH (1.2 eq.), DMAP (0.2 eq.) and EDC (1.2 eq). The mixture is stirred at room temperature for 4 h. After evaporation of the solvent, the residue is partitioned between chloroform-methanol and water. Organic layer is dried over MgSO$_4$ and filtered. Solvents are removed in vacuo and the residue is chromatographed on silica gel eluting with chloroform-methanol (9:1). The fractions containing the desired product are pooled and solvents are evaporated in vacuo.

Example 44

N—BOC-Doxorubicin-14-O—[(N-succinyl)glycine] ester

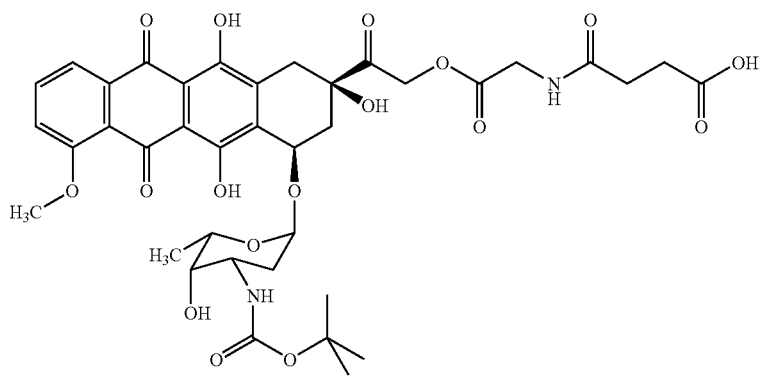 [SMILES: COc1cccc2c1C(=O)c1c(O)c3c(c(O)c1C2=O)C[C@@](O)(C(=O)COC(=O)CNC(=O)CCC(=O)O)C[C@H]3OC1CC(NC(=O)OC(C)(C)C)C(O)C(C)O1]

To a solution of Boc-doxorubicin-14-O-(Fmoc-glycine) ester (100 mg) in DMF (5 mL) is added 1 mL of piperidine. After stirring for 2 hours at room temperature, the mixture is diluted with chloroform (20 mL). The mixture is washed with brine, dried over MgSO$_4$, and filtered. The solvents are removed in vacuo to a small volume (~5 mL). To the mixture are added succinic anhydride (4 eq.), DMAP (2 eq.) and triethylamine (4 eq.). The solution is stirred at room temperature overnight. Volatile substances are removed in vacuo. The residue is triturated with 5% aqueous citric acid. Precipitate is collected by filtration, washed with water, and dried.

Example 45 pGlu-His-Trp-Ser-Tyr-DLys[N$^\epsilon$-(doxorubicin-14-O-glycyl-succinyl-Aepa-(Doc)$_4$-)]-Leu-Arg-Pro-Gly-NH$_2$

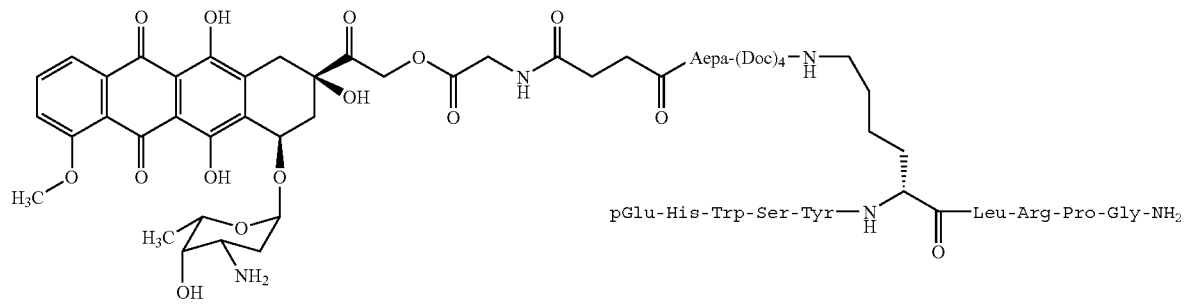

The titled compound is synthesized substantially according to the procedure for Example 28 by using pGlu-His(Trt)-Trp(Boc)-Ser(tBu)-Tyr(tBu)-DLys[N$^\epsilon$-(Aepa-(Doc)$_4$-)]-Leu-Arg(Pbf)-Pro-Gly-Rink Amide MBHA resin (Example 34) and Boc-doxorubicin-14-O—[(N-succinyl)glycine]ester (Example 44).

Example 46 pGlu-His-Trp-Ser-Tyr-DLys[N'-(doxorubicin-14-O-Gly-Succinyl-(Doc)$_4$-Gaba-]-Leu-Arg-Pro-Gly-NH$_2$

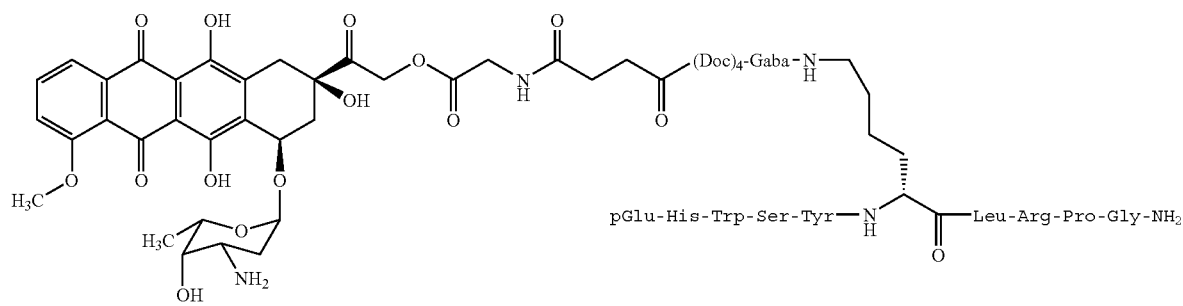

The titled compound was synthesized substantially according to the procedure for Example 45. Fmoc-Gaba-OH was from Novabiochem, San Diego, Calif.

Example 47

Doxorubicin-14-O-glycyl-succinyl-(Doc)$_4$-Aepa-Caeg-cyclo(DCys-3Pal-DTrp-Lys-DCys)-Thr(Bzl)-Tyr-NH$_2$

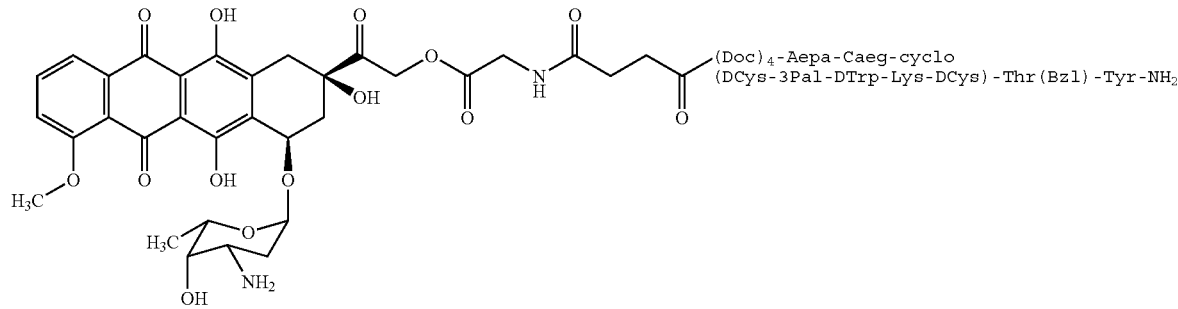

The titled compound is synthesized substantially according to the procedure for Example 19. The H-(Doc)$_4$-Aepa-Caeg-DCys(Trt)-3Pal-Trp(Boc)-Lys(Boc)-DCys(Trt)-Thr(Bzl)-Tyr(tBu)-Rink Amide MBHA resin (Example 35) and BOC-doxorubicin-14-O—[(N-succinyl)glycine]ester (Example 44) are used.

Example 48

Paclitaxel-2'-O-glycyl-succinyl-(Doc)$_4$-Aepa-DPhe-cyclo[Cys-3ITyr-DTrp-Lys-Val-*Cys]-Thr-NH$_2$

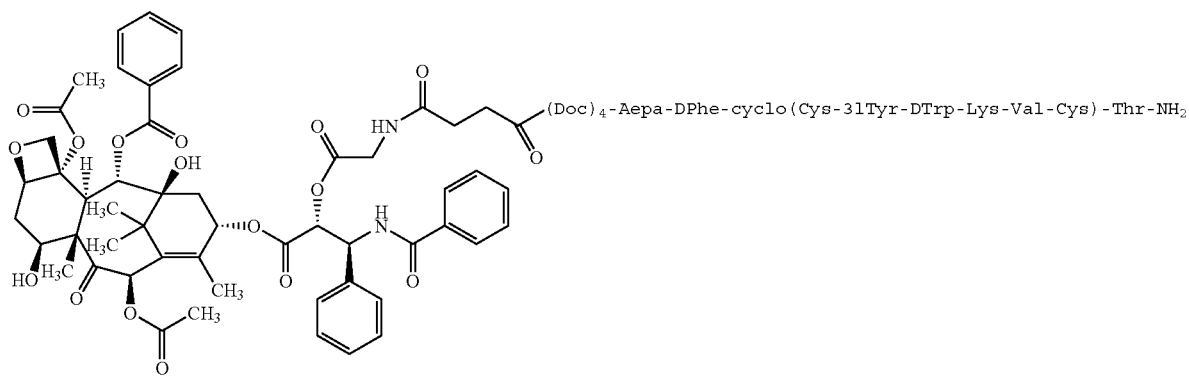

The titled compound is synthesized substantially according to the procedure for Example 40 by using H-(Doc)$_4$-Aepa-DPhe-Cys(Trt)-3ITyr-DTrp(Boc)-Lys(Boc)-Val-Cys(Trt)-Thr(tBu)-Rink Amide MBHA resin (Example 36) and paclitaxel-2'-O-(N-glycyl-succinyl) (Example 38).

Example 49

Paclitaxel-2'-O-glycyl-succinyl-Aepa-(Doc)$_2$-Gln-Trp-Ala-Val-βAla-His-Phe-Nle-NH$_2$

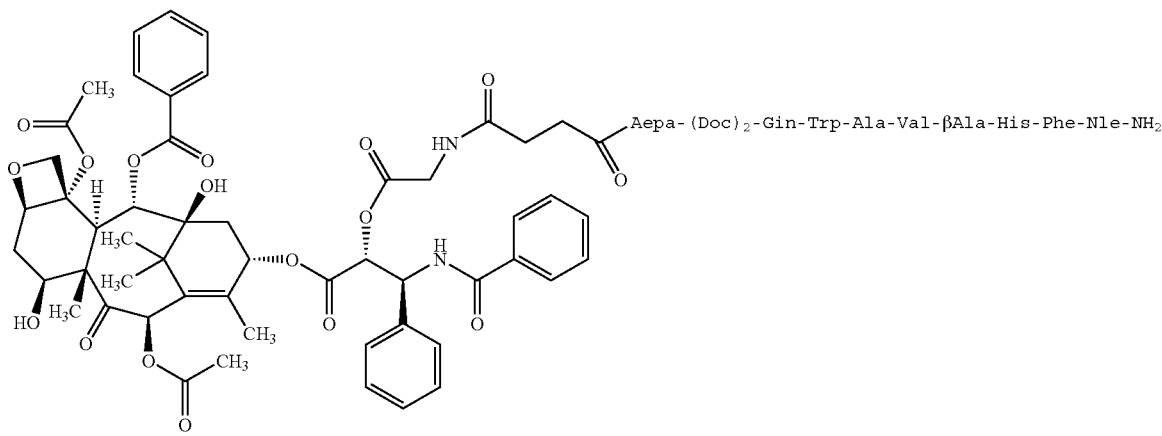

The titled compound is synthesized substantially according to the procedure for Example 28 by using H-Aepa-(Doc)$_2$-Gln(Trt)-Trp(Boc)-Ala-Val-βAla-His(Trt)-Phe-Nle-Rink Amide MBHA resin and paclitaxel-2'-O-(N-glycyl-succinyl) (Example 38).

Example 50 pGlu-His-Trp-Ser-Tyr-DLys[N$^\epsilon$-(paclitaxel-2'-O-glycyl-succinyl-Aepa-(Doc)$_4$-)]-Leu-Arg-Pro-Gly-NH$_2$

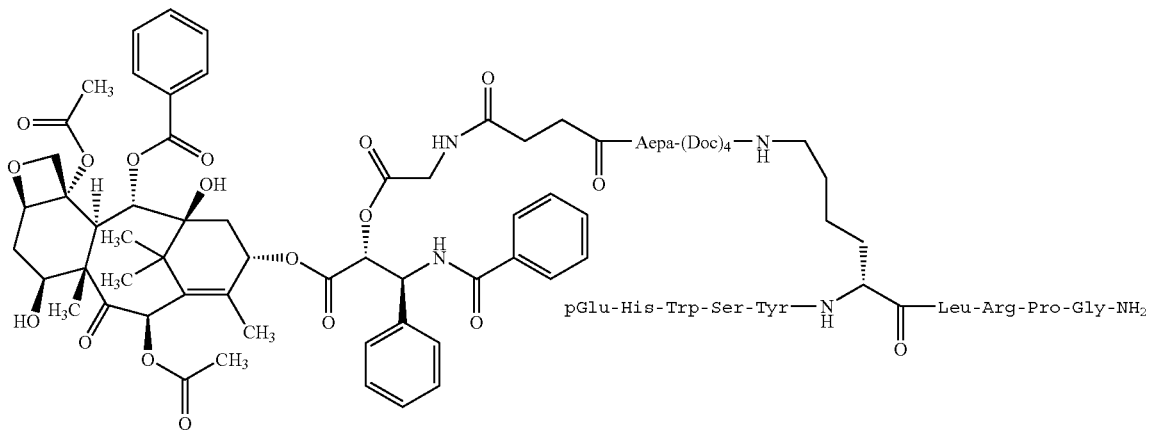

The titled compound was synthesized substantially according to the procedure for Example 45 by using pGlu-His(Trt)-Trp(Boc)-Ser(tBu)-Tyr(tBu)-DLys[N$^\epsilon$-(Aepa-(Doc)$_4$-)]-Leu-Arg(Pbf)-Pro-Gly-Rink Amide MBHA resin (Example 34) and 2'-O-(N-succinyl-glycyl)-paclitaxel (Example 38).

Example 51 pGlu-His-Trp-Ser-Tyr-DLys[N$^\epsilon$-(camptothecin-20-(S)—O-glycinyl-succinyl-(Doc)$_4$-Aepa-)]-Leu-Arg-Pro-Gly-NH$_2$

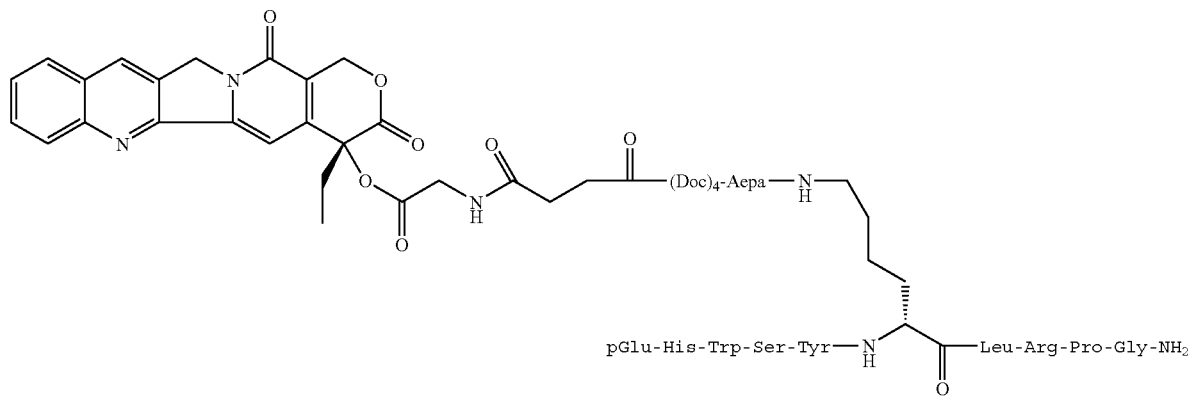

The titled compound is synthesized substantially according to the procedure for Example 50 by using camptothecin-20-(S)-[O—(N-succinyl-glycyl)] (Example 14).

Example 52

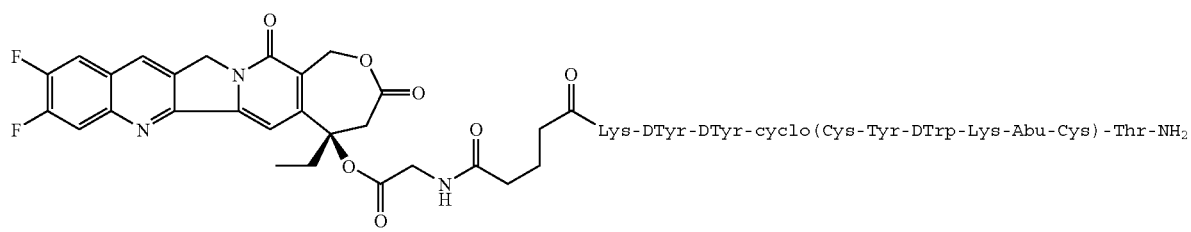

The titled compound was synthesized substantially according to the procedure described in Example 19. Yield=11%. Purity was 99.9% based on analytical HPLC analysis. ESI MS analysis gave the molecular weight at 1891.8 (in agreement with the calculated molecular weight of 1891.1).

Example 53

Camptothecin-Gly-glutaryl-Lys-DTyr-DTyr-cyclo(Cys-Tyr-DTrp-Lys-Abu-Cys)-Thr-NH$_2$

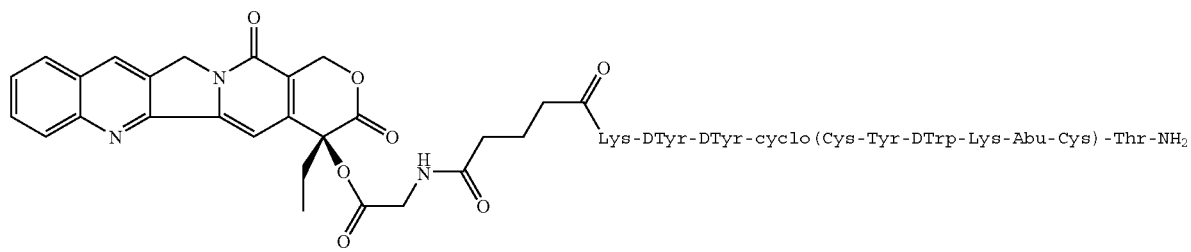

The titled compound was synthesized substantially according to the procedure described in Example 19. Yield=23%. Purity was 99% based on analytical HPLC analysis. ESI MS analysis gave the molecular weight at 1841.9 (in agreement with the calculated molecular weight of 1841.1).

Example 54

Camptothecin-Gly-succinyl-(Doc)$_6$-DPhe-c(Cys-Tyr-DTrp-Lys-Abu-Cys)-Thr-NH$_2$

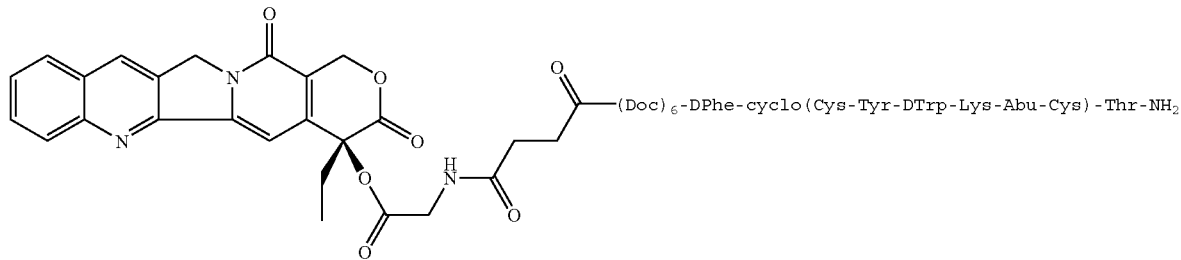

The titled compound was synthesized substantially according to the procedure described in Example 19. Yield=18%. Purity was 98% based on analytical HPLC analysis. ESI MS analysis gave the molecular weight at 2390.0 (in agreement with the calculated molecular weight of 2390.7).

Example 55

Camptothecin-Gly-glutaryl-Lys-Lys-Lys-DTyr-DTyr-cyclo(Cys-Tyr-DTrp-Lys-Abu-Cys)-Thr-NH$_2$

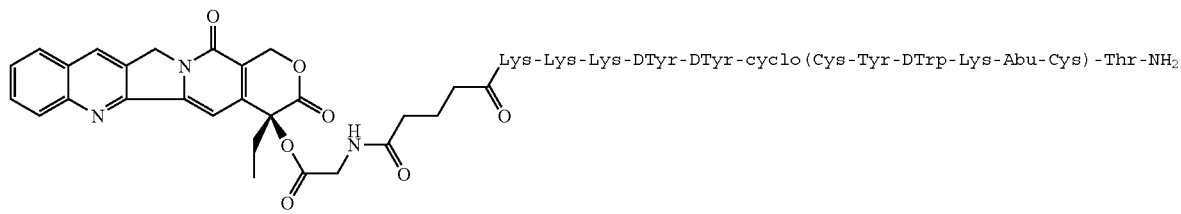

The titled compound was synthesized substantially according to the procedure described in Example 19. Yield=12%. Purity was 100% based on analytical HPLC analysis. ESI MS analysis gave the molecular weight at 2097.0 (in agreement with the calculated molecular weight of 2097.4).

Example 56

Camptothecin-Gly-succinyl-(Doc)$_4$-DPhe-c(Cys-Tyr-DTrp-Lys-Abu-Cys)-Thr-NH$_2$

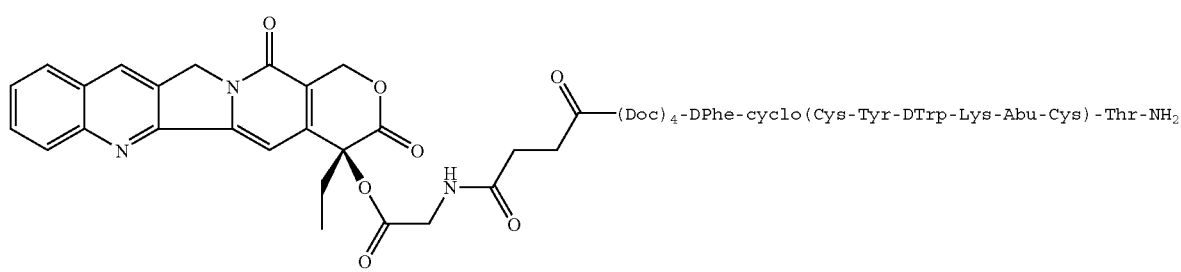

The titled compound was synthesized substantially according to the procedure described in Example 19. Yield=31%. Purity was 100% based on analytical HPLC analysis. ESI MS analysis gave the molecular weight at 2100.9 (in agreement with the calculated molecular weight of 2100.3).

Example 57

Camptothecin-Gly-succinyl-Aepa-DPhe-cyclo(Cys-Tyr-DTrp-Lys-Abu-Cys)-Thr-NH$_2$

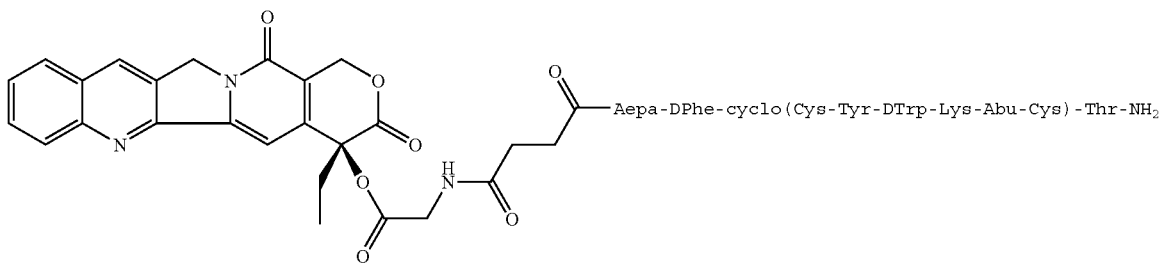

The titled compound was synthesized substantially according to the procedure described in Example 19. Yield=21%. Purity was 97% based on analytical HPLC analysis. ESI MS analysis gave the molecular weight at 1688.0 (in agreement with the calculated molecular weight of 1688.9).

Example 58

Camptothecin-Abu-succinyl-(Doc)$_4$-Lys-DTyr-DTyr-cyclo(Cys-Tyr-DTrp-Lys-Abu-Cys)-Thr-NH$_2$

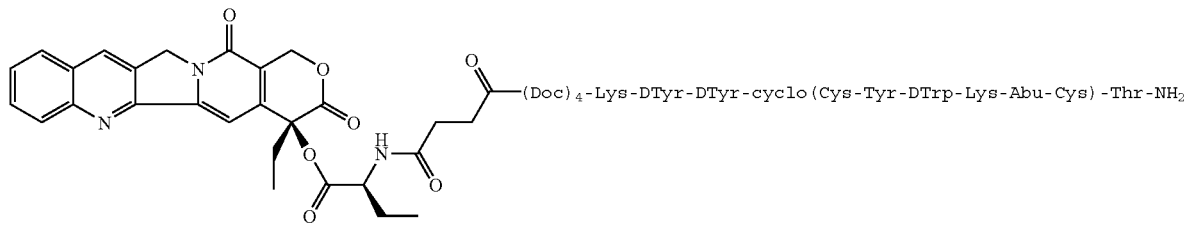

The titled compound was synthesized substantially according to the procedure described in Example 19. Yield=23%. Purity was 95% based on analytical HPLC analysis. ESI MS analysis gave the molecular weight at 2435.2 (in agreement with the calculated molecular weight of 2435.8).

Example 59

Camptothecin-glutaryl-(Doc)$_2$-Lys-DTyr-DTyr-cyclo(Cys-Tyr-DTrp-Lys-Abu-Cys)-Thr-NH$_2$

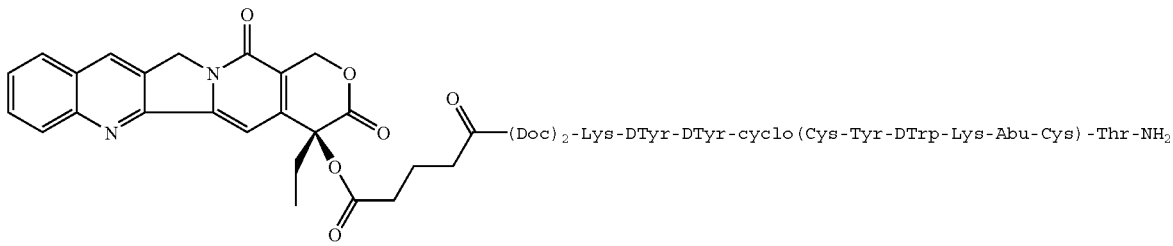

The titled compound was synthesized substantially according to the procedure described in Example 19. Yield=11%. Purity was 95% based on analytical HPLC analysis. ESI MS analysis gave the molecular weight at 2074.0 (in agreement with the calculated molecular weight of 2074.4).

Example 60

Camptothecin-glutaryl-Doc-Lys-DTyr-DTyr-cyclo
(Cys-Tyr-DTrp-Lys-Abu-Cys)-Thr-NH$_2$

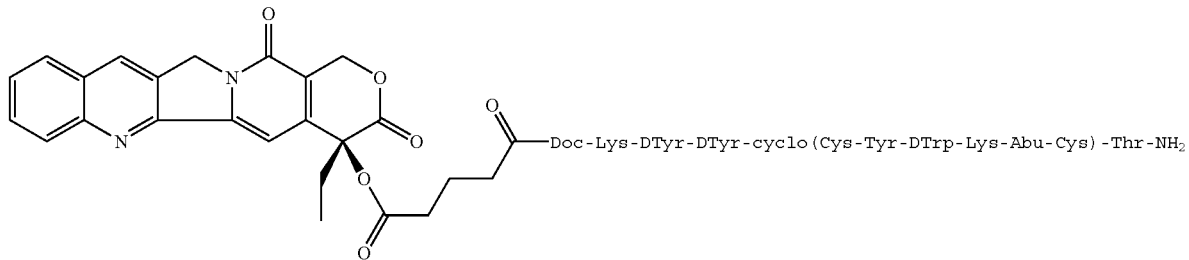

The titled compound was synthesized substantially according to the procedure described in Example 19. Yield=16%. Purity was 95% based on analytical HPLC analysis. ESI MS analysis gave the molecular weight at 1929.5 (in agreement with the calculated molecular weight of 1929.2).

Example 61

Camptothecin-20-glycinyl-succinoyl-DPhe-cyclo
(Cys-Tyr-DTrp-Lys-Abu-Cys)-Thr-NH$_2$

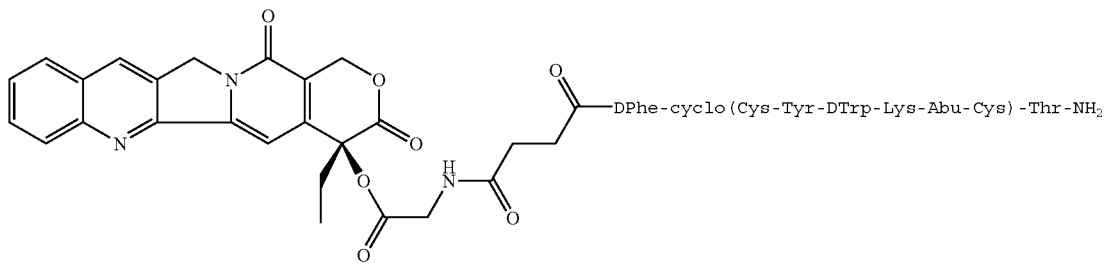

The titled compound was synthesized substantially according to the procedure described in Example 19. Yield=15.6%. Purity was 94% based on analytical HPLC analysis. ESI MS analysis gave the molecular weight at 1520.1 (in agreement with the calculated molecular weight of 1519.71).

Example 62

{5-(R)-Ethyl-9,10-difluoro-1,4,5,13-tetrahydro-3H,
15H-oxepino[3',4':6,7]indolizino[1,2-b]quinoline-3,
15-dione-5-O-glycyl-succinyl}-(Doc)$_4$-Aepa-DPhe-
cyclo(Cys-Tyr-DTrp-Lys-Abu-Cys)-Thr-NH$_2$

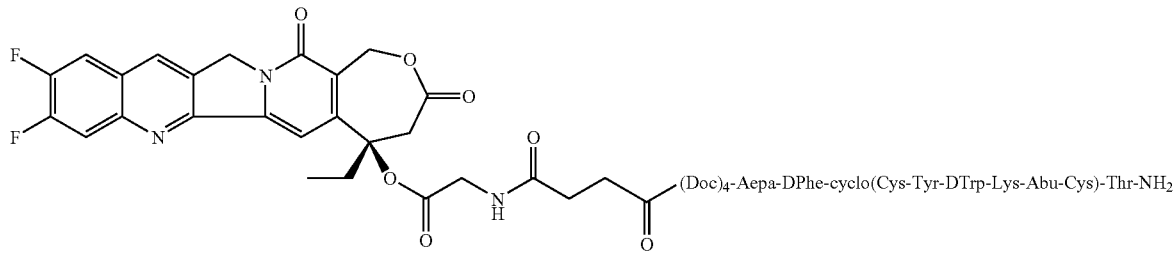

The titled compound was synthesized substantially according to the procedure described in Example 19. Yield=25%. Purity was 97% based on analytical HPLC analysis. ESI MS analysis gave the molecular weight at 2320.0 (in agreement with the calculated molecular weight of 2319.6).

Example 63

{5-(R)-Ethyl-9,10-difluoro-1,4,5,13-tetrahydro-3H, 15H-oxepino[3',4':6,7]indolizino[1,2-b]quinoline-3, 15-dione-5-O-glycyl-glutaryl}-Aepa-Lys-DTyr-DTyr-cyclo(Cys-Tyr-DTrp-Lys-Abu-Cys)-Thr-NH$_2$

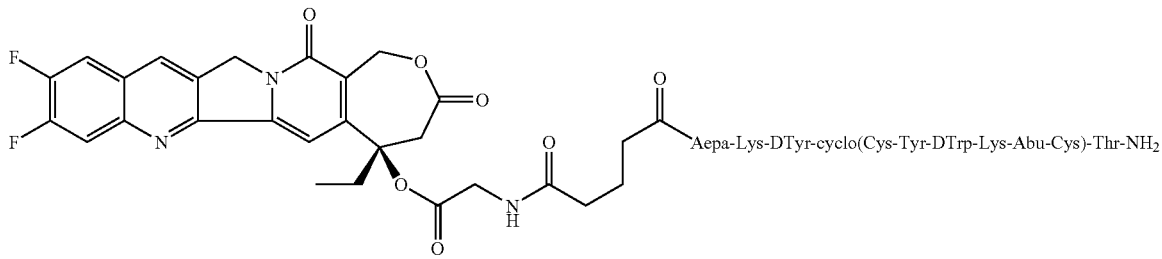

The titled compound was synthesized substantially according to the procedure described in Example 19. Yield=24%. Purity was 95% based on analytical HPLC analysis. ESI MS analysis gave the molecular weight at 2059.4 (in agreement with the calculated molecular weight of 2060.3).

Example 64

{5-(R)-Ethyl-9,10-difluoro-1,4,5,13-tetrahydro-3H, 15H-oxepino[3',4':6,7]indolizino[1,2-b]quinoline-3, 15-dione-5-O-glycyl-succinyl}-(Doc)$_4$-Aepa-Lys-DTyr-DTyr-c(Cys-Tyr-DTrp-Lys-Abu-Cys)-Thr-NH$_2$

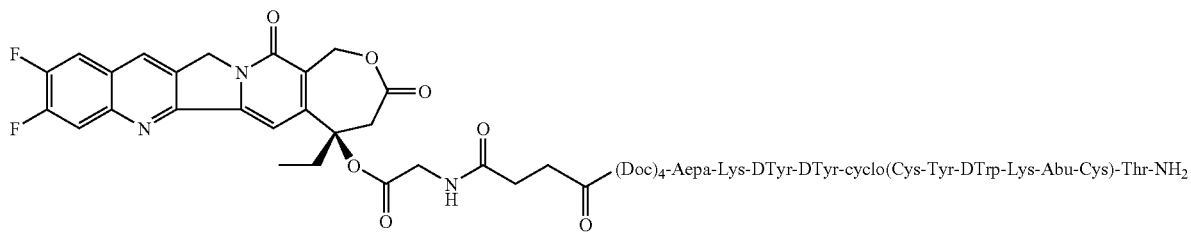

The titled compound was synthesized substantially according to the procedure described in Example 19. Yield=48. Purity was 99.9% based on analytical HPLC analysis. ESI MS analysis gave the molecular weight at 2626.0 (in agreement with the calculated molecular weight of 2626.9).

Example 65

Camptothecin-20-glutaryl-(Doc)$_4$-Lys-DTyr-DTyr-cyclo(Cys-Tyr-DTrp-Lys-Abu-Cys)-Thr-NH$_2$

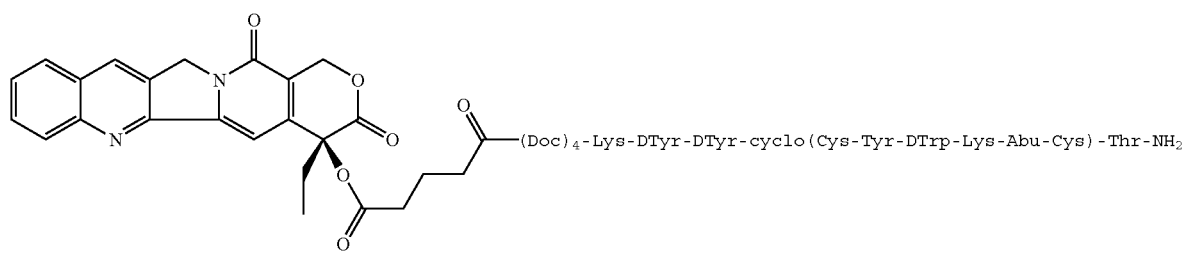

The titled compound was synthesized substantially according to the procedure described in Example 19. Yield=10%. Purity was 98.9% based on analytical HPLC analysis. ESI MS analysis gave the molecular weight at 2365.0 (in agreement with the calculated molecular weight of 2365.0).

Example 66

H-DPhe-Cys(Trt)-Tyr(tBu)-DTrp(Boc)-Lys(Aloc)-Abu-Cys(Trt)-Thr(tBu)-Rink-Amide-MBHA-Resin The titled peptide was automatically synthesized on an Applied Biosystems (Foster City, Calif.) model 433A peptide synthesizer based on Fluorenylmethyloxycarbonyl (Fmoc) chemistry. A Rink Amide MBHA resin (Nova Biochem, San Diego, Calif.) with substitution of 0.72 mmol/g was used. The Fmoc amino acids (AnaSpec, San Jose, Calif.) were used with the following side chain protection: Fmoc-Thr(tBu)-OH, Fmoc-Cys(Trt)-OH, Fmoc-Lys(Aloc)-OH, Fmoc-DTrp(Boc)-OH, Fmoc-Tyr(OtBu)-OH, Fmoc-DPhe-OH, and Fmoc-Abu-OH. The synthesis was carried out on a 0.25 mmol scale. The Fmoc groups were removed by treatment with 20% piperidine in N-methylpyrrolidone (NMP) for 30 min. In each coupling step, the Fmoc amino acid (4 eq, 1 mmol) was first pre-activated by 0.45M 2-(1-H-benzotriazole-1-yl)-1,1,2,3-tetramethyluronium hexafluorophosphate/1-hydroxy-benzotriazole (HBTU/HOBT) in DMF. This activated amino acid ester with 1 ml of diisopropylethylamine (DIEA) and (NMP were added to the resin. The ABI 433A peptide synthesizer was programmed to perform the following reaction cycles: (1) washing with NMP, (2) removing Fmoc protecting group with 20% piperidine in NMP for 30 min, (3) washing with NMP, (4) coupling with pre-activated Fmoc amino acid for 1 h. Single couplings were applied to the Cys(Trt)$^2$,Tyr(tBu)$^3$, and DTrp(Boc)$^4$. For all other amino acids double coupling was used. The resin was coupled successively according to the sequence. After peptide chain was assembled, the Fmoc was removed and washed completely by DMF and DCM.

Example 67

Fmoc-Aepa-DPhe-Cys(Trt)-Tyr(tBu)-DTrp(Boc)-Lys(Aloc)-Abu-Cys(Trt)-Thr(tBu)-Rink-Amide-MBHA-Resin The titled peptide was synthesized starting with the peptide from Example 66. The Fmoc-Aepa-OH (Neosystem Laboratoire, Gennevilliers, France. 1.5 eq, 0.75 mmol) was pre-activated with [O-(7-azabenzotriazol-1-yl)-1,1,3,3-tetramethyluronium hexafluorophosphate] (HATU, 1.4 eq, 0.7 mmol) and 1-hydroxy-7-azabenzotriazole(HOAT, 1.4 eq, 0.7 mmol) in 2 ml of DMF for 5 min. The above resin was transferred into a small reaction vessel and shaken with this activated ester of Fmoc-Aepa-OH and 1 ml of DIEA on a shaker for 2 h. The resin was washed thoroughly with DMF and DCM.

Example 68

H-Doc-Doc-Doc-Doc-Aepa-DPhe-Cys(Trt)-Tyr(tBu)-DTrp(Boc)-Lys(Aloc)-Abu-Cys(Trt)-Thr(tBu)-Rink-Amide-MBHA-Resin The titled peptide was synthesized starting with the peptide from Example 68. The resin was washed with DMF and treated with 25% piperidine in DMF to remove Fmoc. The resin was mixed with a DMF solution of Fmoc-Doc-OH (Chem-Impex International, Wood Dale, Ill., 1.5 eq, 0.75 mmol) N,N-diisopropylcarbodiimide (DIC, 1.5 eq, 0.75 mmol), and HOBT (1.5 eq, 0.75 mmol) for 2 h. The second through fourth Fmoc-Doc-OH were coupled to the resin using the same procedure as described in coupling of the first Fmoc-Doc-OH. The process was repeated until the assembly of peptide chain was completed.

The final Fmoc was removed with 25% piperidine in DMF. The resin was washed with DMF and DCM.

Example 69

H-Doc-Doc-Doc-Doc-Aepa-DPhe-cyclo(Cys-Tyr-DTrp-Lys(Aloc)-Abu-Cys)-Thr-NH$_2$

The peptide was cleaved from the Resin using 19 mL of TFA (Trifluoroacetic Acid, Halocarbon Products Corp. River Edge, N.J.), 1.6 mL of TIS (Triisopropylsilane, Aldrich) and 1.7 mL of water for 2 hours. The resin was filtered and the peptide precipitated by pouring into ether. Dissolve the precipitate in 150 mL of 5% acetic acid and 30 mL of acetonitrile. I$_2$ (20 mg/ml in MeOH) was added dropwise till there was a persistent red color. The flask was placed in a bath of hot tap water and stirred for 2 hours. The reaction was quenched using 10% Na$_2$SSO$_3$. The peptide was purified using a Phenomenex C$_{18}$ column with a gradient 5-60% CH$_3$CN where Buffer A is 0.1% TFA in water and Buffer B is 0.1% TFA in CH$_3$CN over 60 minutes. The fractions containing product were freeze dried to give 186 mg(40% yield) of white powder. MS (Electro Spray): 1722.2

Example 70 H-Doc-Doc-Doc-Aepa-DPhe-Cys(Trt)-Tyr(tBu)-DTrp(Boc)-Lys(Aloc)-Abu-Cys(Trt)-Thr(tBu)-Rink-Amide-MBHA-Resin The titled peptide was synthesized starting with the peptide from Example 67. The resin was washed with DMF and treated with 25% piperidine in DMF to remove Fmoc. The resin was mixed with a DMF solution of Fmoc-Doc-OH (Chem-Impex International, Wood Dale, Ill., 1.5 eq, 0.75 mmol) N,N-diisopropylcarbodiimide (DIC, 1.5 eq, 0.75 mmol), and HOBT (1.5 eq, 0.75 mmol) for 2 h. The second and third Fmoc-Doc-OH were coupled to the resin using the same procedure as described in coupling of the first Fmoc-Doc-OH. The process was repeated until the assembly of peptide chain was completed. The final Fmoc was removed with 25% piperidine in DMF. The resin was washed with DMF and DCM.

Example 71

H-Doc-Doc-Doc-Aepa-DPhe-cyclo(Cys-Tyr-DTrp-Lys(Aloc)-Abu-Cys)-Thr-NH$_2$

The peptide was cleaved from the Resin using 19 mL of TFA (Trifluoroacetic Acid, Halocarbon Products Corp. River Edge, N.J.), 1.6 mL of TIS (Triisopropylsilane, Aldrich) and 1.7 mL of water for 2 hours. The resin was filtered and the peptide precipitated by pouring into ether. Dissolve the precipitate in 150 mL of 5% acetic acid and 30 mL of acetonitrile. I$_2$ (20 mg/mL of MeOH) was added dropwise till there was a persistent red color. The flask was placed in a bath of hot tap water and stirred for 2 hours. The reaction was quenched using 10% Na$_2$SSO$_3$. The peptide was purified using a Phenomenex C$_{18}$ column with a gradient 5-60% CH$_3$CN where Buffer A is 0.1% TFA in water and Buffer B is 0.1% TFA in CH$_3$CN over 60 minutes. The fractions containing product were freeze dried to give 180 mg(42% yield) of white powder. MS (Electro Spray):1722.2,

Example 72

Paclitaxel-2'-glutarate

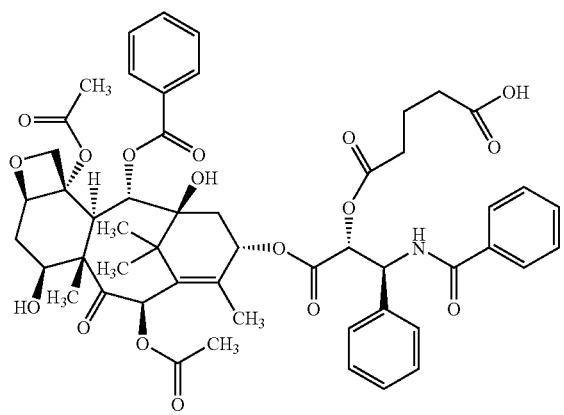 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCCC(=O)O)[C@@H](NC(=O)c4ccccc4)c4ccccc4)C(C)=C1C3(C)C)[C@]1(OC(C)=O)CO[C@@H]1C[C@@H]2O]

To a solution of Paclitaxel (HandeTech USA, Inc, Houston, Tex., 1 g., 1.17 mmol) in 10 mL of pyridine was added glutaric anhydride (Aldrich, 1.6 g, 14.1 mmol, 12 eq.). The resulting solution was stirred at room temperature for 4 hours and then evaporated at reduced pressure. 20 mL of water was added. The sticky solid was collected by filtration. Recrystallization from acetone/water gave 0.842 g of white solid, 0.869 mmole, 74% yield. MS (Electro Spray): 969.0.

Example 73

Paclitaxel-2'-Doc-Suc-OH

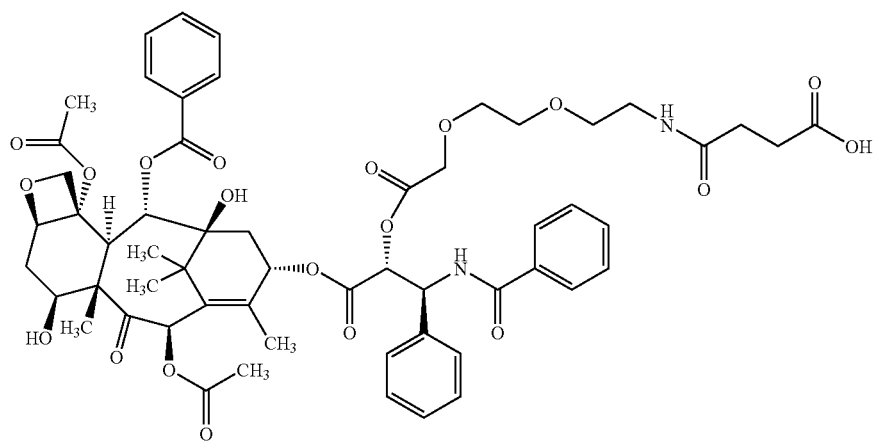

or

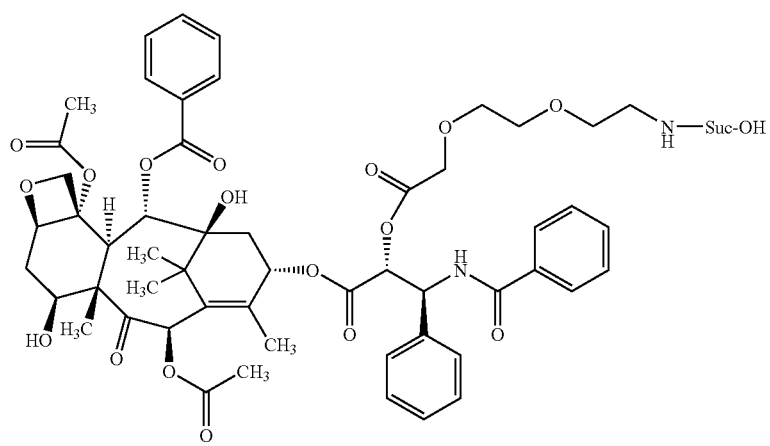

To a solution of paclitaxel (1 g., 1.17 mmol) and the Boc-Doc-OH (0.31 g., 1.17 mmol) in 25 mL of DCM was added DIC (0.241 mL, 1.54 mmol) followed by DMAP (50 mg. 0.4 mmol). The resulting solution was stirred at room temperature for 4 hours. The solution was washed with 3×10% citric acid, 3× saturated NaHCO$_3$, 1× saturated NaCl and dried over MgSO$_4$, filtered and evaporated. The resulting residue was dissolved in EtOAc and then precipitated with hexane. The product was collected by filtration and dried under reduced pressure. Solid (1.19 g, 1.08 mmol) was obtained. Yield was 92%. MS (Electro Spray): m/e=1099.7(+1), Purity was 95% by HPLC. The resulting Boc-Doc-paclitaxel (1.19 g, 1.08 mmol) was dissolved in 20 mL of formic acid, stirred for 30 minutes and then evaporated. The product was dissolved in 15 mL of pyridine. To the solution was added succinic anhydride (1.29 g, 13 mmol). The mixture was stirred at room temperature overnight. Pyridine was removed by evaporation under reduced pressure. The residue was triturated with water and collected (0.99 g, 0.91 mmole, 84% yield). MS (Electo Spray) gave 1099.4(+1), 1121.6 (Na+1). Purity was 75% by HPLC.

then evaporated under reduced pressure. The residue was dissolved in minimal MeOH and precipitated with ether. A solid was obtained (108 mg, 0.04 mmol). Yield was 60% y. MS (Electro Spray) showed 1409.5(+2). To remove the Aloc from the Lys, the peptide was dissolved in DCM/THF (anhydrous, 15 mL/5 mL). To is were added glacial acetic acid (15)IL, 5 eq.), Pd(PPh$_3$)$_4$ (Tetrakis(triphenylphosphine) palladium (0); 12 mg, 0.3 eq.) and Bu$_3$SnH (Tributyltin hydride; 2×31 μL, 3 eq) at 0° C. After stirring 1 hour, the solution was quenched using 0.5M HCl in ether (0.7 mL, 10 eq.). The peptide was precipitated with ether. The crude peptide was purified on a PLRP-S column (Polymer Labs, 100A, 8μ) using a gradient of 5-90% over 1 hour where solvent A was 5% MeOH in water and solvent B was CH$_3$CN. Pure fractions were combined and lyophilized, yielding 42 mg of the peptide. MS (Electro Spray) gave 2731.4 (in agreement with the calculated molecular weight of 2732.1). Purity was 99.9% based on HPLC analysis.

Example 74

Paclitaxel-2'-glutaryl-(Doc)$_4$-Aepa-DPhe-cyclo(Cys-Tyr-DTrp-Lys-Abu-Cys)-Thr-NH$_2$ Example 75

Paclitaxel-2'-Doc-Suc-(Doc)$_3$-Aepa-DPhe-cyclo(Cys-Tyr-DTrp-Lys-Abu-Cys)-Thr-NH$_2$

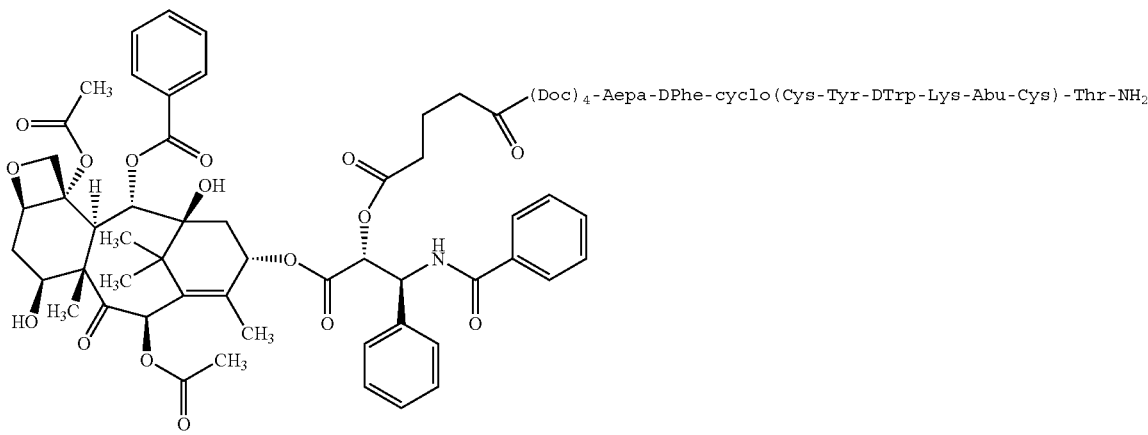

To a DMF (10 mL) solution of the peptide (125 mg, 0.067 mmol) from Example 69 was added paclitaxel-2'-Glut-OH (Example 72, 65 mg, 0.067 mmol), HOBT (20 mg, 0.147 mmol), BOP (Benzotriazole-1-yl-oxy-tris-(dimethylamino)-phosphonium hexafluorophosphate; 29 mg, 0.067 mmol) and DIEA (8 eq., 93 μL). The solution was stirred overnight and

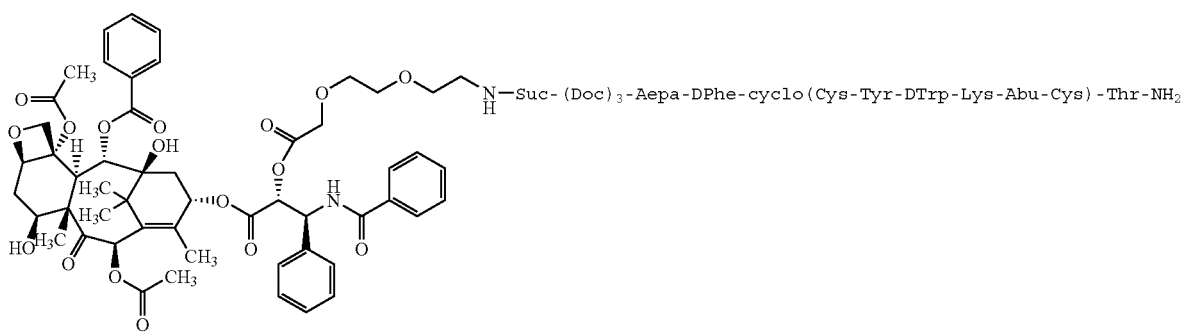

To a DMF (10 ml) solution of the peptide (200 mg, 0.12 mmol) from Example 71 was added paclitaxel-2'-Doc-Suc-OH (Example 73, 140 mg, 0.128 mmol), HOBT (39 mg, 0.281 mmol), BOP (74 mg, 0.166 mmol) and DIEA (8 eq., 177 µL). The solution was stirred overnight and evaporated under reduced pressure. A solid was obtained (355 mg, 0.126 mmol).

To remove the Aloc from the Lys, the product was dissolved in DCM/THF (anhydrous, 15 mL/5 mL). To it were added glacial acetic acid (19 µL, 5 eq.), Pd(PPh$_3$)$_4$ (12 mg, 0.3 eq.) and Bu$_3$SnH (2×54 µL, 3 eq) at 0° C. The solution was stirred for 1 hour and then quenched using 0.5M HCl in ether (0.7 mL, 10 eq.). The product was precipitated with ether.

Purify was done on a PLRP-S column (Polymer Labs, 100A, 8µ) using a gradient of 5-90% over 1 hour where solvent A was 5% MeOH in water and solvent B was CH$_3$CN. Pure fractions were combined and lyophilized. MS (Electro Spray) gave 2717.3 (in agreement with the calculated molecular weight of 2718.1). Purity was 99.9% based on HPLC analysis.

Example 76

Paclitaxel-Sar-Suc-(Doc)$_4$-Aepa-DPhe-cyclo(Cys-Tyr-DTrp-Lys-Abu-Cys)-Thr-NH$_2$

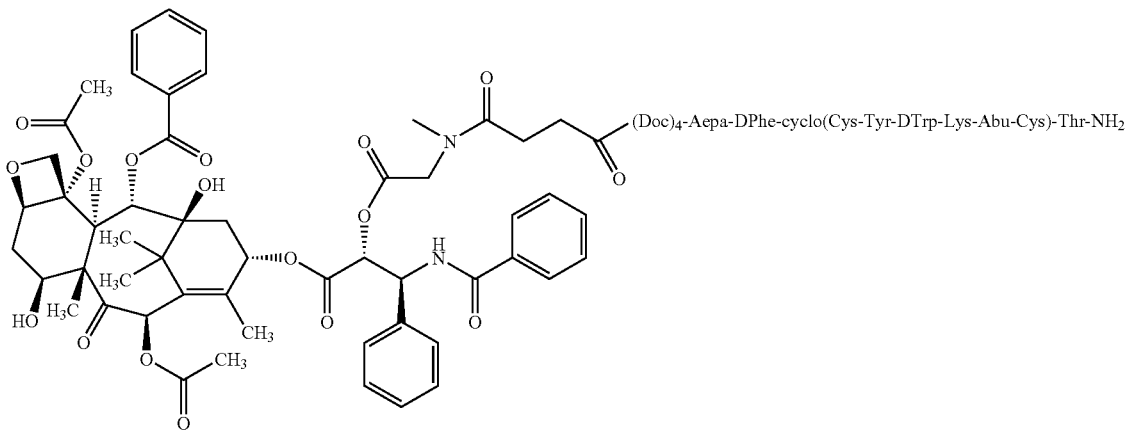

The titled compound was synthesized substantially according to the procedure described in Example 28 by using 2'-O-(N-succinyl-N-methyl-glycyl)-paclitaxel (Example 38) and H-Doc-Doc-Doc-Doc-Aepa-DPhe-cyclo(Cys-Tyr-DTrp-Lys(Aloc)-Abu-Cys)-Thr-NH$_2$ (Example 69). The yield was 18.8%, and the purity was 95% based on HPLC analysis. The molecular weight was determined to be 2789.2.

Example 77

Paclitaxel-Suc-(Doc)$_4$-Gaba-Gln-Trp-Ala-Val-βAla-His-Leu-Nle-NH$_2$

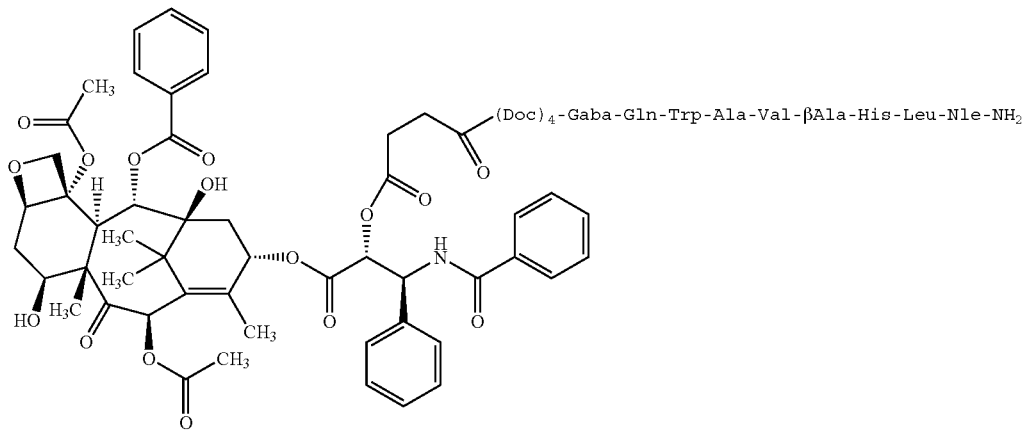

The titled compound was synthesized substantially according to the procedure described in Example 28 by using paclitaxel-2'-succinyl, prepared as in Example 72, using succinic anhydride instead of glutaric anhydride and H-Doc-Doc-Doc-Doc-Gaba-Gln-Trp-Ala-Val-βAla-His-Leu-Nle-NH₂ in which the peptide was prepared substantially as described in Example 1, then coupled to four Doc residues as substantially described in Example 2. The yield was 12.1%, and the purity was 97% based on HPLC analysis. The molecular weight was determined to be 2537.8.

Example 78

Paclitaxel-Sar-Suc-(Doc)₄-Aepa-Gaba-Gln-Trp-Ala-Val-βAla-His-Leu-Nle-NH₂

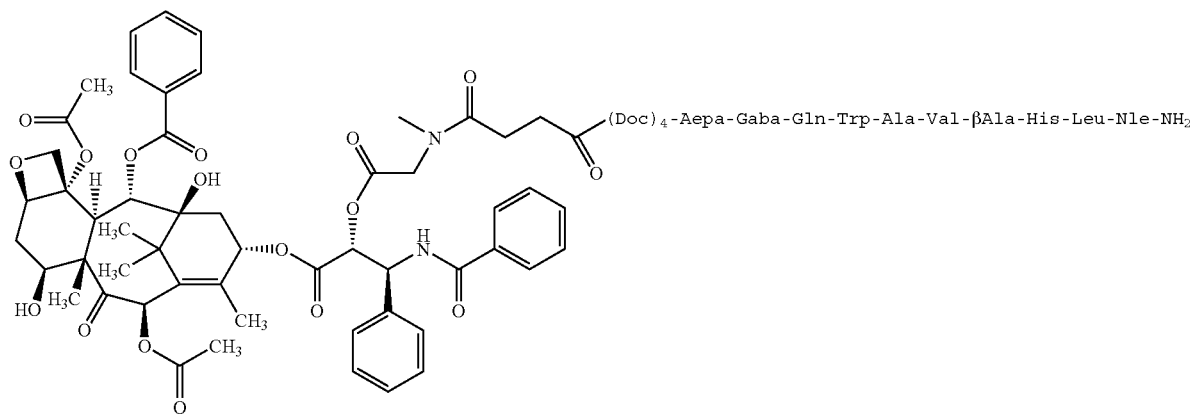

The titled compound was synthesized substantially according to the procedure described in Example 28 by using paclitaxel-2'-O-(N-succinyl-N-methyl-glycyl) prepared substantially as described in Example 38, using Boc-Sar-OH for Boc-Gly-OH) and H-(Doc)₄-Aepa-Gaba-Gln-Trp-Ala-Val-βAla-His-Leu-Nle-NH₂, in which the peptide was synthesized substantially as Example 1, then coupled to an Aepa residue as described in Example 4, followed by coupling to four Doc residues as described in Example 5). The yield was 13.4%, and the purity was 98% based on HPLC analysis. The molecular weight was determined to be 2778.1

Example 79

Camptothecin-Gly-Suc-(Doc)₄-Aepa-Gaba-Gln-Trp-Ala-Val-βAla-His-Leu-Nle-NH₂

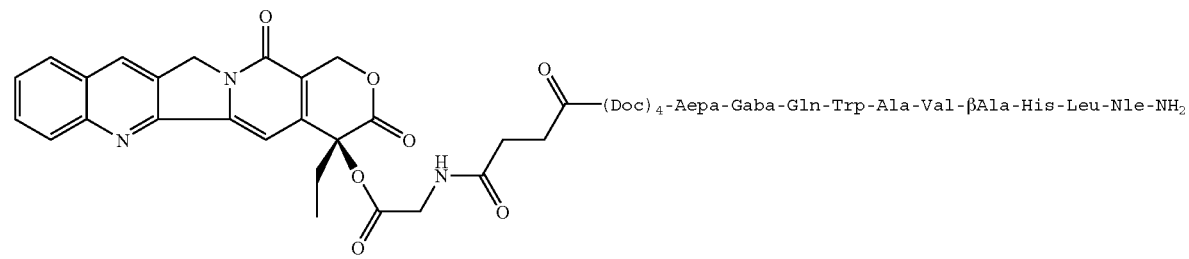

The titled compound was synthesized substantially according to the procedure described in Example 28 by using camptothecin-20-(S)-[O—(N-succinyl-glycyl)] (Example 14) and H-(Doc)₄-Aepa-Gaba-Gln-Trp-Ala-Val-βAla-His-Leu-Nle-NH₂ (Example 78). The yield was 14.4%, and the purity was 99.4% based on HPLC analysis. The molecular weight was determined to be 2258 by mass spectrometry.

Synthesis of Other Compounds

The compounds listed below in Tables A-I can be synthesized according to the procedures described above.

TABLE A

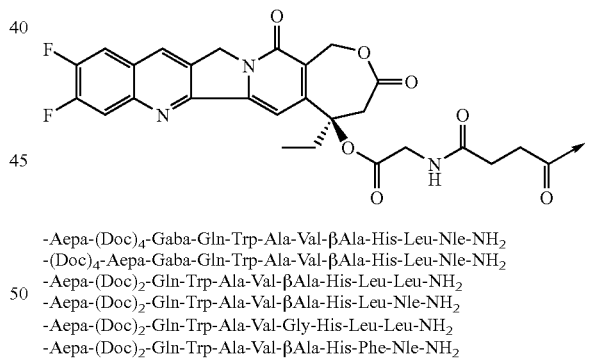

-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
-Aepa-(Doc)₂-Gln-Trp-Ala-Val-βAla-His-Leu-Leu-NH₂
-Aepa-(Doc)₂-Gln-Trp-Ala-Val-βAla-His-Leu-Nle-NH₂
-Aepa-(Doc)₂-Gln-Trp-Ala-Val-Gly-His-Leu-Leu-NH₂
-Aepa-(Doc)₂-Gln-Trp-Ala-Val-βAla-His-Phe-Nle-NH₂

TABLE A-continued

-Aepa-(Doc)$_2$-Gln-Trp-Ala-Ala-βAla-His-Phe-Nle-NH$_2$
-Aepa-Gln-Trp-Ala-Val-βAla-His-Leu-Leu-NH$_2$
-Aepa-Gln-Trp-Ala-Val-βAla-His-Leu-Nle-NH$_2$
-Aepa-Gln-Trp-Ala-Val-Gly-His-Leu-Leu-NH$_2$

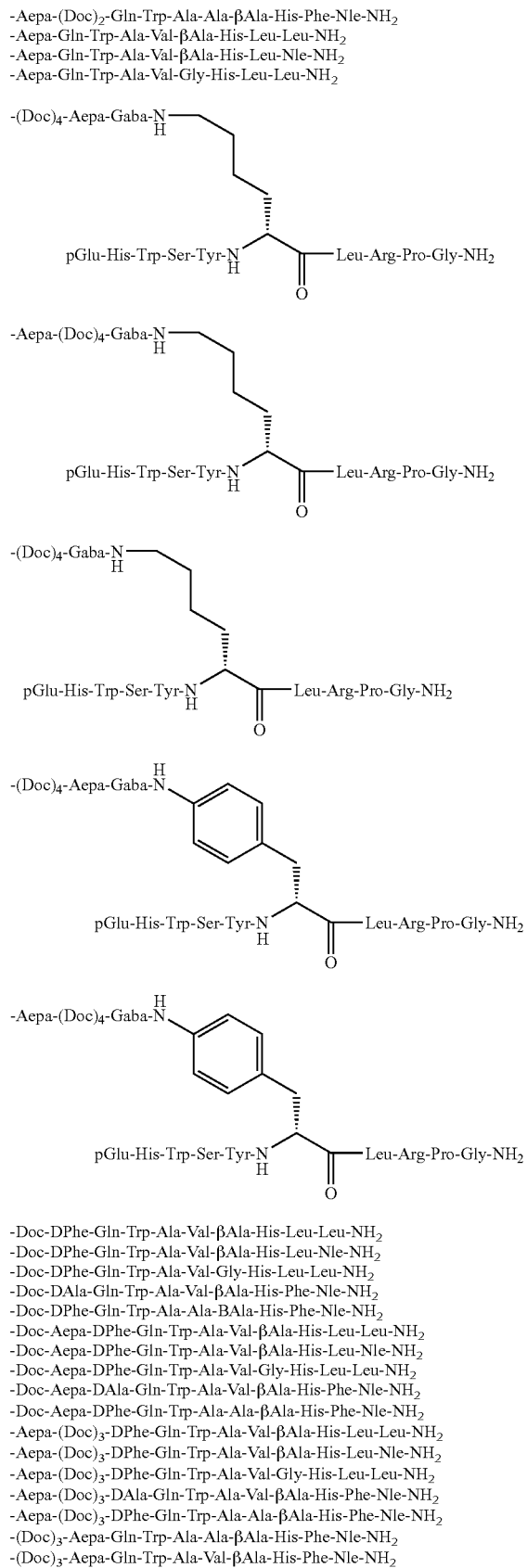

-Doc-DPhe-Gln-Trp-Ala-Val-βAla-His-Leu-Leu-NH$_2$
-Doc-DPhe-Gln-Trp-Ala-Val-βAla-His-Leu-Nle-NH$_2$
-Doc-DPhe-Gln-Trp-Ala-Val-Gly-His-Leu-Leu-NH$_2$
-Doc-DAla-Gln-Trp-Ala-Val-βAla-His-Phe-Nle-NH$_2$
-Doc-DPhe-Gln-Trp-Ala-Ala-BAla-His-Phe-Nle-NH$_2$
-Doc-Aepa-DPhe-Gln-Trp-Ala-Val-βAla-His-Leu-Leu-NH$_2$
-Doc-Aepa-DPhe-Gln-Trp-Ala-Val-βAla-His-Leu-Nle-NH$_2$
-Doc-Aepa-DPhe-Gln-Trp-Ala-Val-Gly-His-Leu-Leu-NH$_2$
-Doc-Aepa-DAla-Gln-Trp-Ala-Val-βAla-His-Phe-Nle-NH$_2$
-Doc-Aepa-DPhe-Gln-Trp-Ala-Ala-βAla-His-Phe-Nle-NH$_2$
-Aepa-(Doc)$_3$-DPhe-Gln-Trp-Ala-Val-βAla-His-Leu-Leu-NH$_2$
-Aepa-(Doc)$_3$-DPhe-Gln-Trp-Ala-Val-βAla-His-Leu-Nle-NH$_2$
-Aepa-(Doc)$_3$-DPhe-Gln-Trp-Ala-Val-Gly-His-Leu-Leu-NH$_2$
-Aepa-(Doc)$_3$-DAla-Gln-Trp-Ala-Val-βAla-His-Phe-Nle-NH$_2$
-Aepa-(Doc)$_3$-DPhe-Gln-Trp-Ala-Ala-βAla-His-Phe-Nle-NH$_2$
-(Doc)$_3$-Aepa-Gln-Trp-Ala-Ala-βAla-His-Phe-Nle-NH$_2$
-(Doc)$_3$-Aepa-Gln-Trp-Ala-Val-βAla-His-Phe-Nle-NH$_2$
-(Doc)$_3$-Aepa-Gln-Trp-Ala-Val-Gly-His-Leu-Leu-NH$_2$
-(Doc)$_3$-Aepa-Gln-Trp-Ala-Val-βAla-His-Leu-Nle-NH$_2$
-(Doc)$_3$-Aepa-Gln-Trp-Ala-Val-βAla-His-Leu-Leu-NH$_2$
-Aepa-Doc-DPhe-Gln-Trp-Ala-Ala-βAla-His-Phe-Nle-NH$_2$
-Aepa-Doc-DAla-Gln-Trp-Ala-Val-βAla-His-Phe-Nle-NH$_2$
-Aepa-Doc-DPhe-Gln-Trp-Ala-Val-Gly-His-Leu-Leu-NH$_2$
-Aepa-Doc-DPhe-Gln-Trp-Ala-Val-βAla-His-Leu-Nle-NH$_2$
-Aepa-Doc-DPhe-Gln-Trp-Ala-Val-βAla-His-Leu-Leu-NH$_2$
-Doc-DPhe-Gln-Trp-Ala-Ala-βAla-His-Phe-Nle-NH$_2$
-Doc-DAla-Gln-Trp-Ala-Val-βAla-His-Phe-Nle-NH$_2$
-Doc-DPhe-Gln-Trp-Ala-Val-Gly-His-Leu-Leu-NH$_2$
-Doc-DPhe-Gln-Trp-Ala-Val-βAla-His-Leu-Nle-NH$_2$
-Doc-DPhe-Gln-Trp-Ala-Val-βAla-His-Leu-Leu-NH$_2$
-(Doc)$_2$-Gln-Trp-Ala-Ala-βAla-His-Phe-Nle-NH$_2$
-(Doc)$_2$-Gln-Trp-Ala-Val-βAla-His-Phe-Nle-NH$_2$
-(Doc)$_2$-Gln-Trp-Ala-Val-Gly-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-βAla-His-Leu-Leu-NH$_2$
-Aepa-Gln-Trp-Ala-Ala-βAla-His-Phe-Nle-NH$_2$
-(Doc)$_4$-Gln-Trp-Ala-Val-Gly-His-Leu-Ψ(CH$_2$NH)-Leu-NH$_2$
-(Doc)$_4$-Aepa-Gln-Trp-Ala-Val-Gly-His-Leu-Ψ(CH$_2$NH)-Leu-NH$_2$
-Aepa-(Doc)$_4$-Gln-Trp-Ala-Val-Gly-His-Leu-Ψ(CH$_2$NH)-Leu-NH$_2$
-(Doc)$_4$-Gaba-Gln-Trp-Ala-Val-Gly-His-Leu-Ψ(CH$_2$NH)-Leu-NH$_2$
-(Doc)$_4$-Aepa-Gaba-Gln-Trp-Ala-Val-Gly-His-Leu-Ψ(CH$_2$NH)-Leu-NH$_2$
-Aepa-(Doc)$_4$-Gaba-Gln-Trp-Ala-Val-Gly-His-Leu-Ψ(CH$_2$NH)-Leu-NH$_2$
-(Doc)$_4$-Gaba-Gln-Trp-Ala-Val-βAla-His-Leu-Leu-NH$_2$
-(Doc)$_4$-Aepa-Gaba-Gln-Trp-Ala-Val-βAla-His-Leu-Leu-NH$_2$
-Aepa-(Doc)$_4$-Gaba-Gln-Trp-Ala-Val-βAla-His-Leu-Leu-NH$_2$
-(Doc)$_4$-Gaba-Gln-Trp-Ala-Val-βAla-His-Leu-Nle-NH$_2$
-(Doc)$_4$-Aepa-Gaba-Gln-Trp-Ala-Val-βAla-His-Leu-Nle-NH$_2$
-Aepa-(Doc)$_4$-Gaba-Gln-Trp-Ala-Val-βAla-His-Leu-Nle-NH$_2$
-(Doc)$_2$-Gln-Trp-Ala-Ala-βAla-His-Phe-Nle-NH$_2$
-(Doc)$_2$-Gln-Trp-Ala-Val-βAla-His-Phe-Nle-NH$_2$
-(Doc)$_2$-Gln-Trp-Ala-Val-Gly-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-βAla-His-Leu-Leu-NH$_2$
-Aepa-Gln-Trp-Ala-Ala-βAla-His-Phe-Nle-NH$_2$
-Aepa-Gln-Trp-Ala-Val-βAla-His-Phe-Nle-NH$_2$
-(Doc)$_4$-Aepa-DPhe-Gln-Trp-Ala-Val-Gly-His-Leu-Leu-NH$_2$
-(Doc)$_4$-Aepa-DPhe-Gln-Trp-Ala-Val-βAla-His-Leu-Nle-NH$_2$
-(Doc)$_4$-Aepa-DPhe-Gln-Trp-Ala-Val-βAla-His-Leu-Leu-NH$_2$
-Aepa-(Doc)$_4$-DPhe-Gln-Trp-Ala-Ala-βAla-His-Phe-Nle-NH$_2$
-Aepa-(Doc)$_4$-DAla-Gln-Trp-Ala-Val-βAla-His-Phe-Nle-NH$_2$
-Aepa-(Doc)$_4$-DPhe-Gln-Trp-Ala-Val-Gly-His-Leu-Leu-NH$_2$
-Aepa-(Doc)$_4$-DPhe-Gln-Trp-Ala-Val-βAla-His-Leu-Nle-NH$_2$
-Aepa-(Doc)$_4$-DPhe-Gln-Trp-Ala-Val-βAla-His-Leu-Leu-NH$_2$
-(Doc)$_4$-DPhe-Gln-Trp-Ala-Ala-βAla-His-Phe-Nle-NH$_2$
-(Doc)$_4$-DAla-Gln-Trp-Ala-Val-βAla-His-Phe-Nle-NH$_2$
-(Doc)$_4$-DPhe-Gln-Trp-Ala-Val-Gly-His-Leu-Leu-NH$_2$
-(Doc)$_4$-DPhe-Gln-Trp-Ala-Val-βAla-His-Leu-Nle-NH$_2$
-(Doc)$_4$-DPhe-Gln-Trp-Ala-Val-βAla-His-Leu-Leu-NH$_2$
-(Doc)$_4$-Aepa-DPhe-Gln-Trp-Ala-Ala-βAla-His-Phe-Nle-NH$_2$
-(Doc)$_4$-Aepa-DAla-Gln-Trp-Ala-Val-βAla-His-Phe-Nle-NH$_2$
-(Doc)$_4$-Aepa-Gln-Trp-Ala-Val-Gly-His-Leu-Leu-NH$_2$
-(Doc)$_4$-Aepa-Gln-Trp-Ala-Val-βAla-His-Leu-Nle-NH$_2$
-(Doc)$_4$-Aepa-Gln-Trp-Ala-Val-βAla-His-Leu-Leu-NH$_2$
-Aepa-(Doc)$_4$-Gln-Trp-Ala-Ala-βAla-His-Phe-Nle-NH$_2$
-Aepa-(Doc)$_4$-Gln-Trp-Ala-Val-βAla-His-Phe-Nle-NH$_2$
-Aepa-(Doc)$_4$-Gln-Trp-Ala-Val-Gly-His-Leu-Leu-NH$_2$
-Aepa-(Doc)$_4$-Gln-Trp-Ala-Val-βAla-His-Leu-Nle-NH$_2$
-Aepa-(Doc)$_4$-Gln-Trp-Ala-Val-βAla-His-Leu-Leu-NH$_2$
-(Doc)$_4$-Gln-Trp-Ala-Ala-βAla-His-Phe-Nle-NH$_2$
-(Doc)$_4$-Gln-Trp-Ala-Val-βAla-His-Phe-Nle-NH$_2$
-(Doc)$_4$-Gln-Trp-Ala-Val-Gly-His-Leu-Leu-NH$_2$
-(Doc)$_4$-Gln-Trp-Ala-Val-βAla-His-Leu-Nle-NH$_2$
-(Doc)$_4$-Gln-Trp-Ala-Val-βAla-His-Leu-Leu-NH$_2$
-(Doc)$_4$-Aepa-Gln-Trp-Ala-Ala-βAla-His-Phe-Nle-NH$_2$
-(Doc)$_4$-Aepa-Gln-Trp-Ala-Val-βAla-His-Phe-Nle-NH$_2$
-Aepa-DPhe-Gln-Trp-Ala-Val-Gly-His-Leu-Leu-NH$_2$
-Aepa-DPhe-Gln-Trp-Ala-Val-βAla-His-Leu-Nle-NH$_2$
-Aepa-DPhe-Gln-Trp-Ala-Val-βAla-His-Leu-Leu-NH$_2$
-Aepa-(Doc)$_2$-DPhe-Gln-Trp-Ala-Ala-βAla-His-Phe-Nle-NH$_2$
-Aepa-(Doc)$_2$-DAla-Gln-Trp-Ala-Val-βAla-His-Phe-Nle-NH$_2$
-Aepa-(Doc)$_2$-DPhe-Gln-Trp-Ala-Val-Gly-His-Leu-Leu-NH$_2$
-Aepa-(Doc)$_2$-DPhe-Gln-Trp-Ala-Val-βAla-His-Leu-Nle-NH$_2$
-Aepa-(Doc)$_2$-DPhe-Gln-Trp-Ala-Val-βAla-His-Leu-Leu-NH$_2$
-(Doc)$_2$-DPhe-Gln-Trp-Ala-Ala-βAla-His-Phe-Nle-NH$_2$
-(Doc)$_2$-DAla-Gln-Trp-Ala-Val-βAla-His-Phe-Nle-NH$_2$
-(Doc)$_2$-DPhe-Gln-Trp-Ala-Val-Gly-His-Leu-Leu-NH$_2$ TABLE A-continued -(Doc)₂-DPhe-Gln-Trp-Ala-Val-βAla-His-Leu-Nle-NH₂
-(Doc)₂-DPhe-Gln-Trp-Ala-Val-βAla-His-Leu-Leu-NH₂
-Aepa-DPhe-Gln-Trp-Ala-Ala-βAla-His-Phe-Nle-NH₂
-Aepa-DAla-Gln-Trp-Ala-Val-βAla-His-Phe-Nle-NH₂
-Aepa-(Doc)₄-Gln-Trp-Ala-Val-βAla-His-Ala-Nle-NH₂
-Aepa-(Doc)₄-Gln-Trp-Ala-Val-βAla-His-Ala-Nle-NH₂
-Aepa-DPhe-Gln-Trp-Ala-Val-βAla-His-Ala-Nle-NH₂
-Aepa-(Doc)₂-DPhe-Gln-Trp-Ala-Val-βAla-His-Ala-Nle-NH₂
-(Doc)₂-Gln-Trp-Ala-Val-βAla-His-Ala-Nle-NH₂
-Aepa-Gln-Trp-Ala-Val-βAla-His-Ala-Nle-NH₂
-Aepa-(Doc)₂-Gln-Trp-Ala-Val-βAla-His-Ala-Nle-NH₂
-(Doc)₂-Aepa-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-Aepa-(Doc)₂-Gln-Trp-Ala-Val-βAla-His-Ala-Nle-NH₂
-Aepa-Gln-Trp-Ala-Val-βAla-His-Ala-Nle-NH₂
-(Doc)₂-Gln-Trp-Ala-Val-βAla-His-Ala-Nle-NH₂
-Aepa-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-(Doc)₂-DPhe-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-(Doc)₄-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₂-Aepa-DPhe-Gln-Trp-Ala-Val-βAla-His-Ala-Nle-NH₂
-Aepa-(Doc)₃-Gln-Trp-Ala-Val-βAla-His-Leu-Leu-NH₂
-Aepa-(Doc)₃-Gln-Trp-Ala-Val-βAla-His-Leu-Nle-NH₂
-Aepa-(Doc)₃-Gln-Trp-Ala-Val-Gly-His-Leu-Leu-NH₂
-Aepa-(Doc)₃-Gln-Trp-Ala-Val-βAla-His-Phe-Nle-NH₂
-Aepa-(Doc)₃-Gln-Trp-Ala-Ala-βAla-His-Phe-Nle-NH₂
-Aepa-Doc-Gln-Trp-Ala-Val-βAla-His-Leu-Leu-NH₂
-Aepa-Doc-Gln-Trp-Ala-Val-βAla-His-Leu-Nle-NH₂
-Aepa-Doc-Gln-Trp-Ala-Val-Gly-His-Leu-Leu-NH₂
-Aepa-Doc-Gln-Trp-Ala-Val-βAla-His-Phe-Nle-NH₂
-Aepa-Doc-Gln-Trp-Ala-Ala-βAla-His-Phe-Nle-NH₂
-(Doc)₃-Gln-Trp-Ala-Val-βAla-His-Leu-Leu-NH₂
-(Doc)₃-Gln-Trp-Ala-Val-βAla-His-Leu-Nle-NH₂
-(Doc)₃-Gln-Trp-Ala-Val-Gly-His-Leu-Leu-NH₂
-(Doc)₃-Gln-Trp-Ala-Val-βAla-His-Phe-Nle-NH₂
-(Doc)₃-Gln-Trp-Ala-Ala-βAla-His-Phe-Nle-NH₂
-(Doc)₃-DPhe-Gln-Trp-Ala-Ala-βAla-His-Phe-Nle-NH₂
-(Doc)₃-DAla-Gln-Trp-Ala-Val-βAla-His-Phe-Nle-NH₂
-(Doc)₃-DPhe-Gln-Trp-Ala-Val-Gly-His-Leu-Leu-NH₂
-(Doc)₃-DPhe-Gln-Trp-Ala-Val-βAla-His-Leu-Nle-NH₂
-(Doc)₃-DPhe-Gln-Trp-Ala-Val-βAla-His-Leu-Leu-NH₂
-(Doc)₃-Aepa-DPhe-Gln-Trp-Ala-Ala-βAla-His-Phe-Nle-NH₂
-(Doc)₃-Aepa-DAla-Gln-Trp-Ala-Val-βAla-His-Phe-Nle-NH₂
-(Doc)₃-Aepa-DPhe-Gln-Trp-Ala-Val-Gly-His-Leu-Leu-NH₂
-(Doc)₃-Aepa-DPhe-Gln-Trp-Ala-Val-βAla-His-Leu-Nle-NH₂
-(Doc)₃-Aepa-DPhe-Gln-Trp-Ala-Val-βAla-His-Leu-Leu-NH₂
-Doc-Gln-Trp-Ala-Val-βAla-His-Leu-Leu-NH₂
-Doc-Aepa-Gln-Trp-Ala-Ala-βAla-His-Phe-Nle-NH₂
-Doc-Aepa-Gln-Trp-Ala-Val-βAla-His-Phe-Nle-NH₂
-Doc-Aepa-Gln-Trp-Ala-Val-Gly-His-Leu-Leu-NH₂
-Doc-Aepa-Gln-Trp-Ala-Val-βAla-His-Leu-Nle-NH₂
-Doc-Aepa-Gln-Trp-Ala-Val-βAla-His-Leu-Leu-NH₂
-Doc-Gln-Trp-Ala-Ala-βAla-His-Phe-Nle-NH₂
-Doc-Gln-Trp-Ala-Val-βAla-His-Phe-Nle-NH₂
-Doc-Gln-Trp-Ala-Val-Gly-His-Leu-Leu-NH₂
-Doc-Gln-Trp-Ala-Val-βAla-His-Leu-Nle-NH₂
-Doc-Gln-Trp-Ala-Val-βAla-His-Leu-Leu-NH₂
-(Doc)₄-Aepa-DPhe-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂

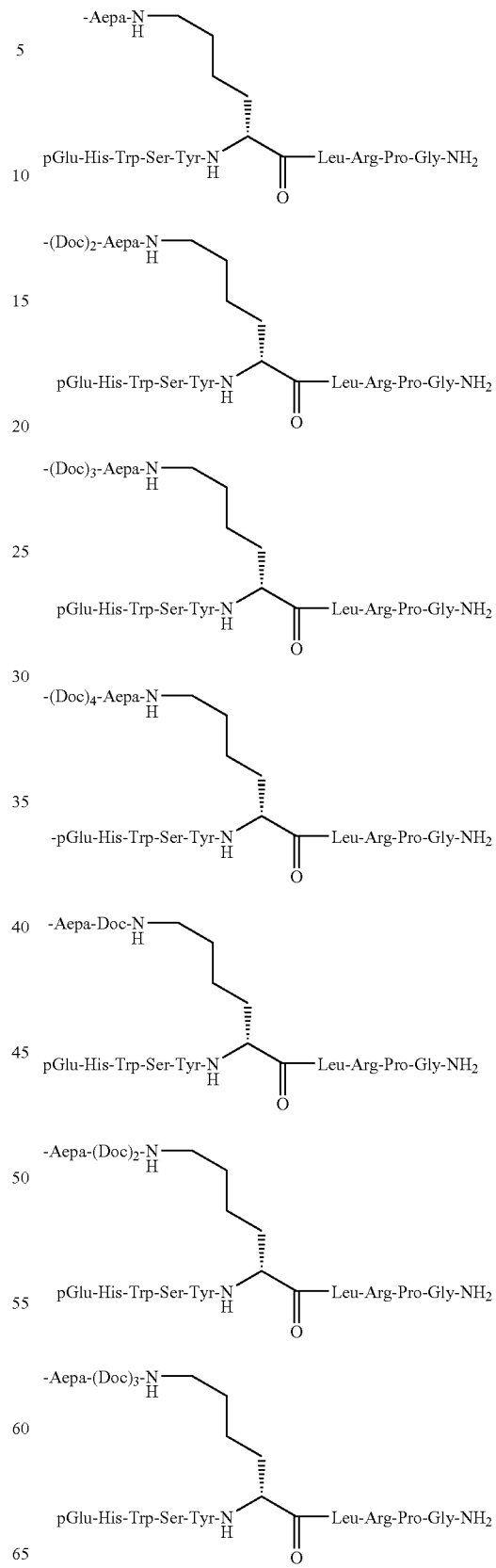

TABLE A-continued
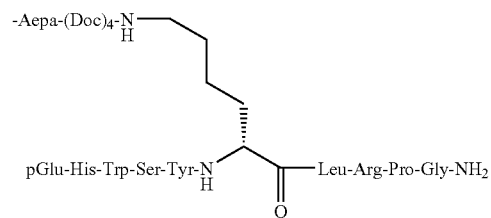
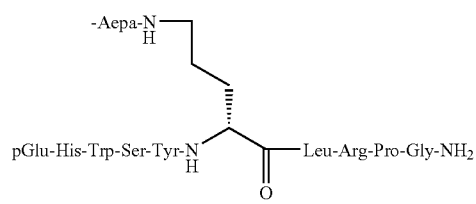
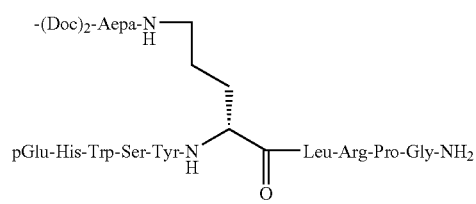
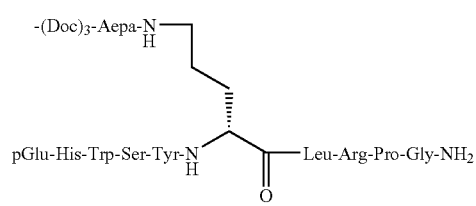
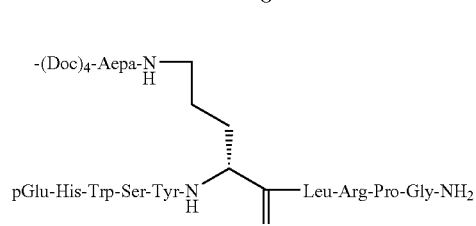
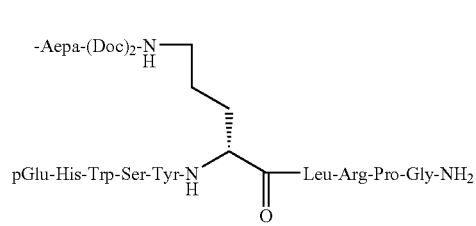
TABLE A-continued
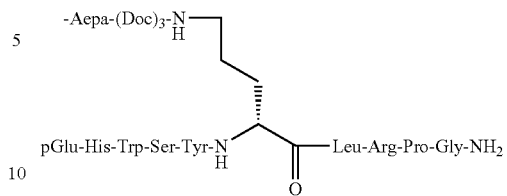
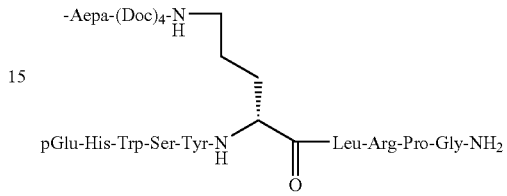
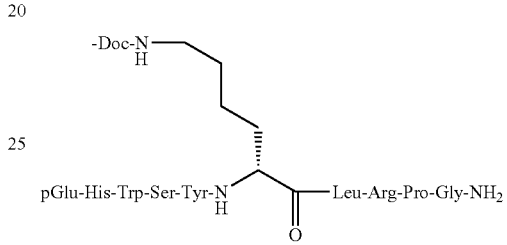
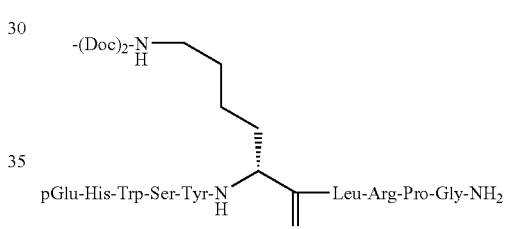
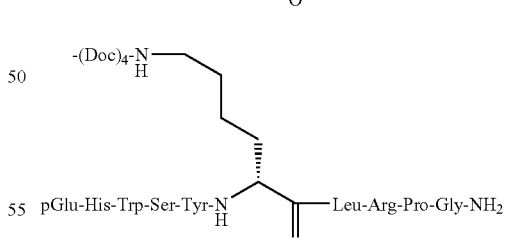

TABLE A-continued

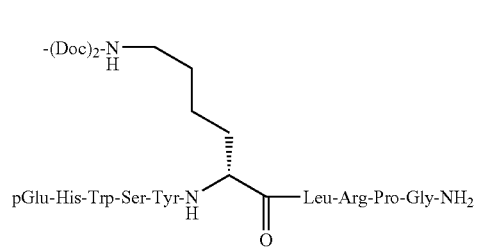

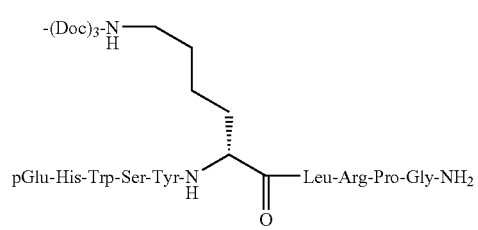

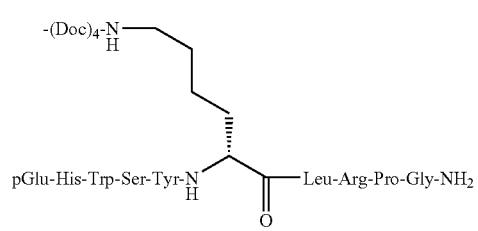

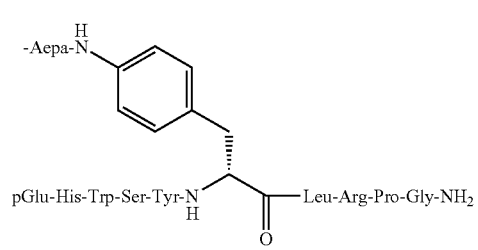

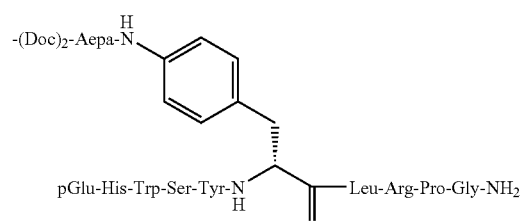

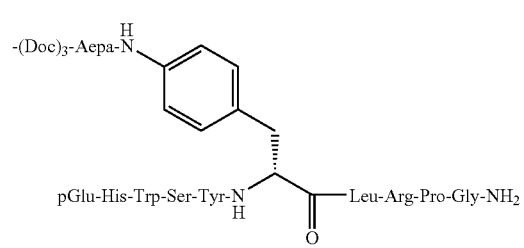

TABLE A-continued

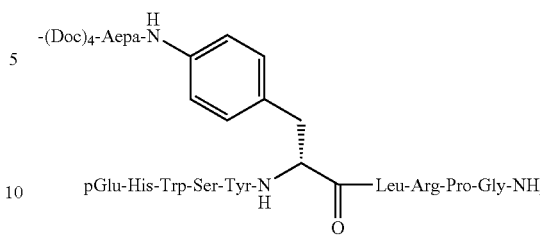

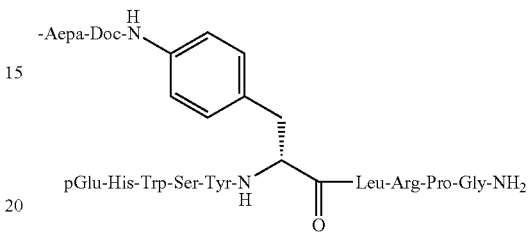

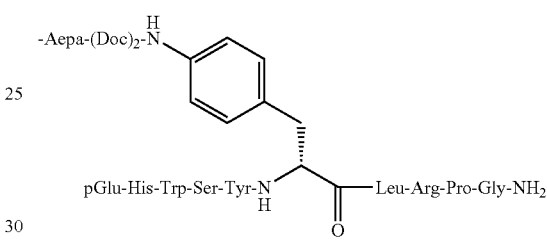

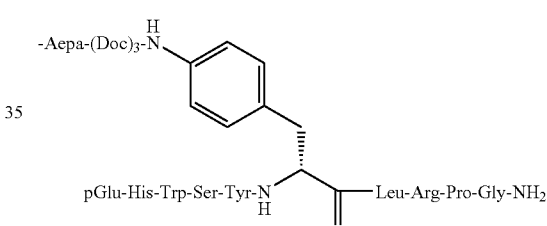

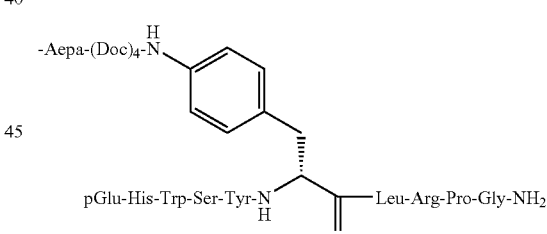

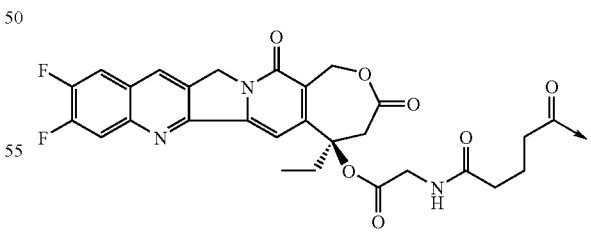

-(Doc)$_2$-Gln-Trp-Ala-Ala-βAla-His-Phe-Nle-NH$_2$
-(Doc)$_2$-Gln-Trp-Ala-Val-βAla-His-Phe-Nle-NH$_2$
-(Doc)$_2$-Gln-Trp-Ala-Val-Gly-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-βAla-His-Leu-Leu-NH$_2$
-Aepa-Gln-Trp-Ala-Ala-βAla-His-Phe-Nle-NH$_2$
-Aepa-Gln-Trp-Ala-Val-βAla-His-Phe-Nle-NH$_2$
-Aepa-Gln-Trp-Ala-Val-Gly-His-Leu-Leu-NH$_2$
-Aepa-Gln-Trp-Ala-Val-βAla-His-Leu-Nle-NH$_2$ TABLE A-continued -Aepa-Gln-Trp-Ala-Val-βAla-His-Leu-Leu-NH₂
-Aepa-(Doc)₂-Gln-Trp-Ala-Ala-βAla-His-Phe-Nle-NH₂
-Aepa-(Doc)₂-Gln-Trp-Ala-Val-βAla-His-Phe-Nle-NH₂
-Aepa-(Doc)₂-Gln-Trp-Ala-Val-Gly-His-Leu-Leu-NH₂
-Aepa-(Doc)₂-Gln-Trp-Ala-Val-βAla-His-Leu-Nle-NH₂
-Aepa-(Doc)₂-Gln-Trp-Ala-Val-βAla-His-Leu-Leu-NH₂
-(Doc)₄-DPhe-Gln-Trp-Ala-Ala-βAla-His-Phe-Nle-NH₂
-(Doc)₄-DAla-Gln-Trp-Ala-Val-βAla-His-Phe-Nle-NH₂
-(Doc)₄-DPhe-Gln-Trp-Ala-Val-Gly-His-Leu-Leu-NH₂
-(Doc)₄-DPhe-Gln-Trp-Ala-Val-βAla-His-Leu-Nle-NH₂
-(Doc)₄-DPhe-Gln-Trp-Ala-Val-βAla-His-Leu-Leu-NH₂
-(Doc)₄-Aepa-DPhe-Gln-Trp-Ala-Ala-βAla-His-Phe-Nle-NH₂
-(Doc)₄-Aepa-DAla-Gln-Trp-Ala-Val-βAla-His-Phe-Nle-NH₂
-(Doc)₄-Aepa-DPhe-Gln-Trp-Ala-Val-Gly-His-Leu-Leu-NH₂
-(Doc)₄-Aepa-DPhe-Gln-Trp-Ala-Val-βAla-His-Leu-Nle-NH₂
-(Doc)₄-Aepa-DPhe-Gln-Trp-Ala-Val-βAla-His-Leu-Leu-NH₂
-Aepa-(Doc)₄-DPhe-Gln-Trp-Ala-Ala-βAla-His-Phe-Nle-NH₂
-Aepa-(Doc)₄-DAla-Gln-Trp-Ala-Val-βAla-His-Phe-Nle-NH₂
-Aepa-(Doc)₄-DPhe-Gln-Trp-Ala-Val-Gly-His-Leu-Leu-NH₂
-Aepa-(Doc)₄-DPhe-Gln-Trp-Ala-Val-βAla-His-Leu-Nle-NH₂
-Aepa-(Doc)₄-DPhe-Gln-Trp-Ala-Val-βAla-His-Leu-Leu-NH₂
-(Doc)₄-Gln-Trp-Ala-Ala-βAla-His-Phe-Nle-NH₂
-(Doc)₄-Gln-Trp-Ala-Val-βAla-His-Phe-Nle-NH₂
-(Doc)₄-Gln-Trp-Ala-Val-Gly-His-Leu-Leu-NH₂
-(Doc)₄-Gln-Trp-Ala-Val-βAla-His-Leu-Nle-NH₂
-(Doc)₄-Gln-Trp-Ala-Val-βAla-His-Leu-Leu-NH₂
-(Doc)₄-Aepa-Gln-Trp-Ala-Ala-βAla-His-Phe-Nle-NH₂
-(Doc)₄-Aepa-Gln-Trp-Ala-Val-βAla-His-Phe-Nle-NH₂
-(Doc)₄-Aepa-Gln-Trp-Ala-Val-Gly-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-βAla-His-Leu-Leu-NH₂
-Aepa-(Doc)₄-Gln-Trp-Ala-Ala-βAla-His-Phe-Nle-NH₂
-Aepa-(Doc)₄-Gln-Trp-Ala-Val-βAla-His-Phe-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-βAla-His-Leu-Leu-NH₂
-(Doc)₂-DPhe-Gln-Trp-Ala-Ala-βAla-His-Phe-Nle-NH₂
-(Doc)₂-DAla-Gln-Trp-Ala-Val-βAla-His-Phe-Nle-NH₂
-(Doc)₂-DPhe-Gln-Trp-Ala-Val-Gly-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-βAla-His-Leu-Leu-NH₂
-Aepa-DPhe-Gln-Trp-Ala-Ala-βAla-His-Phe-Nle-NH₂
-Aepa-DAla-Gln-Trp-Ala-Val-βAla-His-Phe-Nle-NH₂
-Aepa-DPhe-Gln-Trp-Ala-Val-Gly-His-Leu-Leu-NH₂
-Aepa-DPhe-Gln-Trp-Ala-Val-βAla-His-Leu-Nle-NH₂
-Aepa-DPhe-Gln-Trp-Ala-Val-βAla-His-Leu-Leu-NH₂
-Aepa-(Doc)₂-DPhe-Gln-Trp-Ala-Ala-βAla-His-Phe-Nle-NH₂
-Aepa-(Doc)₂-DAla-Gln-Trp-Ala-Val-βAla-His-Phe-Nle-NH₂
-Aepa-(Doc)₂-DPhe-Gln-Trp-Ala-Val-Gly-His-Leu-Leu-NH₂
-Aepa-(Doc)₂-DPhe-Gln-Trp-Ala-Val-βAla-His-Leu-Nle-NH₂
-Aepa-(Doc)₂-DPhe-Gln-Trp-Ala-Val-βAla-His-Leu-Leu-NH₂
-(Doc)₂-Aepa-DPhe-Gln-Trp-Ala-Ala-βAla-His-Phe-Nle-NH₂
-(Doc)₂-Aepa-DAla-Gln-Trp-Ala-Val-βAla-His-Phe-Nle-NH₂
-(Doc)₂-Aepa-DPhe-Gln-Trp-Ala-Val-Gly-His-Leu-Leu-NH₂
-(Doc)₂-Aepa-DPhe-Gln-Trp-Ala-Val-βAla-His-Leu-Nle-NH₂
-(Doc)₂-Aepa-DPhe-Gln-Trp-Ala-Val-βAla-His-Leu-Leu-NH₂
-(Doc)₂-Aepa-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-Aepa-(Doc)₂-DPhe-Gln-Trp-Ala-Val-βAla-His-Ala-Nle-NH₂
-(Doc)₂-Gln-Trp-Ala-Val-βAla-His-Ala-Nle-NH₂
-Aepa-Gln-Trp-Ala-Val-βAla-His-Ala-Nle-NH₂
-Aepa-(Doc)₂-Gln-Trp-Ala-Val-βAla-His-Ala-Nle-NH₂
-Aepa-Lys-DTyr-DTyr-cyclo(Cys-Tyr-DTrp-Lys-Abu-Cys)-Thr-NH₂

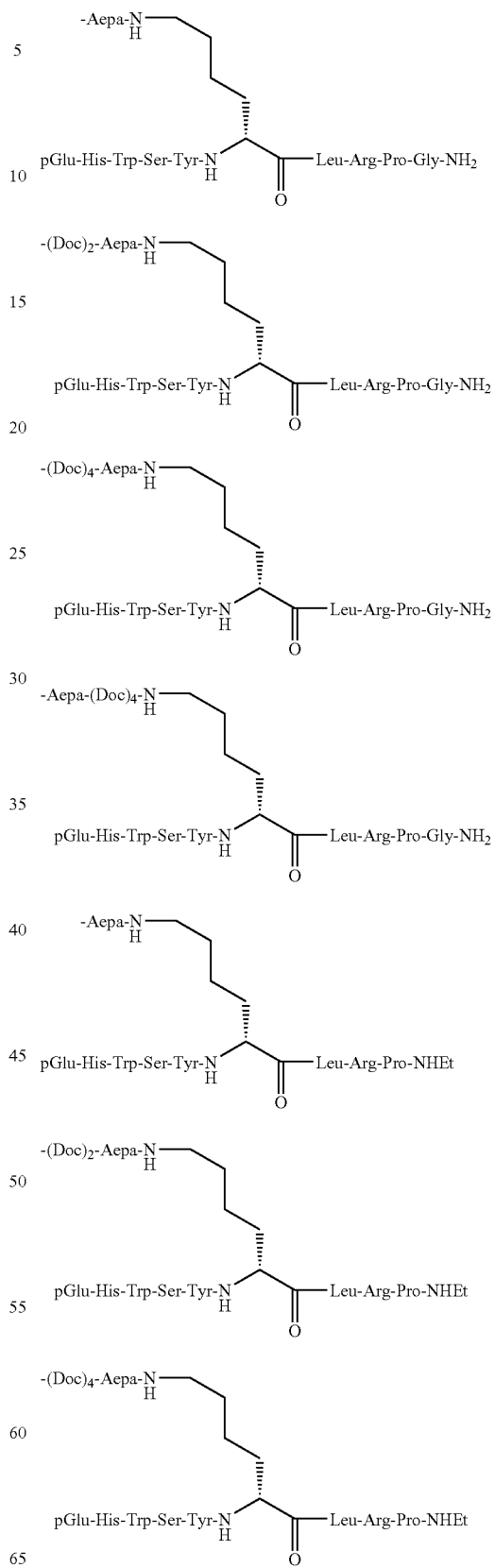

TABLE A-continued
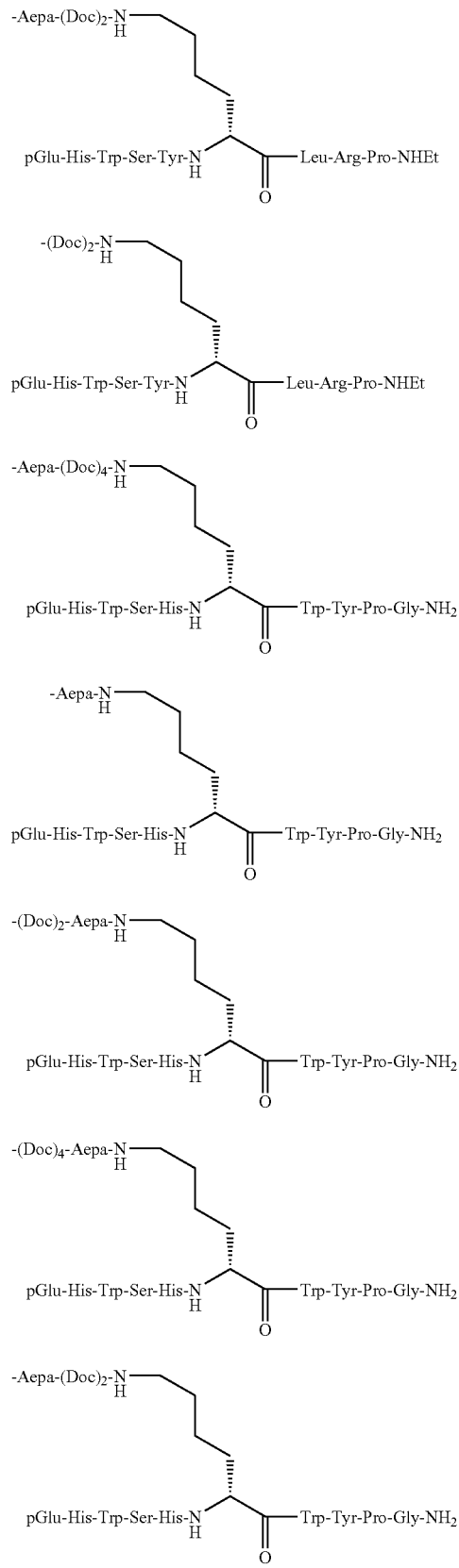
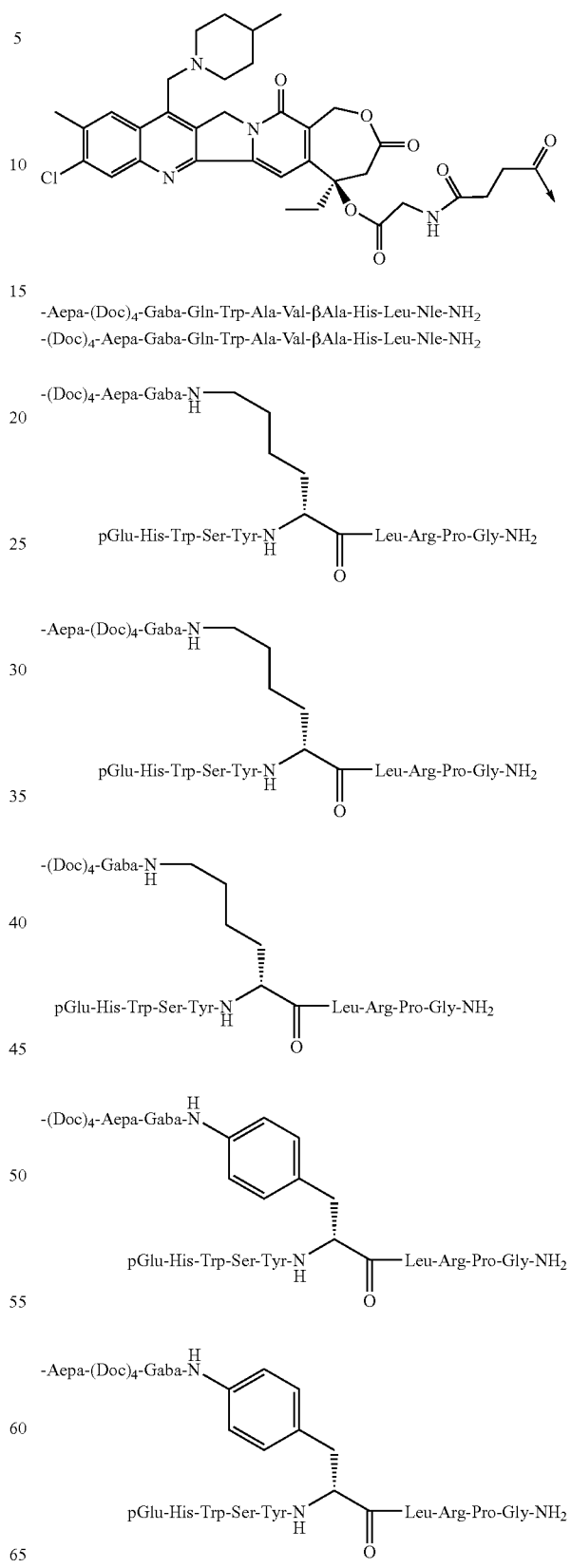
-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂

TABLE A-continued
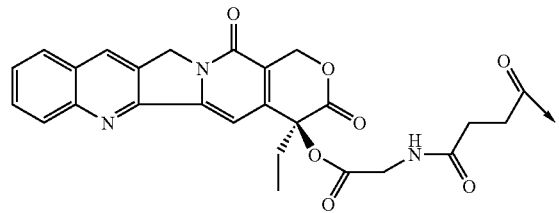 [SMILES: CC[C@@]1(OC(=O)CNC(=O)CCC=O)C(=O)OCc2c1cc1n(c2=O)Cc2cc3ccccc3nc2-1]
-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
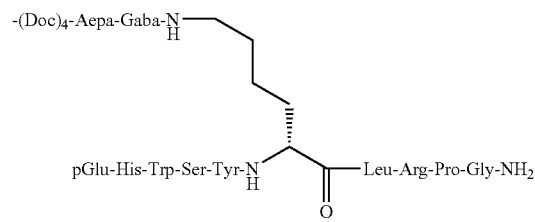
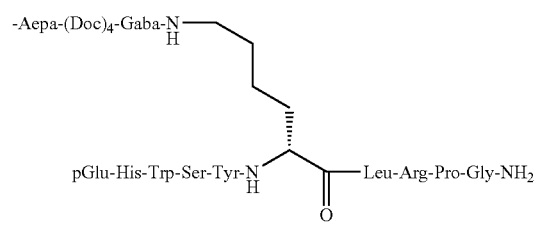
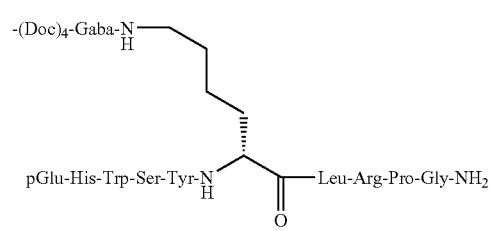
TABLE A-continued
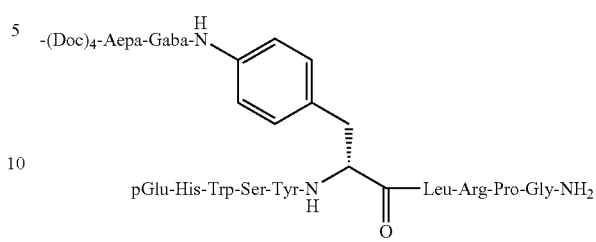
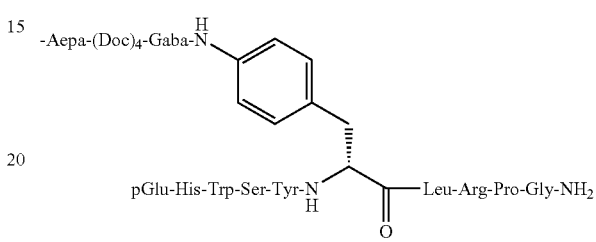
-DPhe-cyclo(Cys-Tyr-DTrp-Lys-Abu-Cys)-Thr-NH₂
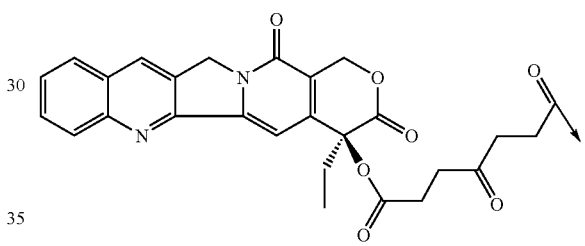
-(Doc)₄-Lys-DTyr-DTyr-cyclo(Cys-Tyr-DTrp-Lys-Abu-Cys)-Thr-NH₂
TABLE B
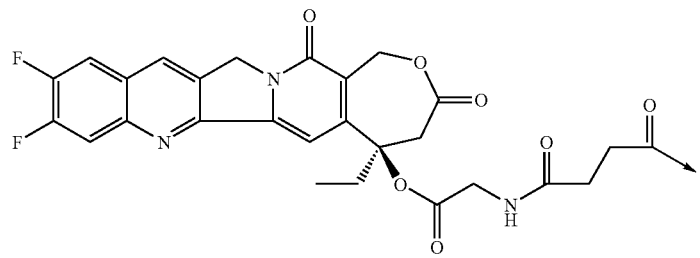 [SMILES: CC[C@@]1(OC(=O)CNC(=O)CCC=O)CC(=O)OCc2c1cc1n(c2=O)Cc2cc3cc(F)c(F)cc3nc2-1]
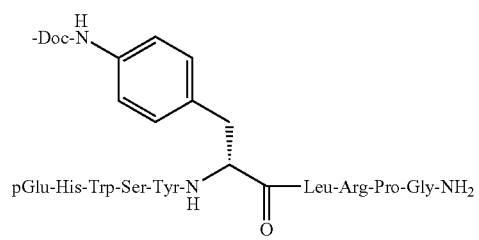

TABLE B-continued

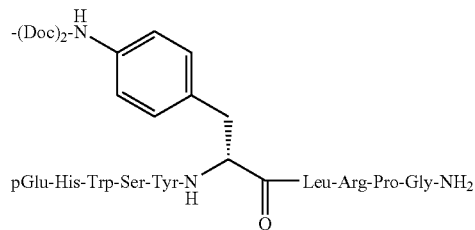

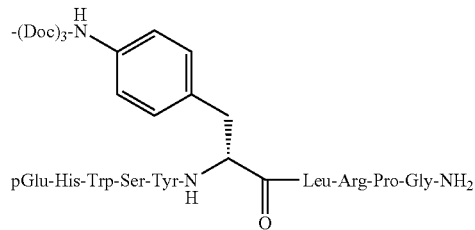

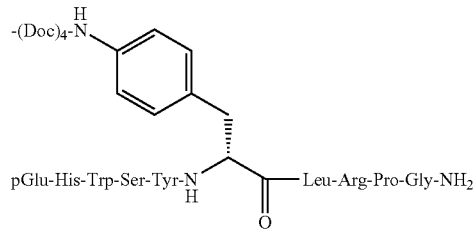

-(Doc)₄-Aepa-Lys-DTyr-DTyr-cyclo(Cys-Tyr-DTrp-Lys-Abu-Cys)-Thr-NH₂
-(Doc)₄-Aepa-DPhe-cyclo(Cys-Tyr-DTrp-Lys-Abu-Cys)-Thr-NH₂
-DPhe-cyclo(Cys-Tyr-DTrp-Lys-Abu-Cys)-Thr-NH₂
-Aepa-DPhe-cyclo(Cys-Tyr-DTrp-Lys-Abu-Cys)-Thr-NH₂
-(Doc)₆-DPhe-cyclo(Cys-3lTyr-DTrp-Lys-Val-Cys)-Thr-NH₂
-(Doc)₅-DPhe-cyclo(Cys-3lTyr-DTrp-Lys-Val-Cys)-Thr-NH₂
-(Doc)₄-DPhe-cyclo(Cys-3lTyr-DTrp-Lys-Val-Cys)-Thr-NH₂
-(Doc)₃-DPhe-cyclo(Cys-3lTyr-DTrp-Lys-Val-Cys)-Thr-NH₂
-(Doc)₂-DPhe-cyclo(Cys-3lTyr-DTrp-Lys-Val-Cys)-Thr-NH₂
-Doc-DPhe-cyclo(Cys-3lTyr-DTrp-Lys-Val-Cys)-Thr-NH₂
-(Aepa)₂-DPhe-cyclo(Cys-3lTyr-DTrp-Lys-Val-Cys)-Thr-NH₂
-(Doc)₆-Aepa-DPhe-cyclo(Cys-3lTyr-DTrp-Lys-Val-Cys)-Thr-NH₂
-(Doc)₅-Aepa-DPhe-cyclo(Cys-3lTyr-DTrp-Lys-Val-Cys)-Thr-NH₂
-(Doc)₃-Aepa-DPhe-cyclo(Cys-3lTyr-DTrp-Lys-Val-Cys)-Thr-NH₂
-(Doc)₂-Aepa-DPhe-cyclo(Cys-3lTyr-DTrp-Lys-Val-Cys)-Thr-NH₂
-Doc-Aepa-DPhe-cyclo(Cys-3lTyr-DTrp-Lys-Val-Cys)-Thr-NH₂
-Aepa-(Doc)₄-DPhe-cyclo(Cys-3lTyr-DTrp-Lys-Val-Cys)-Thr-NH₂
-Aepa-(Doc)₃-DPhe-cyclo(Cys-3lTyr-DTrp-Lys-Val-Cys)-Thr-NH₂
-Aepa-(Doc)₂-DPhe-cyclo(Cys-3lTyr-DTrp-Lys-Val-Cys)-Thr-NH₂
-Aepa-Doc-DPhe-cyclo(Cys-3lTyr-DTrp-Lys-Val-Cys)-Thr-NH₂
-(Doc)₆-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂
-(Doc)₅-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-(Doc)₃-DPhe-cyclo(Cys-3lTyr-DTrp-Lys-Thr-Cys)-Thr-NH₂
-(Doc)₂-DPhe-cyclo(Cys-3lTyr-DTrp-Lys-Thr-Cys)-Thr-NH₂
-Doc-DPhe-cyclo(Cys-3lTyr-DTrp-Lys-Thr-Cys)-Thr-NH₂
-(Aepa)₂-DPhe-cyclo(Cys-3lTyr-DTrp-Lys-Thr-Cys)-Thr-NH₂
-(Doc)₆-Aepa-DPhe-cyclo(Cys-3lTyr-DTrp-Lys-Thr-Cys)-Thr-NH₂
-(Doc)₅-Aepa-DPhe-cyclo(Cys-3lTyr-DTrp-Lys-Thr-Cys)-Thr-NH₂
-(Doc)₄-Aepa-DPhe-cyclo(Cys-3lTyr-DTrp-Lys-Thr-Cys)-Thr-NH₂
-(Doc)₃-Aepa-DPhe-cyclo(Cys-3lTyr-DTrp-Lys-Thr-Cys)-Thr-NH₂
-(Doc)₂-Aepa-DPhe-cyclo(Cys-3lTyr-DTrp-Lys-Thr-Cys)-Thr-NH₂
-Doc-Aepa-DPhe-cyclo(Cys-3lTyr-DTrp-Lys-Thr-Cys)-Thr-NH₂
-Aepa-(Doc)₄-DPhe-cyclo(Cys-3lTyr-DTrp-Lys-Thr-Cys)-Thr-NH₂
-Aepa-(Doc)₃-DPhe-cyclo(Cys-3lTyr-DTrp-Lys-Thr-Cys)-Thr-NH₂
-Aepa-(Doc)₂-DPhe-cyclo(Cys-3lTyr-DTrp-Lys-Thr-Cys)-Thr-NH₂
-Aepa-Doc-DPhe-cyclo(Cys-3lTyr-DTrp-Lys-Thr-Cys)-Thr-NH₂
-Aepa-DPhe-cyclo(Cys-3lTyr-DTrp-Lys-Thr-Cys)-Thr-NH₂
-DPhe-cyclo(Cys-3lTyr-DTrp-Lys-Thr-Cys)-Thr-NH₂
-(Doc)₄-Aepa-DPhe-cyclo(Cys-3lTyr-DTrp-Lys-Thr-Cys)-Thr-NH₂
-(Doc)₆-DPhe-cyclo(Cys-3lTyr-DTrp-Lys-Abu-Cys)-Thr-NH₂
-(Doc)₅-DPhe-cyclo(Cys-3lTyr-DTrp-Lys-Abu-Cys)-Thr-NH₂

TABLE B-continued

-(Doc)$_4$-DPhe-cyclo(Cys-3lTyr-DTrp-Lys-Abu-Cys)-Thr-NH$_2$
-(Doc)$_3$-DPhe-cyclo(Cys-3lTyr-DTrp-Lys-Abu-Cys)-Thr-NH$_2$
-(Doc)$_2$-DPhe-cyclo(Cys-3lTyr-DTrp-Lys-Abu-Cys)-Thr-NH$_2$
-Doc-DPhe-cyclo(Cys-3lTyr-DTrp-Lys-Abu-Cys)-Thr-NH$_2$
-(Aepa)$_2$-DPhe-cyclo(Cys-3lTyr-DTrp-Lys-Abu-Cys)-Thr-NH$_2$
-(Doc)$_6$-Aepa-DPhe-cyclo(Cys-3lTyr-DTrp-Lys-Abu-Cys)-Thr-NH$_2$
-(Doc)$_5$-Aepa-DPhe-cyclo(Cys-3lTyr-DTrp-Lys-Abu-Cys)-Thr-NH$_2$
-(Doc)$_4$-Aepa-DPhe-cyclo(Cys-3lTyr-DTrp-Lys-Abu-Cys)-Thr-NH$_2$
-(Doc)$_3$-Aepa-DPhe-cyclo(Cys-3lTyr-DTrp-Lys-Abu-Cys)-Thr-NH$_2$
-(Doc)$_2$-Aepa-DPhe-cyclo(Cys-3lTyr-DTrp-Lys-Abu-Cys)-Thr-NH$_2$
-Doc-Aepa-DPhe-cyclo(Cys-3lTyr-DTrp-Lys-Abu-Cys)-Thr-NH$_2$
-Aepa-(Doc)$_4$-DPhe-cyclo(Cys-3lTyr-DTrp-Lys-Abu-Cys)-Thr-NH$_2$
-Aepa-(Doc)$_3$-D Phe-cyclo(Cys-3lTyr-DTrp-Lys-Abu-Cys)-Thr-NH$_2$
-Aepa-(Doc)$_2$-DPhe-cyclo(Cys-3lTyr-DTrp-Lys-Abu-Cys)-Thr-NH$_2$
-Aepa-Doc-DPhe-cyclo(Cys-3lTyr-DTrp-Lys-Abu-Cys)-Thr-NH$_2$
-Aepa-DPhe-cyclo(Cys-3lTyr-DTrp-Lys-Val-Cys)-Thr-NH$_2$
-DPhe-cyclo(Cys-3lTyr-DTrp-Lys-Val-Cys)-Thr-NH$_2$
-(Doc)$_4$-Aepa-DPhe-cyclo(Cys-3lTyr-DTrp-Lys-Val-Cys)-Thr-NH$_2$
-(Doc)$_6$-DPhe-cyclo(Cys-Tyr-DTrp-Lys-Abu-Cys)-Thr-NH$_2$
-(Doc)$_5$-DPhe-cyclo(Cys-Tyr-DTrp-Lys-Abu-Cys)-Thr-NH$_2$
-(Doc)$_4$-DPhe-cyclo(Cys-Tyr-DTrp-Lys-Abu-Cys)-Thr-NH$_2$
-(Doc)$_3$-DPhe-cyclo(Cys-Tyr-DTrp-Lys-Abu-Cys)-Thr-NH$_2$
-(Doc)$_2$-DPhe-cyclo(Cys-Tyr-DTrp-Lys-Abu-Cys)-Thr-NH$_2$
-Doc-DPhe-cyclo(Cys-Tyr-DTrp-Lys-Abu-Cys)-Thr-NH$_2$
-(Aepa)$_2$-DPhe-cyclo(Cys-Tyr-DTrp-Lys-Abu-Cys)-Thr-NH$_2$
-(Doc)$_6$-Aepa-DPhe-cyclo(Cys-Tyr-DTrp-Lys-Abu-Cys)-Thr-NH$_2$
-(DoG) 5-Aepa-DPhe-cyclo(Cys-Tyr-DTrp-Lys-Abu-Cys)-Thr-NH$_2$
-(Doc)$_3$-Aepa-DPhe-cyclo(Cys-Tyr-DTrp-Lys-Abu-Cys)-Thr-NH$_2$
-(Doc)$_2$-Aepa-DPhe-cyclo(Cys-Tyr-DTrp-Lys-Abu-Cys)-Thr-NH$_2$
-Doc-Aepa-DPhe-cyclo(Cys-Tyr-DTrp-Lys-Abu-Cys)-Thr-NH$_2$
-(Doc)$_6$-Aepa-Lys-DTyr-DTyr-cyclo(Cys-Tyr-DTrp-Lys-Abu-Cys)-Thr-NH$_2$
-(Doc)$_5$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_3$-Aepa-Lys-DTyr-DTyr-cyclo(Cys-Tyr-DTrp-Lys-Abu-Cys)-Thr-NH$_2$
-(Doc)$_2$-Aepa-Lys-DTyr-DTyr-cyclo(Cys-Tyr-DTrp-Lys-Abu-Cys)-Thr-NH$_2$
-Doc-Aepa-Lys-DTyr-DTyr-cyclo(Cys-Tyr-DTrp-Lys-Abu-Cys)-Thr-NH$_2$
-Lys-DTyr-DTyr-cyclo(Cys-Tyr-DTrp-Lys-Abu-Cys)-Thr-NH$_2$
-Doc-Lys-DTyr-DTyr-cyclo(Cys-Tyr-DTrp-Lys-Abu-Cys)-Thr-NH$_2$
-(Doc)$_2$-Lys-DTyr-DTyr-cyclo(Cys-Tyr-DTrp-Lys-Abu-Cys)-Thr-NH$_2$
-(Doc)$_3$-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-(Doc)$_5$-Lys-DTyr-DTyr-cyclo(Cys-Tyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-Aepa-(Doc)$_3$-DPhe-cyclo(Cys-Tyr-DTrp-Lys-Abu-Cys)-Thr-NH$_2$
-Aepa-(Doc)$_2$-DPhe-cyclo(Cys-Tyr-DTrp-Lys-Abu-Cys)-Thr-NH$_2$
-Aepa-Doc-DPhe-cyclo(Cys-Tyr-DTrp-Lys-Abu-Cys)-Thr-NH$_2$
-Aepa-(Doc)$_4$-Lys-DTyr-DTyr-cyclo(Cys-Tyr-DTrp-Lys-Abu-Cys)-Thr-NH$_2$
-Aepa-(Doc)$_3$-Lys-DTyr-DTyr-cyclo(Cys-Tyr-DTrp-Lys-Abu-Cys)-Thr-NH$_2$
-Aepa-(Doc)$_2$-Lys-DTyr-DTyr-cyclo(Cys-Tyr-DTrp-Lys-Abu-Cys)-Thr-NH$_2$
-Aepa-Doc-Lys-DTyr-DTyr-cyclo(Cys-Tyr-DTrp-Lys-Abu-Cys)-Thr-NH$_2$
-Aepa-DPhe-cyclo(Cys-3lTyr-DTrp-Lys-Abu-Cys)-Thr-NH$_2$
-DPhe-cyclo(Cys-3lTyr-DTrp-Lys-Abu-Cys)-Thr-NH$_2$
-(Doc)$_4$-Aepa-DPhe-cyclo(Cys-3lTyr-DTrp-Lys-Abu-Cys)-Thr-NH$_2$
-(Aepa)$_2$-Caeg-cyclo(DCys-3Pal-DTrp-Lys-DCys)-Thr(Bzl)-Tyr-NH$_2$
-(Doc)$_6$-Aepa-Caeg-cyclo(DCys-3Pal-DTrp-Lys-DCys)-Thr(Bzl)-Tyr-NH$_2$
-(Doc)$_5$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-(Doc)$_3$-Aepa-Caeg-cyclo(DCys-3Pal-DTrp-Lys-DCys)-Thr(Bzl)-Tyr-NH$_2$
-(Doc)$_2$-Aepa-Caeg-cyclo(DCys-3Pal-DTrp-Lys-DCys)-Thr(Bzl)-Tyr-NH$_2$
-Doc-Aepa-Caeg-cyclo(DCys-3Pal-DTrp-Lys-DCys)-Thr(Bzl)-Tyr-NH$_2$
-(Doc)$_6$-Caeg-cyclo(DCys-3Pal-DTrp-Lys-DCys)-Thr(Bzl)-Tyr-NH$_2$
-(Doc) 5-Caeg-cyclo(DCys-3Pal-DTrp-Lys-DCys)-Thr(Bzl)-Tyr-NH$_2$
-(Doc)$_4$-Caeg-cyclo(DCys-3Pal-DTrp-Lys-DCys)-Thr(Bzl)-Tyr-NH$_2$
-(Doc)$_3$-Caeg-cyclo(DCys-3Pal-DTrp-Lys-DCys)-Thr(Bzl)-Tyr-NH$_2$
-(Doc)$_2$-Caeg-cyclo(DCys-3Pal-DTrp-Lys-DCys)-Thr(Bzl)-Tyr-NH$_2$
-Doc-Caeg-cyclo(DCys-3Pal-DTrp-Lys-DCys)-Thr(Bzl)-Tyr-NH$_2$
-Aepa-Doc-Caeg-cyclo(DCys-3Pal-DTrp-Lys-DCys)-Thr(Bzl)-Tyr-NH$_2$
-Aepa-(Doc)$_2$-Caeg-cyclo(DCys-3Pal-DTrp-Lys-DCys)-Thr(Bzl)-Tyr-NH$_2$
-Aepa-(Doc)$_3$-Caeg-cyclo(DCys-3Pal-DTrp-Lys-DCys)-Thr(Bzl)-Tyr-NH$_2$
-Aepa-(Doc)$_4$-Caeg-cyclo(DCys-3Pal-DTrp-Lys-DCys)-Thr(Bzl)-Tyr-NH$_2$
-(Doc)$_6$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-(Doc)$_4$-DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-DPhe-cyclo(Cys-Tyr-DTrp-Lys-Abu-Cys)-Thr-NH$_2$
-(Doc)$_4$-Aepa-DPhe-cyclo(Cys-Tyr-DTrp-Lys-Abu-Cys)-Thr-NH$_2$
-(Doc)$_6$-Aepa-DPhe-cyclo(Cys-Tyr-DTrp-Lys-Abu-Cys)-Thr-NH$_2$
-(Aepa)$_2$-DPhe-cyclo(Cys-Tyr-DTrp-Lys-Abu-Cys)-Thr-NH$_2$ TABLE B-continued -(Doc)₂-Aepa-DPhe-cyclo(Cys-Tyr-DTrp-Lys-Abu-Cys)-Thr-NH₂
-(Doc)₄-Aepa-DPhe-cyclo(Cys-Tyr-DTrp-Lys-Abu-Cys)-Thr-NH₂
-(Doc)₆-Aepa-DPhe-cyclo(Cys-Tyr-DTrp-Lys-Abu-Cys)-Thr-NH₂
-(Doc)8-Aepa-D Phe-cyclo(Cys-Tyr-DTrp-Lys-Abu-Cys)-Thr-NH₂
-(Aepa)HSDAVFTDNYTRLRKQMAVKKLLNSILN-NH₂
-(Aepa)HSDAVFTDNYTRLRKQMAVKKALNSILN-NH₂
-(Aepa)HSDAVFTDNYTRLRKQMAVKKFLNSILN-NH₂
-(Aepa)HSDAVFTDNYTRLRKQMAVKKYLNSILN-NH₂
-(Aepa)HSDAVFTDNYTRLRKQ(Nle)AVKKYLNSILN-NH₂
-HSDAVFTDNYTRLRKQMAVKKLLNSILN-NH₂ (SEQ ID NO: 4)
-HSDAVFTDNYTRLRKQMAVKKALNSILN-NH₂ (SEQ ID NO: 5)
-HSDAVFTDNYTRLRKQMAVKKFLNSILN-NH₂ (SEQ ID NO: 6)
-HSDAVFTDNYTRLRKQMAVKKYLNSILN-NH₂ (SEQ ID NO: 7)
-HSDAVFTDNYTRLRKQ(Nle)AVKKYLNSILN-NH₂
-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂

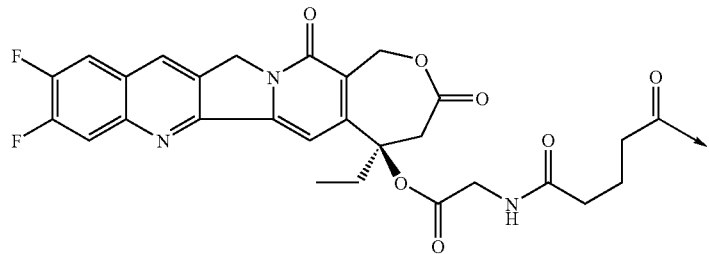 [SMILES: CC[C@@]1(OC(=O)CNC(=O)CCCC=O)CC(=O)OCc2c1cc1n(c2=O)Cc2cc3cc(F)c(F)cc3nc2-1]

-(Aepa)HSDGIFTDSYSRYRKQMA(A5c)KKYLAAVLGKRYKQRVKNK-NH₂
-(Aepa)HSDGIFTDSYSRYRKQMAVKKYLAAVLGKRYKQR(A6c)KNK-NH₂
-(Aepa)HSDGIFTDSYSRYRKQMAVKKYLAAVL(Ava)KRYKQRVKNK-NH₂
-(Aepa)HSDGIFTDSYSRYRKQMAVKKYLAAVL(βAla)KRYKQRVKNK-NH₂.
-HSDGIFTDSYSRYRKQMA(A5c)KKYLAAVLGKRYKQRVKNK-NH₂
-HSDGIFTDSYSRYRKQMAVKKYLAAVLGKRYKQR(A6c)KNK-NH₂
-HSDGIFTDSYSRYRKQMAVKKYLAAVL(Ava)KRYKQRVKNK-NH₂
-HSDGIFTDSYSRYRKQMAVKKYLAAVL(βAla)KRYKQRVKNK-NH₂
-Aepa-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-Aepa-DPhe-cyclo(Cys-3lTyr-DTrp-Lys-Thr-Cys)-Thr-NH₂
-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂
-Aepa-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂
-(Doc)₄-DPhe-cyclo(Cys-3lTyr-DTrp-Lys-Val-Cys)-Thr-NH₂
-(Doc)₆-DPhe-cyclo(Cys-3lTyr-DTrp-Lys-Val-Cys)-Thr-NH₂
-(Aepa)₂-Lys-DTyr-DTyr-cyclo(Cys-Tyr-DTrp-Lys-Abu-Cys)-Thr-NH₂
-Aepa-DPhe-cyclo(Cys-3lTyr-DTrp-Lys-Abu-Cys)-Thr-NH₂
-DPhe-cyclo(Cys-3lTyr-DTrp-Lys-Abu-Cys)-Thr-NH₂
-(Doc)₄-DPhe-cyclo(Cys-3lTyr-DTrp-Lys-Abu-Cys)-Thr-NH₂
-(Doc)₆-DPhe-cyclo(Cys-3lTyr-DTrp-Lys-Abu-Cys)-Thr-NH₂
-(Aepa)₂-Lys-DTyr-DTyr-cyclo(Cys-Tyr-DTrp-Lys-Abu-Cys)-Thr-NH₂
-(Doc)₆-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₂-Aepa-Lys-DTyr-DTyr-cyclo(Cys-Tyr-DTrp-Lys-Abu-Cys)-Thr-NH₂
-Aepa-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-Aepa-(Doc)₆-Lys-DTyr-DTyr-cyclo(Cys-Tyr-DTrp-Lys-Abu-Cys)-Thr-NH₂
-Aepa-(Doc)₄-Lys-DTyr-DTyr-cyclo(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂

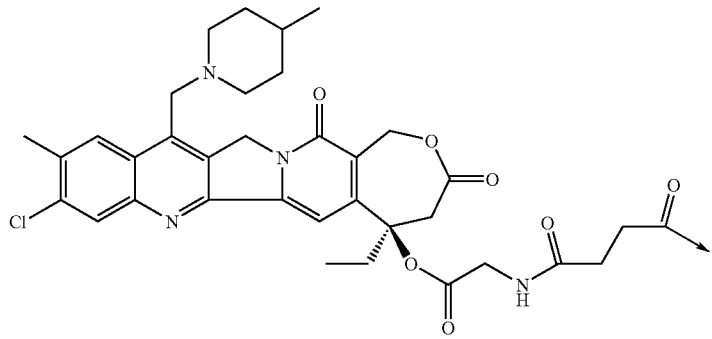 [SMILES: CC[C@@]1(OC(=O)CNC(=O)CCC=O)CC(=O)OCc2c1cc1n(c2=O)Cc2c-1nc1cc(Cl)c(C)cc1c2CN1CCC(C)CC1]

-Doc-Gln-Trp-Ala-Ala-βAla-His-Phe-Nle-NH₂
-Doc-Gln-Trp-Ala-Val-βAla-His-Phe-Nle-NH₂
-Doc-Gln-Trp-Ala-Val-Gly-His-Leu-Leu-NH₂
-Doc-Gln-Trp-Ala-Val-βAla-His-Leu-Nle-NH₂
-Doc-Gln-Trp-Ala-Val-βAla-His-Leu-Leu-NH₂
-Doc-DPhe-Gln-Trp-Ala-Val-βAla-His-Leu-Leu-NH₂
-Doc-DPhe-Gln-Trp-Ala-Val-βAla-His-Leu-Nle-NH₂
-Doc-DPhe-Gln-Trp-Ala-Val-Gly-His-Leu-Leu-NH₂
-Doc-DAla-Gln-Trp-Ala-Val-βAla-His-Phe-Nle-NH₂
-Doc-DPhe-Gln-Trp-Ala-Ala-βAla-His-Phe-Nle-NH₂
-Doc-Aepa-DPhe-Gln-Trp-Ala-Ala-βAla-His-Phe-Nle-NH₂
-Doc-Aepa-DAla-Gln-Trp-Ala-Val-βAla-His-Phe-Nle-NH₂
-Doc-Aepa-DPhe-Gln-Trp-Ala-Val-Gly-His-Leu-Leu-NH₂
-Doc-Aepa-DPhe-Gln-Trp-Ala-Val-βAla-His-Leu-Nle-NH₂
-Doc-Aepa-DPhe-Gln-Trp-Ala-Val-βAla-His-Leu-Leu-NH₂
-Aepa-(Doc)₃-DPhe-Gln-Trp-Ala-Ala-βAla-His-Phe-Nle-NH₂
-Aepa-(Doc)₃-DAla-Gln-Trp-Ala-Val-βAla-His-Phe-Nle-NH₂
-Aepa-(Doc)₃-DPhe-Gln-Trp-Ala-Val-Gly-His-Leu-Leu-NH₂
-Aepa-(Doc)₃-DPhe-Gln-Trp-Ala-Val-βAla-His-Leu-Nle-NH₂
-Aepa-(Doc)₃-DPhe-Gln-Trp-Ala-Val-βAla-His-Leu-Leu-NH₂
-(Doc)₃-Aepa-Gln-Trp-Ala-Ala-βAla-His-Phe-Nle-NH₂
-(Doc)₃-Aepa-Gln-Trp-Ala-Val-βAla-His-Phe-Nle-NH₂
-(Doc)₃-Aepa-Gln-Trp-Ala-Val-Gly-His-Leu-Leu-NH₂
-(Doc)₃-Aepa-Gln-Trp-Ala-Val-βAla-His-Leu-Nle-NH₂
-(Doc)₃-Aepa-Gln-Trp-Ala-Val-βAla-His-Leu-Leu-NH₂
-Aepa-Doc-DPhe-Gln-Trp-Ala-Ala-βAla-His-Phe-Nle-NH₂
-Aepa-Doc-DAla-Gln-Trp-Ala-Val-βAla-His-Phe-Nle-NH₂
-Aepa-Doc-DPhe-Gln-Trp-Ala-Val-Gly-His-Leu-Leu-NH₂
-Aepa-Doc-DPhe-Gln-Trp-Ala-Val-βAla-His-Leu-Nle-NH₂
-Aepa-Doc-DPhe-Gln-Trp-Ala-Val-βAla-His-Leu-Leu-NH₂
-(Doc)₄-Gln-Trp-Ala-Val-Gly-His-Leu-Ψ(CH₂NH)-Leu-NH₂
-(Doc)₄-Aepa-Gln-Trp-Ala-Val-Gly-His-Leu-Ψ(CH₂NH)-Leu-NH₂
-Aepa-(Doc)₄-Gln-Trp-Ala-Val-Gly-His-Leu-Ψ(CH₂NH)-Leu-NH₂
-(Doc)₄-Gaba-Gln-Trp-Ala-Val-Gly-His-Leu-Ψ(CH₂NH)-Leu-NH₂
-(Doc)₄-Aepa-Gaba-Gln-Trp-Ala-Val-Gly-His-Leu-Ψ(CH₂NH)-Leu-NH₂
-Aepa-(Doc)₄-Gaba-Gln-Trp-Ala-Val-Gly-His-Leu-Ψ(CH₂NH)-Leu-NH₂
-(Doc)₄-Gaba-Gln-Trp-Ala-Val-βAla-His-Leu-Leu-NH₂
-(Doc)₄-Aepa-Gaba-Gln-Trp-Ala-Val-βAla-His-Leu-Leu-NH₂
-Aepa-(Doc)₄-Gaba-Gln-Trp-Ala-Val-βAla-His-Leu-Leu-NH₂
-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
-Aepa-(Doc)₄-Gaba-Gln-Trp-Ala-Val-βAla-His-Leu-Nle-NH₂
-Aepa-Gln-Trp-Ala-Val-Gly-His-Leu-Leu-NH₂
-Aepa-Gln-Trp-Ala-Val-βAla-His-Leu-Nle-NH₂
-Aepa-Gln-Trp-Ala-Val-βAla-His-Leu-Leu-NH₂
-Aepa-(Doc)₂-Gln-Trp-Ala-Ala-βAla-His-Phe-Nle-NH₂
-Aepa-(Doc)₂-Gln-Trp-Ala-Val-βAla-His-Phe-Nle-NH₂
-Aepa-(Doc)₂-Gln-Trp-Ala-Val-Gly-His-Leu-Leu-NH₂
-Aepa-(Doc)₂-Gln-Trp-Ala-Val-βAla-His-Leu-Nle-NH₂
-Aepa-(Doc)₂-Gln-Trp-Ala-Val-βAla-His-Leu-Leu-NH₂
-(Doc)₂-Gln-Trp-Ala-Ala-βAla-His-Phe-Nle-NH₂
-(Doc)₂-Gln-Trp-Ala-Val-βAla-His-Phe-Nle-NH₂
-(Doc)₂-Gln-Trp-Ala-Val-Gly-His-Leu-Leu-NH₂
-(Doc)₂-Gln-Trp-Ala-Val-βAla-His-Leu-Nle-NH₂
-(Doc)₂-Gln-Trp-Ala-Val-βAla-His-Leu-Leu-NH₂
-Aepa-Gln-Trp-Ala-Ala-βAla-His-Phe-Nle-NH₂
-Aepa-Gln-Trp-Ala-Val-βAla-His-Phe-Nle-NH₂
-(Doc)₄-Aepa-DPhe-Gln-Trp-Ala-Val-Gly-His-Leu-Leu-NH₂
-(Doc)₄-Aepa-DPhe-Gln-Trp-Ala-Val-βAla-His-Leu-Nle-NH₂
-(Doc)₄-Aepa-DPhe-Gln-Trp-Ala-Val-βAla-His-Leu-Leu-NH₂
-Aepa-(Doc)₄-DPhe-Gln-Trp-Ala-Ala-βAla-His-Phe-Nle-NH₂
-Aepa-(Doc)₄-DAla-Gln-Trp-Ala-Val-βAla-His-Phe-Nle-NH₂

TABLE B-continued

-Aepa-(Doc)₄-DPhe-Gln-Trp-Ala-Val-Gly-His-Leu-Leu-NH₂
-Aepa-(Doc)₄-DPhe-Gln-Trp-Ala-Val-βAla-His-Leu-Nle-NH₂
-Aepa-(Doc)₄-DPhe-Gln-Trp-Ala-Val-βAla-His-Leu-Leu-NH₂
-(Doc)₄-DPhe-Gln-Trp-Ala-Ala-βAla-His-Phe-Nle-NH₂
-(Doc)₄-DAla-Gln-Trp-Ala-Val-βAla-His-Phe-Nle-NH₂
-(Doc)₄-DPhe-Gln-Trp-Ala-Val-Gly-His-Leu-Leu-NH₂
-(Doc)₄-DPhe-Gln-Trp-Ala-Val-βAla-His-Leu-Nle-NH₂
-(Doc)₄-DPhe-Gln-Trp-Ala-Val-βAla-His-Leu-Leu-NH₂
-(Doc)₄-Aepa-DPhe-Gln-Trp-Ala-Ala-βAla-His-Phe-Nle-NH₂
-(Doc)₄-Aepa-DAla-Gln-Trp-Ala-Val-βAla-His-Phe-Nle-NH₂
-(Doc)₄-Aepa-Gln-Trp-Ala-Val-Gly-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-βAla-His-Leu-Leu-NH₂
-Aepa-(Doc)₄-Gln-Trp-Ala-Ala-βAla-His-Phe-Nle-NH₂
-Aepa-(Doc)₄-Gln-Trp-Ala-Val-βAla-His-Phe-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-βAla-His-Leu-Leu-NH₂
-(Doc)₄-Gln-Trp-Ala-Ala-βAla-His-Phe-Nle-NH₂
-(Doc)₄-Gln-Trp-Ala-Val-βAla-His-Phe-Nle-NH₂
-(Doc)₄-Gln-Trp-Ala-Val-Gly-His-Leu-Leu-NH₂
-(Doc)₄-Gln-Trp-Ala-Val-βAla-His-Leu-Nle-NH₂
-(Doc)₄-Gln-Trp-Ala-Val-βAla-His-Leu-Leu-NH₂
-(Doc)₄-Aepa-Gln-Trp-Ala-Ala-βAla-His-Phe-Nle-NH₂
-(Doc)₄-Aepa-Gln-Trp-Ala-Val-βAla-His-Phe-Nle-NH₂
-Aepa-DAla-Gln-Trp-Ala-Val-βAla-His-Phe-Nle-NH₂
-Aepa-DPhe-Gln-Trp-Ala-Ala-βAla-His-Phe-Nle-NH₂
-(Doc)₂-DPhe-Gln-Trp-Ala-Val-βAla-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-Gly-His-Leu-Leu-NH₂
-(Doc)₂-DAla-Gln-Trp-Ala-Val-βAla-His-Phe-Nle-NH₂
-(Doc)₂-DPhe-Gln-Trp-Ala-Ala-βAla-His-Phe-Nle-NH₂

TABLE C

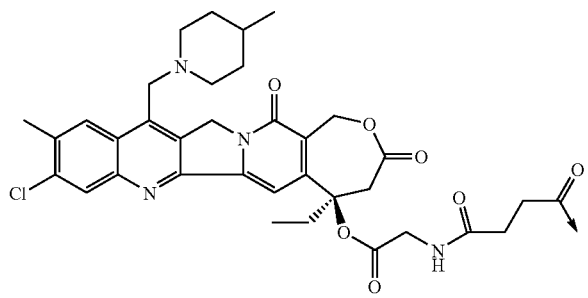

-(Doc)₂-DPhe-Gln-Trp-Ala-Ala-βAla-His-Phe-Nle-NH₂
-(Doc)₂-DAla-Gln-Trp-Ala-Val-βAla-His-Phe-Nle-NH₂
-(Doc)₂-DPhe-Gln-Trp-Ala-Val-Gly-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-βAla-His-Leu-Leu-NH₂
-Aepa-DPhe-Gln-Trp-Ala-Ala-βAla-His-Phe-Nle-NH₂
-Aepa-DAla-Gln-Trp-Ala-Val-βAla-His-Phe-Nle-NH₂
-(Doc)₂-Aepa-DPhe-Gln-Trp-Ala-Ala-βAla-His-Phe-Nle-NH₂
-(Doc)₂-Aepa-DAla-Gln-Trp-Ala-Val-βAla-His-Phe-Nle-NH₂
-(Doc)₂-Aepa-DPhe-Gln-Trp-Ala-Val-Gly-His-Leu-Leu-NH₂
-(Doc)₂-Aepa-DPhe-Gln-Trp-Ala-Val-βAla-His-Leu-Nle-NH₂
-(Doc)₂-Aepa-DPhe-Gln-Trp-Ala-Val-βAla-His-Leu-Leu-NH₂
-Aepa-(Doc)₂-Gln-Trp-Ala-Val-βAla-His-Ala-Nle-NH₂
-Aepa-Gln-Trp-Ala-Val-βAla-His-Ala-Nle-NH₂
-(Doc)₂-Gln-Trp-Ala-Val-βAla-His-Ala-Nle-NH₂
-Aepa-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-(Doc)₂-DPhe-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₂-Aepa-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-Aepa-(Doc)₄-DPhe-Gln-Trp-Ala-Val-βAla-His-Ala-Nle-NH₂

TABLE C-continued

-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-Aepa-Doc-Gln-Trp-Ala-Val-Gly-His-Leu-Leu-NH₂
-Aepa-Doc-Gln-Trp-Ala-Val-βAla-His-Leu-Nle-NH₂
-Aepa-Doc-Gln-Trp-Ala-Val-βAla-His-Leu-Leu-NH₂
-Aepa-(Doc)₃-Gln-Trp-Ala-Ala-βAla-His-Phe-Nle-NH₂
-Aepa-(Doc)₃-Gln-Trp-Ala-Val-βAla-His-Phe-Nle-NH₂
-Aepa-(Doc)₃-Gln-Trp-Ala-Val-Gly-His-Leu-Leu-NH₂
-Aepa-(Doc)₃-Gln-Trp-Aia-Val-βAla-His-Leu-Nle-NH₂
-Aepa-(Doc)₃-Gln-Trp-Ala-Val-βAla-His-Leu-Leu-NH₂
-(Doc)₃-Gln-Trp-Ala-Ala-βAla-His-Phe-Nle-NH₂
-(Doc)₃-Gln-Trp-Ala-Val-βAla-His-Phe-Nle-NH₂
-(Doc)₃-Gln-Trp-Ala-Val-Gly-His-Leu-Leu-NH₂
-(Doc)₃-Gln-Trp-Ala-Val-βAla-His-Leu-Nle-NH₂
-(Doc)₃-Gln-Trp-Ala-Val-βAla-His-Leu-Leu-NH₂
-Aepa-Doc-Gln-Trp-Ala-Ala-βAla-His-Phe-Nle-NH₂
-Aepa-Doc-Gln-Trp-Ala-Val-βAla-His-Phe-Nle-NH₂
-(Doc)₃-Aepa-DPhe-Gln-Trp-Ala-Val-Gly-His-Leu-Leu-NH₂
-(Doc)₃-Aepa-DPhe-Gln-Trp-Ala-Val-βAla-His-Leu-Nle-NH₂
-(Doc)₃-Aepa-DPhe-Gln-Trp-Ala-Val-βAla-His-Leu-Leu-NH₂
-(Doc)₃-DPhe-Gln-Trp-Ala-Ala-βAla-His-Phe-Nle-NH₂
-(Doc)₃-DAla-Gln-Trp-Ala-Val-βAla-His-Phe-Nle-NH₂
-(Doc)₃-DPhe-Gln-Trp-Ala-Val-Gly-His-Leu-Leu-NH₂
-(Doc)₃-DPhe-Gln-Trp-Ala-Val-βAla-His-Leu-Nle-NH₂
-(Doc)₃-DPhe-Gln-Trp-Ala-Val-βAla-His-Leu-Leu-NH₂
-Doc-Gln-Trp-Ala-Ala-βAla-His-Phe-Nle-NH₂
-Doc-Gln-Trp-Ala-Val-βAla-His-Phe-Nle-NH₂
-Doc-Gln-Trp-Ala-Val-Gly-His-Leu-Leu-NH₂
-Doc-Gln-Trp-Ala-Val-βAla-His-Leu-Nle-NH₂
-Doc-Gln-Trp-Ala-Val-βAla-His-Leu-Leu-NH₂
-Doc-Aepa-Gln-Trp-Ala-Ala-βAla-His-Phe-Nle-NH₂
-Doc-Aepa-Gln-Trp-Ala-Val-βAla-His-Phe-Nle-NH₂
-Doc-Aepa-Gln-Trp-Ala-Val-Gly-His-Leu-Leu-NH₂
-Doc-Aepa-Gln-Trp-Ala-Val-βAla-His-Leu-Nle-NH₂
-Doc-Aepa-Gln-Trp-Ala-Val-βAla-His-Leu-Leu-NH₂

TABLE C-continued
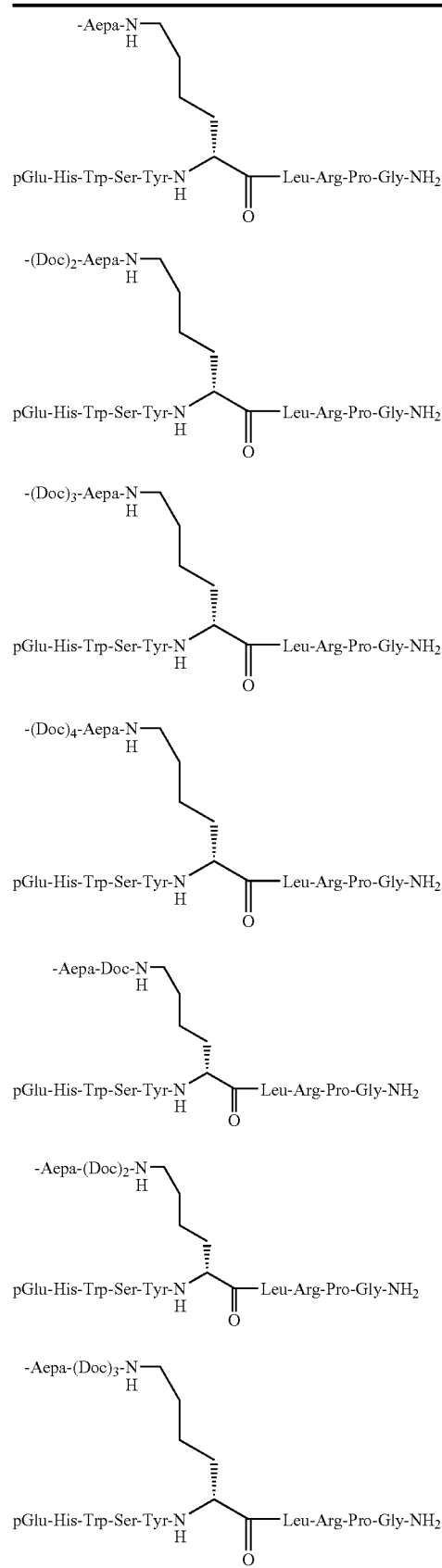
TABLE C-continued
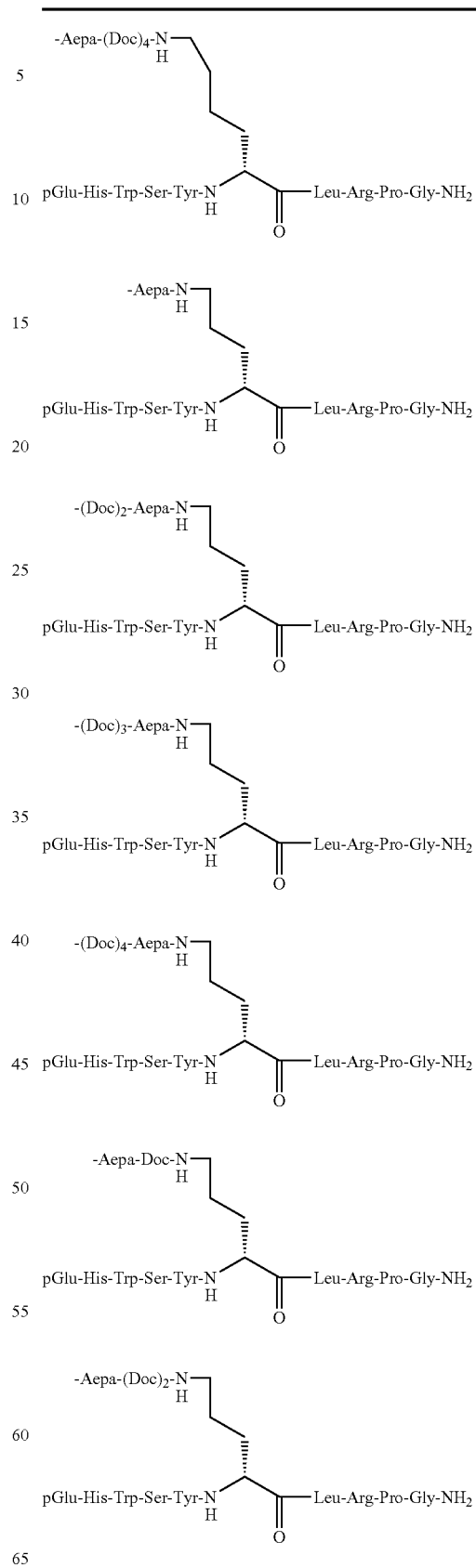

TABLE C-continued
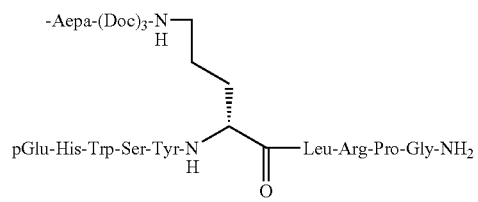
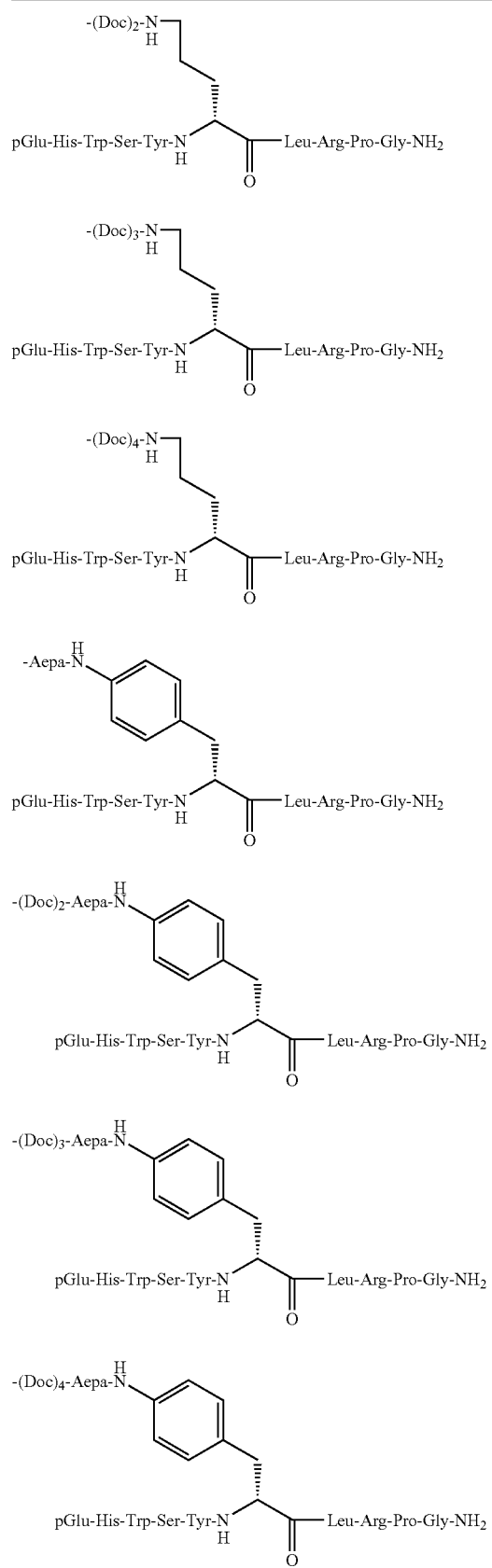

TABLE C-continued

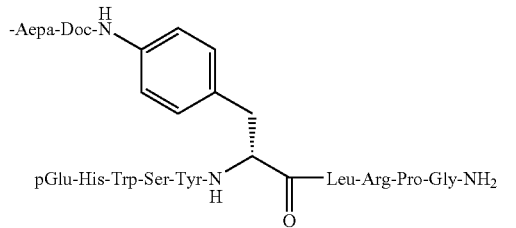

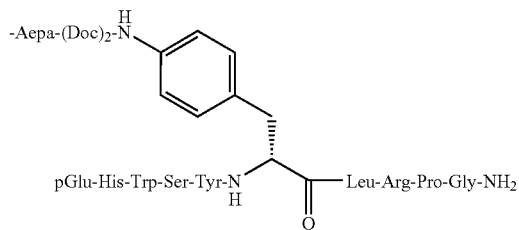

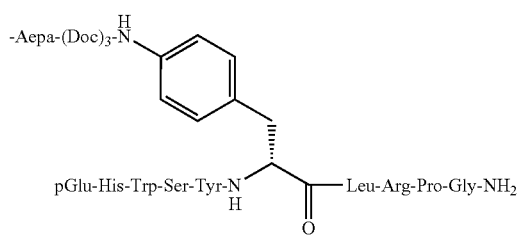

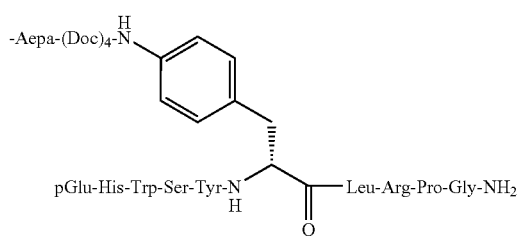

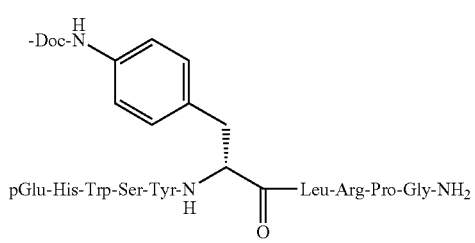

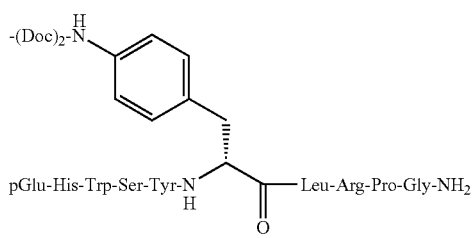

TABLE C-continued

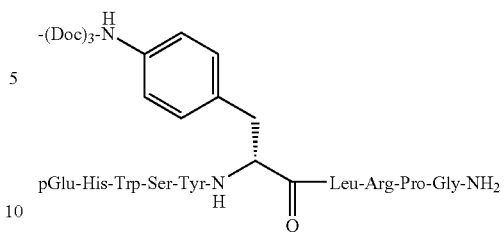

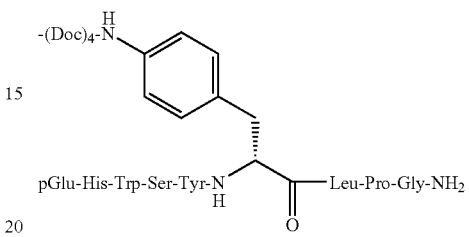

-Aepa-DPhe-cyclo(Cys-Tyr-DTrp-Lys-Abu-Cys)-Thr-NH$_2$
-DPhe-cyclo(Cys-Tyr-DTrp-Lys-Abu-Cys)-Thr-NH$_2$
-(Doc)$_4$-Aepa-DPhe-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_4$-Aepa-DPhe-cyclo(Cys-3lTyr-DTrp-Lys-Val-Cys)-Thr-NH$_2$
-Aepa-DPhe-cyclo(Cys-3lTyr-DTrp-Lys-Val-Cys)-Thr-NH$_2$
-DPhe-cyclo(Cys-3lTyr-DTrp-Lys-Val-Cys)-Thr-NH$_2$
-(Doc)$_4$-DPhe-cyclo(Cys-3lTyr-DTrp-Lys-Val-Cys)-Thr-NH$_2$
-(Doc)$_6$-DPhe-cyclo(Cys-3lTyr-DTrp-Lys-Val-Cys)-Thr-NH$_2$
-Doc-Aepa-DPhe-cyclo(Cys-3lTyr-DTrp-Lys-Val-Cys)-Thr-NH$_2$
-(Doc)$_2$-Aepa-DPhe-cyclo(Cys-3lTyr-DTrp-Lys-Val-Cys)-Thr-NH$_2$
-(Doc)$_3$-Aepa-DPhe-cyclo(Cys-3lTyr-DTrp-Lys-Val-Cys)-Thr-NH$_2$
-(Doc)$_5$-Aepa-DPhe-cyclo(Cys-3lTyr-DTrp-Lys-Val-Cys)-Thr-NH$_2$
-(Doc)$_6$-Aepa-DPhe-cyclo(Cys-3lTyr-DTrp-Lys-Val-Cys)-Thr-NH$_2$
-(Aepa)$_2$-DPhe-cyclo(Cys-3lTyr-DTrp-Lys-Val-Cys)-Thr-NH$_2$
-Doc-DPhe-cyclo-(Cys-3lTyr-DTrp-Lys-Val-Cys)-Thr-NH$_2$
-(Doc)$_2$-DPhe-cyclo-(Cys-3lTyr-DTrp-Lys-Val-Cys)-Thr-NH$_2$
-(Doc)$_3$-DPhe-cyclo-(Cys-3lTyr-DTrp-Lys-Val-Cys)-Thr-NH$_2$
-(Doc)$_5$-DPhe-cyclo-(Cys-3lTyr-DTrp-Lys-Val-Cys)-Thr-NH$_2$
-Aepa-(Doc)$_4$-DPhe-cyclo-(Cys-3lTyr-DTrp-Lys-Val-Cys)-Thr-NH$_2$
-Aepa-(Doc)$_3$-DPhe-cyclo-(Cys-3lTyr-DTrp-Lys-Val-Cys)-Thr-NH$_2$
-Aepa-(Doc)$_2$-DPhe-cyclo-(Cys-3lTyr-DTrp-Lys-Val-Cys)-Thr-NH$_2$
-Aepa-Doc-DPhe-cyclo-(Cys-3lTyr-DTrp-Lys-Val-Cys)-Thr-NH$_2$
-(Doc)$_6$-DPhe-cyclo-(Cys-3lTyr-DTrp-Lys-Thr-Cys)-Thr-NH$_2$
-(Doc)$_5$-DPhe-cyclo-(Cys-3lTyr-DTrp-Lys-Thr-Cys)-Thr-NH$_2$
-(Doc)$_4$-DPhe-cyclo-(Cys-3lTyr-DTrp-Lys-Thr-Cys)-Thr-NH$_2$
-(Doc)$_3$-DPhe-cyclo-(Cys-3lTyr-DTrp-Lys-Thr-Cys)-Thr-NH$_2$
-(Doc)$_2$-DPhe-cyclo-(Cys-3lTyr-DTrp-Lys-Thr-Cys)-Thr-NH$_2$
-Doc-DPhe-cyclo-(Cys-3lTyr-DTrp-Lys-Thr-Cys)-Thr-NH$_2$
-(Aepa)$_2$-DPhe-cyclo-(Cys-3lTyr-DTrp-Lys-Thr-Cys)-Thr-NH$_2$
-(Doc)$_6$-Aepa-DPhe-cyclo-(Cys-3lTyr-DTrp-Lys-Thr-Cys)-Thr-NH$_2$
-(Doc)$_5$-Aepa-DPhe-cyclo-(Cys-3lTyr-DTrp-Lys-Thr-Cys)-Thr-NH$_2$
-(Doc)$_3$-Aepa-DPhe-cyclo-(Cys-3lTyr-DTrp-Lys-Thr-Cys)-Thr-NH$_2$
-(Doc)$_2$-Aepa-DPhe-cyclo-(Cys-3lTyr-DTrp-Lys-Thr-Cys)-Thr-NH$_2$
-Doc-Aepa-DPhe-cyclo-(Cys-3lTyr-DTrp-Lys-Thr-Cys)-Thr-NH$_2$
-Aepa-(Doc)$_4$-DPhe-cyclo-(Cys-3lTyr-DTrp-Lys-Thr-Cys)-Thr-NH$_2$
-Aepa-(Doc)$_3$-DPhe-cyclo-(Cys-3lTyr-DTrp-Lys-Thr-Cys)-Thr-NH$_2$
-Aepa-(Doc)$_2$-DPhe-cyclo-(Cys-3lTyr-DTrp-Lys-Thr-Cys)-Thr-NH$_2$
-Aepa-Doc-DPhe-cyclo-(Cys-3lTyr-DTrp-Lys-Thr-Cys)-Thr-NH$_2$
-Aepa-DPhe-cyclo-(Cys-3lTyr-DTrp-Lys-Thr-Cys)-Thr-NH$_2$
-DPhe-cyclo-(Cys-3lTyr-DTrp-Lys-Thr-Cys)-Thr-NH$_2$
-(Doc)$_4$-Aepa-DPhe-cyclo-(Cys-3lTyr-DTrp-Lys-Thr-Cys)-Thr-NH$_2$
-Aepa-DPhe-cyclo-(Cys-3lTyr-DTrp-Lys-Thr-Cys)-Thr-NH$_2$
-DPhe-cyclo-(Cys-3lTyr-DTrp-Lys-Thr-Cys)-Thr-NH$_2$
-(Doc)$_4$-DPhe-cyclo-(Cys-3lTyr-DTrp-Lys-Thr-Cys)-Thr-NH$_2$
-(Doc)$_6$-DPhe-cyclo-(Cys-3lTyr-DTrp-Lys-Thr-Cys)-Thr-NH$_2$
-(Doc)$_6$-DPhe-cyclo-(Cys-3lTyr-DTrp-Lys-Abu-Cys)-Thr-NH$_2$
-(Doc)$_5$-DPhe-cyclo-(Cys-3lTyr-DTrp-Lys-Abu-Cys)-Thr-NH$_2$
-(Doc)$_4$-DPhe-cyclo(Cys-3lTyr-DTrp-Lys-Abu-Cys)-Thr-NH$_2$
-(Doc)$_3$-DPhe-cyclo(Cys-3lTyr-DTrp-Lys-Abu-Cys)-Thr-NH$_2$
-(Doc)$_2$-DPhe-cyclo(Cys-3lTyr-DTrp-Lys-Abu-Cys)-Thr-NH$_2$
-Doc-DPhe-cyclo(Cys-3lTyr-DTrp-Lys-Abu-Cys)-Thr-NH$_2$
-(Aepa)$_2$-DPhe-cyclo(Cys-3lTyr-DTrp-Lys-Abu-Cys)-Thr-NH$_2$
-(Doc)$_6$-Aepa-DPhe-cyclo(Cys-3lTyr-DTrp-Lys-Abu-Cys)-Thr-NH$_2$
-(Doc)$_5$-Aepa-DPhe-cyclo(Cys-3lTyr-DTrp-Lys-Abu-Cys)-Thr-NH$_2$ TABLE C-continued -(Doc)₃-Aepa-DPhe-cyclo(Cys-3lTyr-DTrp-Lys-Abu-Cys)-Thr-NH₂
-(Doc)₂-Aepa-DPhe-cyclo(Cys-3lTyr-DTrp-Lys-Abu-Cys)-Thr-NH₂
-Doc-Aepa-DPhe-cyclo(Cys-3lTyr-DTrp-Lys-Abu-Cys)-Thr-NH₂
-Aepa-(Doc)₄-DPhe-cyclo(Cys-3lTyr-DTrp-Lys-Abu-Cys)-Thr-NH₂
-Aepa-(Doc)₃-DPhe-cyclo(Cys-3lTyr-DTrp-Lys-Abu-Cys)-Thr-NH₂
-Aepa-(Doc)₂-DPhe-cyclo(Cys-3lTyr-DTrp-Lys-Abu-Cys)-Thr-NH₂
-Aepa-Doc-DPhe-cyclo(Cys-3lTyr-DTrp-Lys-Abu-Cys)-Thr-NH₂
-Aepa-DPhe-cyclo(Cys-3lTyr-DTrp-Lys-Abu-Cys)-Thr-NH₂
-DPhe-cyclo(Cys-3lTyr-DTrp-Lys-Abu-Cys)-Thr-NH₂
-(Doc)₄-Aepa-DPhe-cyclo(Cys-3lTyr-DTrp-Lys-Abu-Cys)-Thr-NH₂
-Aepa-DPhe-cyclo(Cys-3lTyr-DTrp-Lys-Abu-Cys)-Thr-NH₂
-DPhe-cyclo(Cys-3lTyr-DTrp-Lys-Abu-Cys)-Thr-NH₂
-(Doc)₄-DPhe-cyclo(Cys-3lTyr-DTrp-Lys-Abu-Cys)-Thr-NH₂
-(Doc)₆-DPhe-cyclo(Cys-3lTyr-DTrp-Lys-Abu-Cys)-Thr-NH₂
-(Doc)₆-DPhe-cyclo(Cys-Tyr-DTrp-Lys-Abu-Cys)-Thr-NH₂
-(Doc)₅-DPhe-cyclo(Cys-Tyr-DTrp-Lys-Abu-Cys)-Thr-NH₂
-(Doc)₄-DPhe-cyclo(Cys-Tyr-DTrp-Lys-Abu-Cys)-Thr-NH₂
-(Doc)₃-DPhe-cyclo(Cys-Tyr-DTrp-Lys-Abu-Cys)-Thr-NH₂
-(Doc)₂-DPhe-cyclo(Cys-Tyr-DTrp-Lys-Abu-Cys)-Thr-NH₂
-Doc-DPhe-cyclo(Cys-Tyr-DTrp-Lys-Abu-Cys)-Thr-NH₂
-(Aepa)₂-DPhe-cyclo(Cys-Tyr-DTrp-Lys-Abu-Cys)-Thr-NH₂
-(Doc)₆-Aepa-D Phe-cyclo(Cys-Tyr-DTrp-Lys-Abu-Cys)-Thr-NH₂
-(Doc)₅-Aepa-DPhe-cyclo(Cys-Tyr-DTrp-Lys-Abu-Cys)-Thr-NH₂
-(Doc)₃-Aepa-DPhe-cycto(Cys-Tyr-DTrp-Lys-Abu-Cys)-Thr-NH₂
-(Doc)₂-Aepa-DPhe-cyclo(Cys-Tyr-DTrp-Lys-Abu-Cys)-Thr-NH₂
-Doc-Aepa-DPhe-cyclo(Cys-Tyr-DTrp-Lys-Abu-Cys)-Thr-NH₂
-(Aepa)₂-Lys-DTyr-DTyr-cyclo(Cys-Tyr-DTrp-Lys-Abu-Cys)-Thr-NH₂
-(Doc)₆-Aepa-Lys-DTyr-DTyr-cyclo(Cys-Tyr-DTrp-Lys-Abu-Cys)-Thr-NH₂
-(Doc)₅-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₃-Aepa-Lys-DTyr-DTyr-cyclo(Cys-Tyr-DTrp-Lys-Abu-Cys)-Thr-NH₂
-(Doc)₂-Aepa-Lys-DTyr-DTyr-cyclo(Cys-Tyr-DTrp-Lys-Abu-Cys)-Thr-NH₂
-Doc-Aepa-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-(Doc)₄-Aepa-Gln-Trp-Ala-Val-βAla-His-Phe-Nle-NH₂
-(Doc)₄-Aepa-Gln-Trp-Ala-Val-Gly-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-βAla-His-Leu-Leu-NH₂
-Aepa-(Doc)₄-Gln-Trp-Ala-Ala-βAla-His-Phe-Nle-NH₂
-Aepa-(Doc)₄-Gln-Trp-Ala-Val-βAla-His-Phe-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-βAla-His-Leu-Leu-NH₂
-(Doc)₄-Gln-Trp-Ala-Ala-βAla-His-Phe-Nle-NH₂
-(Doc)₄-Gln-Trp-Ala-Val-βAla-His-Phe-Nle-NH₂
-(Doc)₄-Gln-Trp-Ala-Val-Gly-His-Leu-Leu-NH₂
-(Doc)₄-Gln-Trp-Ala-Val-βAla-His-Leu-Nle-NH₂
-(Doc)₄-Gln-Trp-Ala-Val-βAla-His-Leu-Leu-NH₂
-(Doc)₄-Aepa-Gln-Trp-Ala-Ala-βAla-His-Phe-Nle-NH₂
-(Doc)₆-Lys-DTyr-DTyr-cyclo(Cys-Tyr-DTrp-Lys-Abu-Cys)-Thr-NH₂
-(Doc)₅-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₃-Lys-DTyr-DTyr-cyclo(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-Doc-Lys-DTyr-DTyr-cyclo(Cys-Tyr-DTrp-Lys-Abu-Cys)-Thr-NH₂
-Aepa-(Doc)₄-DPhe-cyclo(Cys-Tyr-DTrp-Lys-Abu-Cys)-Thr-NH₂
-Aepa-(Doc)₃-DPhe-cyclo(Cys-Tyr-DTrp-Lys-Abu-Cys)-Thr-NH₂
-Aepa-(Doc)₂-DPhe-cyclo(Cys-Tyr-DTrp-Lys-Abu-Cys)-Thr-NH₂
-Aepa-Doc-DPhe-cyclo(Cys-Tyr-DTrp-Lys-Abu-Cys)-Thr-NH₂
-Aepa-(Doc)₄-Lys-DTyr-DTyr-cyclo(Cys-Tyr-DTrp-Lys-Abu-Cys)-Thr-NH₂
-Aepa-(Doc)₃-Lys-DTyr-DTyr-cyclo(Cys-Tyr-DTrp-Lys-Abu-Cys)-Thr-NH₂
-Aepa-(Doc)₂-Lys-DTyr-DTyr-cyclo(Cys-Tyr-DTrp-Lys-Abu-Cys)-Thr-NH₂
-Aepa-Doc-Lys-DTyr-DTyr-cyclo(Cys-Tyr-DTrp-Lys-Abu-Cys)-Thr-NH₂
-(Doc)₆-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Th r(Bzl)-Tyr-NH₂
-(Doc)₄-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂
-(Aepa)₂-Caeg-cyclo(DCys-3Pal-DTrp-Lys-DCys)-Thr(Bzl)-Tyr-NH₂
-(Doc)₆-Aepa-Caeg-cyclo(DCys-3Pal-DTrp-Lys-DCys)-Thr(Bzl)-Tyr-NH₂
-(Doc)₅-Aepa-Caeg-cyclo(DCys-3Pal-DTrp-Lys-DCys)-Thr(Bzl)-Tyr-NH₂

TABLE C-continued

-(Doc)₄-Aepa-Caeg-cyclo(DCys-3Pal-DTrp-Lys-DCys)-Thr(Bzl)-Tyr-NH₂
-(Doc)₃-Aepa-Caeg-cyclo(DCys-3Pal-DTrp-Lys-DCys)-Thr(Bzl)-Tyr-NH₂
-(Doc)₂-Aepa-Caeg-cyclo(DCys-3Pal-DTrp-Lys-DCys)-Thr(Bzl)-Tyr-NH₂
-Doc-Aepa-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Th r(Bzl)-Tyr-NH₂
-(Doc)₅-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)₃-Caeg-cyclo(DCys-3Pal-DTrp-Lys-DCys)-Thr(Bzl)-Tyr-NH₂
-(Doc)₂-Caeg-cyclo(DCys-3Pal-DTrp-Lys-DCys)-Th r(Bzl)-Tyr-NH₂
-Doc-Caeg-cyclo(DCys-3Pal-DTrp-Lys-DCys)-Thr(Bzl)-Tyr-NH₂
-Aepa-(Doc)₄-Caeg-cyclo(DCys-3Pal-DTrp-Lys-DCys)-Thr(Bzl)-Tyr-NH₂
-Aepa-(Doc)₃-Caeg-cyclo(DCys-3Pal-DTrp-Lys-DCys)-Thr(Bzl)-Tyr-NH₂
-Aepa-(Doc)₂-Caeg-cyclo(DCys-3Pal-DTrp-Lys-DCys)-Thr(Bzl)-Tyr-NH₂
-Aepa-Doc-Caeg-cyclo(DCys-3Pal-DTrp-Lys-DCys)-Thr(Bzl)-Tyr-NH₂

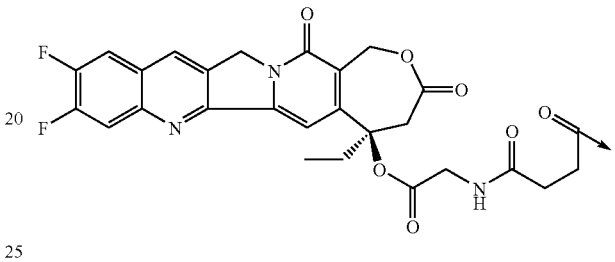

-Aepa-(Doc)₂-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-(Doc)₂-DPhe-cyclo(Cys-3lTyr-DTrp-Lys-Val-Cys)-Thr-NH₂
-(Doc)₄-Aepa-D Phe-cyclo(Cys-3lTyr-DTrp-Lys-Val-Cys)-Thr-NH₂
-Aepa-D Phe-cyclo(Cys-3lTyr-DTrp-Lys-Val-Cys)-Thr-NH₂
-DPhe-cyclo(Cys-3lTyr-DTrp-Lys-Val-Cys)-Thr-NH₂

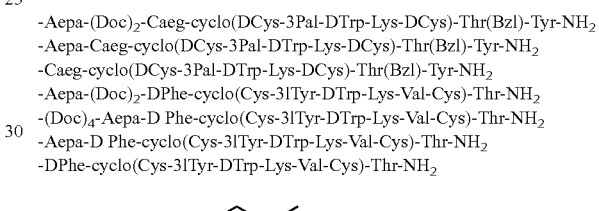

-Aepa-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂

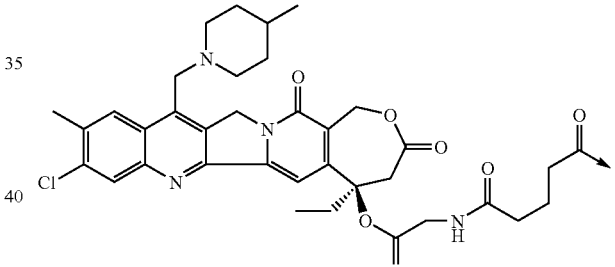

-Aepa-(Doc)₂-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-(Doc)₂-D Phe-cyclo(Cys-3lTyr-DTrp-Lys-Val-Cys)-Thr-NH₂
-(Doc)₄-Aepa-DPhe-cyclo(Cys-3lTyr-DTrp-Lys-Val-Cys)-Thr-NH₂
-Aepa-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂

TABLE D

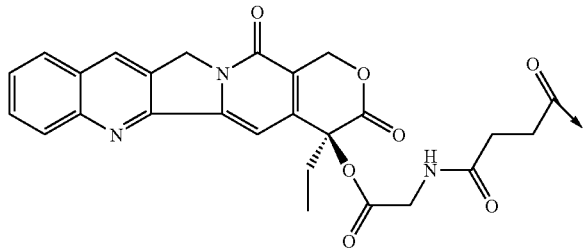

-(Doc)₂-Gln-Trp-Ala-Ala-βAla-His-Phe-Nle-NH₂
-(Doc)₂-Gln-Trp-Ala-Val-βAla-His-Phe-Nle-NH₂
-(Doc)₂-Gln-Trp-Ala-Val-Gly-His-Leu-Leu-NH₂
-(Doc)₂-Gln-Trp-Ala-Val-βAla-His-Leu-Nle-NH₂
-(Doc)₂-Gln-Trp-Ala-Val-βAla-His-Leu-Leu-NH₂
-Aepa-Gln-Trp-Ala-Ala-βAla-His-Phe-Nle-NH₂
-Aepa-Gln-Trp-Ala-Val-βAla-His-Phe-Nle-NH₂
-Aepa-Gln-Trp-Ala-Val-Gly-His-Leu-Leu-NH₂
-Aepa-Gln-Trp-Ala-Val-βAla-His-Leu-Nle-NH₂
-Aepa-Gln-Trp-Ala-Val-βAla-His-Leu-Leu-NH₂
-Aepa-(Doc)₂-Gln-Trp-Ala-Ala-βAla-His-Phe-Nle-NH₂
-Aepa-(Doc)₂-Gln-Trp-Ala-Val-βAla-His-Phe-Nle-NH₂
-Aepa-(Doc)₂-Gln-Trp-Ala-Val-Gly-His-Leu-Leu-NH₂
-Aepa-(Doc)₂-Gln-Trp-Ala-Val-βAla-His-Leu-Nle-NH₂
-Aepa-(Doc)₂-Gln-Trp-Ala-Val-βAla-His-Leu-Leu-NH₂
-(Doc)₂-Gln-Trp-Ala-Ala-βAla-His-Phe-Nle-NH₂
-(Doc)₂-Gln-Trp-Ala-Val-βAla-His-Phe-Nle-NH₂
-(Doc)₂-Gln-Trp-Ala-Val-Gly-His-Leu-Leu-NH₂
-(Doc)₂-Gln-Trp-Ala-Val-βAla-His-Leu-Nle-NH₂
-Aepa-Gln-Trp-Ala-Ala-βAla-His-Phe-Nle-NH₂
-Aepa-Gln-Trp-Ala-Val-βAla-His-Phe-Nte-NH₂
-Aepa-Gln-Trp-Ala-Val-Gly-His-Leu-Leu-NH₂
-Aepa-Gln-Trp-Ala-Val-βAla-His-Leu-Nle-NH₂
-Aepa-Gln-Trp-Ala-Val-βAla-His-Leu-Leu-NH₂
-Aepa-(Doc)₂-Gln-Trp-Ala-Ala-βAla-His-Phe-Nle-NH₂
-Aepa-(Doc)₂-Gln-Trp-Ala-Val-βAla-His-Phe-Nle-NH₂
-Aepa-(Doc)₂-Gln-Trp-Ala-Val-Gly-His-Leu-Leu-NH₂
-Aepa-(Doc)₂-Gln-Trp-Ala-Val-βAla-His-Leu-Nle-NH₂
-Aepa-(Doc)₂-Gln-Trp-Ala-Val-βAla-His-Leu-Leu-NH₂
-Aepa-(Doc)₂-Gln-Trp-Ala-Val-βAla-His-Leu-Leu-NH₂
-(Doc)₄-DPhe-Gln-Trp-Ala-Ala-βAla-His-Phe-Nle-NH₂
-(Doc)₄-DAla-Gln-Trp-Ala-Val-βAla-His-Phe-Nle-NH₂
-(Doc)₄-DPhe-Gln-Trp-Ala-Val-Gly-His-Leu-Leu-NH₂
-(Doc)₄-DPhe-Gln-Trp-Ala-Val-βAla-His-Leu-Nle-NH₂
-(Doc)₄-DPhe-Gln-Trp-Ala-Val-βAla-His-Leu-Leu-NH₂
-(Doc)₄-Aepa-DPhe-Gln-Trp-Ala-Ala-βAla-His-Phe-Nle-NH₂
-(Doc)₄-Aepa-DAla-Gln-Trp-Ala-Val-βAla-His-Phe-Nle-NH₂
-(Doc)₄-Aepa-DPhe-Gln-Trp-Ala-Val-Gly-His-Leu-Leu-NH₂
-(Doc)₄-Aepa-DPhe-Gln-Trp-Ala-Val-βAla-His-Leu-Nle-NH₂
-(Doc)₄-Aepa-DPhe-Gln-Trp-Ala-Val-βAla-His-Leu-Leu-NH₂
-Aepa-(Doc)₄-DPhe-Gln-Trp-Ala-Ala-βAla-His-Phe-Nle-NH₂
-Aepa-(Doc)₄-DAla-Gln-Trp-Ala-Val-βAla-His-Phe-Nle-NH₂
-Aepa-(Doc)₄-DPhe-Gln-Trp-Ala-Val-Gly-His-Leu-Leu-NH₂
-Aepa-(Doc)₄-DPhe-Gln-Trp-Ala-Val-βAla-His-Leu-Nle-NH₂
-Aepa-(Doc)₄-DPhe-Gln-Trp-Ala-Val-βAla-His-Leu-Leu-NH₂
-(Doc)₄-Gln-Trp-Ala-Ala-βAla-His-Phe-Nle-NH₂
-(Doc)₄-Gln-Trp-Ala-Val-βAla-His-Phe-Nle-NH₂
-(Doc)₄-Gln-Trp-Ala-Val-Gly-His-Leu-Leu-NH₂
-(Doc)₄-Gln-Trp-Ala-Val-βAla-His-Leu-Nle-NH₂
-(Doc)₄-Gln-Trp-Ala-Val-βAla-His-Leu-Leu-NH₂
-(Doc)₄-Aepa-Gln-Trp-Ala-Ala-βAla-His-Phe-Nle-NH₂
-(Doc)₄-Aepa-Gln-Trp-Ala-Val-βAla-His-Phe-Nle-NH₂
-(Doc)₄-Aepa-Gln-Trp-Ala-Val-Gly-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-βAla-His-Leu-Leu-NH₂
-Aepa-(Doc)₄-Gln-Trp-Ala-Val-βAla-His-Phe-Nle-NH₂
-Aepa-(Doc)₄-Gln-Trp-Ala-Val-βAla-His-Phe-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-βAla-His-Leu-Leu-NH₂
-Aepa-(Doc)₂-DPhe-Gln-Trp-Ala-Val-βAla-His-Leu-Leu-NH₂
-Aepa-(Doc)₂-DPhe-Gln-Trp-Ala-Val-βAla-His-Leu-Nle-NH₂
-Aepa-(Doc)₂-DPhe-Gln-Trp-Ala-Val-Gly-His-Leu-Leu-NH₂
-Aepa-(Doc)₂-DAla-Gln-Trp-Ala-Val-βAla-His-Phe-Nle-NH₂
-Aepa-(Doc)₂-DPhe-Gln-Trp-Ala-Ala-βAla-His-Phe-Nle-NH₂
-Aepa-DPhe-Gln-Trp-Ala-Val-βAla-His-Leu-Leu-NH₂

TABLE D-continued

-Aepa-DPhe-Gln-Trp-Ala-Val-βAla-His-Leu-Nle-NH₂
-Aepa-DPhe-Gln-Trp-Ala-Val-Gly-His-Leu-Leu-NH₂
-Aepa-DAla-Gln-Trp-Ala-Val-βAla-His-Phe-Nle-NH₂
-Aepa-DPhe-Gln-Trp-Ala-Ala-βAla-His-Phe-Nle-NH₂
-(Doc)₂-DPhe-Gln-Trp-Ala-Val-βAla-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-Gly-His-Leu-Leu-NH₂
-(Doc)₂-DAla-Gln-Trp-Ala-Val-βAla-His-Phe-Nle-NH₂
-(Doc)₂-DPhe-Gln-Trp-Ala-Ala-βAla-His-Phe-Nle-NH₂
-(Doc)₂-Aepa-DPhe-Gln-Trp-Ala-Val-βAla-His-Leu-Leu-NH₂
-(Doc)₂-Aepa-DPhe-Gln-Trp-Ala-Val-βAla-His-Leu-Nle-NH₂
-(Doc)₂-Aepa-DPhe-Gln-Trp-Ala-Val-Gly-His-Leu-Leu-NH₂
-(Doc)₂-Aepa-DAla-Gln-Trp-Ala-Val-βAla-His-Phe-Nle-NH₂
-(Doc)₂-Aepa-DPhe-Gln-Trp-Ala-Ala-βAla-His-Phe-Nle-NH₂
-Aepa-(Doc)₂-Gln-Trp-Ala-Val-βAla-His-Ala-Nle-NH₂
-Aepa-Gln-Trp-Ala-Val-βAla-His-Ala-Nle-NH₂
-(Doc)₂-Gln-Trp-Ala-Val-aAla-His-Ala-Nle-NH₂
-Aepa-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-(Doc)₂-DPhe-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-(Doc)₄-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₂-Aepa-DPhe-Gln-Trp-Ala-Val-βAla-His-Ala-Nle-NH₂
-Aepa-(Doc)₄-Gaba-Gln-Trp-Ala-Val-βAla-His-Leu-Leu-NH₂
-(Doc)₄-Aepa-Gaba-Gln-Trp-Ala-Val-βAla-His-Leu-Leu-NH₂
-Aepa-(Doc)₄-Gln-Trp-Ala-Val-Gly-His-Leu-Ψ(CH₂NH)-Leu-NH₂
-(Doc)₄-Gaba-Gln-Trp-Ala-Val-βAla-His-Leu-Leu-NH₂
-(Doc)₄-Aepa-Gaba-Gln-Trp-Ala-Val-Gly-His-Leu-Ψ(CH₂NH)-Leu-NH₂
-(Doc)₄-Gaba-Gln-Trp-Ala-Val-Gly-His-Leu-Ψ(CH₂NH)-Leu-NH₂
-Aepa-(Doc)₄-Gln-Trp-Ala-Val-Gly-His-Leu-Ψ(CH₂NH)-Leu-NH₂
-(Doc)₄-Aepa-Gln-Trp-Ala-Val-Gly-His-Leu-Ψ(CH₂NH)-Leu-NH₂
-(Doc)₄-Gln-Trp-Ala-Val-Gly-His-Leu-Ψ(CH₂NH)-Leu-NH₂
-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
-(Doc)₄-Gaba-Gln-Trp-Ala-Val-βAla-His-Leu-Nle-NH₂

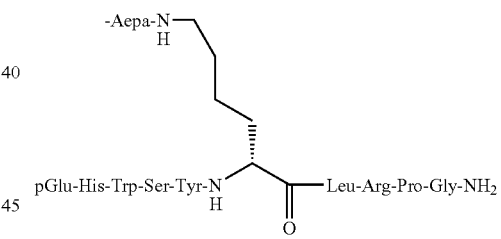

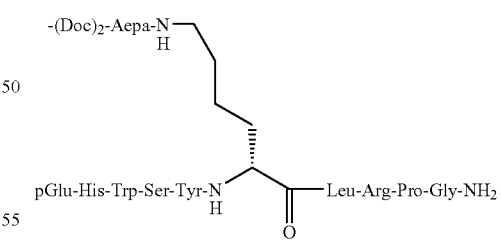

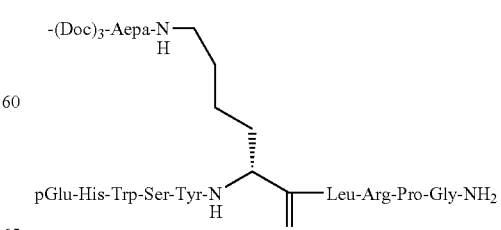

TABLE D-continued
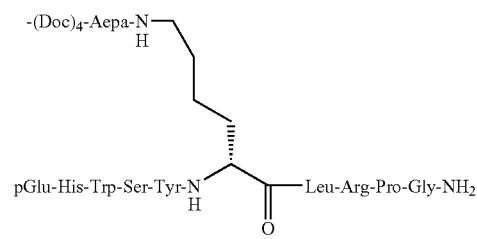
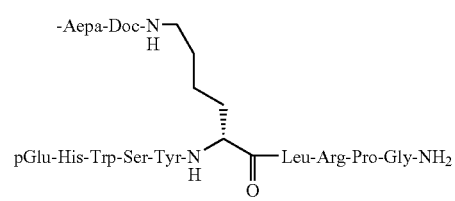
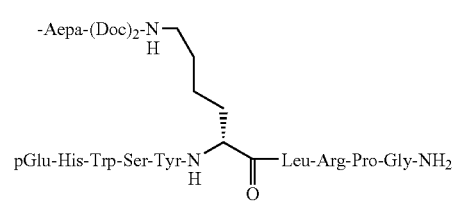
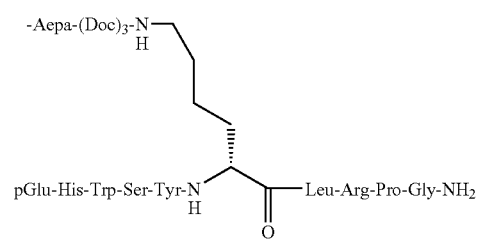
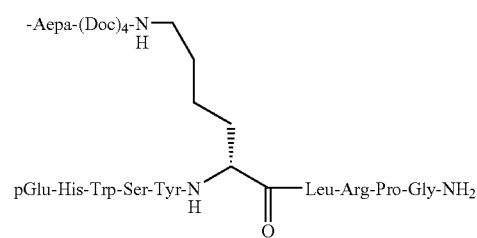
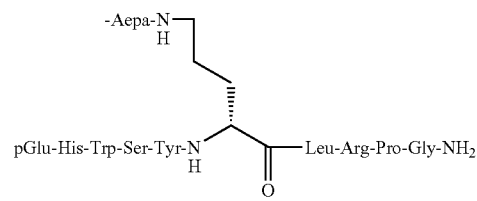
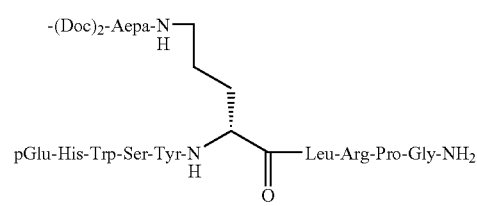
TABLE D-continued
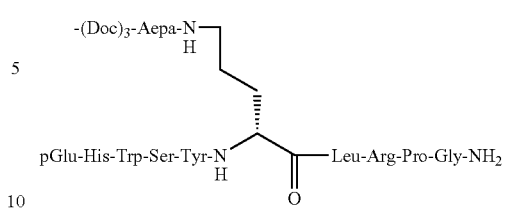
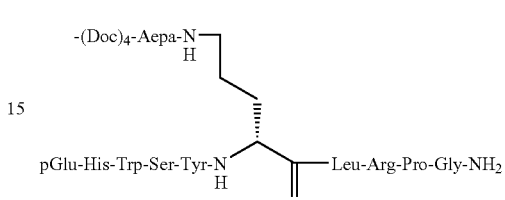
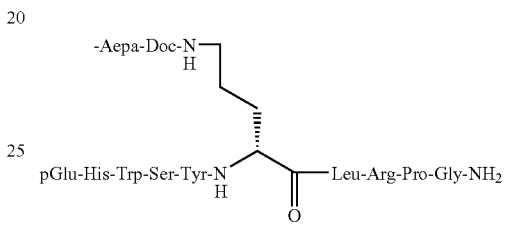
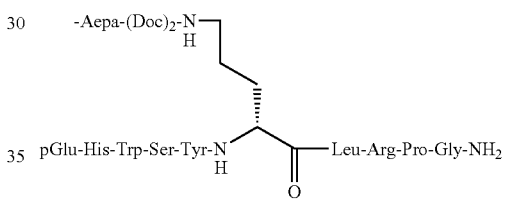
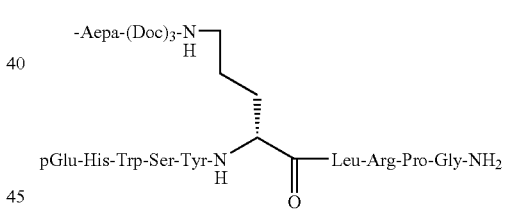
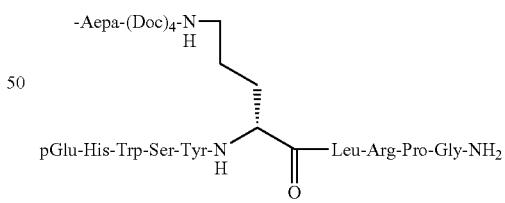
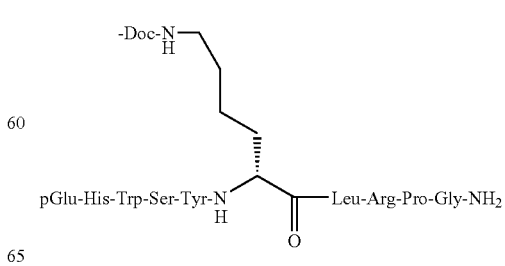

TABLE D-continued
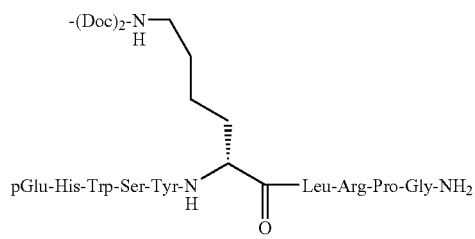
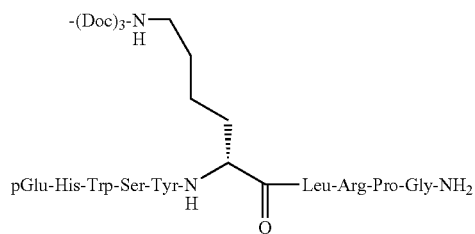
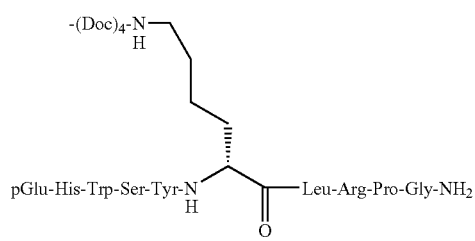
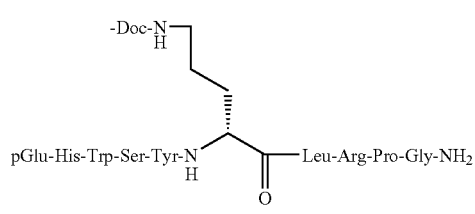
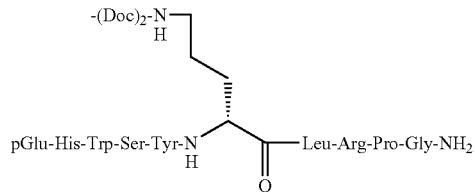
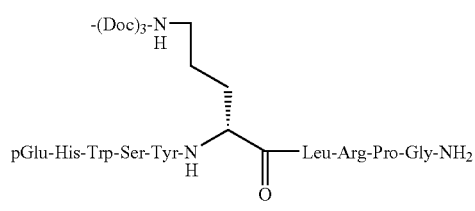
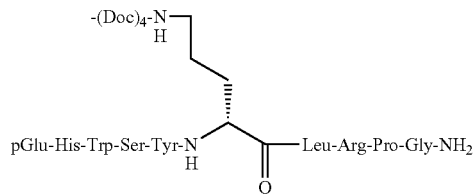
TABLE D-continued
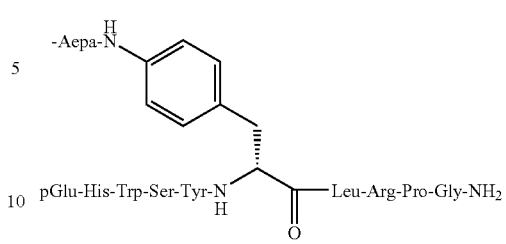
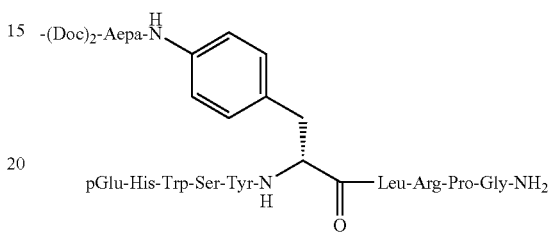
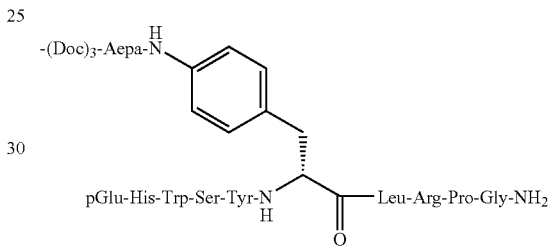
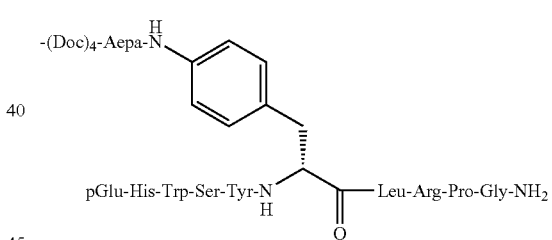
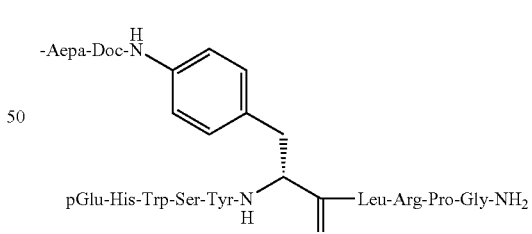
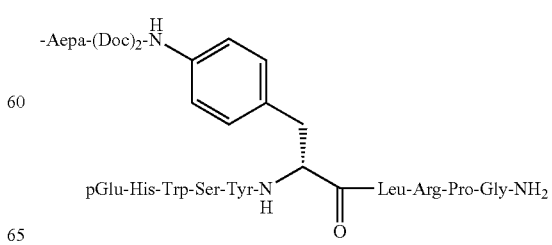

TABLE D-continued

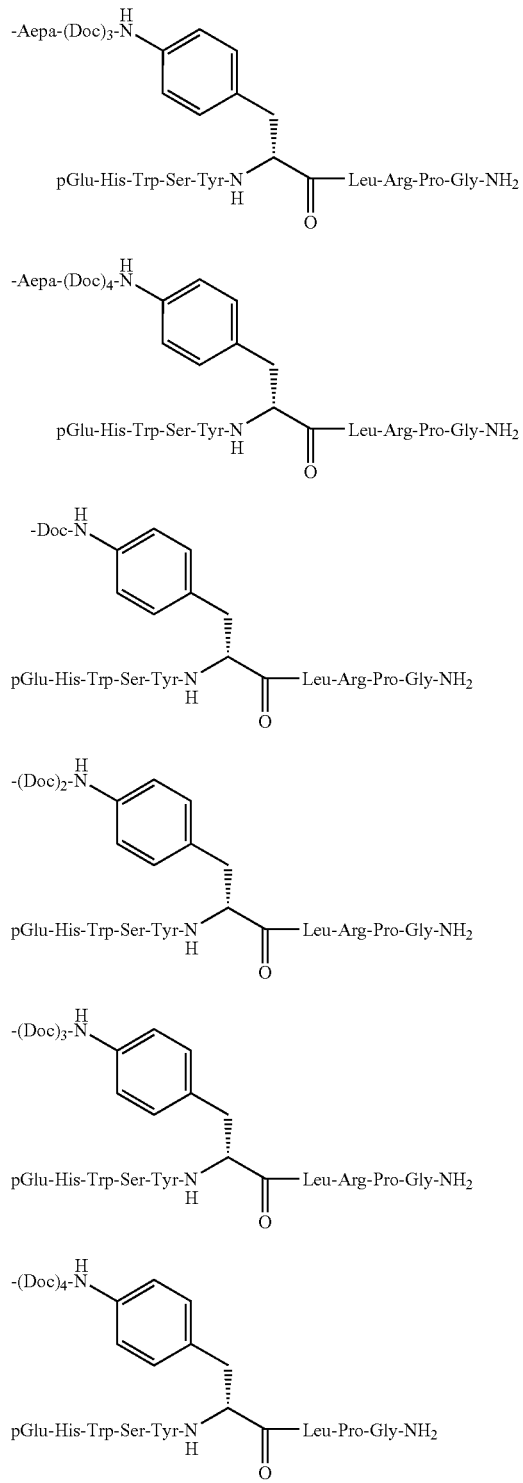

-HSDGIFTDSYSRYRKQMAVKKYLAAVL(βAla)KRYKQRVKNK-NH₂
-HSDGIFTDSYSRYRKQMAVKKYLAAVL(Ava)KRYKQRVKNK-NH₂
-HSDGIFTDSYSRYRKQMAVKKYLAAVLGKRYKQR(A₆c)KNK-NH₂
-HSDGIFTDSYSRYRKQMA(A₅c)KKYLAAVLGKRYKQRVKNK-NH₂
-(Aepa)HSDGIFTDSYSRYRKQMAVKKYLAAVL(βAla)KRYKQRVKNK-NH₂
-(Aepa)HSDGIFTDSYSRYRKQMAVKKYLAAVL(Ava)KRYKQRVKNK-NH₂

TABLE D-continued

-(Aepa)HSDGIFTDSYSRYRKQMAVKKYLAAVLGKRYKQR(A₆c)KNK-NH₂
-(Aepa)HSDGIFTDSYSRYRKQMA(A₅c)KKYLAAVLGKRYKQRVKNK-NH₂
-Aepa-Doc-Caeg-cyclo(DCys-3Pal-DTrp-Lys-DCys)-Thr(Bzl)-Tyr-NH₂
-Aepa-(Doc)₂-Caeg-cyclo(DCys-3Pal-DTrp-Lys-DCys)-Thr(Bzl)-Tyr-NH₂
-Aepa-(Doc)₃-Caeg-cyclo(DCys-3Pal-DTrp-Lys-DCys)-Thr(Bzl)-Tyr-NH₂
-Aepa-(Doc)₄-Caeg-cyclo(DCys-3Pal-DTrp-Lys-DCys)-Thr(Bzl)-Tyr-NH₂
-(Doc)₆-DPhe-cyclo(Cys-3lTyr-DTrp-Lys-Val-Cys)-Thr-NH₂
-(Doc)₄-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂
-Aepa-D Phe-cyclo(Cys-3lTyr-DTrp-Lys-Val-Cys)-Thr-NH₂
-(Doc)₄-Aepa-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂
-Aepa-DPhe-cyclo(Cys-3lTyr-DTrp-Lys-Val-Cys)-Thr-NH₂
-Doc-Aepa-DPhe-cyclo(Cys-3lTyr-DTrp-Lys-Val-Cys)-Thr-NH₂
-(Doc)₂-Aepa-DPhe-cyclo(Cys-3lTyr-DTrp-Lys-Val-Cys)-Thr-NH₂
-(Doc)₃-Aepa-DPhe-cyclo(Cys-3lTyr-DTrp-Lys-Val-Cys)-Thr-NH₂
-(Doc)₅-Aepa-DPhe-cyclo(Cys-3lTyr-DTrp-Lys-Val-Cys)-Thr-NH₂
-(Doc)₆-Aepa-DPhe-cyclo(Cys-3lTyr-DTrp-Lys-Val-Cys)-Thr-NH₂
-(Aepa)₂-DPhe-cyclo(Cys-3lTyr-DTrp-Lys-Val-Cys)-Thr-NH₂
-Doc-DPhe-cyclo(Cys-3lTyr-DTrp-Lys-Val-Cys)-Thr-NH₂
-(Doc)₂-DPhe-cyclo(Cys-3lTyr-DTrp-Lys-Val-Cys)-Thr-NH₂
-(Doc)₃-DPhe-cyclo(Cys-3lTyr-DTrp-Lys-Val-Cys)-Thr-NH₂
-(Doc)₄-DPhe-cyclo(Cys-3lTyr-DTrp-Lys-Val-Cys)-Thr-NH₂
-(Doc)₅-DPhe-cyclo(Cys-3lTyr-DTrp-Lys-Val-Cys)-Thr-NH₂
-(Doc)₆-DPhe-cyclo(Cys-3lTyr-DTrp-Lys-Val-Cys)-Thr-NH₂
-Aepa-Doc-D Phe-cyclo(Cys-3lTyr-DTrp-Lys-Val-Cys)-Thr-NH₂
-Aepa-(Doc)₂-DPhe-cyclo(Cys-3lTyr-DTrp-Lys-Val-Cys)-Thr-NH₂
-Aepa-(Doc)₃-DPhe-cyclo(Cys-3lTyr-DTrp-Lys-Val-Cys)-Thr-NH₂
-Aepa-(Doc)₄-DPhe-cyclo(Cys-3lTyr-DTrp-Lys-Val-Cys)-Thr-NH₂
-Doc-Aepa-DPhe-cyclo(Cys-3lTyr-DTrp-Lys-Thr-Cys)-Thr-NH₂
-(Doc)₂-Aepa-DPhe-cyclo(Cys-3lTyr-DTrp-Lys-Thr-Cys)-Thr-NH₂
-(Doc)₃-Aepa-DPhe-cyclo(Cys-3lTyr-DTrp-Lys-Thr-Cys)-Thr-NH₂
-(Doc)₅-Aepa-DPhe-cyclo(Cys-3lTyr-DTrp-Lys-Thr-Cys)-Thr-NH₂
-(Doc)₆-Aepa-DPhe-cyclo(Cys-3lTyr-DTrp-Lys-Thr-Cys)-Thr-NH₂
-(Aepa)₂-DPhe-cyclo(Cys-3lTyr-DTrp-Lys-Thr-Cys)-Thr-NH₂
-Doc-DPhe-cyclo(Cys-3lTyr-DTrp-Lys-Thr-Cys)-Thr-NH₂
-(Doc)₂-DPhe-cyclo(Cys-3lTyr-DTrp-Lys-Thr-Cys)-Thr-NH₂
-(Doc)₃-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-(Doc)₅-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂
-Aepa-Doc-DPhe-cyclo(Cys-3lTyr-DTrp-Lys-Thr-Cys)-Thr-NH₂
-Aepa-(Doc)₂-DPhe-cyclo(Cys-3lTyr-DTrp-Lys-Thr-Cys)-Thr-NH₂
-Aepa-(Doc)₃-DPhe-cyclo(Cys-3lTyr-DTrp-Lys-Thr-Cys)-Thr-NH₂
-Aepa-(Doc)₄-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-DPhe-cyclo(Cys-3lTyr-DTrp-Lys-Thr-Cys)-Thr-NH₂
-Aepa-DPhe-cyclo(Cys-3lTyr-DTrp-Lys-Thr-Cys)-Thr-NH₂
-(Doc)₄-Aepa-DPhe-cyclo(Cys-3lTyr-DTrp-Lys-Thr-Cys)-Thr-NH₂
-DPhe-cyclo(Cys-3lTyr-DTrp-Lys-Thr-Cys)-Thr-NH₂
-Aepa-DPhe-cyclo(Cys-3lTyr-DTrp-Lys-Thr-Cys)-Th r-NH₂
-Doc-Aepa-D Phe-cyclo(Cys-3lTyr-DTrp-Lys-Abu-Cys)-Thr-NH₂
-(Doc)₂-Aepa-DPhe-cyclo(Cys-3lTyr-DTrp-Lys-Abu-Cys)-Thr-NH₂
-(Doc)₃-Aepa-DPhe-cyclo(Cys-3lTyr-DTrp-Lys-Abu-Cys)-Thr-NH₂
-(Doc)₅-Aepa-DPhe-cyclo(Cys-3lTyr-DTrp-Lys-Abu-Cys)-Thr-NH₂
-(Doc)₆-Aepa-DPhe-cyclo(Cys-3lTyr-DTrp-Lys-Abu-Cys)-Thr-NH₂
-(Aepa)₂-DPhe-cyclo(Cys-3lTyr-DTrp-Lys-Abu-Cys)-Thr-NH₂
-Doc-DPhe-cyclo(Cys-3lTyr-DTrp-Lys-Abu-Cys)-Thr-NH₂
-(Doc)₂-DPhe-cyclo(Cys-3lTyr-DTrp-Lys-Abu-Cys)-Thr-NH₂
-(Doc)₃-DPhe-cyclo(Cys-3lTyr-DTrp-Lys-Abu-Cys)-Thr-NH₂
-(Doc)₄-DPhe-cyclo(Cys-3lTyr-DTrp-Lys-Abu-Cys)-Th r-NH₂
-(Doc)₅-DPhe-cyclo(Cys-3lTyr-DTrp-Lys-Abu-Cys)-Thr-NH₂
-(Doc)₆-DPhe-cyclo(Cys-3lTyr-DTrp-Lys-Abu-Cys)-Thr-NH₂
-Aepa-Doc-DPhe-cyclo(Cys-3lTyr-DTrp-Lys-Abu-Cys)-Thr-NH₂
-Aepa-(Doc)₂-DPhe-cyclo(Cys-3lTyr-DTrp-Lys-Abu-Cys)-Thr-NH₂
-Aepa-(Doc)₃-DPhe-cyclo(Cys-3lTyr-DTrp-Lys-Abu-Cys)-Thr-NH₂
-Aepa-(Doc)₄-DPhe-cyclo(Cys-3lTyr-DTrp-Lys-Abu-Cys)-Thr-NH₂
-(Doc)₆-DPhe-cyclo(Cys-3lTyr-DTrp-Lys-Abu-Cys)-Thr-NH₂
-(Doc)₄-DPhe-cyclo(Cys-3lTyr-DTrp-Lys-Abu-Cys)-Thr-NH₂
-DPhe-cyclo(Cys-3lTyr-DTrp-Lys-Abu-Cys)-Thr-NH₂
-Aepa-DPhe-cyclo(Cys-3lTyr-DTrp-Lys-Abu-Cys)-Thr-NH₂
-(Doc)₄-DPhe-cyclo(Cys-3lTyr-DTrp-Lys-Abu-Cys)-Thr-NH₂
-Aepa-DPhe-cyclo(Cys-3lTyr-DTrp-Lys-Abu-Cys)-Thr-NH₂
-DPhe-cyclo(Cys-Tyr-DTrp-Lys-Abu-Cys)-Thr-NH₂
-Aepa-DPhe-cyclo(Cys-Tyr-DTrp-Lys-Abu-Cys)-Thr-NH₂
-(Doc)₄-DPhe-cyclo(Cys-Tyr-DTrp-Lys-Abu-Cys)-Thr-NH₂

TABLE D-continued

-(Doc)₆-DPhe-cyclo(Cys-Tyr-DTrp-Lys-Abu-Cys)-Thr-NH₂
-(Doc)₄-Aepa-DPhe-cyclo(Cys-Tyr-DTrp-Lys-Abu-Cys)-Thr-NH₂
-(Aepa)₂-(Doc)₂-DPhe-cyclo(Cys-Tyr-DTrp-Lys-Abu-Cys)-Thr-NH₂
-Aepa-Doc-Aepa-DPhe-cyclo(Cys-Tyr-DTrp-Lys-Abu-Cys)-Thr-NH₂
-(Aepa)₂-DPhe-cyclo(Cys-Tyr-DTrp-Lys-Abu-Cys)-Thr-NH₂
-(Doc)₂-DPhe-cyclo(Cys-Tyr-DTrp-Lys-Abu-Cys)-Thr-NH₂
-(Aepa)₂-(Doc)₄-DPhe-cyclo(Cys-Tyr-DTrp-Lys-Abu-Cys)-Thr-NH₂
-Aepa-(Doc)₆-DPhe-cyclo(Cys-Tyr-DTrp-Lys-Abu-Cys)-Thr-NH₂
-(Doc)₂-Aepa-DPhe-cyclo(Cys-Tyr-DTrp-Lys-Abu-Cys)-Thr-NH₂
-Aepa-(Doc)₄-Aepa-DPhe-cyclo(Cys-Tyr-DTrp-Lys-Abu-Cys)-Thr-NH₂
-(Doc)₆-Aepa-DPhe-cyclo(Cys-Tyr-DTrp-Lys-Abu-Cys)-Thr-NH₂
-(Doc)₂-(Aepa)₂-DPhe-cyclo(Cys-Tyr-DTrp-Lys-Abu-Cys)-Thr-NH₂
-Doc-Aepa-DPhe-cyclo(Cys-Tyr-DTrp-Lys-Abu-Cys)-Thr-NH₂
-(Doc)₂-Aepa-DPhe-cyclo(Cys-Tyr-DTrp-Lys-Abu-Cys)-Thr-NH₂
-(Doc)₃-Aepa-DPhe-cyclo(Cys-Tyr-DTrp-Lys-Abu-Cys)-Thr-NH₂
-(Doc)₅-Aepa-DPhe-cyclo(Cys-Tyr-DTrp-Lys-Abu-Cys)-Thr-NH₂
-(Doc)₆-Aepa-DPhe-cyclo(Cys-Tyr-DTrp-Lys-Abu-Cys)-Thr-NH₂
-(Aepa)₂-DPhe-cyclo(Cys-Tyr-DTrp-Lys-Abu-Cys)-Thr-NH₂
-Doc-DPhe-cyclo(Cys-Tyr-DTrp-Lys-Abu-Cys)-Thr-NH₂
-(Doc)₂-DPhe-cyclo(Cys-Tyr-DTrp-Lys-Abu-Cys)-Thr-NH₂
-(Doc)₃-DPhe-cyclo(Cys-Tyr-DTrp-Lys-Abu-Cys)-Thr-NH₂
-(Doc)₄-DPhe-cyclo(Cys-Tyr-DTrp-Lys-Abu-Cys)-Thr-NH₂
-(Doc)₅-DPhe-cyclo(Cys-Tyr-DTrp-Lys-Abu-Cys)-Thr-NH₂
-(Doc)₆-DPhe-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-Doc-Aepa-Lys-DTyr-DTyr-cyclo(Cys-Tyr-DTrp-Lys-Abu-Cys)-Thr-NH₂
-(Doc)₂-Aepa-Lys-DTyr-DTyr-cyclo(Cys-Tyr-DTrp-Lys-Abu-Cys)-Thr-NH₂
-(Doc)₃-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₅-Aepa-Lys-DTyr-DTyr-cyclo(Cys-Tyr-DTrp-Lys-Abu-Cys)-Thr-NH₂
-(Doc)₆-Aepa-Lys-DTyr-DTyr-cyclo(Cys-Tyr-DTrp-Lys-Abu-Cys)-Thr-NH₂
-(Aepa)₂-Lys-DTyr-DTyr-cyclo(Cys-Tyr-DTrp-Lys-Abu-Cys)-Thr-NH₂
-Doc-Lys-DTyr-DTyr-cyclo(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-(Doc)₃-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₅-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-Aepa-Doc-Lys-DTyr-DTyr-cyclo(Cys-Tyr-DTrp-Lys-Abu-Cys)-Thr-NH₂
-Aepa-(Doc)₂-Lys-DTyr-DTyr-cyclo(Cys-Tyr-DTrp-Lys-Abu-Cys)-Thr-NH₂
-Aepa-(Doc)₃-Lys-DTyr-DTyr-cyclo(Cys-Tyr-DTrp-Lys-Abu-Cys)-Thr-NH₂
-Aepa-(Doc)₄-Lys-DTyr-DTyr-cyclo(Cys-Tyr-DTrp-Lys-Abu-Cys)-Thr-NH₂
-Aepa-Doc-DPhe-cyclo(Cys-Tyr-DTrp-Lys-Abu-Cys)-Thr-NH₂
-Aepa-(Doc)₂-DPhe-cyclo(Cys-Tyr-DTrp-Lys-Abu-Cys)-Thr-NH₂
-Aepa-(Doc)₃-DPhe-cyclo(Cys-Tyr-DTrp-Lys-Abu-Cys)-Thr-NH₂
-Aepa-(Doc)₄-DPhe-cyclo(Cys-Tyr-DTrp-Lys-Abu-Cys)-Thr-NH₂

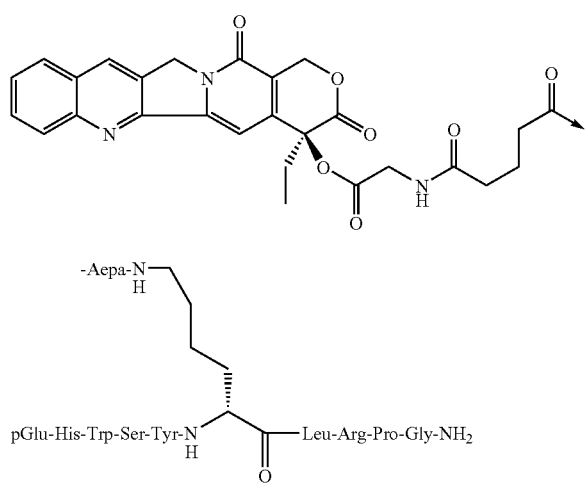

TABLE D-continued
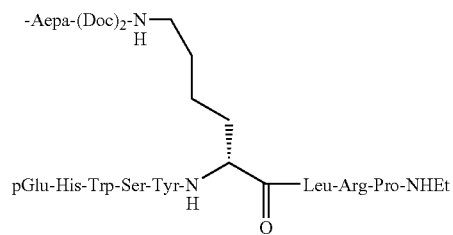
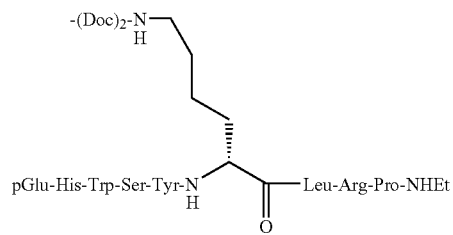
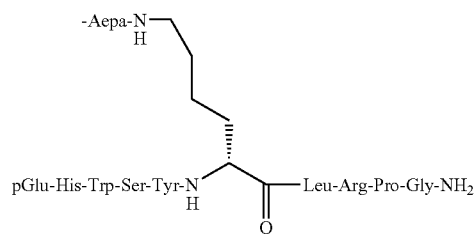
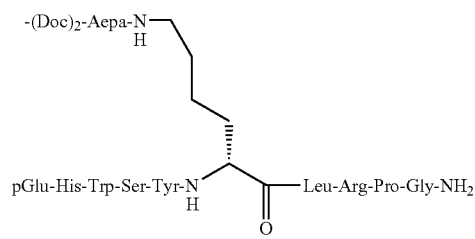
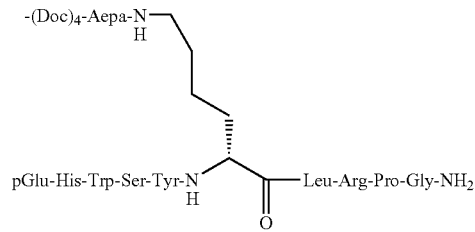
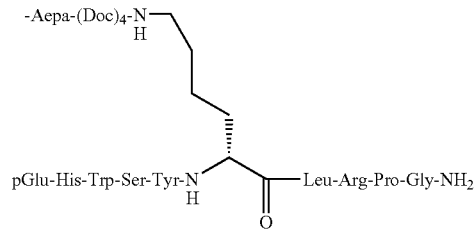
TABLE D-continued
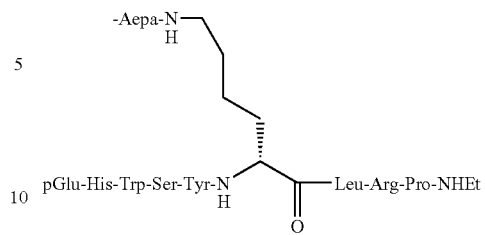
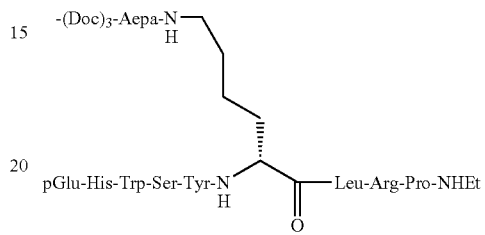
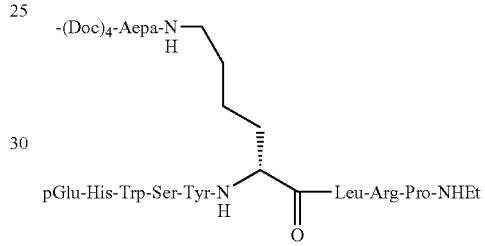
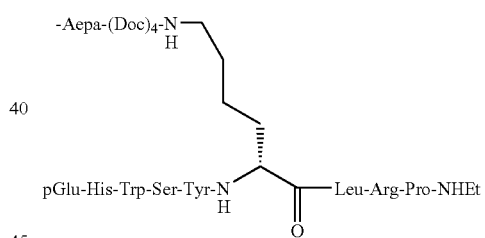
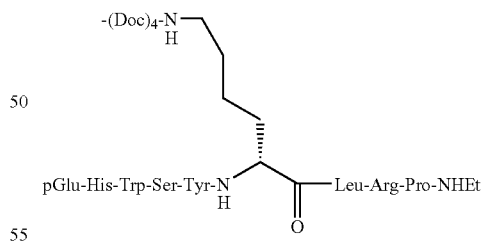
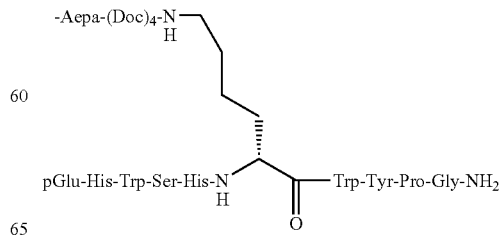

141
TABLE D-continued

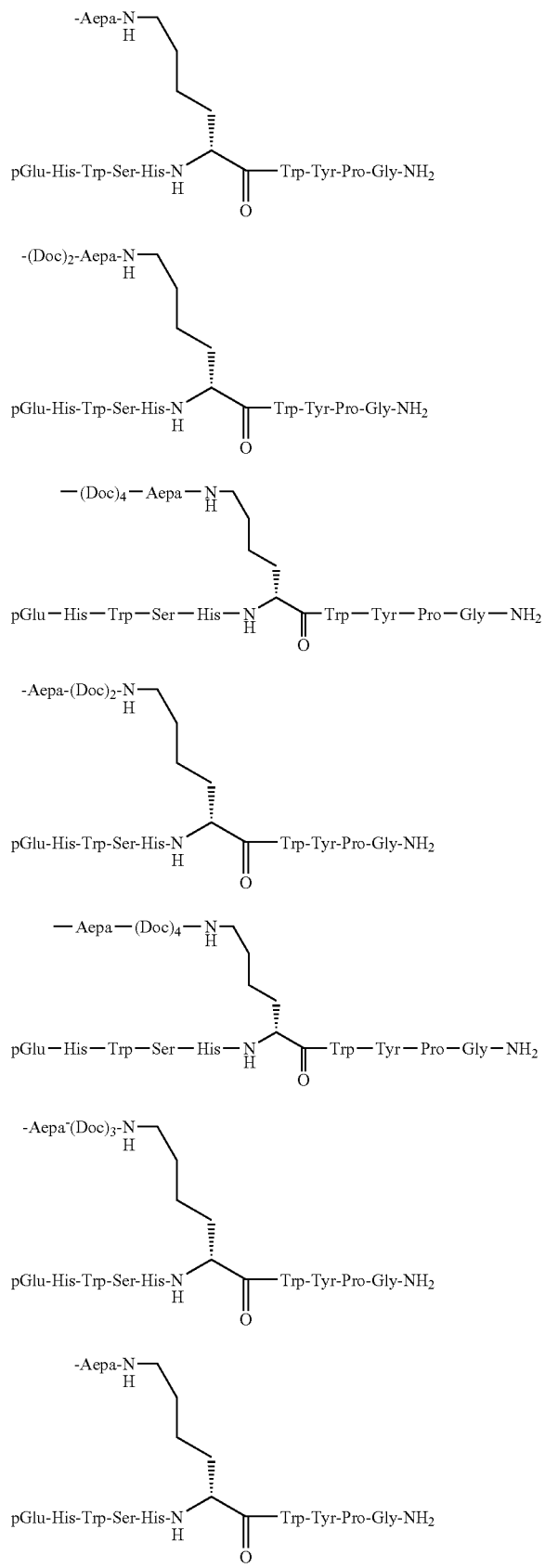

142
TABLE D-continued

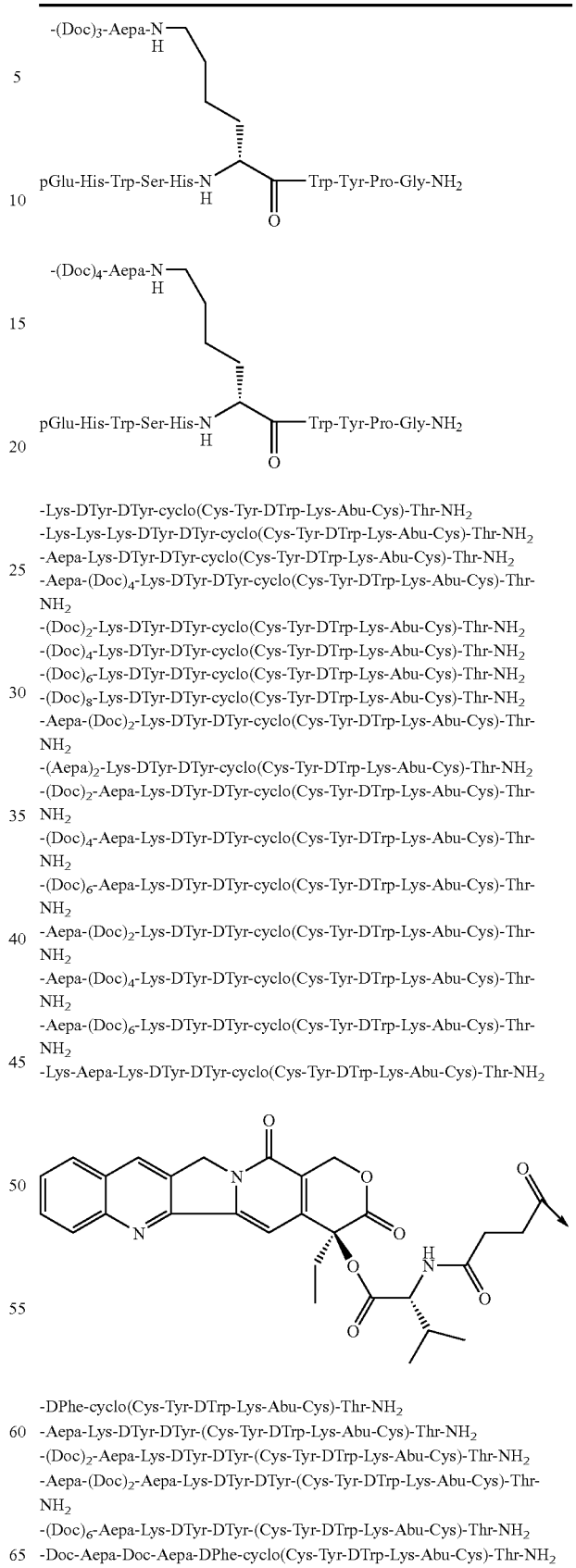

-Lys-DTyr-DTyr-cyclo(Cys-Tyr-DTrp-Lys-Abu-Cys)-Thr-NH$_2$
-Lys-Lys-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-Aepa-(Doc)$_4$-Lys-DTyr-DTyr-cyclo(Cys-Tyr-DTrp-Lys-Abu-Cys)-Thr-NH$_2$
-(Doc)$_2$-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-(Doc)$_8$-Lys-DTyr-DTyr-cyclo(Cys-Tyr-DTrp-Lys-Abu-Cys)-Thr-NH$_2$
-Aepa-(Doc)$_2$-Lys-DTyr-DTyr-cyclo(Cys-Tyr-DTrp-Lys-Abu-Cys)-Thr-NH$_2$
-(Aepa)$_2$-Lys-DTyr-DTyr-cyclo(Cys-Tyr-DTrp-Lys-Abu-Cys)-Thr-NH$_2$
-(Doc)$_2$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_6$-Aepa-Lys-DTyr-DTyr-cyclo(Cys-Tyr-DTrp-Lys-Abu-Cys)-Thr-NH$_2$
-Aepa-(Doc)$_2$-Lys-DTyr-DTyr-cyclo(Cys-Tyr-DTrp-Lys-Abu-Cys)-Thr-NH$_2$
-Aepa-(Doc)$_4$-Lys-DTyr-DTyr-cyclo(Cys-Tyr-DTrp-Lys-Abu-Cys)-Thr-NH$_2$
-Aepa-(Doc)$_6$-Lys-DTyr-DTyr-cyclo(Cys-Tyr-DTrp-Lys-Abu-Cys)-Thr-NH$_2$
-Lys-Aepa-Lys-DTyr-DTyr-cyclo(Cys-Tyr-DTrp-Lys-Abu-Cys)-Thr-NH$_2$ -DPhe-cyclo(Cys-Tyr-DTrp-Lys-Abu-Cys)-Thr-NH$_2$
-Aepa-Lys-DTyr-DTyr-(Cys-Tyr-DTrp-Lys-Abu-Cys)-Thr-NH$_2$
-(Doc)$_2$-Aepa-Lys-DTyr-DTyr-(Cys-Tyr-DTrp-Lys-Abu-Cys)-Thr-NH$_2$
-Aepa-(Doc)$_2$-Aepa-Lys-DTyr-DTyr-(Cys-Tyr-DTrp-Lys-Abu-Cys)-Thr-NH$_2$
-(Doc)$_6$-Aepa-Lys-DTyr-DTyr-(Cys-Tyr-DTrp-Lys-Abu-Cys)-Thr-NH$_2$
-Doc-Aepa-Doc-Aepa-DPhe-cyclo(Cys-Tyr-DTrp-Lys-Abu-Cys)-Thr-NH$_2$

TABLE D-continued

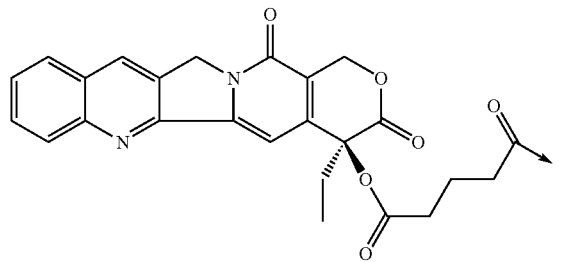

-(Doc)₄-Lys-DTyr-DTyr-cyclo(Cys-Tyr-DTrp-Lys-Abu-Cys)-Thr-NH₂
-Doc-Aepa-Lys-DTyr-DTyr-(Cys-Tyr-DTrp-Lys-Abu-Cys)-Thr-NH₂
-(Doc)₂-Aepa-Lys-DTyr-DTyr-(Cys-Tyr-DTrp-Lys-Abu-Cys)-Thr-NH₂
-(Doc)₃-Aepa-Lys-DTyr-DTyr-(Cys-Tyr-DTrp-Lys-Abu-Cys)-Thr-NH₂
-(Doc)₄-Aepa-Lys-DTyr-DTyr-(Cys-Tyr-DTrp-Lys-Abu-Cys)-Thr-NH₂
-Aepa-Doc-Aepa-Lys-DTyr-DTyr-(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-Doc-Lys-DTyr-DTyr-cyclo(Cys-Tyr-DTrp-Lys-Abu-Cys)-Thr-NH₂

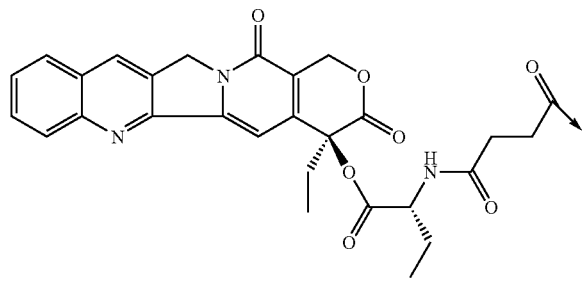

-(Doc)₄-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂

TABLE E

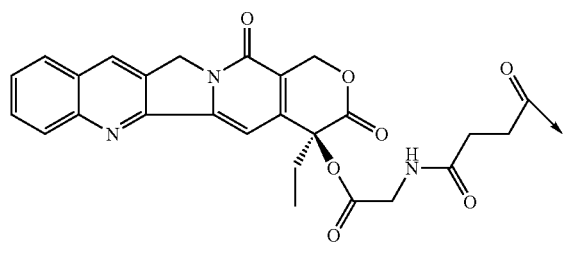 [SMILES: CC[C@@]1(OC(=O)CNC(=O)CCC=O)C(=O)OCc2c1cc1n(c2=O)Cc2cc3ccccc3nc2-1]

-(Doc)₆-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-(Doc)₆-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-Doc-Aepa-Caeg-cyclo(DCys-3Pal-DTrp-Lys-DCys)-Thr(Bzl)-Tyr-NH₂
-(Doc)₂-Aepa-Caeg-cyclo(DCys-3Pal-DTrp-Lys-DCys)-Thr(Bzl)-Tyr-NH₂
-(Doc)₃-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-(Doc)₅-Aepa-Caeg-cyclo(DCys-3Pal-DTrp-Lys-DCys)-Thr(Bzl)-Tyr-NH₂
-(Doc)₆-Aepa-Caeg-cyclo(DCys-3Pal-DTrp-Lys-DCys)-Thr(Bzl)-Tyr-NH₂
-(Aepa)₂-Caeg-cyclo(DCys-3Pal-DTrp-Lys-DCys)-Thr(Bzl)-Tyr-NH₂
-Doc-Caeg-cyclo(DCys-3Pal-DTrp-Lys-DCys)-Thr(Bzl)-Tyr-NH₂
-(Doc)₂-Caeg-cyclo(DCys-3Pal-DTrp-Lys-DCys)-Thr(Bzl)-Tyr-NH₂
-(Doc)₃-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)s-Caeg-cyclo(DCys-3Pal-DTrp-Lys-DCys)-Thr(Bzl)-Tyr-NH₂
-(Doc)s-Caeg-cyclo(DCys-3Pal-DTrp-Lys-DCys)-Thr(Bzl)-Tyr-NH₂
-(Aepa)₂-(Doc)₂-DPhe-cyclo(Cys-Tyr-DTrp-Lys-Abu-Cys)-Thr-NH₂
-Aepa-Doc-Aepa-DPhe-cyclo(Cys-Tyr-DTrp-Lys-Abu-Cys)-Thr-NH₂

TABLE E-continued

-(Aepa)₂-DPhe-cyclo(Cys-Tyr-DTrp-Lys-Abu-Cys)-Thr-NH₂
-Doc-Aepa-Doc-Aepa-DPhe-cyclo(Cys-Tyr-DTrp-Lys-Abu-Cys)-Thr-NH₂
-(Doc)₂-DPhe-cyclo(Cys-Tyr-DTrp-Lys-Abu-Cys)-Thr-NH₂
-(Aepa)₂-(Doc)₄-DPhe-cyclo(Cys-Tyr-DTrp-Lys-Abu-Cys)-Thr-NH₂
-Aepa-(Doc)₆-DPhe-cyclo(Cys-Tyr-DTrp-Lys-Abu-Cys)-Thr-NH₂
-(Doc)₂-Aepa-DPhe-cyclo(Cys-Tyr-DTrp-Lys-Abu-Cys)-Thr-NH₂
-Aepa-(Doc)₄-Aepa-DPhe-cyclo(Cys-Tyr-DTrp-Lys-Abu-Cys)-Thr-NH₂
-(Doc)₆-Aepa-DPhe-cyclo(Cys-Tyr-DTrp-Lys-Abu-Cys)-Thr-NH₂
-(Doc)₂-(Aepa)₂-DPhe-cyclo(Cys-Tyr-DTrp-Lys-Abu-Cys)-Thr-NH₂
-HSDAVFTDNYTRLRKQ(Nle)AVKKYLNSILN-NH₂
-HSDAVFTDNYTRLRKQMAVKKYLNSILN-NH₂(SEQ ID NO: 7)
-HSDAVFTDNYTRLRKQMAVKKFLNSILN-NH₂(SEQ ID NO: 6)
-HSDAVFTDNYTRLRKQMAVKKALNSILN-NH₂(SEQ ID NO: 5)
-HSDAVFTDNYTRLRKQMAVKKLLNSILN-NH₂(SEQ ID NO: 4)
-(Aepa)HSDAVFTDNYTRLRKQ(Nle)AVKKYLNSILN-NH₂
-(Aepa)HSDAVFTDNYTRLRKQMAVKKYLNSILN-NH₂
-(Aepa)HSDAVFTDNYTRLRKQMAVKKFLNSILN-NH₂
-(Aepa)HSDAVFTDNYTRLRKQMAVKKALNSILN-NH₂
-(Aepa)HSDAVFTDNYTRLRKQMAVKKLLNSILN-NH₂

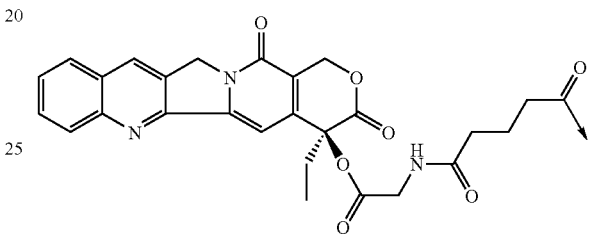

-Aepa-(Doc)₄-Lys-DTyr-DTyr-cyclo(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-(Doc)₈-Lys-DTyr-DTyr-cyclo(Cys-Tyr-DTrp-Lys-Abu-Cys)-Thr-NH₂
-Aepa-(Doc)₂-Lys-DTyr-DTyr-cyclo(Cys-Tyr-DTrp-Lys-Abu-Cys)-Thr-NH₂
-(Aepa)₂-Lys-DTyr-DTyr-cyclo(Cys-Tyr-DTrp-Lys-Abu-Cys)-Thr-NH₂
-(Doc)₂-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₆-Aepa-Lys-DTyr-DTyr-cyclo(Cys-Tyr-DTrp-Lys-Abu-Cys)-Thr-NH₂
-Aepa-(Doc)₂-Lys-DTyr-DTyr-cyclo(Cys-Tyr-DTrp-Lys-Abu-Cys)-Thr-NH₂
-Aepa-(Doc)₄-Lys-DTyr-DTyr-cyclo(Cys-Tyr-DTrp-Lys-Abu-Cys)-Thr-NH₂
-Aepa-(Doc)₆-Lys-DTyr-DTyr-cyclo(Cys-Tyr-DTrp-Lys-Abu-Cys)-Thr-NH₂
-Lys-Aepa-Lys-DTyr-DTyr-cyclo(Cys-Tyr-DTrp-Lys-Abu-Cys)-Thr-NH₂

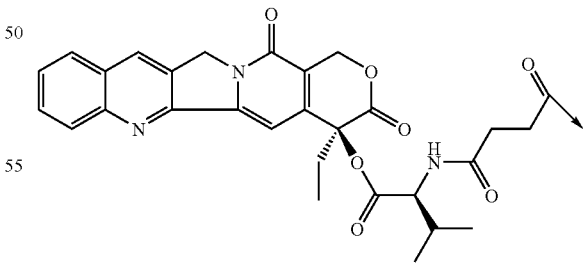

-Aepa-Lys-DTyr-DTyr-cyclo(Cys-Tyr-DTrp-Lys-Abu-Cys)-Thr-NH₂
-(Doc)₂-Aepa-Lys-DTyr-DTyr-cyclo(Cys-Tyr-DTrp-Lys-Abu-Cys)-Thr-NH₂
-Aepa-(Doc)₂-Aepa-Lys-DTyr-DTyr-cyclo(Cys-Tyr-DTrp-Lys-Abu-Cys)-Thr-NH₂
-(Doc)₆-Aepa-Lys-DTyr-DTyr-cyclo(Cys-Tyr-DTrp-Lys-Abu-Cys)-Thr-NH₂

TABLE E-continued

[Camptothecin-like structure with pendant linker ending in ketone]

-(Doc)$_2$-Aepa-Lys-DTyr-DTyr-cyclo(Cys-Tyr-DTrp-Lys-Abu-Cys)-Thr-NH$_2$
-Doc-Aepa-Lys-DTyr-DTyr-cyclo(Cys-Tyr-DTrp-Lys-Abu-Cys)-Thr-NH$_2$
-(Doc)$_3$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-Doc-Aepa-Lys-DTyr-DTyr-cyclo(Cys-Tyr-DTrp-Lys-Abu-Cys)-Thr-NH$_2$

[Daunorubicin-like anthracycline structure with glycine linker]

-Doc-DPhe-Gln-Trp-Ala-Val-βAla-His-Leu-Leu-NH$_2$
-Doc-DPhe-Gln-Trp-Ala-Val-βAla-His-Leu-Nle-NH$_2$
-Doc-DPhe-Gln-Trp-Ala-Val-Gly-His-Leu-Leu-NH$_2$
-Doc-DAla-Gln-Trp-Ala-Val-βAla-His-Phe-Nle-NH$_2$
-Doc-DPhe-Gln-Trp-Ala-Ala-βAla-His-Phe-Nle-NH$_2$
-Doc-Aepa-DPhe-Gln-Trp-Ala-Val-βAla-His-Leu-Leu-NH$_2$
-Doc-Aepa-DPhe-Gln-Trp-Ala-Val-βAla-His-Leu-Nle-NH$_2$
-Doc-Aepa-DPhe-Gln-Trp-Ala-Val-Gly-His-Leu-Leu-NH$_2$
-Doc-Aepa-DAla-Gln-Trp-Ala-Val-βAla-His-Phe-Nle-NH$_2$
-Doc-Aepa-DPhe-Gln-Trp-Ala-Ala-βAla-His-Phe-Nle-NH$_2$
-Aepa-(Doc)$_3$-DPhe-Gln-Trp-Ala-Val-βAla-His-Leu-Leu-NH$_2$
-Aepa-(Doc)$_3$-DPhe-Gln-Trp-Ala-Val-βAla-His-Leu-Nle-NH$_2$
-Aepa-(Doc)$_3$-DPhe-Gln-Trp-Ala-Val-Gly-His-Leu-Leu-NH$_2$
-Aepa-(Doc)$_3$-DAla-Gln-Trp-Ala-Val-βAla-His-Phe-Nle-NH$_2$
-Aepa-(Doc)$_3$-DPhe-Gln-Trp-Ala-Ala-βAla-His-Phe-Nle-NH$_2$
-(Doc)$_3$-Aepa-Gln-Trp-Ala-Val-βAla-His-Leu-Leu-NH$_2$
-(Doc)$_3$-Aepa-Gln-Trp-Ala-Val-βAla-His-Leu-Nle-NH$_2$
-(Doc)$_3$-Aepa-Gln-Trp-Ala-Val-Gly-His-Leu-Leu-NH$_2$
-(Doc)$_3$-Aepa-Gln-Trp-Ala-Val-βAla-His-Phe-Nle-NH$_2$
-(Doc)$_3$-Aepa-Gln-Trp-Ala-Ala-βAla-His-Phe-Nle-NH$_2$
-Aepa-Doc-DPhe-Gln-Trp-Ala-Val-βAla-His-Leu-Leu-NH$_2$
-Aepa-Doc-DPhe-Gln-Trp-Ala-Val-βAla-His-Leu-Nle-NH$_2$
-Aepa-Doc-DPhe-Gln-Trp-Ala-Val-Gly-His-Leu-Leu-NH$_2$
-Aepa-Doc-DAla-Gln-Trp-Ala-Val-βAla-His-Phe-Nle-NH$_2$
-Aepa-Doc-DPhe-Gln-Trp-Ala-Ala-βAla-His-Phe-Nle-NH$_2$
-Aepa-(Doc)$_2$-Gln-Trp-Ala-Val-βAla-His-Leu-Leu-NH$_2$
-Aepa-(Doc)$_2$-Gln-Trp-Ala-Val-βAla-His-Leu-Nle-NH$_2$
-Aepa-(Doc)$_2$-Gln-Trp-Ala-Val-Gly-His-Leu-Leu-NH$_2$
-Aepa-(Doc)$_2$-Gln-Trp-Ala-Val-βAla-His-Phe-Nle-NH$_2$
-Aepa-(Doc)$_2$-Gln-Trp-Ala-Ala-βAla-His-Phe-Nle-NH$_2$
-Aepa-Gln-Trp-Ala-Val-βAla-His-Leu-Leu-NH$_2$
-Aepa-Gln-Trp-Ala-Val-βAla-His-Leu-Nle-NH$_2$
-Aepa-Gln-Trp-Ala-Val-Gly-His-Leu-Leu-NH$_2$
-Aepa-Gln-Trp-Ala-Val-βAla-His-Phe-Nle-NH$_2$
-Aepa-(Doc)$_2$-Gln-Trp-Ala-Val-βAla-His-Leu-Leu-NH$_2$
-Aepa-(Doc)$_2$-Gln-Trp-Ala-Val-βAla-His-Leu-Nle-NH$_2$
-Aepa-(Doc)$_2$-Gln-Trp-Ala-Val-Gly-His-Leu-Leu-NH$_2$
-Aepa-(Doc)$_2$-Gln-Trp-Ala-Val-βAla-His-Phe-Nle-NH$_2$
-Aepa-(Doc)$_2$-Gln-Trp-Ata-Ala-βAla-His-Phe-Nle-NH$_2$
-Aepa-Gln-Trp-Ala-Val-βAla-His-Leu-Leu-NH$_2$
-Aepa-Gln-Trp-Ala-Val-βAla-His-Leu-Nle-NH$_2$
-Aepa-Gln-Trp-Ala-Val-Gly-His-Leu-Leu-NH$_2$
-Aepa-Gln-Trp-Ala-Val-βAla-His-Phe-Nle-NH$_2$ -Aepa-Gln-Trp-Ala-Ala-βAla-His-Phe-Nle-NH$_2$
-(Doc)$_2$-Gln-Trp-Ala-Val-βAla-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-Gly-His-Leu-Leu-NH$_2$
-(Doc)$_2$-Gln-Trp-Ala-Val-βAla-His-Phe-Nle-NH$_2$
-(Doc)$_2$-Gln-Trp-Ala-Ala-βAla-His-Phe-Nle-NH$_2$
-Aepa-(Doc)$_4$-Gaba-Gln-Trp-Ala-Val-βAla-His-Leu-Leu-NH$_2$
-(Doc)$_4$-Aepa-Gaba-Gln-Trp-Ala-Val-βAla-His-Leu-Leu-NH$_2$
-(Doc)$_4$-Gaba-Gln-Trp-Ala-Val-βAla-His-Leu-Leu-NH$_2$
-Aepa-(Doc)$_4$-Gaba-Gln-Trp-Ala-Val-Gly-His-Leu-Ψ(CH$_2$NH)-Leu-NH$_2$
-(Doc)$_4$-Aepa-Gaba-Gln-Trp-Ala-Val-Gly-His-Leu-Ψ(CH$_2$NH)-Leu-NH$_2$
-(Doc)$_4$-Gaba-Gln-Trp-Ala-Val-Gly-His-Leu-Ψ(CH$_2$NH)-Leu-NH$_2$
-Aepa-(Doc)$_4$-Gln-Trp-Ala-Val-Gly-His-Leu-Ψ(CH$_2$NH)-Leu-NH$_2$
-(Doc)$_4$-Aepa-Gln-Trp-Ala-Val-Gly-His-Leu-Ψ(CH$_2$NH)-Leu-NH$_2$
-(Doc)$_4$-Gln-Trp-Ala-Val-Gly-His-Leu-Ψ(CH$_2$NH)-Leu-NH$_2$
-Aepa-(Doc)$_4$-Gaba-Gln-Trp-Ala-Val-βAla-His-Leu-Nle-NH$_2$
-(Doc)$_4$-Aepa-Gaba-Gln-Trp-Ala-Val-βAla-His-Leu-Nle-NH$_2$
-(Doc)$_4$-Gaba-Gln-Trp-Ala-Val-βAla-His-Leu-Nle-NH$_2$

[Doxorubicin-like anthracycline structure with valine linker]

-Doc-DPhe-Gln-Trp-Ala-Val-βAla-His-Leu-Leu-NH$_2$
-Doc-DPhe-Gln-Trp-Ala-Val-βAla-His-Leu-Nle-NH$_2$
-Doc-DPhe-Gln-Trp-Ala-Val-Gly-His-Leu-Leu-NH$_2$
-Doc-DAla-Gln-Trp-Ala-Val-βAla-His-Phe-Nle-NH$_2$
-Doc-DPhe-Gln-Trp-Ala-Ala-βAla-His-Phe-Nle-NH$_2$
-Aepa-Gln-Trp-Ala-Ala-βAla-His-Phe-Nle-NH$_2$
-(Doc)$_2$-Gln-Trp-Ala-Val-βAla-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-Gly-His-Leu-Leu-NH$_2$
-(Doc)$_2$-Gln-Trp-Ala-Val-βAla-His-Phe-Nle-NH$_2$
-(Doc)$_2$-Gln-Trp-Ala-Ala-βAla-His-Phe-Nle-NH$_2$
-Aepa-(Doc)$_4$-DPhe-Gln-Trp-Ala-Val-βAla-His-Leu-Leu-NH$_2$
-Aepa-(Doc)$_4$-DPhe-Gln-Trp-Ala-Val-βAla-His-Leu-Nle-NH$_2$
-Aepa-(Doc)$_4$-DPhe-Gln-Trp-Ala-Val-Gly-His-Leu-Leu-NH$_2$
-Aepa-(Doc)$_4$-DAla-Gln-Trp-Ala-Val-βAla-His-Phe-Nle-NH$_2$
-Aepa-(Doc)$_4$-DPhe-Gln-Trp-Ala-Ala-βAla-His-Phe-Nle-NH$_2$
-(Doc)$_4$-Aepa-DPhe-Gln-Trp-Ala-Val-βAla-His-Leu-Leu-NH$_2$
-(Doc)$_4$-Aepa-DPhe-Gln-Trp-Ala-Val-βAla-His-Leu-Nle-NH$_2$
-(Doc)$_4$-Aepa-DPhe-Gln-Trp-Ala-Val-Gly-His-Leu-Leu-NH$_2$
-(Doc)$_4$-Aepa-DAla-Gln-Trp-Ala-Val-βAla-His-Phe-Nle-NH$_2$
-(Doc)$_4$-Aepa-DPhe-Gln-Trp-Ala-Ala-βAla-His-Phe-Nle-NH$_2$
-(Doc)$_4$-DPhe-Gln-Trp-Ala-Val-βAla-His-Leu-Leu-NH$_2$
.-(Doc)$_4$-DPhe-Gln-Trp-Ala-Val-βAla-His-Leu-Nle-NH$_2$
-(Doc)$_4$-DPhe-Gln-Trp-Ala-Val-Gly-His-Leu-Leu-NH$_2$
-(Doc)$_4$-DAla-Gln-Trp-Ala-Val-βAla-His-Phe-Nle-NH$_2$
-(Doc)$_4$-DPhe-Gln-Trp-Ala-Ala-βAla-His-Phe-Nle-NH$_2$
-Aepa-(Doc)$_4$-Gln-Trp-Ala-Val-βAla-His-Leu-Leu-NH$_2$
-Aepa-(Doc)$_4$-Gln-Trp-Ala-Val-βAla-His-Leu-Nle-NH$_2$
-Aepa-(Doc)$_4$-Gln-Trp-Ala-Val-Gly-His-Leu-Leu-NH$_2$
-Aepa-(Doc)$_4$-Gln-Trp-Ala-Val-βAla-His-Phe-Nle-NH$_2$
-Aepa-(Doc)$_4$-Gln-Trp-Ala-Ala-βAla-His-Phe-Nle-NH$_2$
-(Doc)$_4$-Aepa-Gln-Trp-Ala-Val-βAla-His-Leu-Leu-NH$_2$
-(Doc)$_4$-Aepa-Gln-Trp-Ala-Val-βAla-His-Leu-Nle-NH$_2$
-(Doc)$_4$-Aepa-Gln-Trp-Ala-Val-Gly-His-Leu-Leu-NH$_2$
-(Doc)$_4$-Aepa-Gln-Trp-Ala-Val-βAla-His-Phe-Nle-NH$_2$
-(Doc)$_4$-Aepa-Gln-Trp-Ala-Ala-βAla-His-Phe-Nle-NH$_2$
-(Doc)$_4$-Gln-Trp-Ala-Val-βAla-His-Leu-Leu-NH$_2$
-(Doc)$_4$-Gln-Trp-Ala-Val-βAla-His-Leu-Nle-NH$_2$
-(Doc)$_4$-Gln-Trp-Ala-Val-Gly-His-Leu-Leu-NH$_2$
-(Doc)$_4$-Gln-Trp-Ala-Val-βAla-His-Phe-Nle-NH$_2$
-(Doc)$_4$-Gln-Trp-Ala-Ala-βAla-His-Phe-Nle-NH$_2$
-Aepa-(Doc)$_2$-DPhe-Gln-Trp-Ala-Val-βAla-His-Leu-Leu-NH$_2$
-Aepa-(Doc)$_2$-DPhe-Gln-Trp-Ala-Val-βAla-His-Leu-Nle-NH$_2$
-Aepa-(Doc)$_2$-DPhe-Gln-Trp-Ala-Val-Gly-His-Leu-Leu-NH$_2$
-Aepa-(Doc)$_2$-DAla-Gln-Trp-Ala-Val-βAla-His-Phe-Nle-NH$_2$
-Aepa-(Doc)$_2$-DPhe-Gln-Trp-Ala-Ala-βAla-His-Phe-Nle-NH$_2$ TABLE E-continued -Aepa-DPhe-Gln-Trp-Ala-Val-βAla-His-Leu-Leu-NH₂
-Aepa-DPhe-Gln-Trp-Ala-Val-βAla-His-Leu-Nle-NH₂
-Aepa-DPhe-Gln-Trp-Ala-Val-Gly-His-Leu-Leu-NH₂
-Aepa-DAla-Gln-Trp-Ala-Val-βAla-His-Phe-Nle-NH₂
-Aepa-DPhe-Gln-Trp-Ala-Ala-βAla-His-Phe-Nle-NH₂
-(Doc)₂-DPhe-Gln-Trp-Ala-Val-βAla-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-Gly-His-Leu-Leu-NH₂
-(Doc)₂-DAla-Gln-Trp-Ala-Val-βAla-His-Phe-Nle-NH₂
-(Doc)₂-DPhe-Gln-Trp-Ala-Ala-βAla-His-Phe-Nle-NH₂
-(Doc)₂-Aepa-DPhe-Gln-Trp-Ala-Val-βAla-His-Leu-Leu-NH₂
-(Doc)₂-Aepa-DPhe-Gln-Trp-Ala-Val-βAla-His-Leu-Nle-NH₂
-(Doc)₂-Aepa-DPhe-Gln-Trp-Ala-Val-Gly-His-Leu-Leu-NH₂
-(Doc)₂-Aepa-DAla-Gln-Trp-Ala-Val-βAla-His-Phe-Nle-NH₂
-(Doc)₂-Aepa-DPhe-Gln-Trp-Ala-Ala-βAla-His-Phe-Nle-NH₂
-Aepa-(Doc)₂-Gln-Trp-Ala-Val-βAla-His-Ala-Nle-NH₂
-Aepa-Gln-Trp-Ala-Val-βAla-His-Ala-Nle-NH₂
-(Doc)₂-Gln-Trp-Ala-Val-βAla-His-Ala-Nle-NH₂
-Aepa-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-(Doc)₂-DPhe-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-(Doc)₄-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₂-Aepa-DPhe-Gln-Trp-Ala-Val-βAla-His-Ala-Nle-NH₂
-Aepa-(Doc)₃-Gln-Trp-Ala-Val-βAla-His-Leu-Leu-NH₂
-Aepa-(Doc)₃-Gln-Trp-Ala-Val-βAla-His-Leu-Nle-NH₂
-Aepa-(Doc)₃-Gln-Trp-Ala-Val-Gly-His-Leu-Leu-NH₂
-Aepa-(Doc)₃-Gln-Trp-Ala-Val-βAla-His-Phe-Nle-NH₂
-Aepa-(Doc)₃-Gln-Trp-Ala-Ala-βAla-His-Phe-Nle-NH₂
-Aepa-Doc-Gln-Trp-Ala-Val-βAla-His-Leu-Leu-NH₂
-Aepa-Doc-Gln-Trp-Ala-Val-βAla-His-Leu-Nle-NH₂
-Aepa-Doc-Gln-Trp-Ala-Val-Gly-His-Leu-Leu-NH₂
-Aepa-Doc-Gln-Trp-Ala-Val-βAla-His-Phe-Nle-NH₂
-Aepa-Doc-Gln-Trp-Ala-Ala-βAla-His-Phe-Nle-NH₂
-(Doc)₃-Gln-Trp-Ala-Val-βAla-His-Leu-Leu-NH₂
-(Doc)₃-Gln-Trp-Ala-Val-βAla-His-Leu-Nle-NH₂
-(Doc)₃-Gln-Trp-Ala-Val-Gly-His-Leu-Leu-NH₂
-(Doc)₃-Gln-Trp-Ala-Val-βAla-His-Phe-Nle-NH₂
-(Doc)₃-Gln-Trp-Ala-Ala-βAla-His-Phe-Nle-NH₂
-(Doc)₃-Aepa-DPhe-Gln-Trp-Ala-Val-βAla-His-Leu-Leu-NH₂
-(Doc)₃-Aepa-DPhe-Gln-Trp-Ala-Val-βAla-His-Leu-Nle-NH₂
-(Doc)₃-Aepa-DPhe-Gln-Trp-Ala-Val-Gly-His-Leu-Leu-NH₂
-(Doc)₃-DPhe-Gln-Trp-Ala-Val-βAla-His-Leu-Leu-NH₂
-(Doc)₃-DPhe-Gln-Trp-Ala-Val-βAla-His-Leu-Nle-NH₂
-(Doc)₃-DPhe-Gln-Trp-Ala-Val-Gly-His-Leu-Leu-NH₂
-(Doc)₃-DAla-Gln-Trp-Ala-Val-βAla-His-Phe-Nle-NH₂
-(Doc)₃-DPhe-Gln-Trp-Ala-Ala-βAla-His-Phe-Nle-NH₂
-Doc-Gln-Trp-Ala-Val-βAla-His-Leu-Leu-NH₂
-Doc-Gln-Trp-Ala-Val-βAla-His-Leu-Nle-NH₂
-Doc-Gln-Trp-Ala-Val-Gly-His-Leu-Leu-NH₂
-Doc-Gln-Trp-Ala-Val-βAla-His-Phe-Nle-NH₂
-Doc-Gln-Trp-Ala-Ala-βAla-His-Phe-Nle-NH₂
-Doc-Aepa-Gln-Trp-Ala-Val-βAla-His-Leu-Leu-NH₂
-Doc-Aepa-Gln-Trp-Ala-Val-βAla-His-Leu-Nle-NH₂
-Doc-Aepa-Gln-Trp-Ala-Val-Gly-His-Leu-Leu-NH₂
-Doc-Aepa-Gln-Trp-Ala-Val-βAla-His-Phe-Nle-NH₂
-Doc-Aepa-Gln-Trp-Ala-Ala-βAla-His-Phe-Nle-NH₂

TABLE F

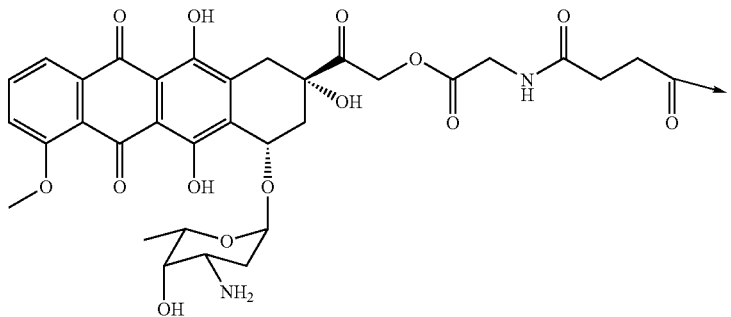 [SMILES: COc1cccc2c1C(=O)c1c(O)c3c(c(O)c1C2=O)C[C@@](O)(C(=O)COC(=O)CNC(=O)CCC=O)C[C@@H]3OC1CC(N)C(O)C(C)O1]

-(Doc)₄-Aepa-DPhe-Gln-Trp-Ala-Ala-βAla-His-Phe-Nle-NH₂
-(Doc)₄-DPhe-Gln-Trp-Ala-Val-βAla-His-Leu-Leu-NH₂
-(Doc)₄-DPhe-Gln-Trp-Ala-Val-βAla-His-Leu-Nle-NH₂
-(Doc)₄-DPhe-Gln-Trp-Ala-Val-Gly-His-Leu-Leu-NH₂
-(Doc)₄-DAla-Gln-Trp-Ala-Val-βAla-His-Phe-Nle-NH₂
-(Doc)₄-DPhe-Gln-Trp-Ala-Ala-βAla-His-Phe-Nle-NH₂
-(Doc)₄-Aepa-Gln-Trp-Ala-Val-βAla-His-Phe-Nle-NH₂
-(Doc)₄-Aepa-Gln-Trp-Ala-Ala-βAla-His-Phe-Nle-NH₂
-(Doc)₄-Gln-Trp-Ala-Val-βAla-His-Leu-Leu-NH₂
-(Doc)₄-Gln-Trp-Ala-Val-βAla-His-Leu-Nle-NH₂
-(Doc)₄-Gln-Trp-Ala-Val-Gly-His-Leu-Leu-NH₂
-(Doc)₄-Gln-Trp-Ala-Val-βAla-His-Phe-Nle-NH₂
-(Doc)₄-Gln-Trp-Ala-Ala-βAla-His-Phe-Nle-NH₂
-Aepa-(Doc)₄-Gln-Trp-Ala-Val-βAla-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Phe-Nle-NH₂
-Aepa-(Doc)₄-Gln-Trp-Ala-Ala-βAla-His-Phe-Nle-NH₂
-(Doc)₄-Aepa-Gln-Trp-Ala-Val-βAla-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-Gly-His-Leu-Leu-NH₂
-Aepa-(Doc)₂-DPhe-Gln-Trp-Ala-Val-βAla-His-Leu-Leu-NH₂
-Aepa-(Doc)₂-DPhe-Gln-Trp-Ala-Val-βAla-His-Leu-Nle-NH₂
-Aepa-(Doc)₂-DPhe-Gln-Trp-Ala-Val-Gly-His-Leu-Leu-NH₂
-Aepa-(Doc)₂-DAla-Gln-Trp-Ala-Val-βAla-His-Phe-Nle-NH₂
-Aepa-(Doc)₂-DPhe-Gln-Trp-Ala-Ala-βAla-His-Phe-Nle-NH₂

TABLE F-continued

-Aepa-DPhe-Gln-Trp-Ala-Val-βAla-His-Leu-Leu-NH$_2$
-Aepa-DPhe-Gln-Trp-Ala-Val-βAla-His-Leu-Nle-NH$_2$
-Aepa-DPhe-Gln-Trp-Ala-Val-Gly-His-Leu-Leu-NH$_2$
-Aepa-DAla-Gln-Trp-Ala-Val-βAla-His-Phe-Nle-NH$_2$
-Aepa-DPhe-Gln-Trp-Ala-Ala-βAla-His-Phe-Nle-NH$_2$
-(Doc)$_2$-DPhe-Gln-Trp-Ala-Val-βAla-His-Leu-Leu-NH$_2$
-(Doc)$_2$-DPhe-Gln-Trp-Ala-Val-βAla-His-Leu-Nle-NH$_2$
-(Doc)$_2$-DPhe-Gln-Trp-Ala-Val-Gly-His-Leu-Leu-NH$_2$
-(Doc)$_2$-DAla-Gln-Trp-Ala-Val-βAla-His-Phe-Nle-NH$_2$
-(Doc)$_2$-DPhe-Gln-Trp-Ala-Ala-βAla-His-Phe-Nle-NH$_2$
-(Doc)$_2$-Aepa-DPhe-Gln-Trp-Ala-Val-βAla-His-Leu-Leu-NH$_2$
-(Doc)$_2$-Aepa-DPhe-Gln-Trp-Ala-Val-βAla-His-Leu-Nle-NH$_2$
-(Doc)$_2$-Aepa-DPhe-Gln-Trp-Ala-Val-Gly-His-Leu-Leu-NH$_2$
-(Doc)$_2$-Aepa-DAla-Gln-Trp-Ala-Val-βAla-His-Phe-Nle-NH$_2$
-(Doc)$_2$-Aepa-DPhe-Gln-Trp-Ala-Ala-βAla-His-Phe-Nle-NH$_2$
-Aepa-(Doc)$_2$-Gln-Trp-Ala-Val-βAla-His-Ala-Nle-NH$_2$
-Aepa-Gln-Trp-Ala-Val-βAla-His-Ala-Nle-NH$_2$
-(Doc)$_2$-Gln-Trp-Ala-Val-βAla-His-Ala-Nle-NH$_2$
-Aepa-(Doc)$_2$-DPhe-Gln-Trp-Ala-Val-βAla-His-Ala-Nle-NH$_2$
-Aepa-DPhe-Gln-Trp-Ala-Val-βAla-His-Ala-Nle-NH$_2$
-(Doc)$_2$-DPhe-Gln-Trp-Ala-Val-βAla-His-Ala-Nle-NH$_2$
-Aepa-(Doc)$_4$-Gln-Trp-Ala-Val-βAla-His-Ala-Nle-NH$_2$
-(Doc)$_4$-Aepa-Gln-Trp-Ala-Val-βAla-His-Ala-Nle-NH$_2$
-(Doc)$_4$-Gln-Trp-Ala-Val-βAla-His-Ala-Nle-NH$_2$
-Aepa-(Doc)$_4$-DPhe-Gln-Trp-Ala-Val-βAla-His-Ala-Nle-NH$_2$
-(Doc)$_4$-Aepa-DPhe-Gln-Trp-Ala-Val-βAla-His-Ala-Nle-NH$_2$
-(Doc)$_4$-DPhe-Gln-Trp-Ala-Val-βAla-His-Ala-Nle-NH$_2$
-(Doc)$_2$-Aepa-Gln-Trp-Ala-Vat-βAla-His-Ala-Nle-NH$_2$
-(Doc)$_2$-Aepa-DPhe-Gln-Trp-Ala-Val-βAla-His-Ala-Nle-NH$_2$
-Aepa-(Doc)$_3$-Gln-Trp-Ala-Val-βAla-His-Leu-Leu-NH$_2$
-Aepa-(Doc)$_3$-Gln-Trp-Ala-Val-βAla-His-Leu-Nle-NH$_2$
-Aepa-(Doc)$_3$-Gln-Trp-Ala-Val-Gly-His-Leu-Leu-NH$_2$
-Aepa-(Doc)$_3$-Gln-Trp-Ala-Val-βAla-His-Phe-Nle-NH$_2$
-Aepa-(Doc)$_3$-Gln-Trp-Ala-Ala-βAla-His-Phe-Nle-NH$_2$
-Aepa-Doc-Gln-Trp-Ala-Val-βAla-His-Leu-Leu-NH$_2$
-Aepa-Doc-Gln-Trp-Ala-Val-βAla-His-Leu-Nle-NH$_2$
-Aepa-Doc-Gln-Trp-Ala-Val-Gly-His-Leu-Leu-NH$_2$
-Aepa-Doc-Gln-Trp-Ala-Val-βAla-His-Phe-Nle-NH$_2$
-Aepa-Doc-Gln-Trp-Ala-Ala-βAla-His-Phe-Nle-NH$_2$
-(Doc)$_3$-Gln-Trp-Ala-Val-βAla-His-Leu-Leu-NH$_2$
-(Doc)$_3$-Gln-Trp-Ala-Val-βAla-His-Leu-Nle-NH$_2$
-(Doc)$_3$-Gln-Trp-Ala-Val-Gly-His-Leu-Leu-NH$_2$
-(Doc)$_3$-Gln-Trp-Ala-Val-βAla-His-Phe-Nle-NH$_2$
-(Doc)$_3$-Gln-Trp-Ala-Ala-βAla-His-Phe-Nle-NH$_2$
-(Doc)$_3$-Aepa-DPhe-Gln-Trp-Ala-Val-βAla-His-Leu-Leu-NH$_2$
-(Doc)$_3$-Aepa-DPhe-Gln-Trp-Ala-Val-βAla-His-Leu-Nle-NH$_2$
-(Doc)$_3$-Aepa-DPhe-Gln-Trp-Ala-Val-Gly-His-Leu-Leu-NH$_2$
-(Doc)$_3$-DPhe-Gln-Trp-Ala-Val-βAla-His-Leu-Leu-NH$_2$
-(Doc)$_3$-DPhe-Gln-Trp-Ala-Val-βAla-His-Leu-Nle-NH$_2$
-(Doc)$_3$-DPhe-Gln-Trp-Ala-Val-Gly-His-Leu-Leu-NH$_2$
-(Doc)$_3$-DAla-Gln-Trp-Ala-Val-βAla-His-Phe-Nle-NH$_2$
-(Doc)$_3$-DPhe-Gln-Trp-Ala-Ala-βAla-His-Phe-Nle-NH$_2$
-Doc-Gln-Trp-Ala-Val-βAla-His-Leu-Leu-NH$_2$
-Doc-Gln-Trp-Ala-Val-βAla-His-Leu-Nle-NH$_2$
-Doc-Gln-Trp-Ala-Val-Gly-His-Leu-Leu-NH$_2$
-Doc-Gln-Trp-Ala-Val-βAla-His-Phe-Nle-NH$_2$
-Doc-Gln-Trp-Ala-Ala-βAla-His-Phe-Nle-NH$_2$
-Doc-Aepa-Gln-Trp-Ala-Val-βAla-His-Leu-Leu-NH$_2$
-Doc-Aepa-Gln-Trp-Ala-Val-βAla-His-Leu-Nle-NH$_2$
-Doc-Aepa-Gln-Trp-Ala-Val-Gly-His-Leu-Leu-NH$_2$
-Doc-Aepa-Gln-Trp-Ala-Val-βAla-His-Phe-Nle-NH$_2$
-Doc-Aepa-Gln-Trp-Ala-Ala-βAla-His-Phe-Nle-NH$_2$

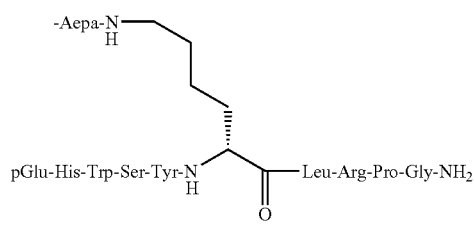

TABLE F-continued
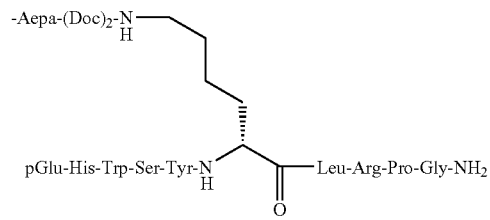
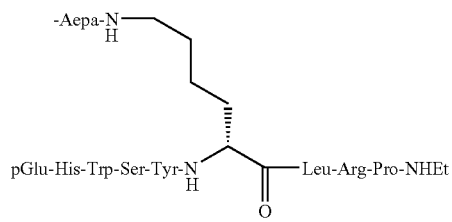
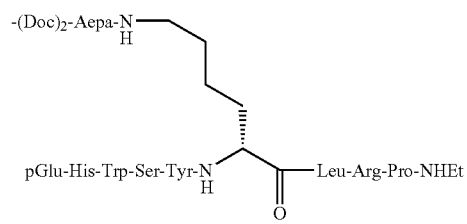
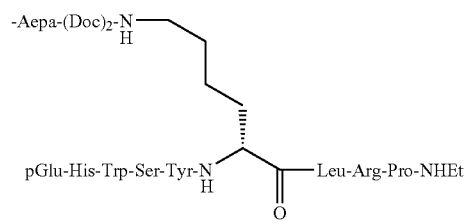
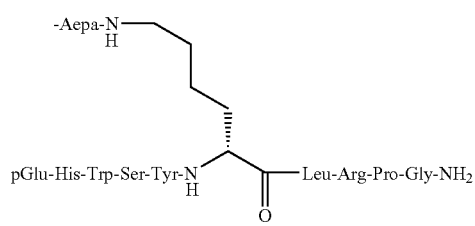
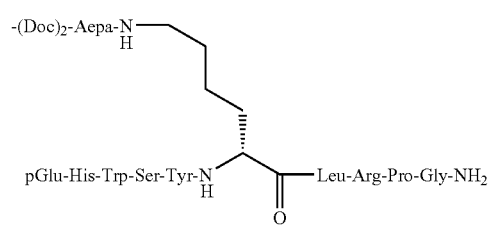
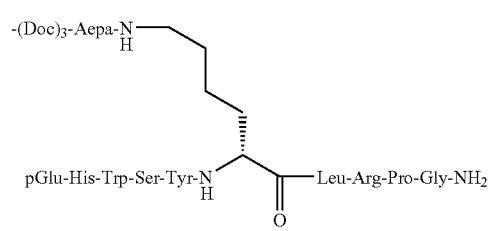

TABLE F-continued
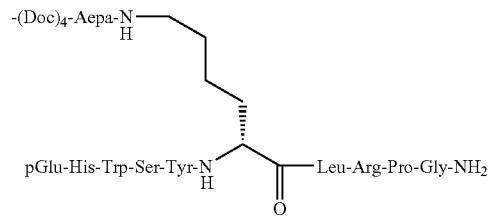
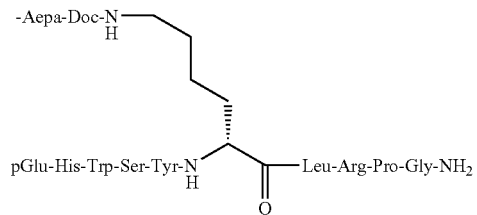
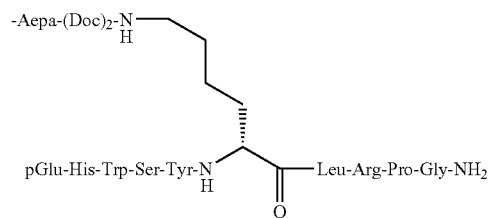
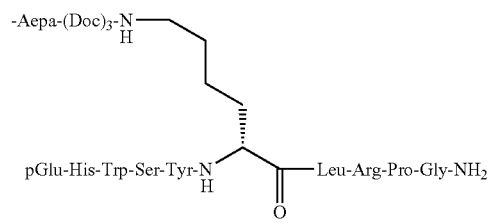
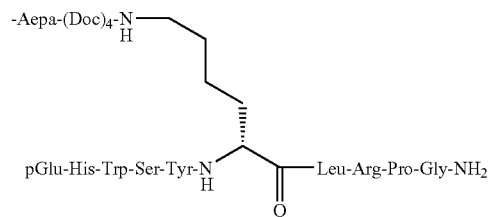
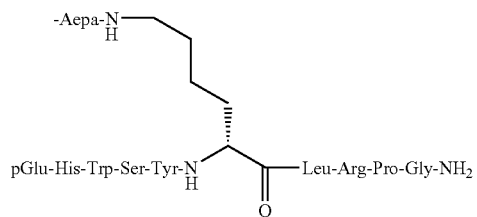
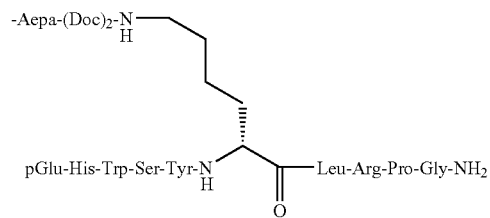

TABLE F-continued
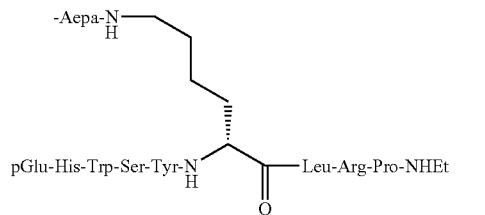
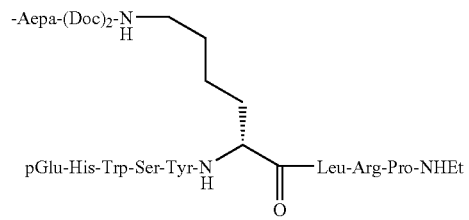
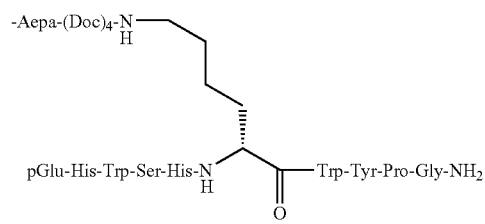
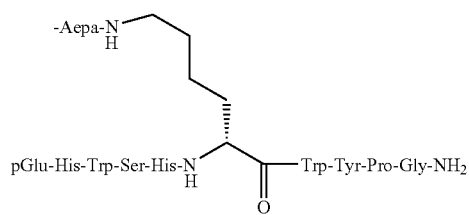
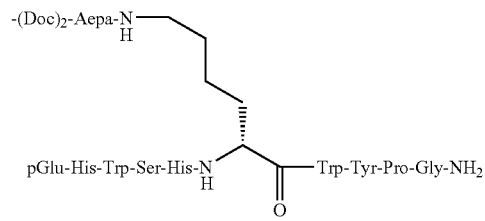
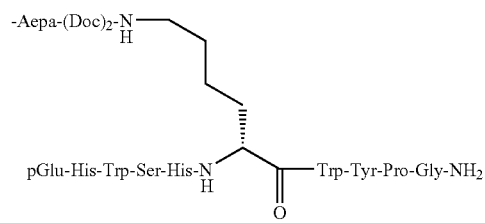
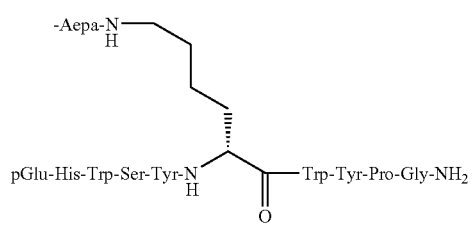

TABLE F-continued
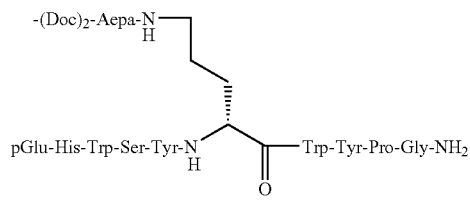
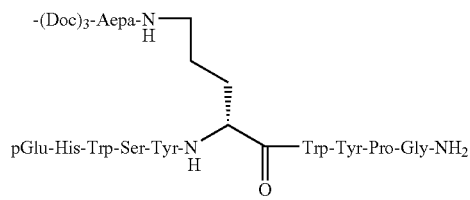
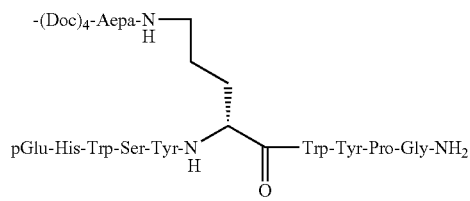
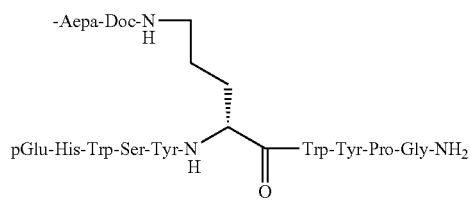
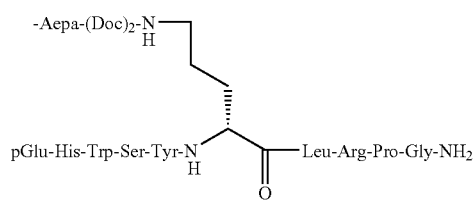
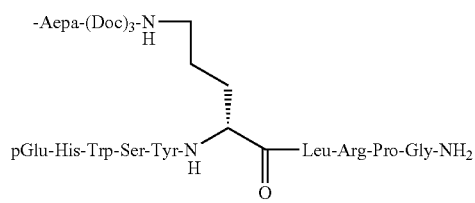
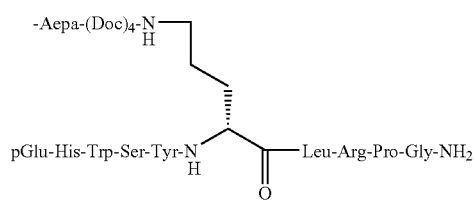

TABLE F-continued
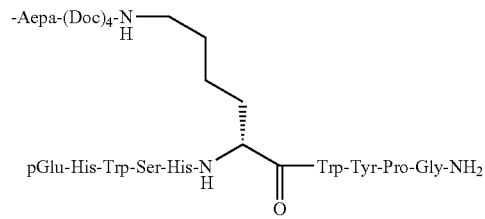
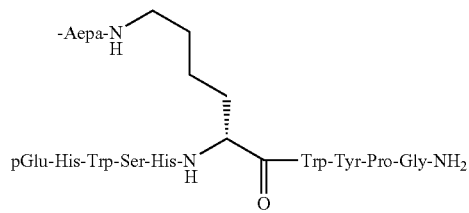
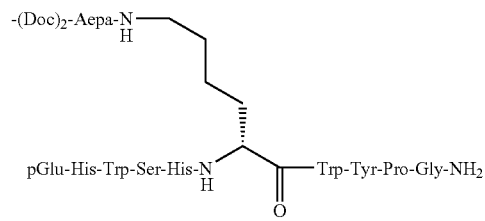
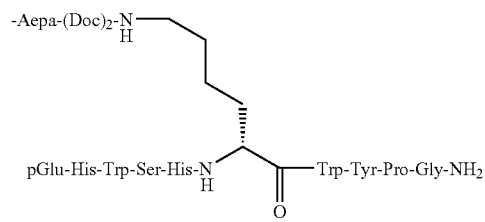
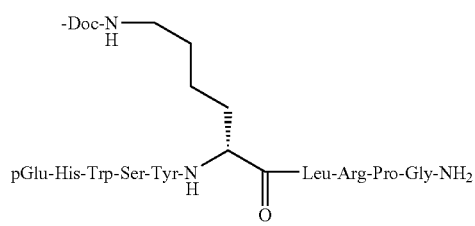
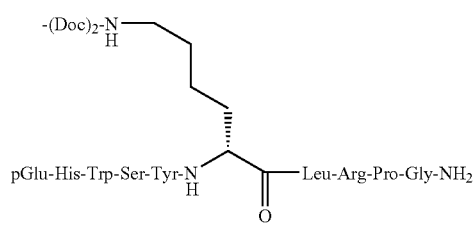
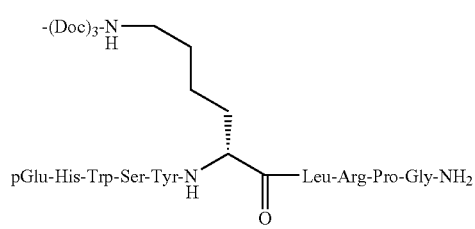

TABLE F-continued
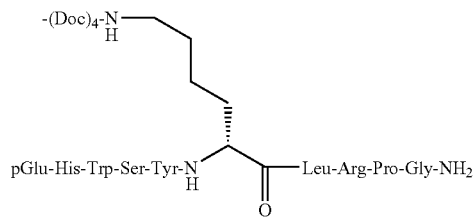
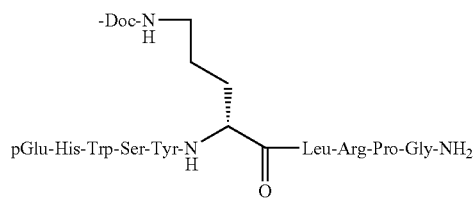
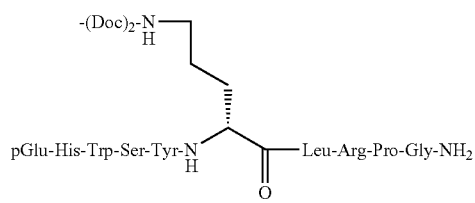
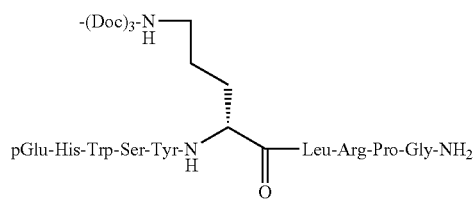
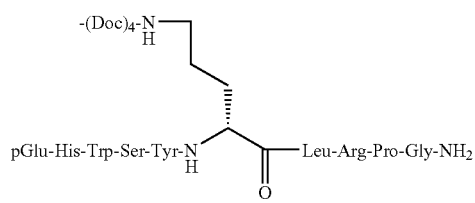
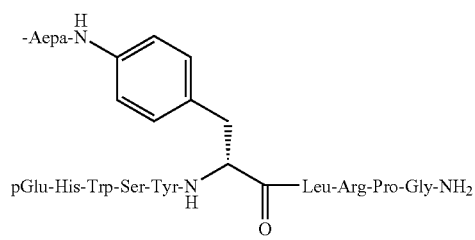
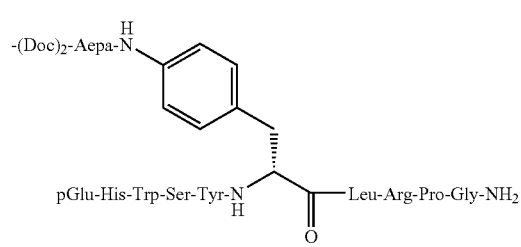

TABLE F-continued
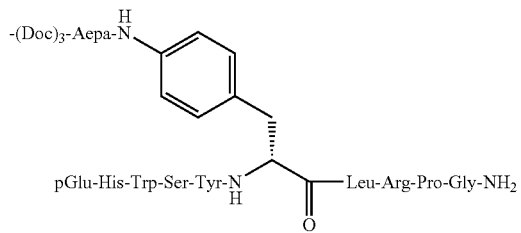
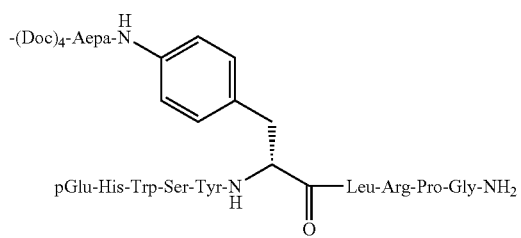
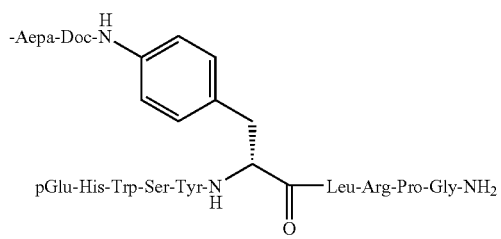
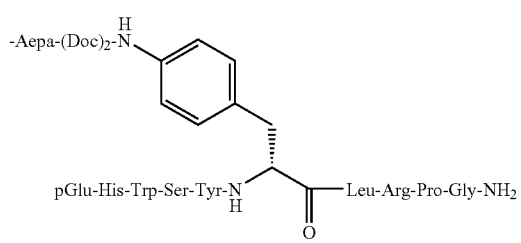
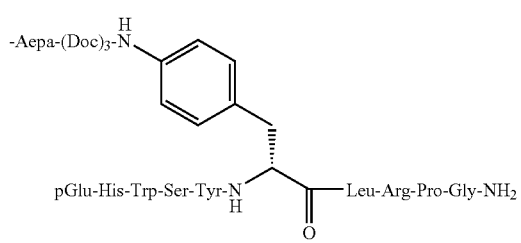
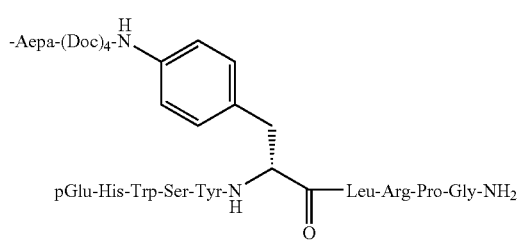

TABLE F-continued

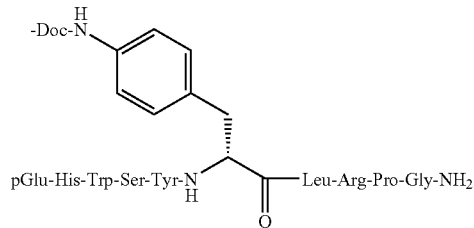

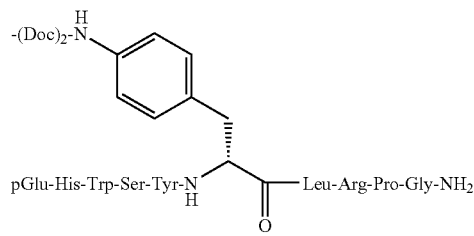

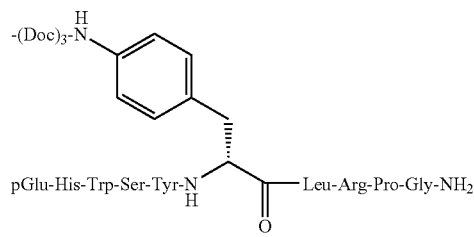

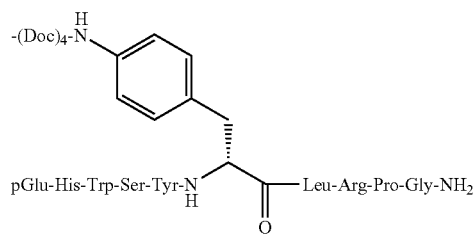

-Aepa-(Doc)₄-DPhe-Gln-Trp-Ala-Val-βAla-His-Leu-Leu-NH₂
-Aepa-(Doc)₄-DPhe-Gln-Trp-Ala-Val-βAla-His-Leu-Nle-NH₂
-Aepa-(Doc)₄-DPhe-Gln-Trp-Ala-Val-Gly-His-Leu-Leu-NH₂
-Aepa-(Doc)₄-DAla-Gln-Trp-Ala-Val-βAla-His-Phe-Nle-NH₂
-Aepa-(Doc)₄-DPhe-Gln-Trp-Ala-Ala-βAla-His-Phe-Nle-NH₂
-(Doc)₄-Aepa-DPhe-Gln-Trp-Ala-Val-βAla-His-Leu-Leu-NH₂
-(Doc)₄-Aepa-DPhe-Gln-Trp-Ala-Val-βAla-His-Leu-Nle-NH₂
-(Doc)₄-Aepa-DPhe-Gln-Trp-Ala-Val-Gly-His-Leu-Leu-NH₂
-(Doc)₄-Aepa-DAla-Gln-Trp-Ala-Val-βAla-His-Phe-Nle-NH₂
-(Doc)HSDGIFTDSYSRYRKQMAVKKYLAAVL(βAla)KRYKQRVKNK-NH₂
-(Doc)HSDGIFTDSYSRYRKQMAVKKYLAAVL(Ava)KRYKQRVKNK-NH₂
-(Doc)HSDGIFTDSYSRYRKQMAVKKYLAAVLGKRYKQR(A₆c)KNK-NH₂
-(Doc)HSDGIFTDSYSRYRKQMA(A₅c)KKYLAAVLGKRYKQRVKNK-NH₂
-(Aepa)HSDGIFTDSYSRYRKQMAVKKYLAAVL(βAla)KRYKQRVKNK-NH₂
-(Aepa)HSDGIFTDSYSRYRKQMAVKKYLAAVL(Ava)KRYKQRVKNK-NH₂
-(Aepa)HSDGIFTDSYSRYRKQMAVKKYLAAVLGKRYKQR(A₆c)KNK-NH₂
-(Aepa)HSDGIFTDSYSRYRKQMA(A₅c)KKYLAAVLGKRYKQRVKNK-NH₂
-(Doc)₆-DPhe-cyclo(Cys-3lTyr-DTrp-Lys-Val-Cys)-Thr-NH₂
-(Doc)₄-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂
-Aepa-DPhe-cyclo(Cys-3lTyr-DTrp-Lys-Val-Cys)-Thr-NH₂
-(Doc)₄-Aepa-DPhe-cyclo(Cys-3lTyr-DTrp-Lys-Val-Cys)-Thr-NH₂
-DPhe-cyclo(Cys-3lTyr-DTrp-Lys-Val-Cys)-Thr-NH₂
-Aepa-DPhe-cyclo(Cys-3lTyr-DTrp-Lys-Val-Cys)-Thr-NH₂

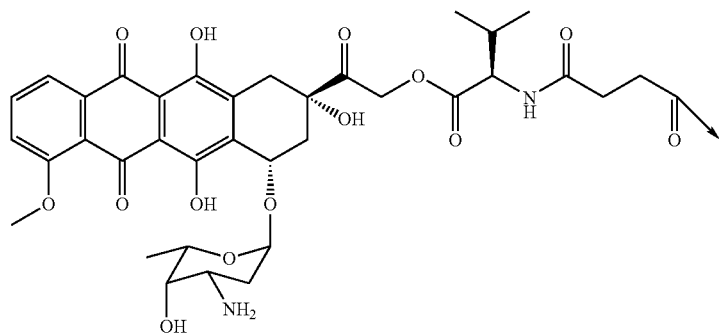 [SMILES: COc1cccc2c1C(=O)c1c(O)c3c(c(O)c1C2=O)C[C@@](O)(C(=O)COC(=O)[C@H](NC(=O)CCC=O)C(C)C)C[C@@H]3OC1CC(N)C(O)C(C)O1]

-Aepa-(Doc)$_4$-Gaba-Gln-Trp-Ala-Val-βAla-His-Leu-Leu-NH$_2$
-(Doc)$_4$-Aepa-Gaba-Gln-Trp-Ala-Val-βAla-His-Leu-Leu-NH$_2$
-(Doc)$_4$-Gaba-Gln-Trp-Ala-Val-βAla-His-Leu-Leu-NH$_2$
-Aepa-(Doc)$_4$-Gaba-Gln-Trp-Ala-Val-Gly-His-Leu-Ψ(CH$_2$NH)-Leu-NH$_2$
-(Doc)$_4$-Aepa-Gaba-Gln-Trp-Ala-Val-Gly-His-Leu-Ψ(CH$_2$NH)-Leu-NH$_2$
-(Doc)$_4$-Gaba-Gln-Trp-Ala-Val-Gly-His-Leu-Ψ(CH$_2$NH)-Leu-NH$_2$
-Aepa-(Doc)$_4$-Gln-Trp-Ala-Val-Gly-His-Leu-Ψ(CH$_2$NH)-Leu-NH$_2$
-(Doc)$_4$-Aepa-Gln-Trp-Ala-Val-Gly-His-Leu-Ψ(CH$_2$NH)-Leu-NH$_2$
-(Doc)$_4$-Gln-Trp-Ala-Val-Gly-His-Leu-Ψ(CH$_2$NH)-Leu-NH$_2$

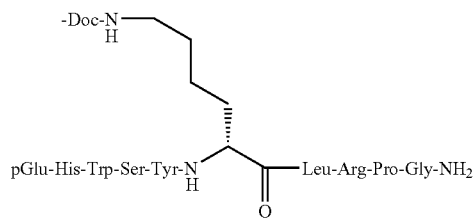

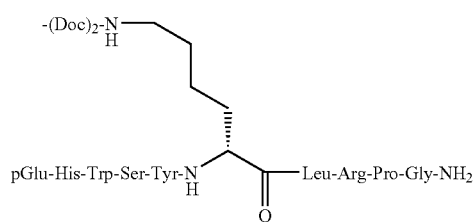

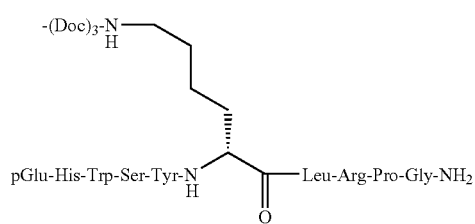

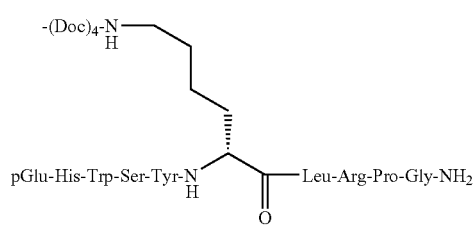

TABLE F-continued
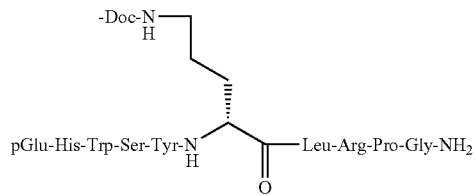
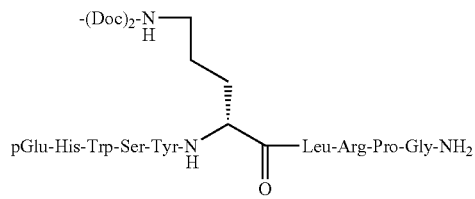
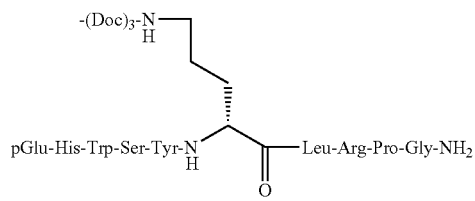
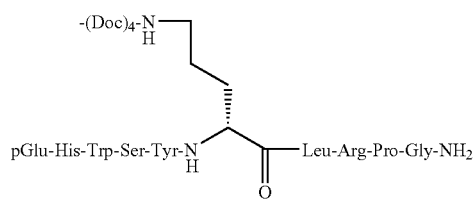
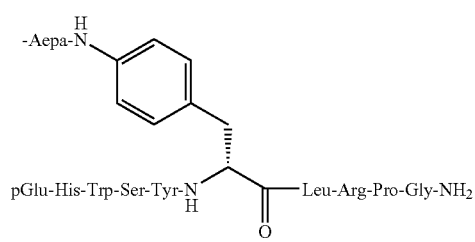
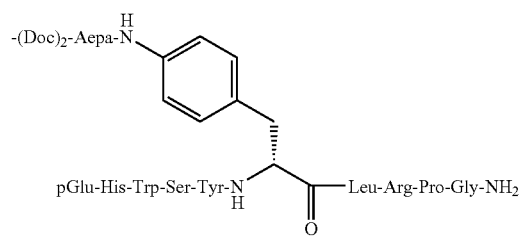
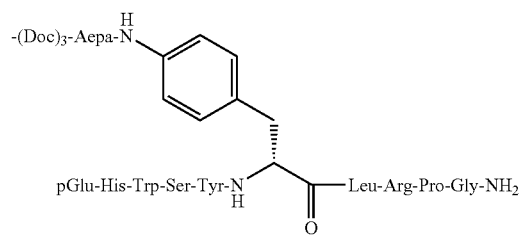

TABLE F-continued
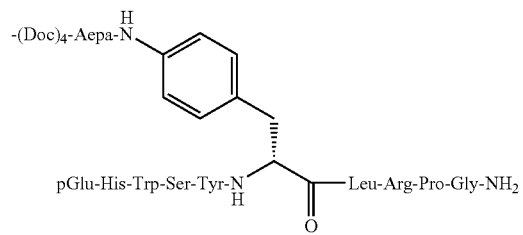
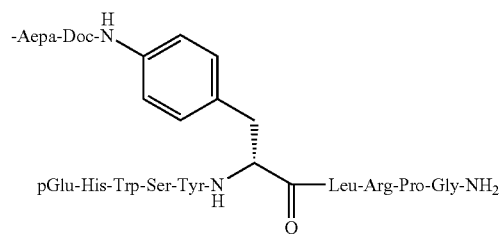
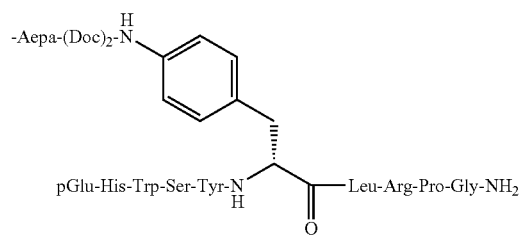
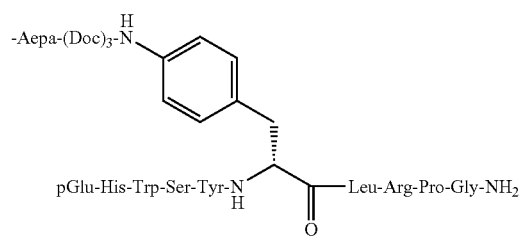
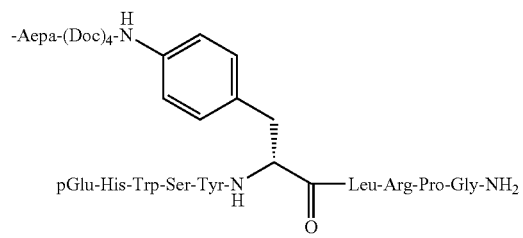
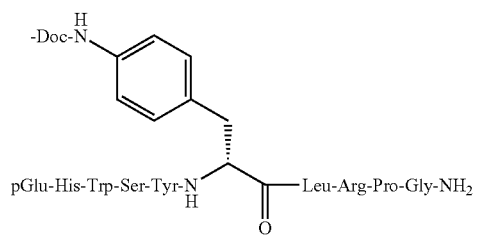

TABLE F-continued
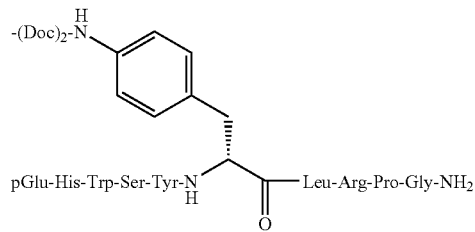
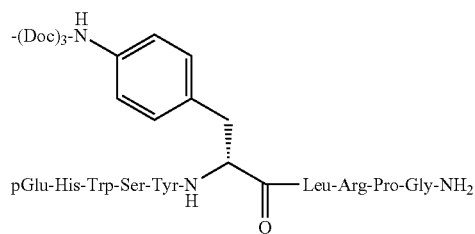
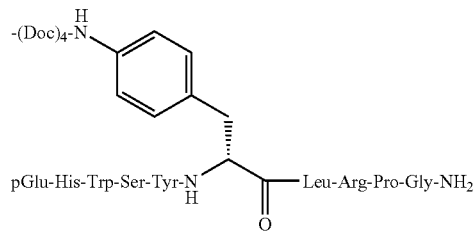
-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
-(Doc)₄-Gaba-Gln-Trp-Ala-Val-βAla-His-Leu-Nle-NH₂
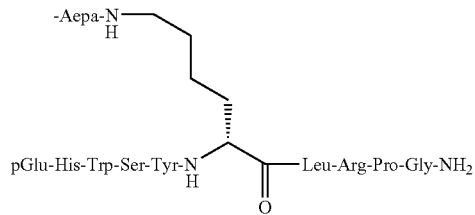
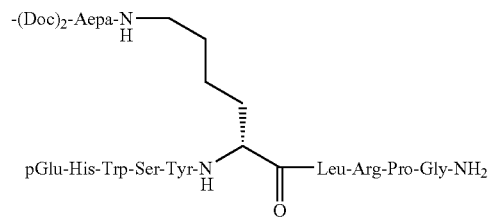
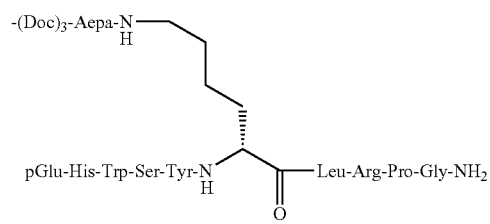

TABLE F-continued
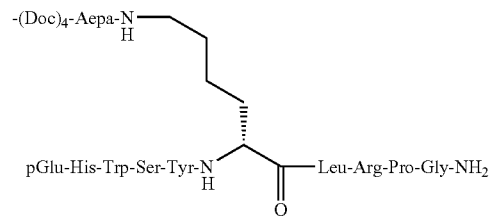
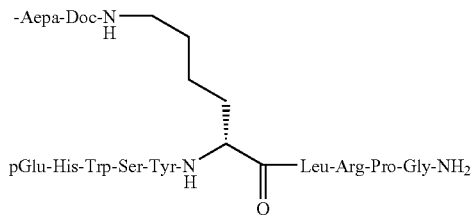
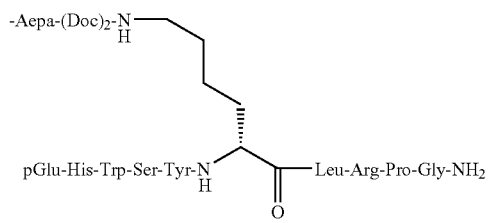
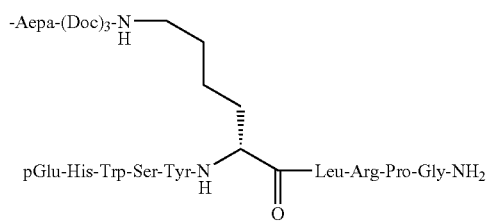
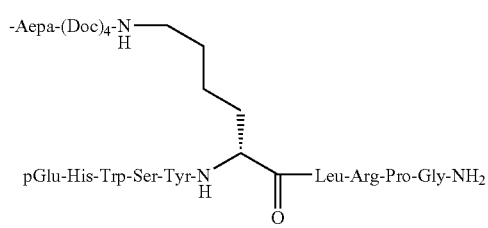
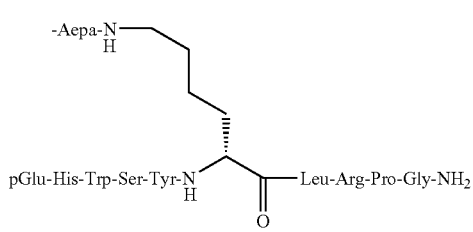
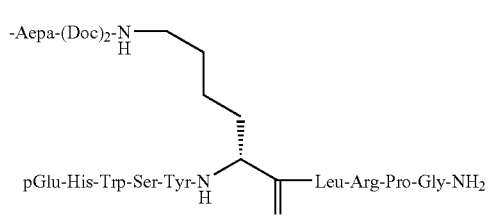

TABLE F-continued
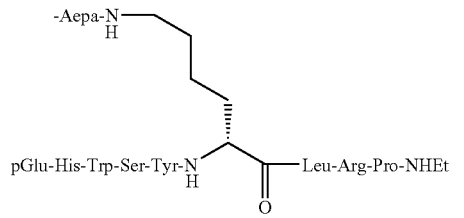
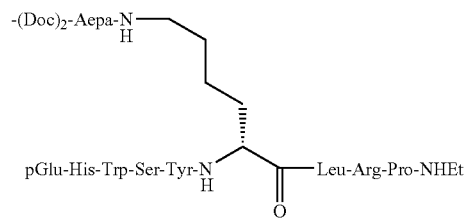
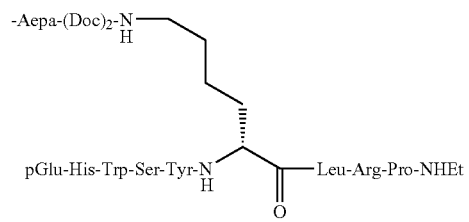
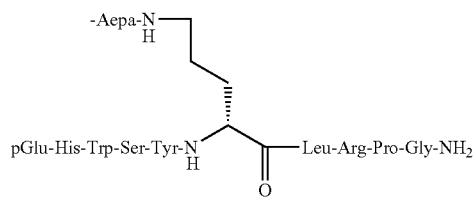
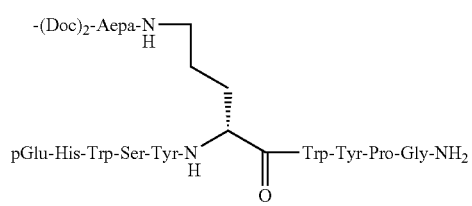
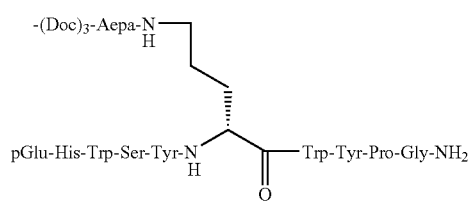
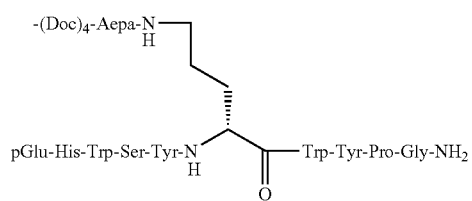

TABLE F-continued
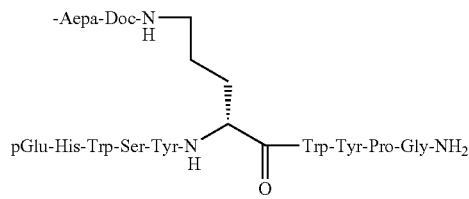
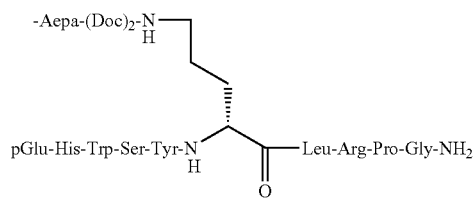
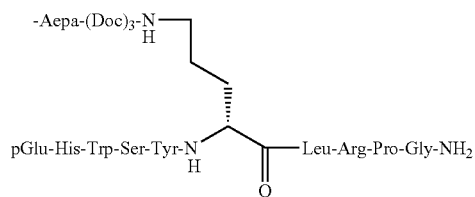
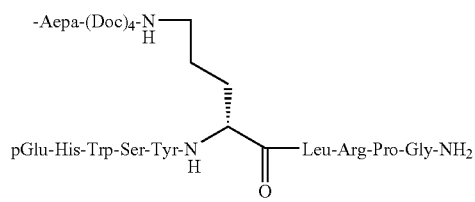
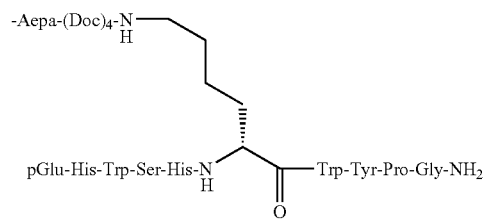
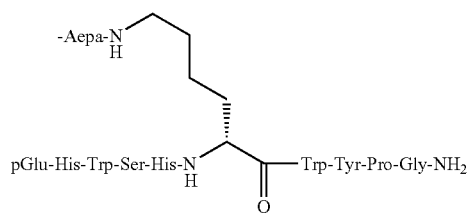
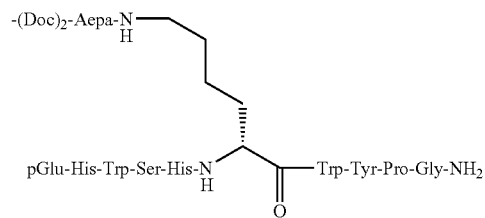

TABLE F-continued

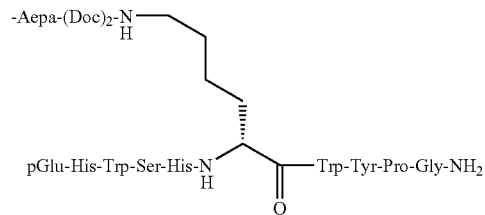

-Doc-DPhe-cyclo(Cys-3lTyr-DTrp-Lys-Val-Cys)-Thr-NH$_2$
-(Doc)$_2$-DPhe-cyclo(Cys-3lTyr-DTrp-Lys-Val-Cys)-Thr-NH$_2$
-(Doc)$_3$-DPhe-cyclo(Cys-3lTyr-DTrp-Lys-Val-Cys)-Thr-NH$_2$
-(Doc)$_4$-DPhe-cyclo(Cys-3lTyr-DTrp-Lys-Val-Cys)-Thr-NH$_2$
-(Doc)$_5$-DPhe-cyclo(Cys-3lTyr-DTrp-Lys-Val-Cys)-Thr-NH$_2$
-(Doc)$_6$-DPhe-cyclo(Cys-3lTyr-DTrp-Lys-Val-Cys)-Thr-NH$_2$
-Doc-Aepa-DPhe-cyclo(Cys-3lTyr-DTrp-Lys-Val-Cys)-Thr-NH$_2$
-(Doc)$_2$-Aepa-DPhe-cyclo(Cys-3lTyr-DTrp-Lys-Val-Cys)-Thr-NH$_2$
-(Doc)$_3$-Aepa-DPhe-cyclo(Cys-3lTyr-DTrp-Lys-Val-Cys)-Thr-NH$_2$
-(Doc)s-Aepa-DPhe-cyclo(Cys-3lTyr-DTrp-Lys-Val-Cys)-Thr-NH$_2$
-(Doc)$_6$-Aepa-DPhe-cyclo(Cys-3lTyr-DTrp-Lys-Val-Cys)-Thr-NH$_2$
-(Aepa)$_2$-DPhe-cyclo(Cys-3lTyr-DTrp-Lys-Val-Cys)-Thr-NH$_2$

TABLE G

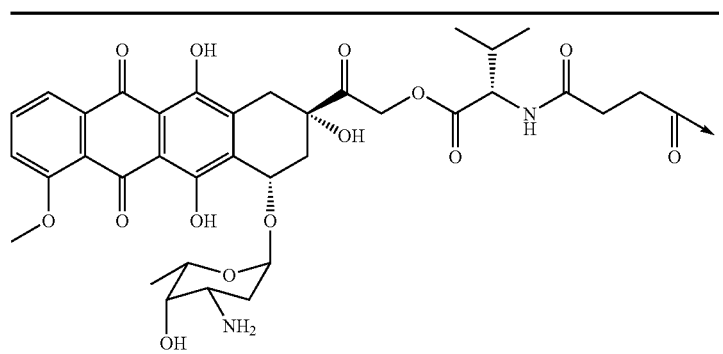

-Aepa-Doc-DPhe-cyclo(Cys-3lTyr-DTrp-Lys-Val-Cys)-Thr-NH$_2$
-Aepa-(Doc)$_2$-DPhe-cyclo(Cys-3lTyr-DTrp-Lys-Val-Cys)-Thr-NH$_2$
-Aepa-(Doc)$_3$-DPhe-cyclo(Cys-3lTyr-DTrp-Lys-Val-Cys)-Thr-NH$_2$
-Aepa-(Doc)$_4$-DPhe-cyclo(Cys-3lTyr-DTrp-Lys-Val-Cys)-Thr-NH$_2$
-Doc-Aepa-DPhe-cyclo(Cys-3lTyr-DTrp-Lys-Thr-Cys)-Thr-NH$_2$
-(Doc)$_2$-Aepa-DPhe-cyclo(Cys-3lTyr-DTrp-Lys-Thr-Cys)-Thr-NH$_2$
-(Doc)$_3$-Aepa-DPhe-cyclo(Cys-3lTyr-DTrp-Lys-Thr-Cys)-Thr-NH$_2$
-(Doc)$_5$-Aepa-DPhe-cyclo(Cys-3lTyr-DTrp-Lys-Thr-Cys)-Thr-NH$_2$
-(Doc)$_6$-Aepa-DPhe-cyclo(Cys-3lTyr-DTrp-Lys-Thr-Cys)-Thr-NH$_2$
-(Aepa)$_2$-DPhe-cyclo(Cys-3lTyr-DTrp-Lys-Thr-Cys)-Thr-NH$_2$
-Doc-DPhe-cyclo(Cys-3lTyr-DTrp-Lys-Thr-Cys)-Thr-NH$_2$
-(Doc)$_2$-DPhe-cyclo(Cys-3lTyr-DTrp-Lys-Thr-Cys)-Thr-NH$_2$
-(Doc)$_3$-DPhe-cyclo(Cys-3lTyr-DTrp-Lys-Thr-Cys)-Thr-NH$_2$
-(Doc)$_4$-DPhe-cyclo(Cys-3lTyr-DTrp-Lys-Thr-Cys)-Thr-NH$_2$
-(Doc)$_5$-DPhe-cyclo(Cys-3lTyr-DTrp-Lys-Thr-Cys)-Thr-NH$_2$
-(Doc)$_6$-DPhe-cyclo(Cys-3lTyr-DTrp-Lys-Thr-Cys)-Thr-NH$_2$
-(Doc)$_6$-DPhe-cyclo(Cys-3lTyr-DTrp-Lys-Thr-Cys)-Thr-NH$_2$
-(Doc)$_4$-DPhe-cyclo(Cys-3lTyr-DTrp-Lys-Thr-Cys)-Thr-NH$_2$
-DPhe-cyclo(Cys-3lTyr-DTrp-Lys-Thr-Cys)-Thr-NH$_2$
-Aepa-DPhe-cyclo(Cys-3lTyr-DTrp-Lys-Thr-Cys)-Thr-NH$_2$
-(Doc)$_4$-Aepa-DPhe-cyclo(Cys-3lTyr-DTrp-Lys-Thr-Cys)-Thr-NH$_2$
-DPhe-cyclo(Cys-3lTyr-DTrp-Lys-Thr-Cys)-Thr-NH$_2$
-Aepa-DPhe-cyclo(Cys-3lTyr-DTrp-Lys-Thr-Cys)-Thr-NH$_2$
-Doc-Aepa-Caeg-cyclo(DCys-3Pal-DTrp-Lys-DCys)-Thr(Bzl)-Tyr-NH$_2$
-(Doc)$_2$-Aepa-Caeg-cyclo(DCys-3Pal-DTrp-Lys-DCys)-Thr(Bzl)-Tyr-NH$_2$
-(Doc)$_3$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-(Doc)$_5$-Aepa-Caeg-cyclo(DCys-3Pal-DTrp-Lys-DCys)-Thr(Bzl)-Tyr-NH$_2$
-(Doc)$_6$-Aepa-Caeg-cyclo(DCys-3Pal-DTrp-Lys-DCys)-Thr(Bzl)-Tyr-NH$_2$
-(Aepa)$_2$-Caeg-cyclo(DCys-3Pal-DTrp-Lys-DCys)-Thr(Bzl)-Tyr-NH$_2$
-Doc-Caeg-cyclo(DCys-3Pal-DTrp-Lys-DCys)-Thr(Bzl)-Tyr-NH$_2$
-(Doc)$_2$-Caeg-cyclo(DCys-3Pal-DTrp-Lys-DCys)-Thr(Bzl)-Tyr-NH$_2$
-(Doc)$_3$-Caeg-cyclo(DCys-3Pal-DTrp-Lys-DCys)-Thr(Bzl)-Tyr-NH$_2$
-(Doc)$_4$-Caeg-cyclo(DCys-3Pal-DTrp-Lys-DCys)-Thr(Bzl)-Tyr-NH$_2$ TABLE G-continued -(Doc)₅-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂
-Doc-Lys-DTyr-DTyr-cyclo(Cys-Tyr-DTrp-Lys-Abu-Cys)-Thr-NH₂
-(Doc)₂-Lys-DTyr-DTyr-cyclo(Cys-Tyr-DTrp-Lys-Abu-Cys)-Thr-NH₂
-(Doc)₃-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₅-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-Lys-DTyr-DTyr-cyclo(Cys-Tyr-DTrp-Lys-Abu-Cys)-Thr-NH₂
-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₄-Aepa-DPhe-cyclo(Cys-Tyr-DTrp-Lys-Abu-Cys)-Thr-NH₂
-DPhe-cyclo(Cys-Tyr-DTrp-Lys-Abu-Cys)-Thr-NH₂
-Aepa-DPhe-cyclo(Cys-Tyr-DTrp-Lys-Abu-Cys)-Thr-NH₂
-Aepa-Lys-DTyr-DTyr-cyclo(Cys-Tyr-DTrp-Lys-Abu-Cys)-Thr-NH₂
-Aepa-DPhe-cyclo(Cys-Tyr-DTrp-Lys-Abu-Cys)-Thr-NH₂
-(Doc)₂-Aepa-DPhe-cyclo(Cys-3lTyr-DTrp-Lys-Val-Cys)-Thr-NH₂
-(Doc)₄-Aepa-Caeg-cyclo(DCys-3Pal-DTrp-Lys-DCys)-Thr(Bzl)-Tyr-NH₂

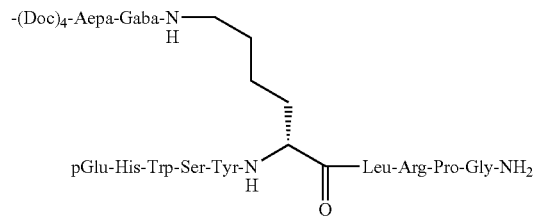

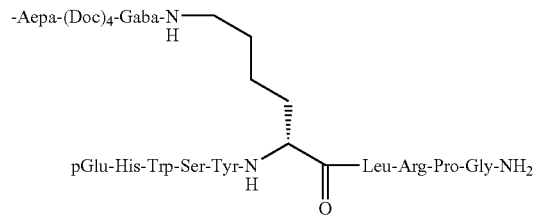

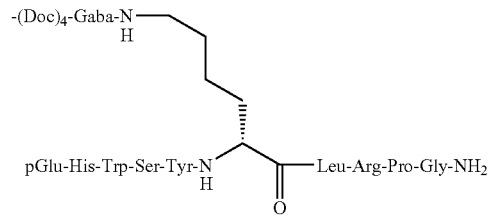

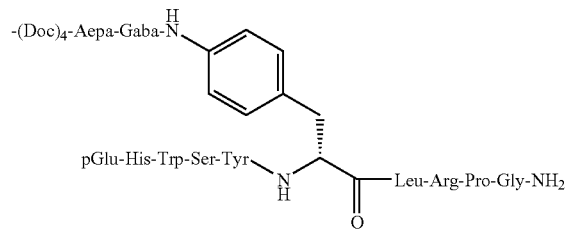

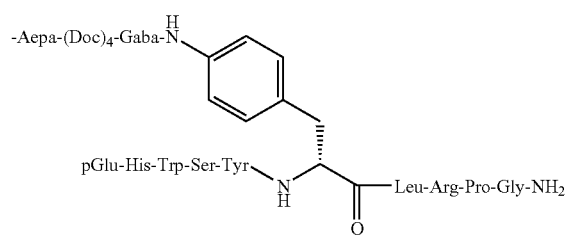

TABLE G-continued

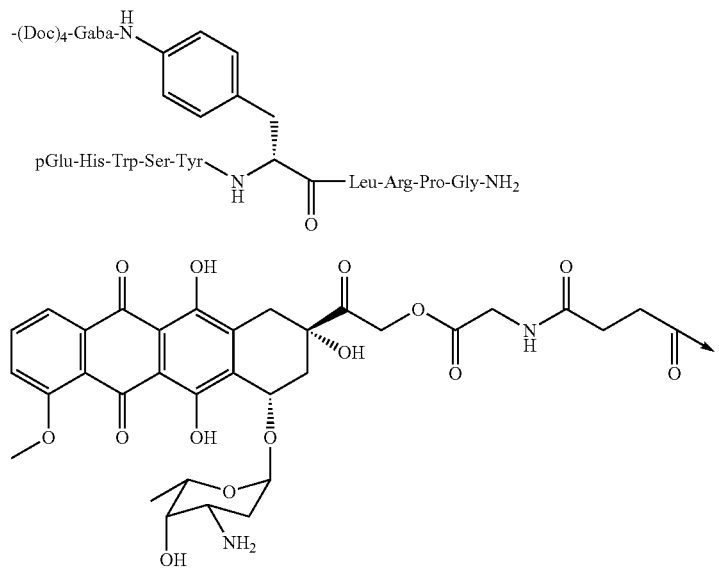

-(Doc)<sub>6</sub>-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_4$-Aepa-DPhe-cyclo(Cys-Tyr-DTrp-Lys-Abu-Cys)-Thr-NH$_2$
DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-DPhe-cyclo(Cys-3lTyr-DTrp-Lys-Val-Cys)-Thr-NH$_2$
-(Doc)$_2$-Aepa-DPhe-cyclo(Cys-3lTyr-DTrp-Lys-Val-Cys)-Thr-NH$_2$
-(Doc)$_2$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-DPhe-cyclo(Cys-3lTyr-DTrp-Lys-Val-Cys)-Thr-NH$_2$
-(Doc)$_2$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-Doc-Aepa-DPhe-cyclo(Cys-Tyr-DTrp-Lys-Abu-Cys)-Thr-NH$_2$
-(Doc)$_2$-Aepa-DPhe-cyclo(Cys-Tyr-DTrp-Lys-Abu-Cys)-Thr-NH$_2$
-(Doc)$_3$-Aepa-DPhe-cyclo(Cys-Tyr-DTrp-Lys-Abu-Cys)-Thr-NH$_2$
-(Doc)$_5$-Aepa-DPhe-cyclo(Cys-Tyr-DTrp-Lys-Abu-Cys)-Thr-NH$_2$
-(Doc)$_6$-Aepa-DPhe-cyclo(Cys-Tyr-DTrp-Lys-Abu-Cys)-Thr-NH$_2$
-(Aepa)$_2$-DPhe-cyclo(Cys-Tyr-DTrp-Lys-Abu-Cys)-Thr-NH$_2$
-Doc-DPhe-cyclo(Cys-Tyr-DTrp-Lys-Abu-Cys)-Thr-NH$_2$
-(Doc)$_2$-DPhe-cyclo(Cys-Tyr-DTrp-Lys-Abu-Cys)-Thr-NH$_2$
-(Doc)$_3$-DPhe-cyclo(Cys-Tyr-DTrp-Lys-Abu-Cys)-Thr-NH$_2$
-(Doc)$_4$-DPhe-cyclo(Cys-Tyr-DTrp-Lys-Abu-Cys)-Thr-NH$_2$
-(Doc)$_5$-DPhe-cyclo(Cys-Tyr-DTrp-Lys-Abu-Cys)-Thr-NH$_2$
-(Doc)$_6$-DPhe-cyclo(Cys-Tyr-DTrp-Lys-Abu-Cys)-Thr-NH$_2$
Lys-DTyr-DTyr-cyclo(Cys-Tyr-DTrp-Lys-Abu-Cys)-Thr-NH$_2$
-Doc-Aepa-Lys-DTyr-DTyr-cyclo(Cys-Tyr-DTrp-Lys-Abu-Cys)-Thr-NH$_2$
-(Doc)$_2$-Aepa-Lys-DTyr-DTyr-cyclo(Cys-Tyr-DTrp-Lys-Abu-Cys)-Thr-NH$_2$
-(Doc)$_3$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_5$-Aepa-Lys-DTyr-DTyr-cyclo(Cys-Tyr-DTrp-Lys-Abu-Cys)-Thr-NH$_2$
-(Doc)$_6$-Aepa-Lys-DTyr-DTyr-cyclo(Cys-Tyr-DTrp-Lys-Abu-Cys)-Thr-NH$_2$
-(Aepa)$_2$-Lys-DTyr-DTyr-cyclo(Cys-Tyr-DTrp-Lys-Abu-Cys)-Thr-NH$_2$
-Doc-Lys-DTyr-DTyr-cyclo(Cys-Tyr-DTrp-Lys-Abu-Cys)-Thr-NH$_2$
-(Doc)$_2$-Lys-DTyr-DTyr-cyclo(Cys-Tyr-DTrp-Lys-Abu-Cys)-Thr-NH$_2$
-(Doc)$_3$-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-(Doc)$_5$-Lys-DTyr-DTyr-cyclo(Cys-Tyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-Aepa-Doc-Lys-DTyr-DTyr-cyclo(Cys-Tyr-DTrp-Lys-Abu-Cys)-Thr-NH$_2$

TABLE G-continued

-Aepa-(Doc)$_2$-Lys-DTyr-DTyr-cyclo(Cys-Tyr-DTrp-Lys-Abu-Cys)-Thr-NH$_2$
-Aepa-(Doc)$_3$-Lys-DTyr-DTyr-cyclo(Cys-Tyr-DTrp-Lys-Abu-Cys)-Thr-NH$_2$
-Aepa-(Doc)$_4$-Lys-DTyr-DTyr-cyclo(Cys-Tyr-DTrp-Lys-Abu-Cys)-Thr-NH$_2$
-Aepa-Doc-DPhe-cyclo(Cys-Tyr-DTrp-Lys-Abu-Cys)-Thr-NH$_2$
-Aepa-(Doc)$_2$-DPhe-cyclo(Cys-Tyr-DTrp-Lys-Abu-Cys)-Thr-NH$_2$
-Aepa-(Doc)$_3$-DPhe-cyclo(Cys-Tyr-DTrp-Lys-Abu-Cys)-Thr-NH$_2$
-Aepa-(Doc)$_4$-DPhe-cyclo(Cys-Tyr-DTrp-Lys-Abu-Cys)-Thr-NH$_2$
-(Doc)$_6$-Caeg-cyclo(DCys-3Pal-DTrp-Lys-DCys)-Thr(Bzl)-Tyr-NH$_2$
-(Doc)$_4$-Caeg-cyclo(DCys-3Pal-DTrp-Lys-DCys)-Thr(Bzl)-Tyr-NH$_2$
Caeg-cyclo(DCys-3Pal-DTrp-Lys-DCys)-Thr(Bzl)-Tyr-NH$_2$
-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
Caeg-cyclo(DCys-3Pal-DTrp-Lys-DCys)-Thr(Bzl)-Tyr-NH$_2$
-Aepa-Caeg-cyclo(DCys-3Pal-DTrp-Lys-DCys)-Thr(Bzl)-Tyr-NH$_2$
Doc-Aepa-Caeg-cyclo(DCys-3Pal-DTrp-Lys-DCys)-Thr(Bzl)-Tyr-NH$_2$
-(Doc)$_2$-Aepa-Caeg-cyclo(DCys-3Pal-DTrp-Lys-DCys)-Thr(Bzl)-Tyr-NH$_2$
-(Doc)$_3$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-(Doc)$_5$-Aepa-Caeg-cyclo(DCys-3Pal-DTrp-Lys-DCys)-Thr(Bzl)-Tyr-NH$_2$
-(Doc)$_6$-Aepa-Caeg-cyclo(DCys-3Pal-DTrp-Lys-DCys)-Thr(Bzl)-Tyr-NH$_2$
-(Aepa)$_2$-Caeg-cyclo(DCys-3Pal-DTrp-Lys-DCys)-Thr(Bzl)-Tyr-NH$_2$
Doc-Caeg-cyclo(DCys-3Pal-DTrp-Lys-DCys)-Thr(Bzl)-Tyr-NH$_2$
-(Doc)$_2$-Caeg-cyclo(DCys-3Pal-DTrp-Lys-DCys)-Thr(Bzl)-Tyr-NH$_2$
-(Doc)$_3$-Caeg-cyclo(DCys-3Pal-DTrp-Lys-DCys)-Thr(Bzl)-Tyr-NH$_2$
-(Doc)$_4$-Caeg-cyclo(DCys-3Pal-DTrp-Lys-DCys)-Thr(Bzl)-Tyr-NH$_2$
-(Doc)$_5$-Caeg-cyclo(DCys-3Pal-DTrp-Lys-DCys)-Thr(Bzl)-Tyr-NH$_2$
-(Doc)$_6$-Caeg-cyclo(DCys-3Pal-DTrp-Lys-DCys)-Thr(Bzl)-Tyr-NH$_2$
-Aepa-Doc-Caeg-cyclo(DCys-3Pal-DTrp-Lys-DCys)-Thr(Bzl)-Tyr-NH$_2$
-Aepa-(Doc)$_2$-Caeg-cyclo(DCys-3Pal-DTrp-Lys-DCys)-Thr(Bzl)-Tyr-NH$_2$
-Aepa-(Doc)$_3$-Caeg-cyclo(DCys-3Pal-DTrp-Lys-DCys)-Thr(Bzl)-Tyr-NH$_2$
-Aepa-(Doc)$_4$-Caeg-cyclo(DCys-3Pal-DTrp-Lys-DCys)-Thr(Bzl)-Tyr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-DPhe-cyclo(Cys-3lTyr-DTrp-Lys-Val-Cys)-Thr-NH$_2$
-(Doc)$_2$-Aepa-Caeg-cyclo(DCys-3Pal-DTrp-Lys-DCys)-Thr(Bzl)-Tyr-NH$_2$
-Aepa-(Doc)$_4$-Gaba-Gln-Trp-Ala-Val-βAla-His-Leu-Nle-NH$_2$
-(Doc)$_4$-Aepa-Gaba-Gln-Trp-Ala-Val-βAla-His-Leu-Nle-NH$_2$
-(Doc)$_4$-Gaba-Gln-Trp-Ala-Val-βAla-His-Leu-Nle-NH$_2$

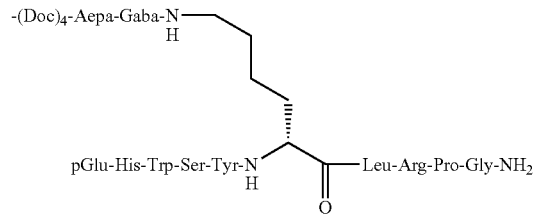

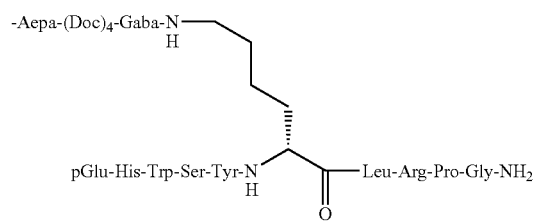

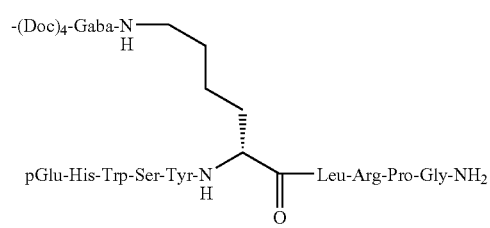

TABLE G-continued

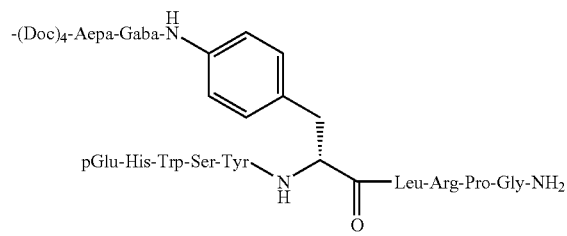

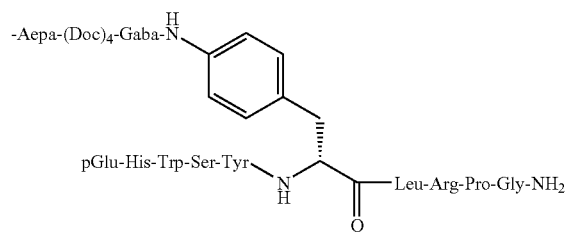

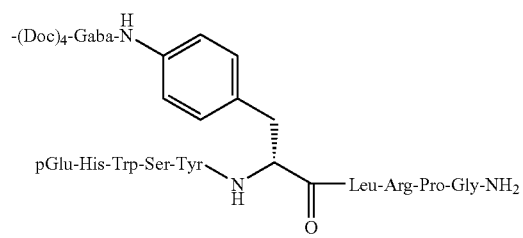

-(Doc)HSDAVFTDNYTRLRKQ(Nle)AVKKYLNSILN-NH$_2$
-(Doc)HSDAVFTDNYTRLRKQMAVKKYLNSILN-NH$_2$
-(Doc)HSDAVFTDNYTRLRKQMAVKKALNSILN-NH$_2$
-(Doc)HSDAVFTDNYTRLRKQMAVKKLLNSILN-NH$_2$
-(Aepa)HSDAVFTDNYTRLRKQ(Nle)AVKKYLNSILN-NH$_2$
-(Aepa)HSDAVFTDNYTRLRKQMAVKKYLNSILN-NH$_2$
-(Aepa)HSDAVFTDNYTRLRKQMAVKKALNSILN-NH$_2$
-(Aepa)HSDAVFTDNYTRLRKQMAVKKLLNSILN-NH$_2$
-Aepa-(Doc)$_2$-Gln-Trp-Ala-Val-βAla-His-Leu-Leu-NH$_2$

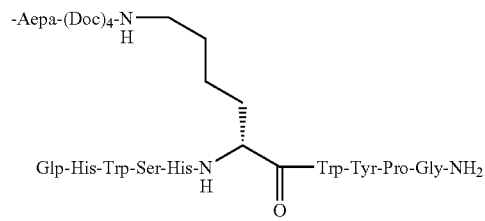

-(Doc)$_2$-Aepa-Caeg-cyclo(DCys-3Pal-DTrp-Lys-DCys)-Thr(Bzl)-Tyr-NH$_2$

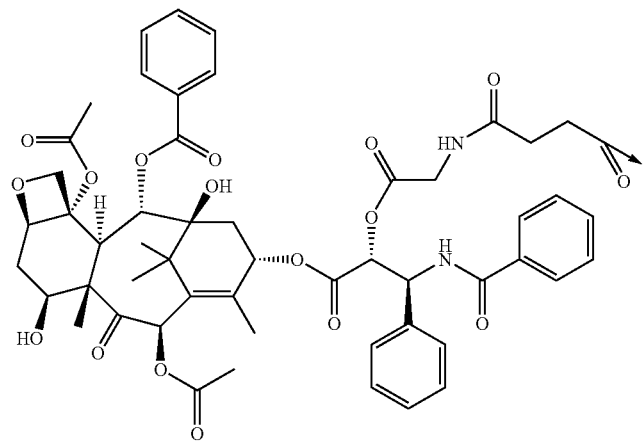

TABLE G-continued
-Aepa-(Doc)₄-Gaba-Gln-Trp-Ala-Val-βAla-His-Leu-Nle-NH₂
-(Doc)₄-Aepa-Gaba-Gln-Trp-Ala-Val-βAla-His-Leu-Nle-NH₂
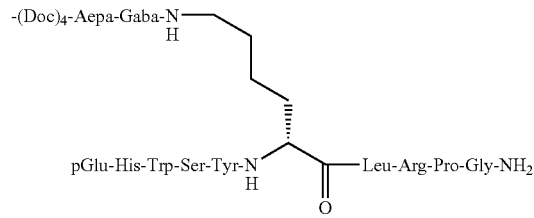
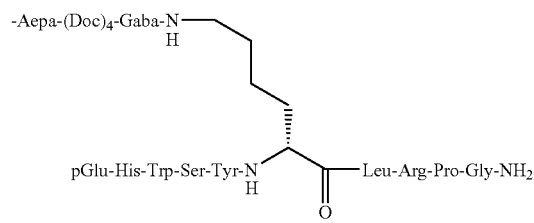
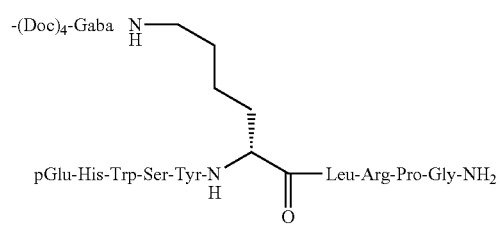
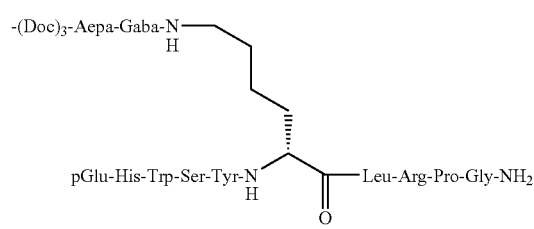
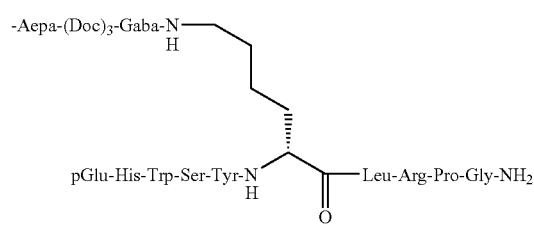
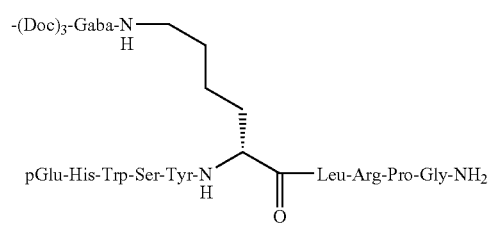

TABLE G-continued

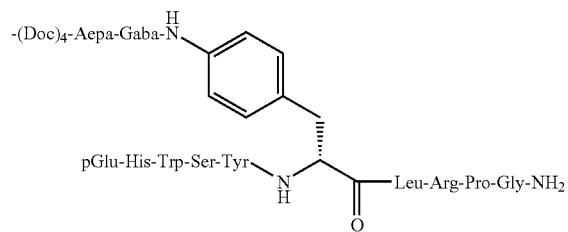

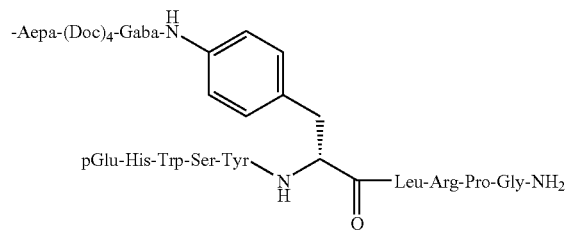

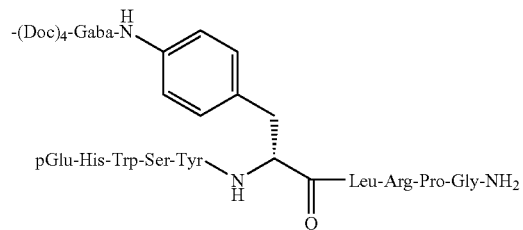

-(Doc)$_2$-Aepa-DPhe-cyclo(Cys-3lTyr-DTrp-Lys-Val-Cys)-Thr-NH$_2$
-Aepa-(Doc)$_2$-Gln-Trp-Ala-Val-βAla-His-Phe-Nle-NH$_2$

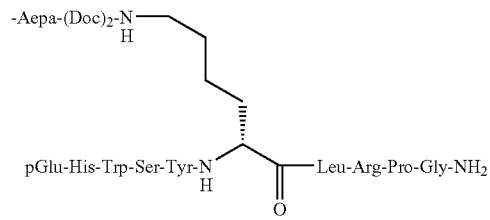

-Aepa-(Doc)$_2$-Gln-Trp-Ala-Val-βAla-His-Leu-Leu-NH$_2$
-Aepa-(Doc)$_2$-Gln-Trp-Ala-Val-βAla-His-Leu-Nle-NH$_2$
-Aepa-(Doc)$_2$-Gln-Trp-Ala-Val-βAla-His-Phe-Nle-NH$_2$
-Aepa-Gln-Trp-Ala-Val-βAla-His-Leu-Leu-NH$_2$
-Aepa-Gln-Trp-Ala-Val-βAla-His-Leu-Nle-NH$_2$
-Aepa-Gln-Trp-Ala-Val-βAla-His-Phe-Nle-NH$_2$
-(Aepa)$_2$-(Doc)$_2$-Gln-Trp-Ala-Val-βAla-His-Leu-Leu-NH$_2$
-(Aepa)$_2$-(Doc)$_2$-Gln-Trp-Ala-Val-βAla-His-Leu-Nle-NH$_2$
-Doc-DPhe-Gln-Trp-Ala-Val-βAla-His-Leu-Leu-NH$_2$
-Doc-DPhe-Gln-Trp-Ala-Val-βAla-His-Leu-Nle-NH$_2$
-Doc-DPhe-Gln-Trp-Ala-Val-Gly-His-Leu-Leu-NH$_2$
-Doc-DAla-Gln-Trp-Ala-Val-βAla-His-Phe-Nle-NH$_2$
-Doc-DPhe-Gln-Trp-Ala-Ala-βAla-His-Phe-Nle-NH$_2$
-Doc-Aepa-DPhe-Gln-Trp-Ala-Val-βAla-His-Leu-Leu-NH$_2$
-Doc-Aepa-DPhe-Gln-Trp-Ala-Val-βAla-His-Leu-Nle-NH$_2$
-Doc-Aepa-DPhe-Gln-Trp-Ala-Val-Gly-His-Leu-Leu-NH$_2$
-Doc-Aepa-DAla-Gln-Trp-Ala-Val-βAla-His-Phe-Nle-NH$_2$
-Doc-Aepa-DPhe-Gln-Trp-Ala-Ala-βAla-His-Phe-Nle-NH$_2$
-Aepa-(Doc)$_3$-DPhe-Gln-Trp-Ala-Val-βAla-His-Leu-Leu-NH$_2$
-Aepa-(Doc)$_3$-DPhe-Gln-Trp-Ala-Val-βAla-His-Leu-Nle-NH$_2$
-Aepa-(Doc)$_3$-DPhe-Gln-Trp-Ala-Val-Gly-His-Leu-Leu-NH$_2$
-Aepa-(Doc)$_3$-DAla-Gln-Trp-Ala-Val-βAla-His-Phe-Nle-NH$_2$
-Aepa-(Doc)$_3$-DPhe-Gln-Trp-Ala-Ala-βAla-His-Phe-Nle-NH$_2$
-(Doc)$_3$-Aepa-Gln-Trp-Ala-Val-βAla-His-Leu-Leu-NH$_2$
-(Doc)$_3$-Aepa-Gln-Trp-Ala-Val-βAla-His-Leu-Nle-NH$_2$
-(Doc)$_3$-Aepa-Gln-Trp-Ala-Val-Gly-His-Leu-Leu-NH$_2$
-(Doc)$_3$-Aepa-Gln-Trp-Ala-Val-βAla-His-Phe-Nle-NH$_2$
-(Doc)$_3$-Aepa-Gln-Trp-Ala-Ala-βAla-His-Phe-Nle-NH$_2$
-Aepa-Doc-DPhe-Gln-Trp-Ala-Val-βAla-His-Leu-Leu-NH$_2$
-Aepa-Doc-DPhe-Gln-Trp-Ala-Val-βAla-His-Leu-Nle-NH$_2$ TABLE G-continued -Aepa-Doc-DPhe-Gln-Trp-Ala-Val-Gly-His-Leu-Leu-NH$_2$
-Aepa-Doc-DAla-Gln-Trp-Ala-Val-βAla-His-Phe-Nle-NH$_2$
-Aepa-Doc-DPhe-Gln-Trp-Ala-Ala-βAla-His-Phe-Nle-NH$_2$
-Aepa-(Doc)$_4$-Gaba-Gln-Trp-Ala-Val-βAla-His-Leu-Leu-NH$_2$
-(Doc)$_4$-Aepa-Gaba-Gln-Trp-Ala-Val-βAla-His-Leu-Leu-NH$_2$
-(Doc)$_4$-Gaba-Gln-Trp-Ala-Val-βAla-His-Leu-Leu-NH$_2$
-Aepa-(Doc)$_4$-Gaba-Gln-Trp-Ala-Val-Gly-His-Leu-Ψ(CH$_2$NH)-Leu-NH$_2$
-(Doc)$_4$-Aepa-Gaba-Gln-Trp-Ala-Val-Gly-His-Leu-Ψ(CH$_2$NH)-Leu-NH$_2$
-(Doc)$_4$-Gaba-Gln-Trp-Ala-Val-Gly-His-Leu-Ψ(CH$_2$NH)-Leu-NH$_2$
-Aepa-(Doc)$_4$-Gaba-Gln-Trp-Ala-Val-βAla-His-Leu-Nle-NH$_2$
-(Doc)$_4$-Aepa-Gaba-Gln-Trp-Ala-Val-βAla-His-Leu-Nle-NH$_2$
-(Doc)$_4$-Gaba-Gln-Trp-Ala-Val-βAla-His-Leu-Nle-NH$_2$
-Aepa-(Doc)$_4$-Gln-Trp-Ala-Val-Gly-His-Leu-Ψ(CH$_2$NH)-Leu-NH$_2$
-(Doc)$_4$-Aepa-Gln-Trp-Ala-Val-Gly-His-Leu-Ψ(CH$_2$NH)-Leu-NH$_2$
-(Doc)$_4$-Gln-Trp-Ala-Val-Gly-His-Leu-Ψ(CH$_2$NH)-Leu-NH$_2$ -Aepa-(Doc)$_2$-Gln-Trp-Ala-Val-βAla-His-Leu-Leu-NH$_2$ Glp-His-Trp-Ser-Tyr-N(H)-[Lys(-Aepa-NH-)]-Leu-Arg-Pro-Gly-NH$_2$ -(Doc)$_4$-Aepa-Gaba-Gln-Trp-Ala-Val-βAla-His-Leu-Nle-NH$_2$
-(Doc)$_4$-Aepa-Gln-Trp-Ala-Val-βAla-His-Leu-Nle-NH$_2$
-(Doc)$_4$-Aepa-DPhe-Gln-Trp-Ala-Val-βAla-His-Leu-Nle-NH$_2$ TABLE G-continued

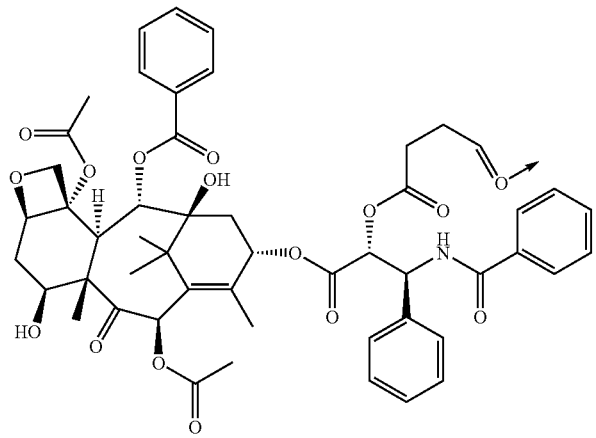

-(Doc)₄-Aepa-Gaba-Gln-Trp-Ala-Val-βAla-His-Leu-Nle-NH₂
-(Doc)₄-Aepa-Gln-Trp-Ala-Val-βAla-His-Leu-Nle-NH₂
-(Doc)₄-Gaba-Gln-Trp-Ala-Val-βAla-His-Leu-Nle-NH₂
-(Doc)₄-Aepa-DPhe-Gln-Trp-Ala-Val-βAla-His-Leu-Nle-NH₂

TABLE H

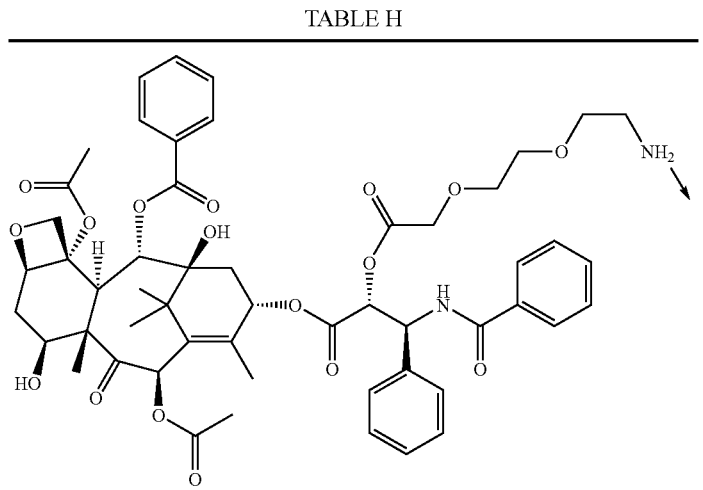

-Suc-(Doc)₃-Aepa-Gaba-Gln-Trp-Ala-Val-βAla-His-Leu-Nle-NH₂
-Suc-Aepa-(Doc)₃-Gaba-Gln-Trp-Ala-Val-βAla-His-Leu-Nle-NH₂
-Suc-Aepa-(Doc)₃-Gln-Trp-Ala-Val-βAla-His-Leu-Nle-NH₂
-Suc-(Doc)₃-Aepa-Gln-Trp-Ala-Val-βAla-His-Leu-Nle-NH₂
-Suc-(Doc)₃-Gln-Trp-Ala-Val-βAla-His-Leu-Nle-NH₂
-Suc-Aepa-(Doc)₃-DPhe-Gln-Trp-Ala-Val-βAla-His-Leu-Nle-NH₂
-Suc-(Doc)₃-Aepa-DPhe-Gln-Trp-Ala-Val-βAla-His-Leu-Nle-NH₂

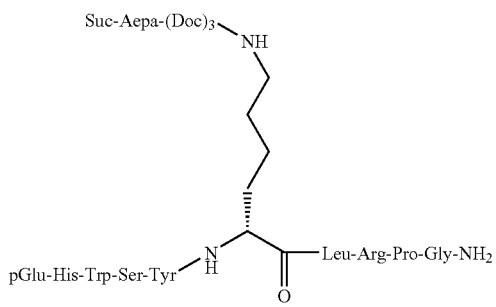

TABLE H-continued

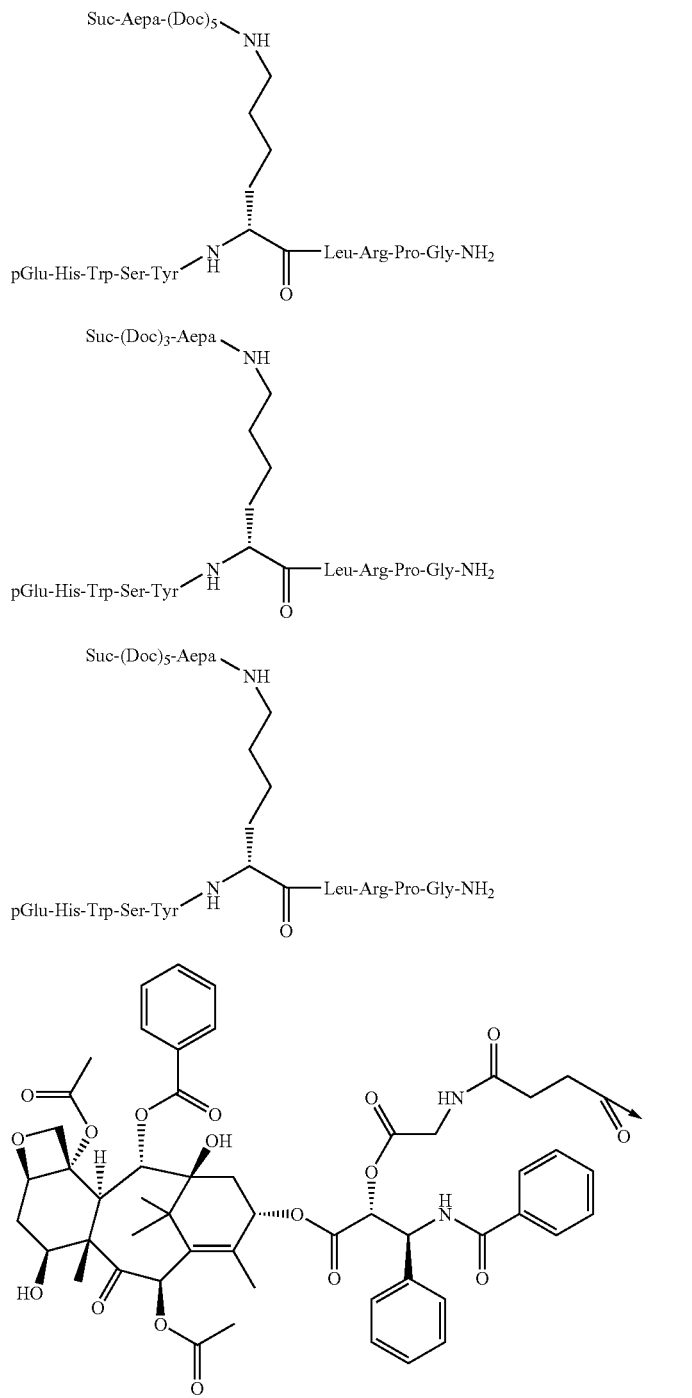

-Aepa-(Doc)$_2$-Gln-Trp-Ala-Val-βAla-His-Leu-Leu-NH$_2$
-Aepa-(Doc)$_2$-Gln-Trp-Ala-Val-βAla-His-Leu-Nle-NH$_2$
-Aepa-(Doc)$_2$-Gln-Trp-Ala-Val-Gly-His-Leu-Leu-NH$_2$
-Aepa-(Doc)$_2$-Gln-Trp-Ala-Val-βAla-His-Phe-Nle-NH$_2$
-Aepa-(Doc)$_2$-Gln-Trp-Ala-Ala-βAla-His-Phe-Nle-NH$_2$
-Aepa-Gln-Trp-Ala-Val-βAla-His-Leu-Leu-NH$_2$
-Aepa-Gln-Trp-Ala-Val-βAla-His-Leu-Nle-NH$_2$
-Aepa-Gln-Trp-Ala-Val-Gly-His-Leu-Leu-NH$_2$
-Aepa-Gln-Trp-Ala-Val-βAla-His-Phe-Nle-NH$_2$
-Aepa-Gln-Trp-Ala-Ala-βAla-His-Phe-Nle-NH$_2$
-(Doc)$_2$-Gln-Trp-Ala-Val-βAla-His-Leu-Leu-NH$_2$
-(Doc)$_2$-Gln-Trp-Ala-Val-βAla-His-Leu-Nle-NH$_2$
-(Doc)$_2$-Gln-Trp-Ala-Val-Gly-His-Leu-Leu-NH$_2$ TABLE H-continued -(Doc)₂-Gln-Trp-Ala-Val-βAla-His-Phe-Nle-NH₂
-(Doc)₂-Gln-Trp-Ala-Ala-βAla-His-Phe-Nle-NH₂
-Aepa-(Doc)₂-DPhe-Gln-Trp-Ala-Val-βAla-His-Leu-Leu-NH₂
-Aepa-(Doc)₂-DPhe-Gln-Trp-Ala-Val-βAla-His-Leu-Nle-NH₂
-Aepa-(Doc)₂-DPhe-Gln-Trp-Ala-Val-βAla-His-Phe-Nle-NH₂
-Aepa-DPhe-Gln-Trp-Ala-Val-βAla-His-Leu-Leu-NH₂
-Aepa-DPhe-Gln-Trp-Ala-Val-βAla-His-Leu-Nle-NH₂
-Aepa-DPhe-Gln-Trp-Ala-Val-βAla-His-Phe-Nle-NH₂
-(Aepa)₂-(Doc)₂-DPhe-Gln-Trp-Ala-Val-βAla-His-Leu-Leu-NH₂
-(Aepa)₂-(Doc)₂-DPhe-Gln-Trp-Ala-Val-βAla-His-Leu-Nle-NH₂
-Aepa-(Doc)₄-DPhe-Gln-Trp-Ala-Val-βAla-His-Leu-Leu-NH₂
-Aepa-(Doc)₄-DPhe-Gln-Trp-Ala-Val-βAla-His-Leu-Nle-NH₂
-Aepa-(Doc)₄-DPhe-Gln-Trp-Ala-Val-Gly-His-Leu-Leu-NH₂
-Aepa-(Doc)₄-DAla-Gln-Trp-Ala-Val-βAla-His-Phe-Nle-NH₂
-Aepa-(Doc)₄-DPhe-Gln-Trp-Ala-Ala-βAla-His-Phe-Nle-NH₂
-(Doc)₄-Aepa-DPhe-Gln-Trp-Ala-Val-βAla-His-Leu-Leu-NH₂
-(Doc)₄-Aepa-DPhe-Gln-Trp-Ala-Val-βAla-His-Leu-Nle-NH₂
-(Doc)₄-Aepa-DPhe-Gln-Trp-Ala-Val-Gly-His-Leu-Leu-NH₂
-(Doc)₄-Aepa-DAla-Gln-Trp-Ala-Val-βAla-His-Phe-Nle-NH₂
-(Doc)₄-Aepa-DPhe-Gln-Trp-Ala-Ala-βAla-His-Phe-Nle-NH₂
-(Doc)₄-Aepa-DPhe-Gln-Trp-Ala-Ala-βAla-His-Phe-Nle-NH₂
-(Doc)₄-DPhe-Gln-Trp-Ala-Val-βAla-His-Leu-Leu-NH₂
-(Doc)₄-DPhe-Gln-Trp-Ala-Val-βAla-His-Leu-Nle-NH₂
-(Doc)₄-DPhe-Gln-Trp-Ala-Val-Gly-His-Leu-Leu-NH₂
-(Doc)₄-DAla-Gln-Trp-Ala-Val-βAla-His-Phe-Nle-NH₂
-(Doc)₄-DPhe-Gln-Trp-Ala-Ala-βAla-His-Phe-Nle-NH₂
-Aepa-(Doc)₄-Gln-Trp-Ala-Val-βAla-His-Leu-Leu-NH₂
-Aepa-(Doc)₄-Gln-Trp-Ala-Val-βAla-His-Leu-Nle-NH₂
-Aepa-(Doc)₄-Gln-Trp-Ala-Val-Gly-His-Leu-Leu-NH₂
-Aepa-(Doc)₄-Gln-Trp-Ala-Val-βAla-His-Phe-Nle-NH₂
-Aepa-(Doc)₄-Gln-Trp-Ala-Ala-βAla-His-Phe-Nle-NH₂
-(Doc)₄-Aepa-Gln-Trp-Ala-Val-βAla-His-Leu-Leu-NH₂
-(Doc)₄-Aepa-Gln-Trp-Ala-Val-βAla-His-Leu-Nle-NH₂
-(Doc)₄-Aepa-Gln-Trp-Ala-Val-Gly-His-Leu-Leu-NH₂
-(Doc)₄-Aepa-Gln-Trp-Ala-Val-βAla-His-Phe-Nle-NH₂
-(Doc)₄-Aepa-Gln-Trp-Ala-Ala-βAla-His-Phe-Nle-NH₂
-(Doc)₄-Gln-Trp-Ala-Val-βAla-His-Leu-Leu-NH₂
-(Doc)₄-Gln-Trp-Ala-Val-βAla-His-Leu-Nle-NH₂
-(Doc)₄-Gln-Trp-Ala-Val-Gly-His-Leu-Leu-NH₂
-(Doc)₄-Gln-Trp-Ala-Val-βAla-His-Phe-Nle-NH₂
-(Doc)₄-Gln-Trp-Ala-Ala-βAla-His-Phe-Nle-NH₂
-Aepa-(Doc)₂-DPhe-Gln-Trp-Ala-Val-βAla-His-Leu-Leu-NH₂
-Aepa-(Doc)₂-DPhe-Gln-Trp-Ala-Val-βAla-His-Leu-Nle-NH₂
-Aepa-(Doc)₂-DPhe-Gln-Trp-Ala-Val-Gly-His-Leu-Leu-NH₂
-Aepa-(Doc)₂-DAla-Gln-Trp-Ala-Val-βAla-His-Phe-Nle-NH₂
-Aepa-(Doc)₂-DPhe-Gln-Trp-Ala-Ala-βAla-His-Phe-Nle-NH₂
-Aepa-DPhe-Gln-Trp-Ala-Val-βAla-His-Leu-Leu-NH₂
-Aepa-DPhe-Gln-Trp-Ala-Val-βAla-His-Leu-Nle-NH₂
-Aepa-DPhe-Gln-Trp-Ala-Val-Gly-His-Leu-Leu-NH₂
-Aepa-DAla-Gln-Trp-Ala-Val-βAla-His-Phe-Nle-NH₂
-Aepa-DPhe-Gln-Trp-Ala-Ala-βAla-His-Phe-Nle-NH₂
-(Doc)₂-DPhe-Gln-Trp-Ala-Val-βAla-His-Leu-Leu-NH₂
-(Doc)₂-DPhe-Gln-Trp-Ala-Val-βAla-His-Leu-Nle-NH₂
-(Doc)₂-DPhe-Gln-Trp-Ala-Val-Gly-His-Leu-Leu-NH₂
-(Doc)₂-DAla-Gln-Trp-Ala-Val-βAla-His-Phe-Nle-NH₂
-(Doc)₂-DPhe-Gln-Trp-Ala-Ala-βAla-His-Phe-Nle-NH₂
-(Doc)₂-Aepa-DPhe-Gln-Trp-Ala-Val-βAla-His-Leu-Leu-NH₂
-(Doc)₂-Aepa-DPhe-Gln-Trp-Ala-Val-βAla-His-Leu-Nle-NH₂
-(Doc)₂-Aepa-DPhe-Gln-Trp-Ala-Val-Gly-His-Leu-Leu-NH₂
-(Doc)₂-Aepa-DAla-Gln-Trp-Ala-Val-βAla-His-Phe-Nle-NH₂
-(Doc)₂-Aepa-DPhe-Gln-Trp-Ala-Ala-βAla-His-Phe-Nle-NH₂
-Aepa-(Doc)₂-Gln-Trp-Ala-Val-βAla-His-Ala-Nle-NH₂
-Aepa-Gln-Trp-Ala-Val-βAla-His-Ala-Nle-NH₂
-(Doc)₂-Gln-Trp-Ala-Val-βAla-His-Ala-Nle-NH₂
-Aepa-(Doc)₂-DPhe-Gln-Trp-Ala-Val-βAla-His-Ala-Nle-NH₂
-Aepa-DPhe-Gln-Trp-Ala-Val-βAla-His-Ala-Nle-NH₂
-(Doc)₂-DPhe-Gln-Trp-Ala-Val-βAla-His-Ala-Nle-NH₂
-Aepa-(Doc)₄-Gln-Trp-Ala-Val-βAla-His-Ala-Nle-NH₂
-(Doc)₄-Aepa-Gln-Trp-Ala-Val-βAla-His-Ala-Nle-NH₂
-(Doc)₄-Gln-Trp-Ala-Val-βAla-His-Ala-Nle-NH₂
-Aepa-(Doc)₄-DPhe-Gln-Trp-Ala-Val-βAla-His-Ala-Nle-NH₂
-(Doc)₄-Aepa-DPhe-Gln-Trp-Ala-Val-βAla-His-Ala-Nle-NH₂
-(Doc)₄-DPhe-Gln-Trp-Ala-Val-βAla-His-Ala-Nle-NH₂
-(Doc)₂-Aepa-Gln-Trp-Ala-Val-βAla-His-Ala-Nle-NH₂
-(Doc)₂-Aepa-DPhe-Gln-Trp-Ala-Val-βAla-His-Ala-Nle-NH₂
-Aepa-(Doc)₃-Gln-Trp-Ala-Val-βAla-His-Leu-Leu-NH₂
-Aepa-(Doc)₃-Gln-Trp-Ala-Val-βAla-His-Leu-Nle-NH₂
-Aepa-(Doc)₃-Gln-Trp-Ala-Val-Gly-His-Leu-Leu-NH₂
-Aepa-(Doc)₃-Gln-Trp-Ala-Val-βAla-His-Phe-Nle-NH₂
-Aepa-(Doc)₃-Gln-Trp-Ala-Ala-βAla-His-Phe-Nle-NH₂

TABLE H-continued

-Aepa-Doc-Gln-Trp-Ala-Val-βAla-His-Leu-Leu-NH₂
-Aepa-Doc-Gln-Trp-Ala-Val-βAla-His-Leu-Nle-NH₂
-Aepa-Doc-Gln-Trp-Ala-Val-Gly-His-Leu-Leu-NH₂
-Aepa-Doc-Gln-Trp-Ala-Val-βAla-His-Phe-Nle-NH₂
-Aepa-Doc-Gln-Trp-Ala-Ala-βAla-His-Phe-Nle-NH₂
-(Doc)₃-Gln-Trp-Ala-Val-βAla-His-Leu-Leu-NH₂
-(Doc)₃-Gln-Trp-Ala-Val-βAla-His-Leu-Nle-NH₂
-(Doc)₃-Gln-Trp-Ala-Val-Gly-His-Leu-Leu-NH₂
-(Doc)₃-Gln-Trp-Ala-Val-βAla-His-Phe-Nle-NH₂
-(Doc)₃-Gln-Trp-Ala-Ala-βAla-His-Phe-Nle-NH₂
-(Doc)₃-Aepa-DPhe-Gln-Trp-Ala-Val-βAla-His-Leu-Leu-NH₂
-(Doc)₃-Aepa-DPhe-Gln-Trp-Ala-Val-βAla-His-Leu-Nle-NH₂
-(Doc)₃-Aepa-DPhe-Gln-Trp-Ala-Val-Gly-His-Leu-Leu-NH₂
-(Doc)₃-DPhe-Gln-Trp-Ala-Val-βAla-His-Leu-Leu-NH₂
-(Doc)₃-DPhe-Gln-Trp-Ala-Val-βAla-His-Leu-Nle-NH₂
-(Doc)₃-DPhe-Gln-Trp-Ala-Val-Gly-His-Leu-Leu-NH₂
-(Doc)₃-DAla-Gln-Trp-Ala-Val-βAla-His-Phe-Nle-NH₂
-(Doc)₃-DPhe-Gln-Trp-Ala-Ala-βAla-His-Phe-Nle-NH₂
-Doc-Gln-Trp-Ala-Val-βAla-His-Leu-Leu-NH₂
-Doc-Gln-Trp-Ala-Val-βAla-His-Leu-Nle-NH₂
-Doc-Gln-Trp-Ala-Val-Gly-His-Leu-Leu-NH₂
-Doc-Gln-Trp-Ala-Val-βAla-His-Phe-Nle-NH₂
-Doc-Gln-Trp-Ala-Ala-βAla-His-Phe-Nle-NH₂

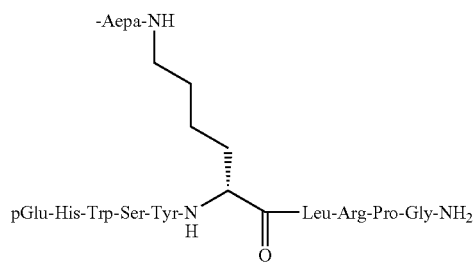

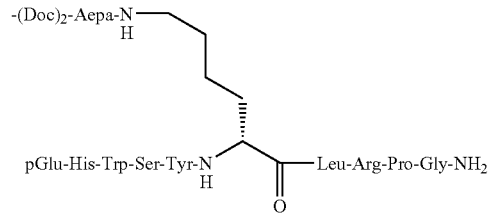

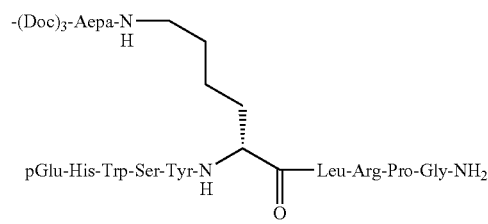

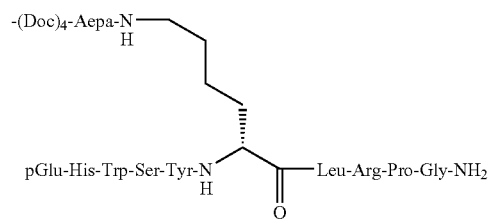

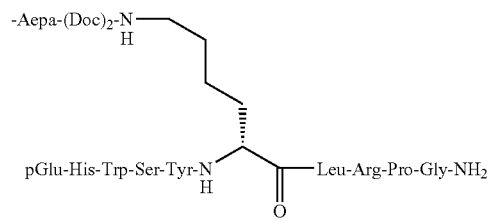

TABLE H-continued
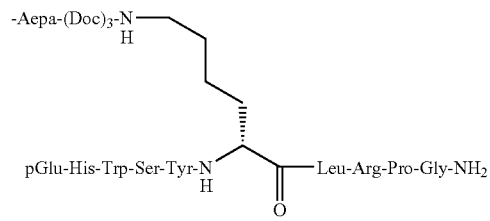
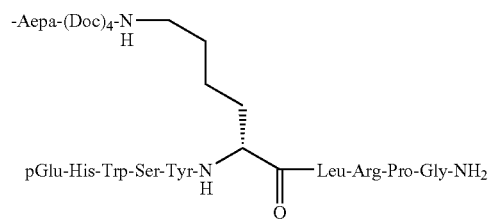
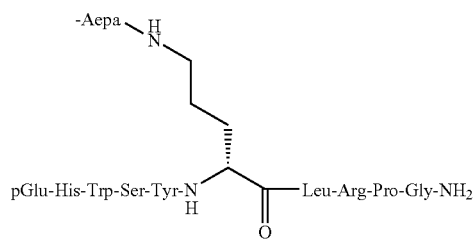
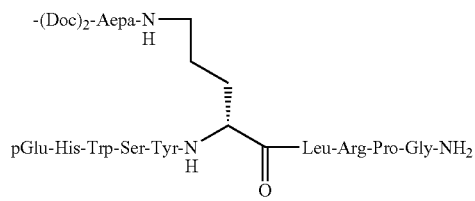
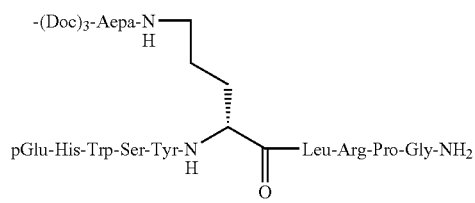
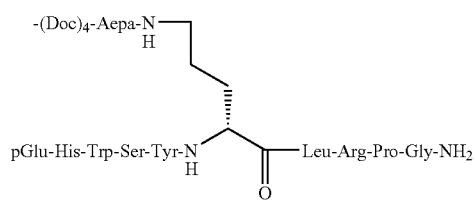
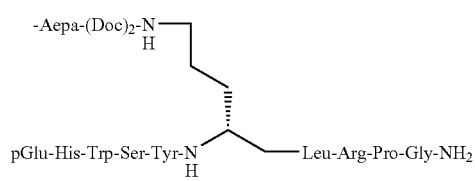

TABLE H-continued
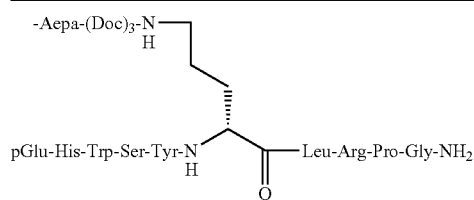
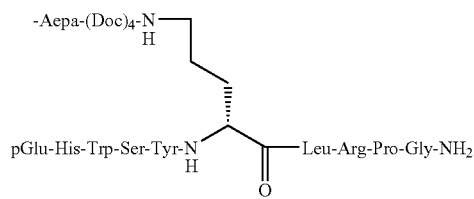
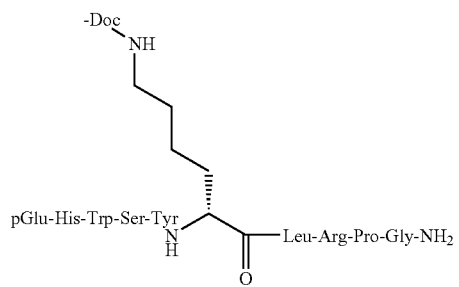
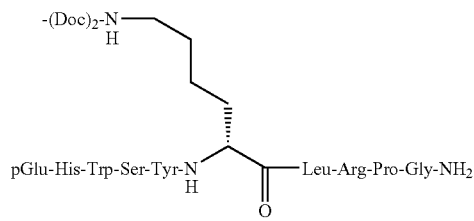
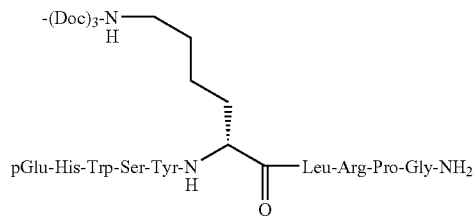
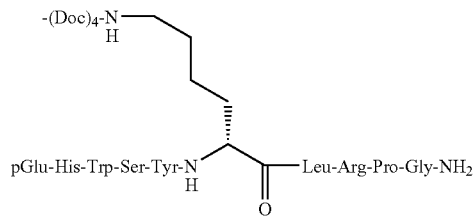
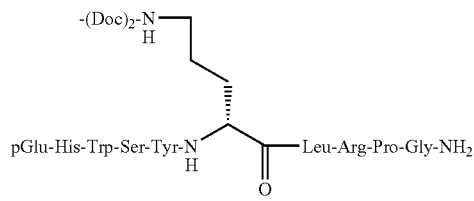

TABLE H-continued
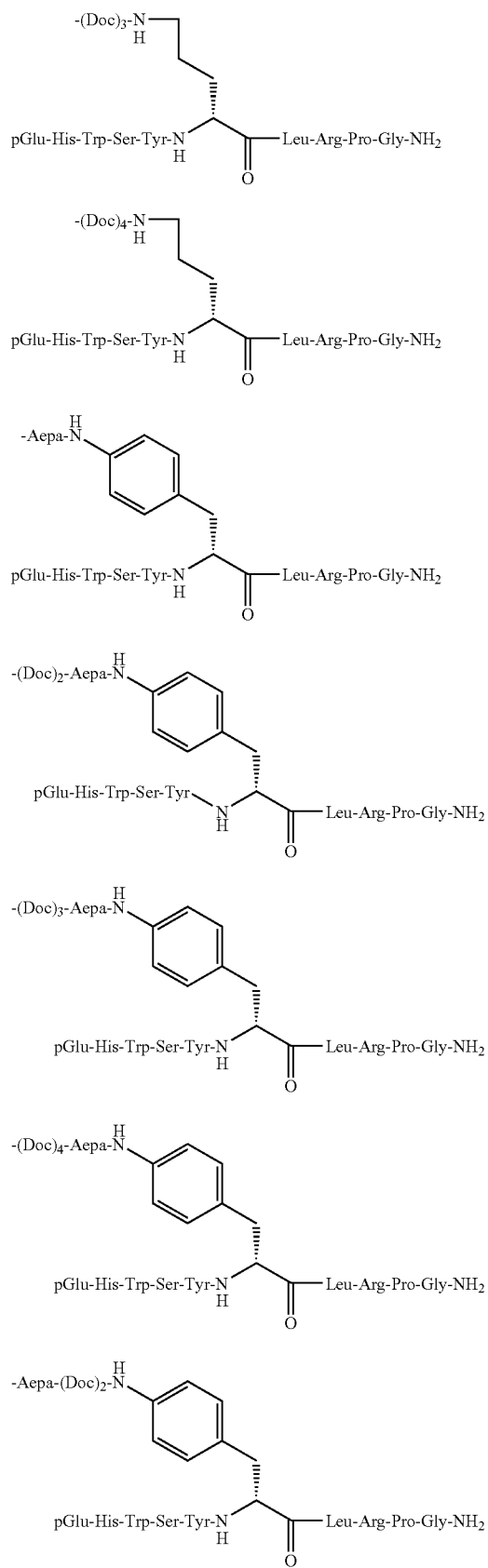

TABLE H-continued

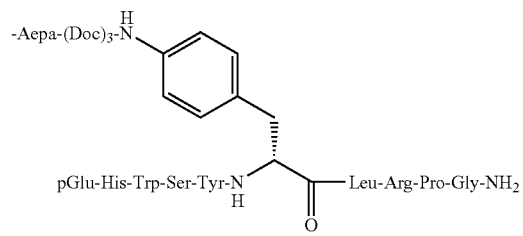

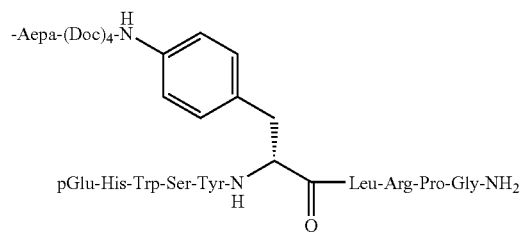

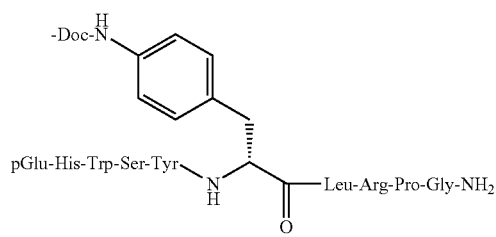

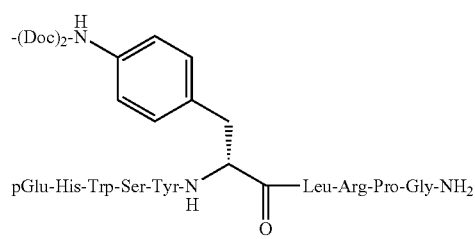

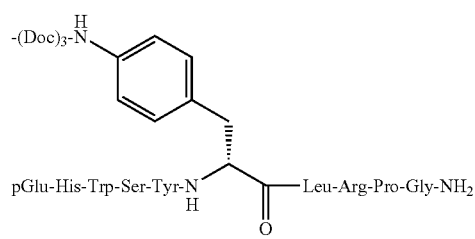

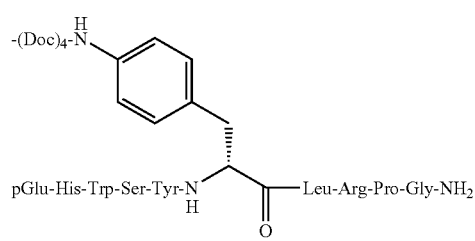

-HSDGIFTDSYSRYRKQMAVKKYLAAVL(βAla)KRYKQRVKNK-NH₂
-HSDGIFTDSYSRYRKQMAVKKYLAAVL(Ava)KRYKQRVKNK-NH₂
-HSDGIFTDSYSRYRKQMAVKKYLAAVLGKRYKQR(A₆c)KNK-NH₂
-HSDGIFTDSYSRYRKQMA(A₅c)KKYLAAVLGKRYKQRVKNK-NH₂
-(Aepa)HSDGIFTDSYSRYRKQMAVKKYLAAVL(βAla)KRYKQRVKNK-NH₂
-(Aepa)HSDGIFTDSYSRYRKQMAVKKYLAAVL(Ava)KRYKQRVKNK-NH₂
-(Aepa)HSDGIFTDSYSRYRKQMAVKKYLAAVLGKRYKQR(A₆c)KNK-NH₂
-(Aepa)HSDGIFTDSYSRYRKQMA(A₅c)KKYLAAVLGKRYKQRVKNK-NH₂
-(Doc)₆-DPhe-cyclo(Cys-3ITyr-DTrp-Lys-Val-Cys)-Thr-NH₂

TABLE H-continued

-(Doc)₄-DPhe-cyclo(Cys-3ITyr-DTrp-Lys-Val-Cys)-Thr-NH₂
-DPhe-cyclo(Cys-3ITyr-DTrp-Lys-Val-Cys)-Thr-NH₂
-Aepa-DPhe-cyclo(Cys-3ITyr-DTrp-Lys-Val-Cys)-Thr-NH₂
-(Doc)₄-Aepa-DPhe-cyclo(Cys-3ITyr-DTrp-Lys-Val-Cys)-Thr-NH₂
-DPhe-cyclo(Cys-3ITyr-DTrp-Lys-Val-Cys)-Thr-NH₂
-Aepa-DPhe-cyclo(Cys-3ITyr-DTrp-Lys-Val-Cys)-Thr-NH₂
-Doc-DPhe-cyclo(Cys-3ITyr-DTrp-Lys-Val-Cys)-Thr-NH₂
-(Doc)₂-DPhe-cyclo(Cys-3ITyr-DTrp-Lys-Val-Cys)-Thr-NH₂
-(Doc)₃-DPhe-cyclo(Cys-3ITyr-DTrp-Lys-Vat-Cys)-Thr-NH₂
-(Doc)₄-DPhe-cyclo(Cys-3ITyr-DTrp-Lys-Val-Cys)-Thr-NH₂
-(Doc)₅-DPhe-cyclo(Cys-3ITyr-DTrp-Lys-Val-Cys)-Thr-NH₂
-(Doc)₆-DPhe-cyclo(Cys-3ITyr-DTrp-Lys-Val-Cys)-Thr-NH₂
-Doc-Aepa-DPhe-cyclo(Cys-3ITyr-DTrp-Lys-Val-Cys)-Thr-NH₂
-(Doc)₂-Aepa-DPhe-cyclo(Cys-3ITyr-DTrp-Lys-Val-Cys)-Thr-NH₂
-(Doc)₃-Aepa-DPhe-cyclo(Cys-3ITyr-DTrp-Lys-Val-Cys)-Thr-NH₂
-(Doc)₅-Aepa-DPhe-cyclo(Cys-3ITyr-DTrp-Lys-Val-Cys)-Thr-NH₂
-(Doc)₆-Aepa-DPhe-cyclo(Cys-3ITyr-DTrp-Lys-Val-Cys)-Thr-NH₂
-(Aepa)₂-DPhe-cyclo(Cys-3ITyr-DTrp-Lys-Val-Cys)-Thr-NH₂
-Aepa-Doc-DPhe-cyclo(Cys-3ITyr-DTrp-Lys-Val-Cys)-Thr-NH₂
-Aepa-(Doc)₂-DPhe-cyclo(Cys-3ITyr-DTrp-Lys-Val-Cys)-Thr-NH₂
-Aepa-(Doc)₃-DPhe-cyclo(Cys-3ITyr-DTrp-Lys-Val-Cys)-Thr-NH₂
-Aepa-(Doc)₄-DPhe-cyclo(Cys-3ITyr-DTrp-Lys-Val-Cys)-Thr-NH₂
-Doc-Aepa-DPhe-cyclo(Cys-3ITyr-DTrp-Lys-Thr-Cys)-Thr-NH₂
-(Doc)₂-Aepa-DPhe-cyclo(Cys-3ITyr-DTrp-Lys-Thr-Cys)-Thr-NH₂
-(Doc)₃-Aepa-DPhe-cyclo(Cys-3ITyr-DTrp-Lys-Thr-Cys)-Thr-NH₂
-(Doc)₅-Aepa-DPhe-cyclo(Cys-3ITyr-DTrp-Lys-Thr-Cys)-Thr-NH₂
-(Doc)₆-Aepa-DPhe-cyclo(Cys-3ITyr-DTrp-Lys-Thr-Cys)-Thr-NH₂
-(Aepa)₂-DPhe-cyclo(Cys-3ITyr-DTrp-Lys-Thr-Cys)-Thr-NH₂
-Doc-DPhe-cyclo(Cys-3ITyr-DTrp-Lys-Thr-Cys)-Thr-NH₂
-(Doc)₂-DPhe-cyclo(Cys-3ITyr-DTrp-Lys-Thr-Cys)-Thr-NH₂
-(Doc)₃-DPhe-cyclo(Cys-3ITyr-DTrp-Lys-Thr-Cys)-Thr-NH₂
-(Doc)₄-DPhe-cyclo(Cys-3ITyr-DTrp-Lys-Thr-Cys)-Thr-NH₂
-(Doc)₅-DPhe-cyclo(Cys-3ITyr-DTrp-Lys-Thr-Cys)-Thr-NH₂
-(Doc)₆-DPhe-cyclo(Cys-3ITyr-DTrp-Lys-Thr-Cys)-Thr-NH₂
-(Doc)₆-DPhe-cyclo(Cys-3ITyr-DTrp-Lys-Thr-Cys)-Thr-NH₂
-(Doc)₄-DPhe-cyclo(Cys-3ITyr-DTrp-Lys-Thr-Cys)-Thr-NH₂
-DPhe-cyclo(Cys-3ITyr-DTrp-Lys-Thr-Cys)-Thr-NH₂
-Aepa-DPhe-cyclo(Cys-3ITyr-DTrp-Lys-Thr-Cys)-Thr-NH₂
-(Doc)₄-Aepa-DPhe-cyclo(Cys-3ITyr-DTrp-Lys-Thr-Cys)-Thr-NH₂
-DPhe-cyclo(Cys-3ITyr-DTrp-Lys-Thr-Cys)-Thr-NH₂
-Aepa-DPhe-cyclo(Cys-3ITyr-DTrp-Lys-Thr-Cys)-Thr-NH₂

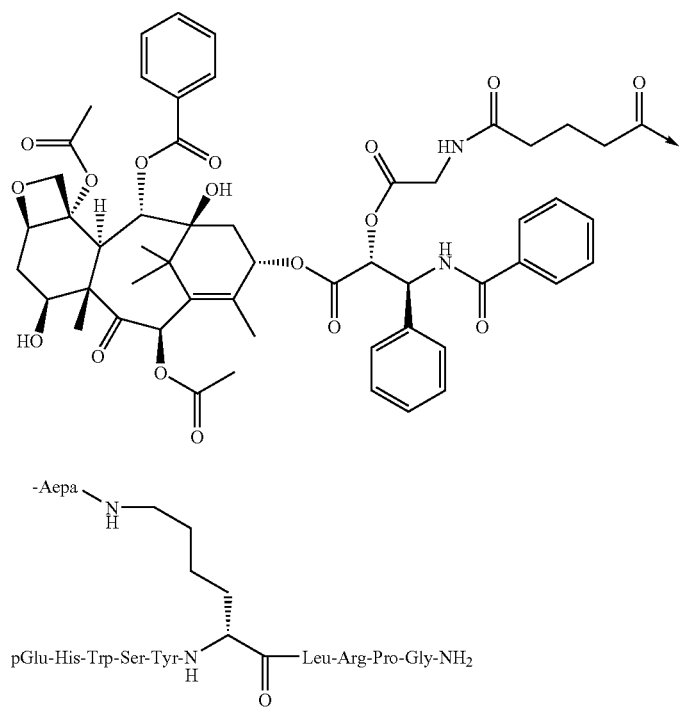

TABLE H-continued
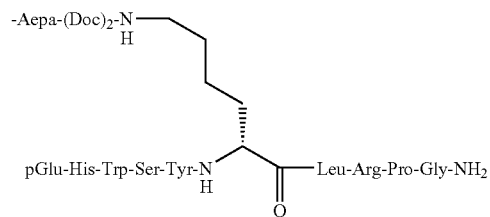
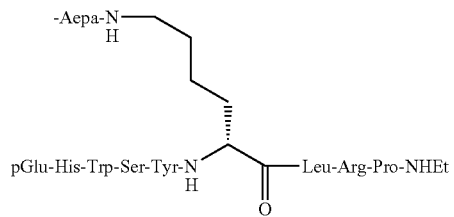
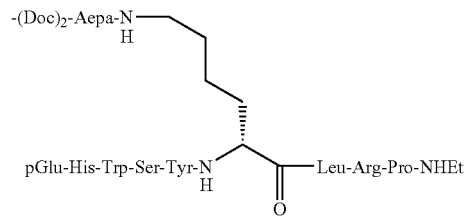
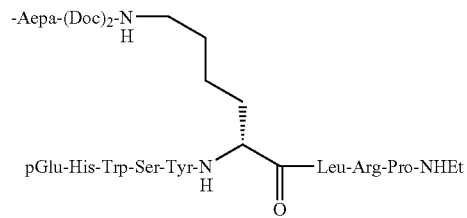
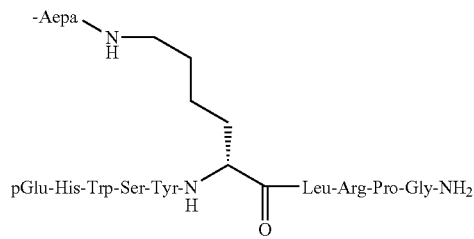
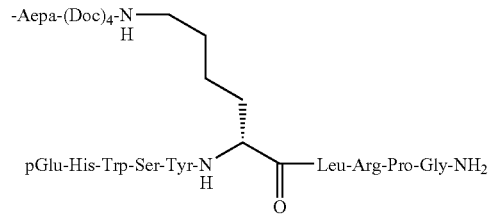
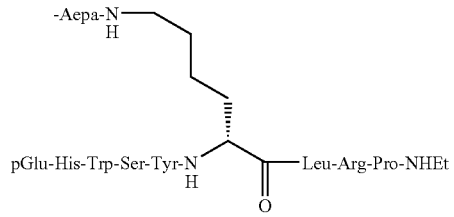

TABLE H-continued
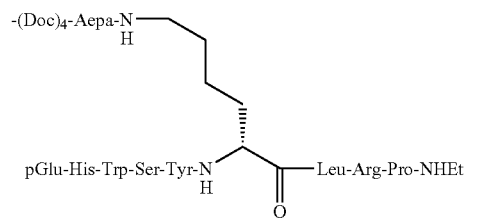
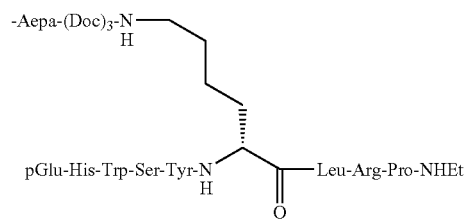
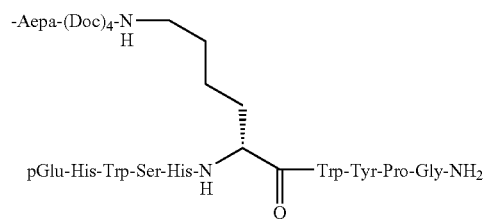
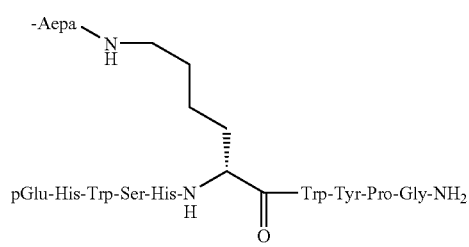
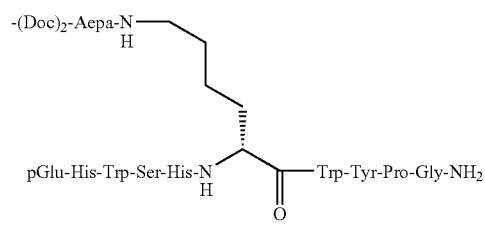
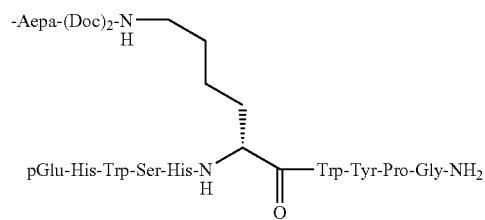
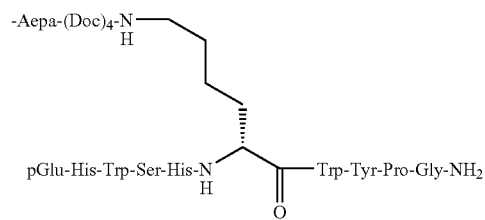

TABLE H-continued
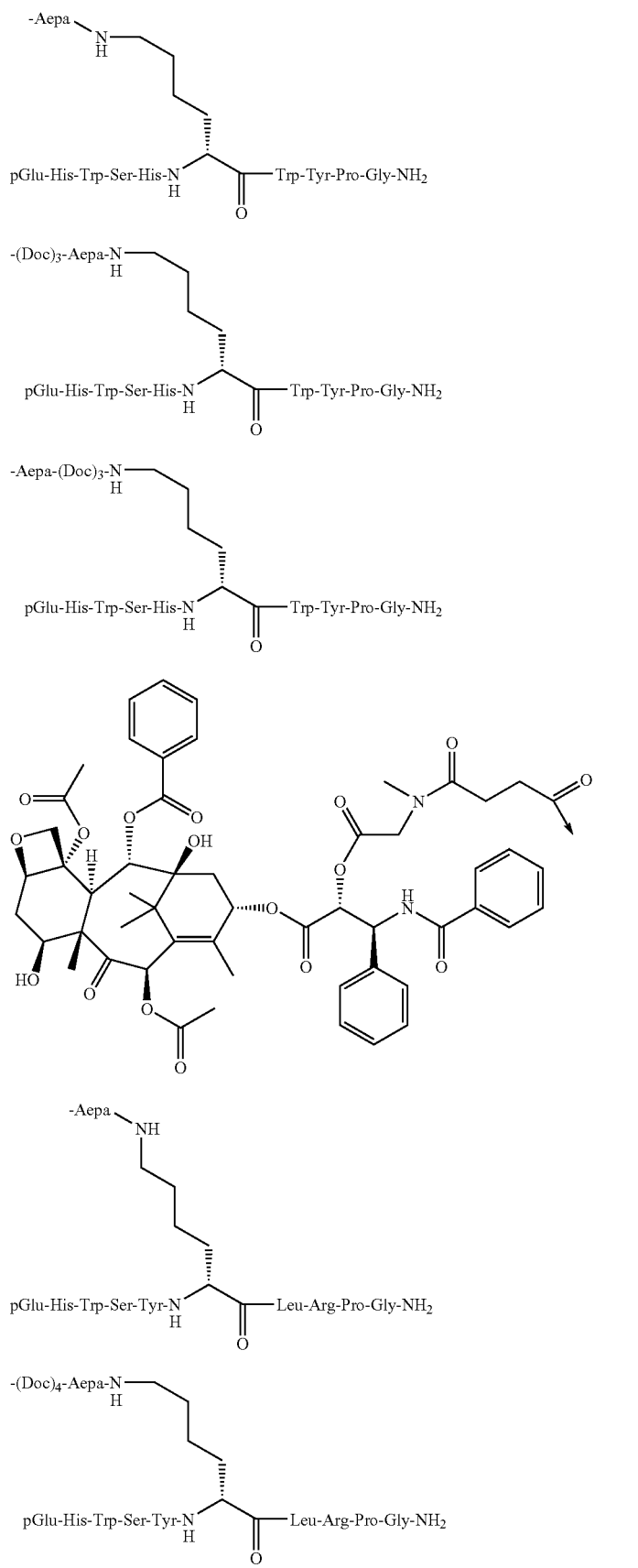

TABLE H-continued
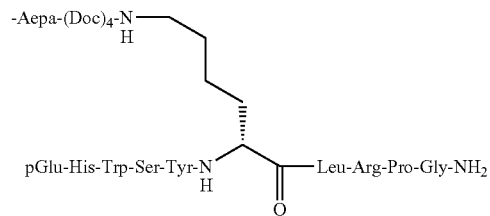
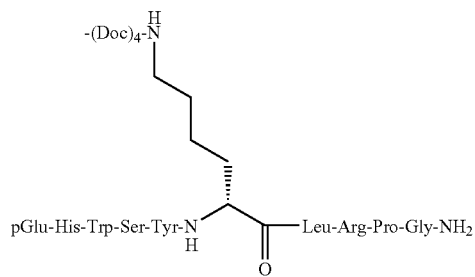
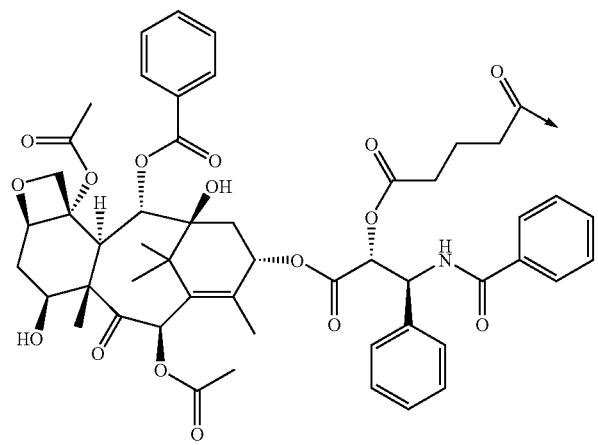
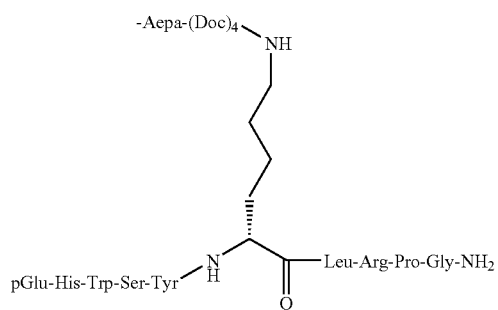
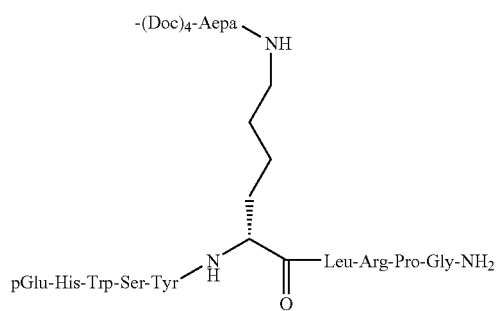

TABLE H-continued

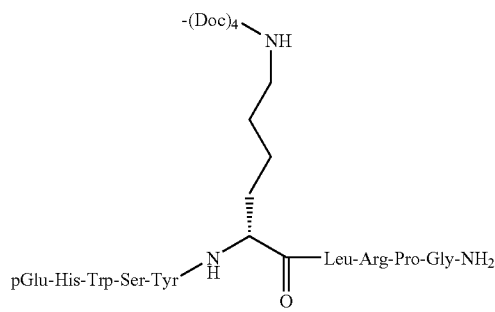

TABLE I

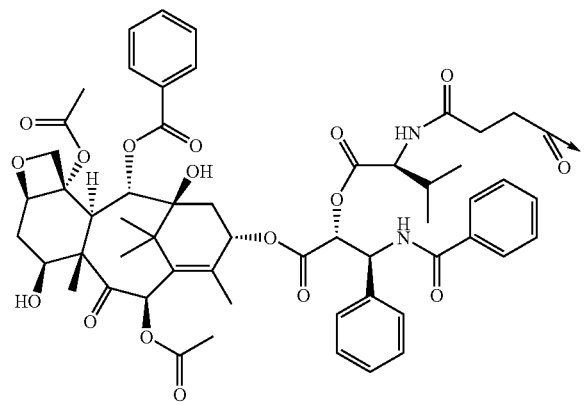

-Aepa-Lys-DTyr-DTyr-cyclo(Cys-Tyr-DTrp-Lys-Abu-Cys)-Thr-NH$_2$
-DPhe-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$

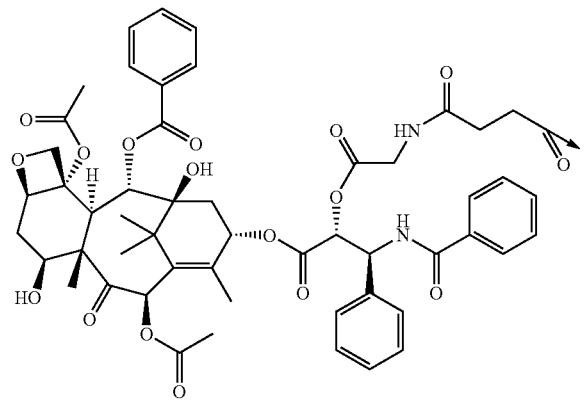

-Aepa-Lys-DTyr-DTyr-cyclo(Cys-Tyr-DTrp-Lys-Abu-Cys)-Thr-NH$_2$
-Doc-Aepa-DPhe-cyclo(Cys-3lTyr-DTrp-Lys-Abu-Cys)-Thr-NH$_2$
-(Doc)$_2$-Aepa-DPhe-cyclo(Cys-3lTyr-DTrp-Lys-Abu-Cys)-Thr-NH$_2$
-(Doc)$_3$-Aepa-DPhe-cyclo(Cys-3lTyr-DTrp-Lys-Abu-Cys)-Thr-NH$_2$
-(Doc)$_5$-Aepa-DPhe-cyclo(Cys-3lTyr-DTrp-Lys-Abu-Cys)-Thr-NH$_2$
-(Doc)$_6$-Aepa-DPhe-cyclo(Cys-3lTyr-DTrp-Lys-Abu-Cys)-Thr-NH$_2$
-(Aepa)$_2$-DPhe-cyclo(Cys-3lTyr-DTrp-Lys-Abu-Cys)-Thr-NH$_2$
-Doc-DPhe-cyclo(Cys-3lTyr-DTrp-Lys-Abu-Cys)-Thr-NH$_2$
-(Doc)$_2$-DPhe-cyclo(Cys-3lTyr-DTrp-Lys-Abu-Cys)-Thr-NH$_2$
-(Doc)$_3$-DPhe-cyclo(Cys-3lTyr-DTrp-Lys-Abu-Cys)-Thr-NH$_2$
-(Doc)$_4$-DPhe-cyclo(Cys-3lTyr-DTrp-Lys-Abu-Cys)-Thr-NH$_2$
-(Doc)$_5$-DPhe-cyclo(Cys-3lTyr-DTrp-Lys-Abu-Cys)-Thr-NH$_2$
-(Doc)$_6$-DPhe-cyclo(Cys-3lTyr-DTrp-Lys-Abu-Cys)-Thr-NH$_2$

TABLE I-continued

-(Doc)$_6$-DPhe-cyclo(Cys-3lTyr-DTrp-Lys-Abu-Cys)-Thr-NH$_2$
-(Doc)$_4$-DPhe-cyclo(Cys-3lTyr-DTrp-Lys-Abu-Cys)-Thr-NH$_2$
-DPhe-cyclo(Cys-3lTyr-DTrp-Lys-Abu-Cys)-Thr-NH$_2$
-Aepa-DPhe-cyclo(Cys-3lTyr-DTrp-Lys-Abu-Cys)-Thr-NH$_2$
-(Doc)$_4$-Aepa-DPhe-cyclo(Cys-3lTyr-DTrp-Lys-Abu-Cys)-Thr-NH$_2$
-DPhe-cyclo(Cys-3lTyr-DTrp-Lys-Abu-Cys)-Thr-NH$_2$
-Aepa-DPhe-cyclo(Cys-3lTyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_4$-Aepa-DPhe-cyclo(Cys-Tyr-DTrp-Lys-Abu-Cys)-Thr-NH$_2$
-DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-Aepa-Lys-DTyr-DTyr-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-Aepa-DPhe-cyclo(Cys-Tyr-DTrp-Lys-Abu-Cys)-Thr-NH$_2$
-(Doc)$_2$-Aepa-DPhe-cyclo(Cys-3lTyr-DTrp-Lys-Val-Cys)-Thr-NH$_2$
-(Doc)$_2$-Aepa-Caeg-cyclo(DCys-3Pal-DTrp-Lys-DCys)-Thr(Bzl)-Tyr-NH$_2$
-(Doc)$_4$-Aepa-Caeg-cyclo(DCys-3Pal-DTrp-Lys-DCys)-Thr(Bzl)-Tyr-NH$_2$
-Doc-Aepa-DPhe-cyclo(Cys-Tyr-DTrp-Lys-Abu-Cys)-Thr-NH$_2$
-(Doc)$_2$-Aepa-DPhe-cyclo(Cys-Tyr-DTrp-Lys-Abu-Cys)-Thr-NH$_2$
-(Doc)$_3$-Aepa-DPhe-cyclo(Cys-Tyr-DTrp-Lys-Abu-Cys)-Thr-NH$_2$
-(Doc)$_5$-Aepa-DPhe-cyclo(Cys-Tyr-DTrp-Lys-Abu-Cys)-Thr-NH$_2$
-(Doc)$_6$-Aepa-DPhe-cyclo(Cys-Tyr-DTrp-Lys-Abu-Cys)-Thr-NH$_2$
-(Aepa)$_2$-DPhe-cyclo(Cys-Tyr-DTrp-Lys-Abu-Cys)-Thr-NH$_2$
-Doc-DPhe-cyclo(Cys-Tyr-DTrp-Lys-Abu-Cys)-Thr-NH$_2$
-(Doc)$_2$-DPhe-cyclo(Cys-Tyr-DTrp-Lys-Abu-Cys)-Thr-NH$_2$
-(Doc)$_3$-DPhe-cyclo(Cys-Tyr-DTrp-Lys-Abu-Cys)-Thr-NH$_2$
-(Doc)$_4$-DPhe-cyclo(Cys-Tyr-DTrp-Lys-Abu-Cys)-Thr-NH$_2$
-(Doc)$_5$-DPhe-cyclo(Cys-Tyr-DTrp-Lys-Abu-Cys)-Thr-NH$_2$
-(Doc)$_6$-DPhe-cyclo(Cys-Tyr-DTrp-Lys-Abu-Cys)-Thr-NH$_2$
-Lys-DTyr-DTyr-cyclo(Cys-Tyr-DTrp-Lys-Abu-Cys)-Thr-NH$_2$
-Doc-Aepa-Lys-DTyr-DTyr-cyclo(Cys-Tyr-DTrp-Lys-Abu-Cys)-Thr-NH$_2$
-(Doc)$_2$-Aepa-Lys-DTyr-DTyr-cyclo(Cys-Tyr-DTrp-Lys-Abu-Cys)-Thr-NH$_2$
-(Doc)$_3$-Aepa-Lys-DTyr-DTyr-cyclo(Cys-Tyr-DTrp-Lys-Abu-Cys)-Thr-NH$_2$
-(Doc)$_4$-Aepa-Lys-DTyr-DTyr-cyclo(Cys-Tyr-DTrp-Lys-Abu-Cys)-Thr-NH$_2$
-(Doc)$_5$-Aepa-Lys-DTyr-DTyr-cyclo(Cys-Tyr-DTrp-Lys-Abu-Cys)-Thr-NH$_2$
-(Doc)$_6$-Aepa-Lys-DTyr-DTyr-cyclo(Cys-Tyr-DTrp-Lys-Abu-Cys)-Thr-NH$_2$
-(Aepa)$_2$-Lys-DTyr-DTyr-cyclo(Cys-Tyr-DTrp-Lys-Abu-Cys)-Thr-NH$_2$
-Doc-Lys-DTyr-DTyr-cyclo(Cys-Tyr-DTrp-Lys-Abu-Cys)-Thr-NH$_2$
-(Doc)$_2$-Lys-DTyr-DTyr-cyclo(Cys-Tyr-DTrp-Lys-Abu-Cys)-Thr-NH$_2$
-(Doc)$_3$-Lys-DTyr-DTyr-cyclo(Cys-Tyr-DTrp-Lys-Abu-Cys)-Thr-NH$_2$
-(Doc)$_4$-Lys-DTyr-DTyr-cyclo(Cys-Tyr-DTrp-Lys-Abu-Cys)-Thr-NH$_2$
-(Doc)$_5$-Lys-DTyr-DTyr-cyclo(Cys-Tyr-DTrp-Lys-Abu-Cys)-Thr-NH$_2$
-(Doc)$_6$-Lys-DTyr-DTyr-cyclo(Cys-Tyr-DTrp-Lys-Abu-Cys)-Thr-NH$_2$
-Aepa-Doc-Lys-DTyr-DTyr-cyclo(Cys-Tyr-DTrp-Lys-Abu-Cys)-Thr-NH$_2$
-Aepa-(Doc)$_2$-Lys-DTyr-DTyr-cyclo(Cys-Tyr-DTrp-Lys-Abu-Cys)-Thr-NH$_2$ TABLE I-continued -Aepa-(Doc)₃-Lys-DTyr-DTyr-cyclo(Cys-Tyr-DTrp-Lys-Abu-Cys)-Thr-NH₂
-Aepa-(Doc)₄-Lys-DTyr-DTyr-cyclo(Cys-Tyr-DTrp-Lys-Abu-Cys)-Thr-NH₂
-Aepa-Doc-DPhe-cyclo(Cys-Tyr-DTrp-Lys-Abu-Cys)-Thr-NH₂
-Aepa-(Doc)₂-DPhe-cyclo(Cys-Tyr-DTrp-Lys-Abu-Cys)-Thr-NH₂
-Aepa-(Doc)₃-DPhe-cyclo(Cys-Tyr-DTrp-Lys-Abu-Cys)-Thr-NH₂
-Aepa-(Doc)₄-DPhe-cyclo(Cys-Tyr-DTrp-Lys-Abu-Cys)-Thr-NH₂
-(Doc)₆-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-Caeg-cyclo(DCys-3Pal-DTrp-Lys-DCys)-Thr(Bzl)-Tyr-NH₂
-Aepa-Caeg-cyclo(DCys-3Pal-DTrp-Lys-DCys)-Thr(Bzl)-Tyr-NH₂
-Doc-Aepa-Caeg-cyclo(DCys-3Pal-DTrp-Lys-DCys)-Thr(Bzl)-Tyr-NH₂
-(Doc)₂-Aepa-Caeg-cyclo(DCys-3Pal-DTrp-Lys-DCys)-Thr(Bzl)-Tyr-NH₂
-(Doc)₃-Aepa-Caeg-cyclo(DCys-3Pal-DTrp-Lys-DCys)-Thr(Bzl)-Tyr-NH₂
-(Doc)₄-Aepa-Caeg-cyclo(DCys-3Pal-DTrp-Lys-DCys)-Thr(Bzl)-Tyr-NH₂
-(Doc)₅-Aepa-Caeg-cyclo(DCys-3Pal-DTrp-Lys-DCys)-Thr(Bzl)-Tyr-NH₂
-(Doc)₆-Aepa-Caeg-cyclo(DCys-3Pal-DTrp-Lys-DCys)-Thr(Bzl)-Tyr-NH₂
-(Aepa)₂-Caeg-cyclo(DCys-3Pal-DTrp-Lys-DCys)-Thr(Bzl)-Tyr-NH₂
-Doc-Caeg-cyclo(DCys-3Pal-DTrp-Lys-DCys)-Thr(Bzl)-Tyr-NH₂
-(Doc)₂-Caeg-cyclo(DCys-3Pal-DTrp-Lys-DCys)-Thr(Bzl)-Tyr-NH₂
-(Doc)₃-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)₅-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂
-Aepa-Doc-Caeg-cyclo(DCys-3Pal-DTrp-Lys-DCys)-Thr(Bzl)-Tyr-NH₂
-Aepa-(Doc)₂-Caeg-cyclo(DCys-3Pal-DTrp-Lys-DCys)-Thr(Bzl)-Tyr-NH₂
-Aepa-(Doc)₃-Caeg-cyclo(DCys-3Pal-DTrp-Lys-DCys)-Thr(Bzl)-Tyr-NH₂
-Aepa-(Doc)₄-Caeg-cyclo(DCys-3Pal-DTrp-Lys-DCys)-Thr(Bzl)-Tyr-NH₂
-HSDAVFTDNYTRLRKQ(Nle)AVKKYLNSILN-NH₂
-HSDAVFTDNYTRLRKQMAVKKYLNSILN-NH₂ (SEQ ID NO: 7)
-HSDAVFTDNYTRLRKQMAVKKALNSILN-NH₂ (SEQ ID NO: 5)
-HSDAVFTDNYTRLRKQMAVKKLLNSILN-NH₂ (SEQ ID NO: 4)
-(Aepa)HSDAVFTDNYTRLRKQ(Nle)AVKKYLNSILN-NH₂
-(Aepa)HSDAVFTDNYTRLRKQMAVKKYLNSILN-NH₂
-(Aepa)HSDAVFTDNYTRLRKQMAVKKALNSILN-NH₂
-(Aepa)HSDAVFTDNYTRLRKQMAVKKLLNSILN-NH₂
-Aepa-Lys-DTyr-DTyr-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-Aepa-DPhe-cyclo(Cys-Tyr-DTrp-Lys-Abu-Cys)-Thr-NH₂
-(Doc)₂-Aepa-DPhe-cyclo(Cys-3lTyr-DTrp-Lys-Val-Cys)-Thr-NH₂

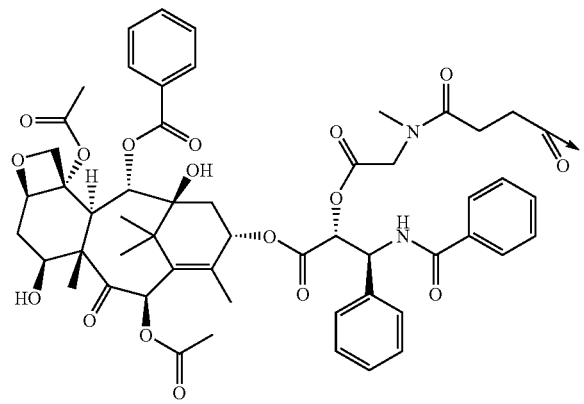

-(Doc)₄-Aepa-DPhe-cyclo(Cys-Tyr-DTrp-Lys-Abu-Cys)-Thr-NH₂
-(Doc)₄-DPhe-cyclo(Cys-Tyr-DTrp-Lys-Abu-Cys)-Thr-NH₂
-(Doc)₆-DPhe-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-(Doc)₄-Aepa-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂

TABLE I-continued

-(Doc)₄-Aepa-Lys-DTyr-DTyr-cyclo(Cys-3lTyr-DTrp-Lys-Thr-Cys)-Thr-NH₂
-(Doc)₄-Lys-DTyr-DTyr-cyclo(Cys-3lTyr-DTrp-Lys-Thr-Cys)-Thr-NH₂
-(Doc)₆-Lys-DTyr-DTyr-cyclo(Cys-3lTyr-DTrp-Lys-Thr-Cys)-Thr-NH₂
-(Doc)₄-Aepa-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂

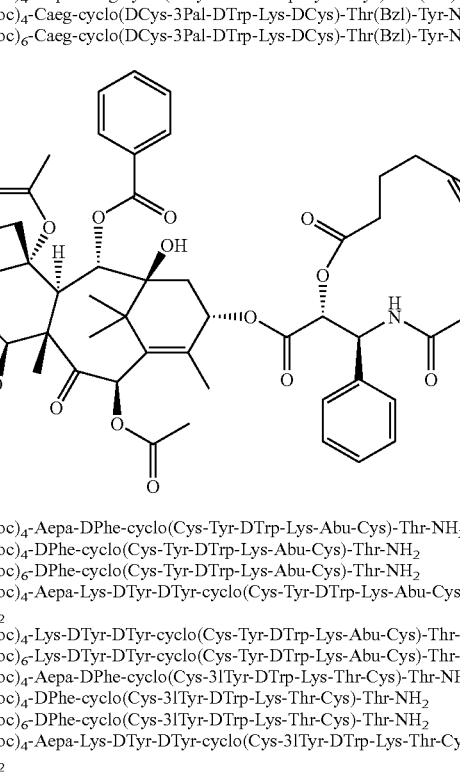

-(Doc)₄-Aepa-DPhe-cyclo(Cys-Tyr-DTrp-Lys-Abu-Cys)-Thr-NH₂
-(Doc)₄-DPhe-cyclo(Cys-Tyr-DTrp-Lys-Abu-Cys)-Thr-NH₂
-(Doc)₆-DPhe-cyclo(Cys-Tyr-DTrp-Lys-Abu-Cys)-Thr-NH₂
-(Doc)₄-Aepa-Lys-DTyr-DTyr-cyclo(Cys-Tyr-DTrp-Lys-Abu-Cys)-Thr-NH₂
-(Doc)₄-Lys-DTyr-DTyr-cyclo(Cys-Tyr-DTrp-Lys-Abu-Cys)-Thr-NH₂
-(Doc)₆-Lys-DTyr-DTyr-cyclo(Cys-Tyr-DTrp-Lys-Abu-Cys)-Thr-NH₂
-(Doc)₄-Aepa-DPhe-cyclo(Cys-3lTyr-DTrp-Lys-Thr-Cys)-Thr-NH₂
-(Doc)₄-DPhe-cyclo(Cys-3lTyr-DTrp-Lys-Thr-Cys)-Thr-NH₂
-(Doc)₆-DPhe-cyclo(Cys-3lTyr-DTrp-Lys-Thr-Cys)-Thr-NH₂
-(Doc)₄-Aepa-Lys-DTyr-DTyr-cyclo(Cys-3lTyr-DTrp-Lys-Thr-Cys)-Thr-NH₂
-(Doc)₄-Lys-DTyr-DTyr-cyclo(Cys-3lTyr-DTrp-Lys-Thr-Cys)-Thr-NH₂
-(Doc)₆-Lys-DTyr-DTyr-cyclo(Cys-3lTyr-DTrp-Lys-Thr-Cys)-Thr-NH₂
-(Doc)₄-Aepa-Caeg-cyclo(DCys-3Pal-DTrp-Lys-DCys)-Thr(Bzl)-Tyr-NH₂
-(Doc)₄-Caeg-cyclo(DCys-3Pal-DTrp-Lys-DCys)-Thr(Bzl)-Tyr-NH₂
-(Doc)₆-Caeg-cyclo(DCys-3Pal-DTrp-Lys-DCys)-Thr(Bzl)-Tyr-NH₂

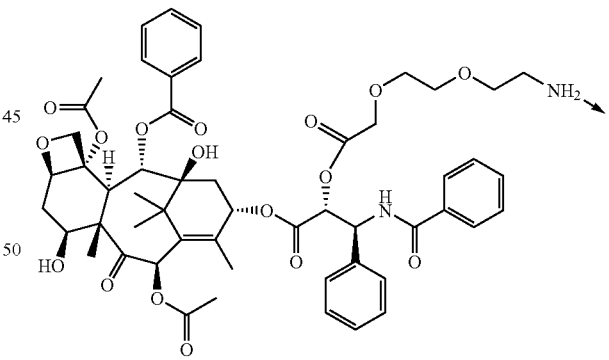

-Suc-(Doc)₃-Aepa-DPhe-cyclo(Cys-Tyr-DTrp-Lys-Abu-Cys)-Thr-NH₂
-Suc-(Doc)₃-DPhe-cyclo(Cys-Tyr-DTrp-Lys-Abu-Cys)-Thr-NH₂
-Suc-(Doc)₅-DPhe-cyclo(Cys-Tyr-DTrp-Lys-Abu-Cys)-Thr-NH₂
-Suc-(Doc)₃-Aepa-Lys-DTyr-DTyr-cyclo(Cys-Tyr-DTrp-Lys-Abu-Cys)-Thr-NH₂
-Suc-(Doc)₃-Lys-DTyr-DTyr-cyclo(Cys-Tyr-DTrp-Lys-Abu-Cys)-Thr-NH₂
-Suc-(Doc)₅-Lys-DTyr-DTyr-cyclo(Cys-Tyr-DTrp-Lys-Abu-Cys)-Thr-NH₂
-Suc-(Doc)₃-Aepa-DPhe-cyclo(Cys-3lTyr-DTrp-Lys-Thr-Cys)-Thr-NH₂
-Suc-(Doc)₃-DPhe-cyclo(Cys-3lTyr-DTrp-Lys-Thr-Cys)-Thr-NH₂
-Suc-(Doc)₅-DPhe-cyclo(Cys-3lTyr-DTrp-Lys-Thr-Cys)-Thr-NH₂
-Suc-(Doc)₃-Aepa-Lys-DTyr-DTyr-cyclo(Cys-3lTyr-DTrp-Lys-Thr-Cys)-Thr-NH₂

TABLE I-continued

-Suc-(Doc)₃-Lys-DTyr-DTyr-cyclo(Cys-3ITyr-DTrp-Lys-Thr-Cys)-Thr-NH₂
-Suc-(Doc)₅-Lys-DTyr-DTyr-cyclo(Cys-3ITyr-DTrp-Lys-Thr-Cys)-Thr-NH₂
-Suc-(Doc)₃-Aepa-Caeg-cyclo(DCys-3Pal-DTrp-Lys-DCys)-Thr(Bzl)-Tyr-NH₂
-Suc-(Doc)₃-Caeg-cyclo(DCys-3Pal-DTrp-Lys-DCys)-Thr(Bzl)-Tyr-NH₂
-Suc-(Doc)₅-Caeg-cyclo(DCys-3Pal-DTrp-Lys-DCys)-Thr(Bzl)-Tyr-NH₂
-Suc-(Doc)₄-Caeg-cyclo(DCys-3Pal-DTrp-Lys-DCys)-Thr(Bzl)-Tyr-NH₂
-Suc-(Doc)₅-Aepa-Caeg-cyclo(DCys-3Pal-DTrp-Lys-DCys)-Thr(Bzl)-Tyr-NH₂
-Suc-(Doc)₄-Aepa-Caeg-cyclo(DCys-3Pal-DTrp-Lys-DCys)-Thr(Bzl)-Tyr-NH₂

Biological Assays

Somatostatin Receptor-Radioligand Binding Assays

Membranes for in vitro receptor binding assays were obtained by homogenizing (Polytron setting 6, 15 sec) the CHO-K1 cells, expressing the human somatostatin receptor subtypes (hSSTR-1, hSSTR-2, hSSTR-3, hSSTR-4, or hSSTR-5), in ice-cold 50 mM Tris-HCl and centrifuging twice at 39,000 g (10 min), with an intermediate resuspension in fresh buffer. The final pellets were resuspended in 10 mM Tris-HCl for assay. For the hSSTR-1, hSSTR-3, and hSSTR-4 assays, aliquots of the membrane preparations were incubated (90 min/25° C. with 0.05 nM [$^{125}$I-Tyr11]SRIF-14 in 50 mM HEPES (pH 7.4) containing BSA (0.2%); MgCl₂ (5 mM). The final assay volume was 0.3 ml. For the hSSTR-2 and hSSTR-5 assays, [$^{125}$I]-[4-(2-hydroxyethyl)]-1-piperazinylacetyl-DPhe-cyclo(Cys-Tyr-DTrp-Lys-Abu-Cys)-Thr-NH₂ (0.05 nM) and [$^{125}$I]-DPhe-cyclo(Cys-Tyr-DTrp-Lys-Val-Cys)-Thr-NH₂ were employed as the radioligands, respectively, and the incubation times were 90 min/25° C. The incubations were terminated by rapid filtration through GF/C filters (pre-soaked in 0.3% polyethylenimine) using a Brandel filtration manifold. Each tube and filter were then washed three times with 5-ml aliquots of ice-cold buffer. Specific binding was defined as the total radioligand bound minus that bound in the presence of 1000 nM SRIF-14 (for hSSTR-1, hSSTR-3, hSSTR-4, or hSSTR-5), or 1000 nM DPhe-c(Cys-Tyr-DTrp-Lys-Abu-Cys)-Thr-NH₂ for hSSTR-2.

In Vitro Growth Assays

For the in vitro proliferation assays, cultured CHO-K1 cells or CHO-K1 cells expressing the hSSTR-2 receptor were seeded into plastic 24-well plates in RPMI 1640 Medium (DMEM) containing 10% fetal bovine serum (FBS) at a density of approximately 104 cells/well/1.0 ml. The test peptides were added at the desired concentration and maintained in culture (5% CO₂, 37° C., humidified air) for one to three days. The cells were rinsed with serum-free RPMI media, trypsinized, resuspended RPMI 1640 (+10% FBS), and counted using a Coulter Counter at 1:20 dilution.

LHRH Radioligand Binding

Membranes were prepared for radioligand binding studies by homogenization of CHO-K1 cells expressing the rat recombinant LHRH receptor in 20 ml of ice-cold 50 mM Tris-HCl with a Brinkman Polytron (Westbury, N.Y.; setting 6, 15 sec). The homogenates were washed twice by centrifugation (39,000 g/10 min), and the final pellets were resuspended in 50 mM Tris-HCl, containing 5 mM MgCl₂, and 0.1% BSA (bovine serum albumin). For the assay, aliquots (0.4 ml) were incubated with 0.05 nM [$^{125}$I]D-Trp6 LHRH (2200 Ci/mmol) with and without 0.05 ml of unlabeled competing test peptides. After a 60 min incubation (4° C.), the bound [$^{125}$I]D-Trp6 LHRH was separated from the free by rapid filtration through GF/B filters (Brandel, Gaithersburg, Md.), which had been previously soaked in 0.5% polyethyleneimine/0.1% BSA. The filters were then washed three times with 5-ml aliquots of ice-cold 50 mM Tris-HCl, and the bound radioactivity trapped on the filters was counted by gamma spectrometry (Wallac L K B, Gaithersburg, Md.). Specific binding was defined as the total [$^{125}$I]D-Trp6 LHRH bound minus that bound in the presence of 1000 nM D-Trp6 LHRH (Bachem, Torrence, Calif.).

Bombesin/GRP Radioligand Binding

Membranes were prepared for radioligand binding studies by homogenization of AR42J rat pancreas cells expressing the native bombesin/GRP receptor, in 20 ml of ice-cold 50 mM Tris-HCl with a Brinkman Polytron (Westbury, N.Y.; setting 6, 15 sec). The homogenates were washed twice by centrifugation (39,000 g/10 min), and the final pellets were resuspended in 50 mM Tris-HCl, containing 2.5 mM MgCl₂, and 0.1% BSA. For the assay, aliquots (0.4 ml) were incubated with 0.05 nM [$^{125}$I-Tyr4]bombesin (2200 Ci/mmol, New England Nuclear, Boston, Mass.), with and without 0.05 ml of unlabeled competing test peptides. After a 30 min incubation (4° C.), the bound [$^{125}$I-Tyr4]bombesin was separated from the free by rapid filtration through GF/B filters (Brandel, Gaithersburg, Md.), which had been previously soaked in 0.3% polyethyleneimine. The filters were then washed three times with 5-ml aliquots of ice-cold 50 mM Tris-HCl, and the bound radioactivity trapped on the filters was counted by gamma spectrometry (Wallac L K B, Gaithersburg, Md.). Specific binding was defined as the total [$^{125}$I-Tyr4]bombesin bound minus that bound in the presence of 1000 nM bombesin (Bachem, Torrence, Calif.).

Some of the compounds of the instant invention have at least one asymmetric center. Additional asymmetric centers may be present in the molecule depending upon the nature of the various substituents of the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The compounds of the instant invention generally can be provided in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention features pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dose of an active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

Preferred dosage ranges are from 0.01 to 10.0 mg/kg of body weight. Such dosages may be administered, for example, daily as a single dose or divided into multiple doses.

Other Embodiments

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if the disclosure of each independent publication was explicitly provided herein.

We claim:

1. A compound according to formula (I):

$X-B^1-B^2-B^3-B^4-Z$  (I)

wherein:

X is a cytotoxic or cytostatic agent;

each of $B^1$, $B^2$, $B^3$, and $B^4$ is, independently for each occurrence, $(Doc)_m$, $(Aepa)_n$, $-(C(O)-A1-A2-A3-A4-A5-C(O))_s-$ or (amino acid)$_p$, provided that at least one of $B^1$, $B^2$, $B^3$, and $B^4$ is $-(C(O)-A1-A2-A3-A4-A5-C(O))_s-$, and that at least one of $B^1$, $B^2$, $B^3$, and $B^4$ is $(Doc)_m$ or $(Aepa)_n$ wherein at least one of m and n is not 0;

each of A1 and A5 is, independently for each occurrence, $CR^1R^2$;

each of $R^1$ and $R^2$ is, independently for each occurrence, H, F, Br, Cl, I, $C_{(1-30)}$alkyl, $C_{(2-30)}$alkenyl, substituted $C_{(1-30)}$alkyl, substituted $C_{(2-30)}$alkenyl, $SR^3$, $S(O)R^4$, or $S(O)_2R^5$, or $R^1$ and $R^2$ together can form a $C_{(3-30)}$cycloalkyl, $C_{(3-30)}$heterocycle, or $C_{(5-30)}$aryl ring;

each of $R^3$, $R^4$, and $R^5$ is, independently for each occurrence, $C_{(1-30)}$alkyl, $C_{(2-30)}$alkenyl, substituted $C_{(1-30)}$alkyl, or substituted $C_{(2-30)}$alkenyl;

each of A2, A3 and A4 is, independently for each occurrence, $CR^6R^7$, O, S, $(CH_2)_t$ or absent;

each of $R^6$ and $R^7$ is, independently for each occurrence, H, F, Br, Cl, I, $C_{(1-30)}$alkyl, $C_{(2-30)}$alkenyl, substituted $C_{(1-30)}$alkyl, substituted $C_{(2-30)}$alkenyl, $SR^3$, $S(O)R^4$, or $S(O)_2R^5$; or $R^6$ and $R^7$ together may form a ring system;

m is, independently for each occurrence, 0, 1, 2, 3, 4, 5, 6, 7, 8, 9, or 10;

n is, independently for each occurrence, 0, 1, 2, 3, 4, 5, 6, 7, 8, 9, or 10;

p is, independently for each occurrence, 0, 1, or 2;

s is, independently for each occurrence, 1, 2, 3, 4, or 5;

t is, independently for each occurrence, 0, 1, 2, or 3; and

Z is selected from the group consisting of somatostatin, a somatostatin analog, luteinizing hormone-releasing hormone (LHRH), an LHRH analog, bombesin, and a bombesin analog;

provided that:

when X is doxorubicin or a doxorubicin derivative, at least one of m and n is not 0; and when X is paclitaxel or a paclitaxel derivative, then $B^1$ is (amino acid)$_p$ and p is 1 or 2;

or a pharmaceutically acceptable salt thereof.

2. The compound according to claim 1, wherein X is a cytotoxic moiety; or a pharmaceutically acceptable salt thereof.

3. The compound according to claim 2, wherein X is an anthracycline; or a pharmaceutically acceptable salt thereof.

4. The compound according to claim 3, wherein X is doxorubicin, or a doxorubicin derivative; or a pharmaceutically acceptable salt thereof.

5. The compound according to claim 2, wherein X is camptothecin, a camptothecin derivative, paclitaxel, or a paclitaxel derivative.

6. The compound according to claim 5, wherein said camptothecin derivative is:

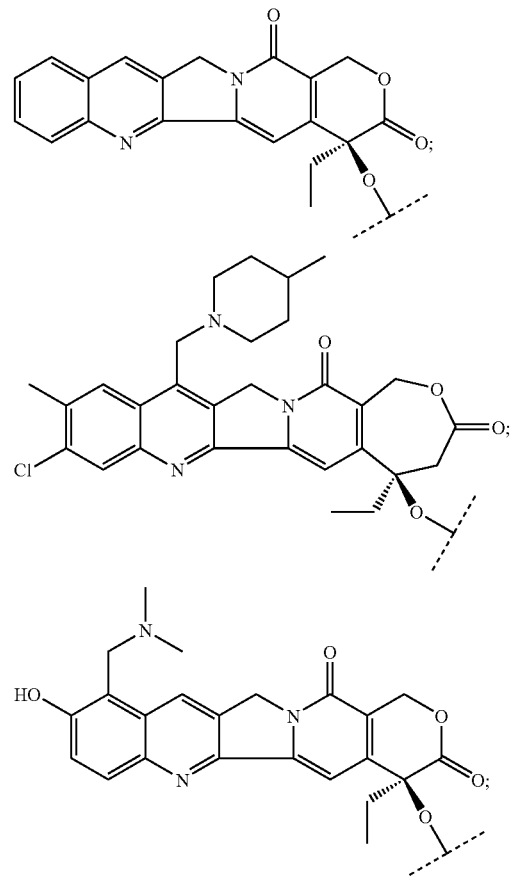

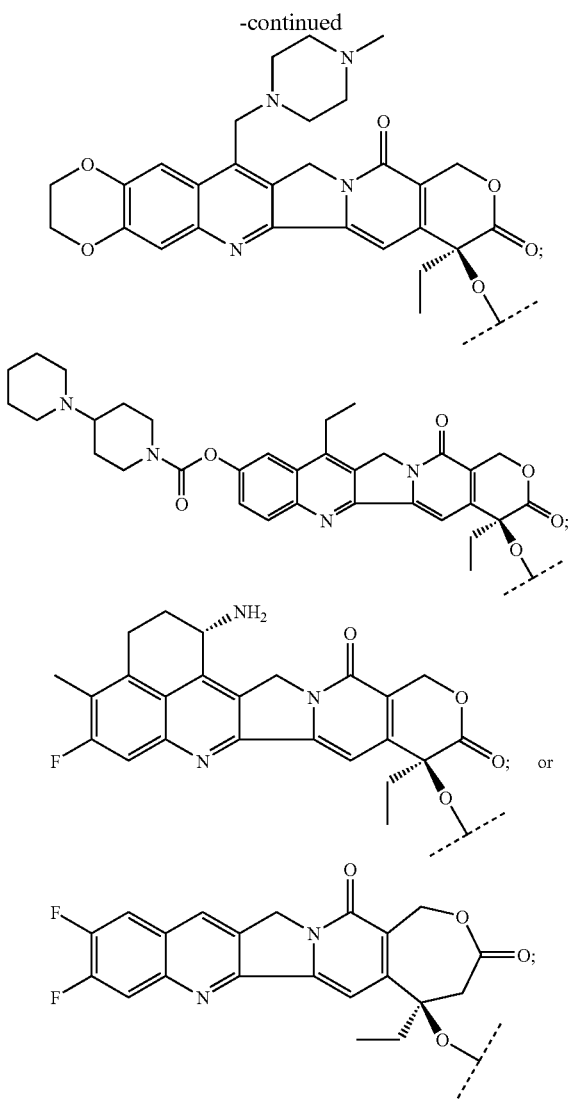

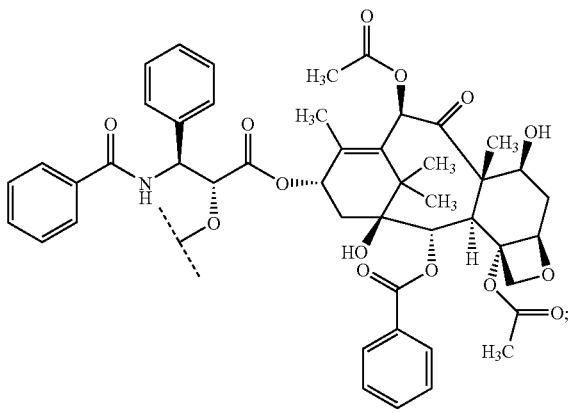

or a pharmaceutically acceptable salt thereof.

7. The compound according to claim 5, wherein X is paclitaxel or a paclitaxel derivative, wherein said paclitaxel derivative is:

or a pharmaceutically acceptable salt thereof.

8. The compound according to claim 4, wherein X is doxorubicin or a doxorubicin derivative, wherein said doxorubicin derivative is:

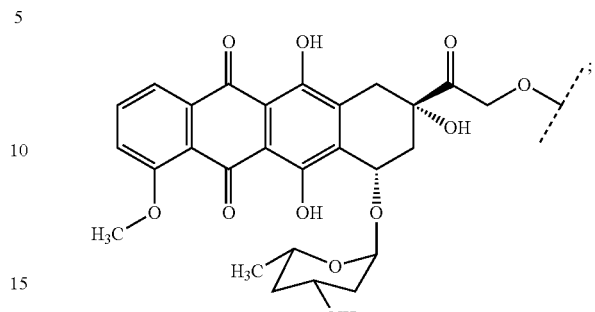

or a pharmaceutically acceptable salt thereof.

9. The compound according to claim 1, wherein Z is a somatostatin analog according to the formula:
- -DPhe-cyclo(Cys-Tyr-DTrp-Lys-Abu-Cys)-Thr-$NH_2$;
- -DPhe-cyclo(Cys-3ITyr-DTrp-Lys-Val-Cys)-Thr-$NH_2$;
- -DPhe-cyclo(Cys-3ITyr-DTrp-Lys-Abu-Cys)-Thr-$NH_2$;
- -DPhe-cyclo(Cys-3ITyr-DTrp-Lys-Thr-Cys)-Thr-$NH_2$;
- -Lys-DTyr-DTyr-cyclo(Cys-Tyr-DTrp-Lys-Abu-Cys)-Thr-$NH_2$;
- -Caeg-cyclo(DCys-Pal-DTrp-Lys-DCys)-Thr(Bzl)-Tyr-$NH_2$;
- -D2Nal-cyclo[Cys-Tyr-DTrp-Lys-Val-Cys]-Thr-$NH_2$;
- -DPhe-cyclo [Cys-Phe-DTrp-Lys-Thr-Cys]-Thr-ol;
- -cyclo({4-(—NH—C2H4—NH—CO—O)Pro}-Phg-DTrp-Lys-Tyr(4-Bzl)-Phe); or
- -DPhe-cyclo[Cys-Tyr-DTrp-Lys-Val-Cys]-Trp-$NH_2$;

or a pharmaceutically acceptable salt thereof.

10. The compound according to claim 1, wherein Z is an LHRH analog according to the formula:
- Glp-His-Trp-Ser-Tyr-DLys(-)-Leu-Arg-Pro-Gly-$NH_2$;
- Glp-His-Trp-Ser-Tyr-DOrn(-)-Leu-Arg-Pro-Gly-$NH_2$;
- Glp-His-Trp-Ser-Tyr-DDab(-)-Leu-Arg-Pro-Gly-$NH_2$;
- Glp-His-Trp-Ser-Tyr-DDap(-)-Leu-Arg-Pro-Gly-$NH_2$;
- Glp-His-Trp-Ser-Tyr-DApa(-)-Leu-Arg-Pro-Gly-$NH_2$;
- Glp-His-Trp-Ser-Tyr-DLys(-)-Leu-Arg-Pro-NHEt;
- Glp-His-Trp-Ser-Tyr-DOrn(-)-Leu-Arg-Pro-NHEt;
- Glp-His-Trp-Ser-Tyr-DDab(-)-Leu-Arg-Pro-NHEt;
- Glp-His-Trp-Ser-Tyr-DDap(-)-Leu-Arg-Pro-NHEt;
- Glp-His-Trp-Ser-His-DLys(-)-Trp-Tyr-Pro-Gly-$NH_2$;
- Glp-His-Trp-Ser-His-DOrn(-)-Trp-Tyr-Pro-Gly-$NH_2$;
- Glp-His-Trp-Ser-His-DDab(-)-Trp-Tyr-Pro-Gly-$NH_2$; or
- Glp-His-Trp-Ser-His-DDap(-)-Trp-Tyr-Pro-Gly-$NH_2$;

or a pharmaceutically acceptable salt thereof.

11. The compound according to claim 1, wherein Z is a bombesin analog according to the formula:
- -Gln-Trp-Ala-Ala-βAla-His-Phe-Nle-$NH_2$; (SEQ ID NO: 8)
- -Gln-Trp-Ala-Val-Gly-His-Leu-Ψ($CH_2$—NH)-Leu-$NH_2$; (SEQ ID NO: 9)
- -Gln-Trp-Ala-Val-Gly-His-Leu-Ψ($CH_2$—NH)-Phe-$NH_2$; (SEQ ID NO: 10)
- -Gln-Trp-Ala-Val-βAla-His-Leu-Leu-$NH_2$; (SEQ ID NO: 11)
- -Gln-Trp-Ala-Val-βAla-His-Leu-Nle-$NH_2$; (SEQ ID NO: 12)
- -Gln-Trp-Ala-Val-βAla-His-Phe-Nle-$NH_2$; (SEQ ID NO: 13)
- -Gln-Trp-Ala-Val-βAla-His-Ala-Nle-$NH_2$; (SEQ ID NO: 14)

-Gln-Trp-Ala-Val-βAla-Ala-Phe-Nle-NH₂; (SEQ ID NO: 15)
-Gln-Trp-Ala-Val-Gly-His-Leu-Leu-NH₂; (SEQ ID NO: 1)
-Gln-Trp-Ala-Val-Gly-His-Leu-Met-NH₂; (SEQ ID NO: 2)
-Gln-Trp-Ala-Val-Gly-His-Phe-Met-NH₂; (SEQ ID NO: 3)
-DAla-Gln-Trp-Ala-Val-βAla-His-Phe-Nle-NH₂;
-DPhe-Gln-Trp-Ala-Ala-βAla-His-Phe-Nle-NH₂;
-DPhe-Gln-Trp-Ala-Val-βAla-Ala-Phe-Nle-NH₂;
-DPhe-Gln-Trp-Ala-Val-βAla-His-Phe-Nle-NH₂;
-DPhe-Gln-Trp-Ala-Val-βAla-His-Phe-Nle-NH₂;
-DPhe-Gln-Trp-Ala-Val-βAla-His-Ala-Nle-NH₂;
-DPhe-Gln-Trp-Ala-Val-βAla-His-Leu-Leu-NH₂;
-DPhe-Gln-Trp-Ala-Val-βAla-His-Leu-Nle-NH₂;
-DPhe-Gln-Trp-Ala-Val-Gly-His-Leu-Ψ(CH₂—NH)-Leu-NH₂;
-DPhe-Gln-Trp-Ala-Val-Gly-His-Leu-Ψ(CH₂—NH)-Phe-NH₂;
-DPhe-Gln-Trp-Ala-Val-Gly-His-Leu-Met-NH₂;
-DPhe-Gln-Trp-Ala-Val-Gly-His-Phe-Met-NH₂;
-DPhe-Gln-Trp-Ala-Val-Gly-His-Leu-Leu-NH₂; or
or a pharmaceutically acceptable salt thereof.

12. The compound according to claim 1, wherein said compound is:

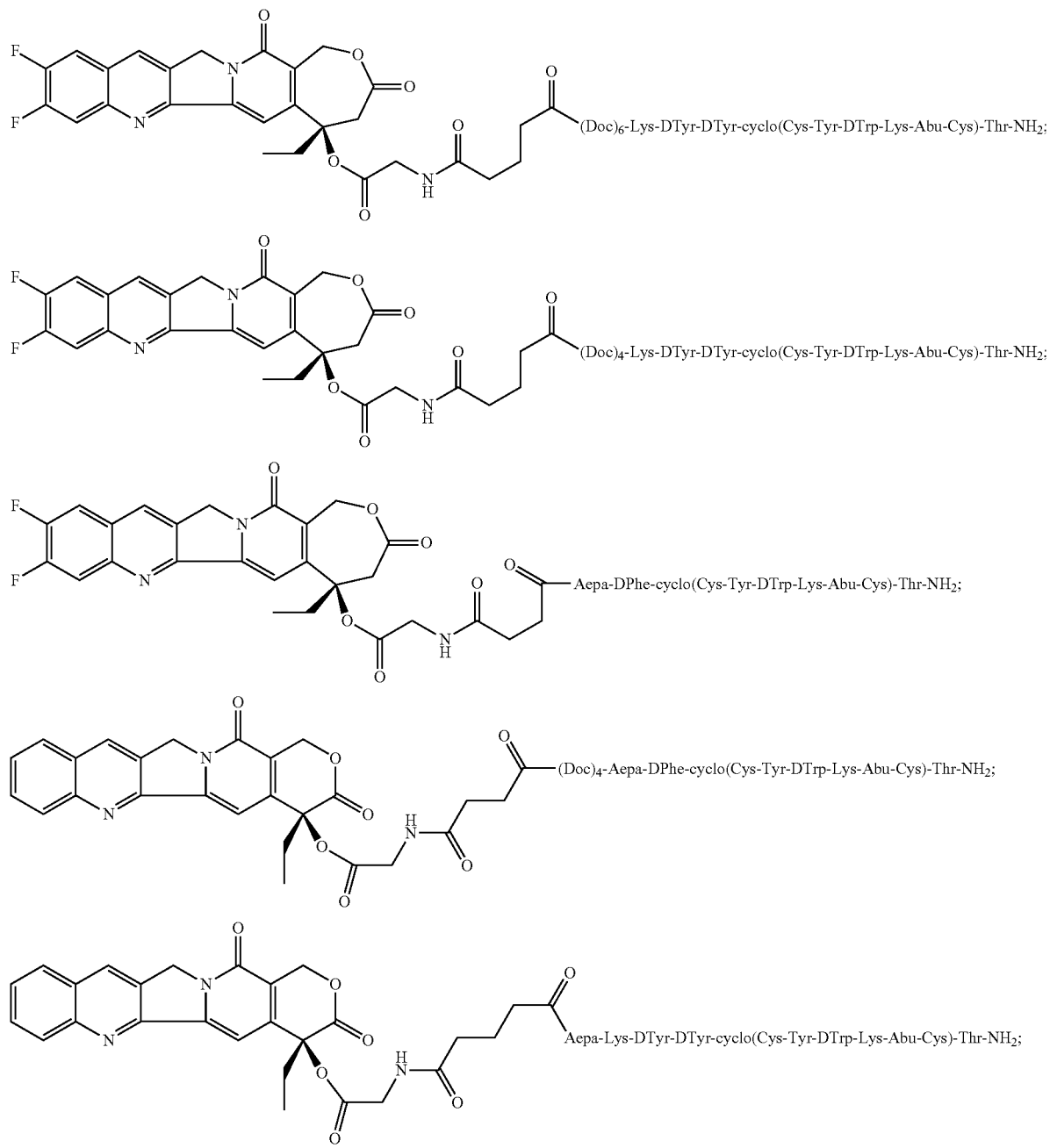

-continued
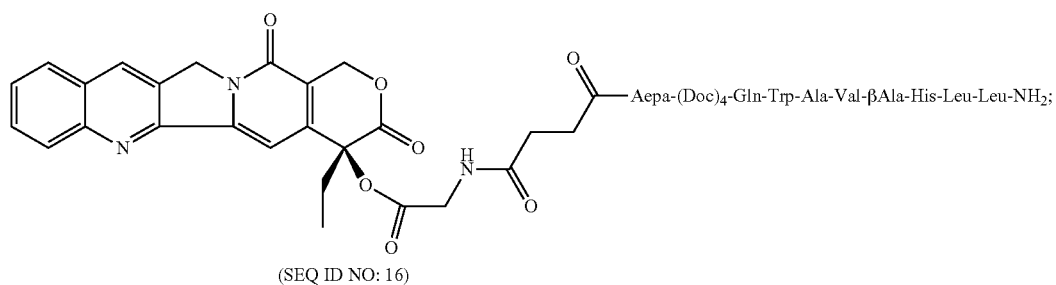
(SEQ ID NO: 16)
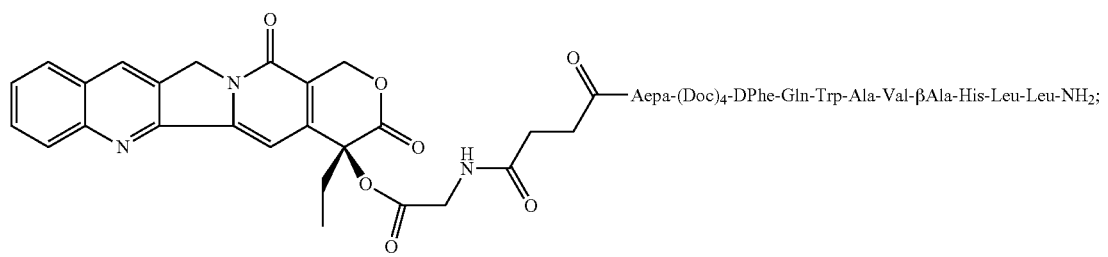
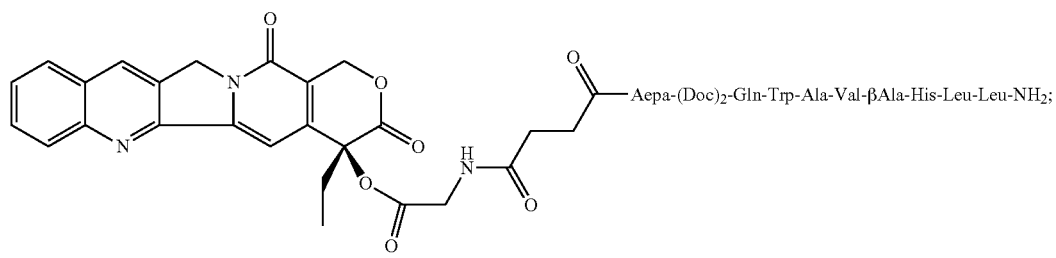
(SEQ ID NO: 16)
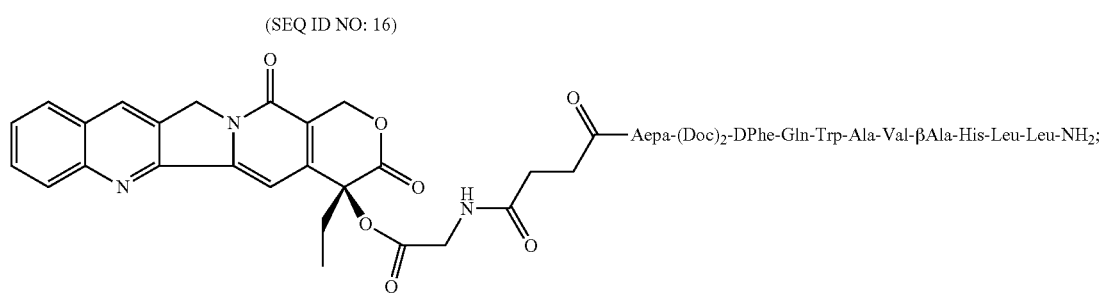
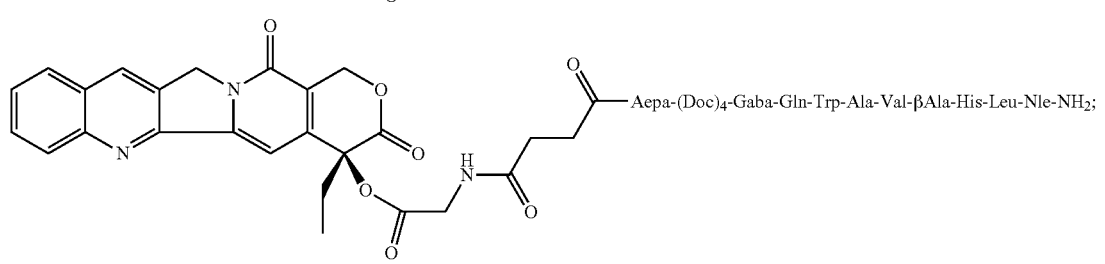
(SEQ ID NO: 17)

-continued
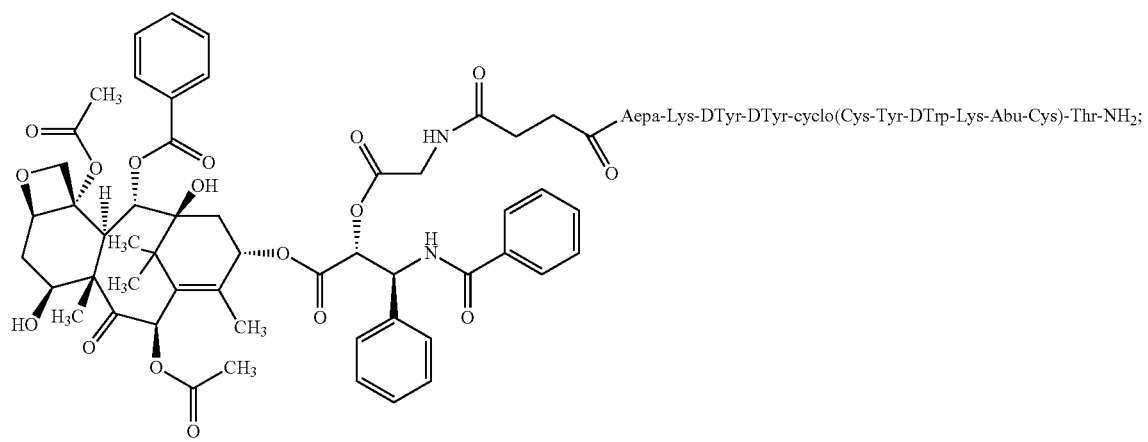
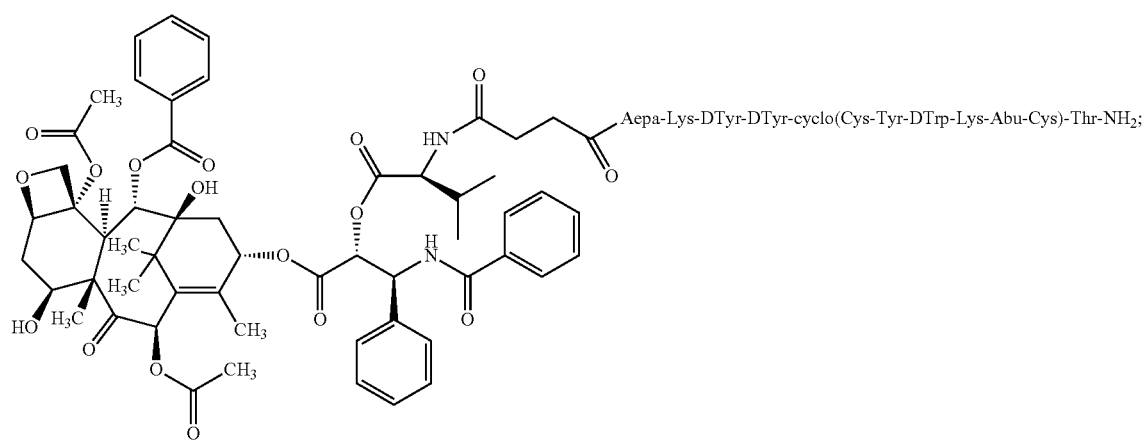
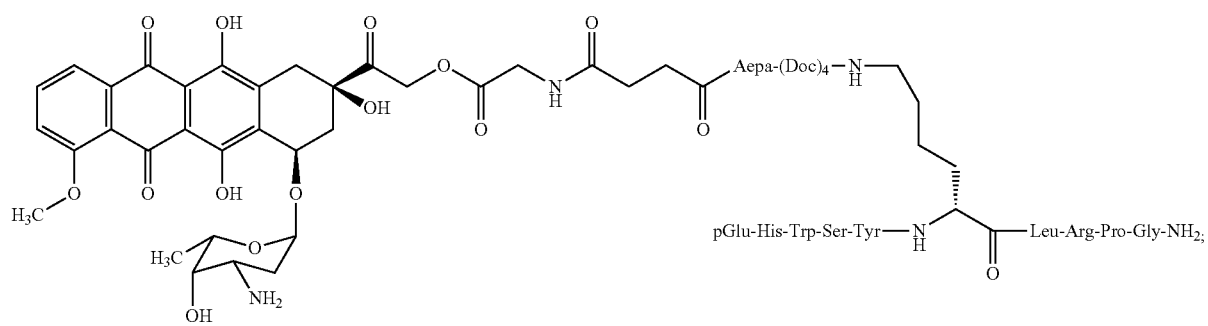
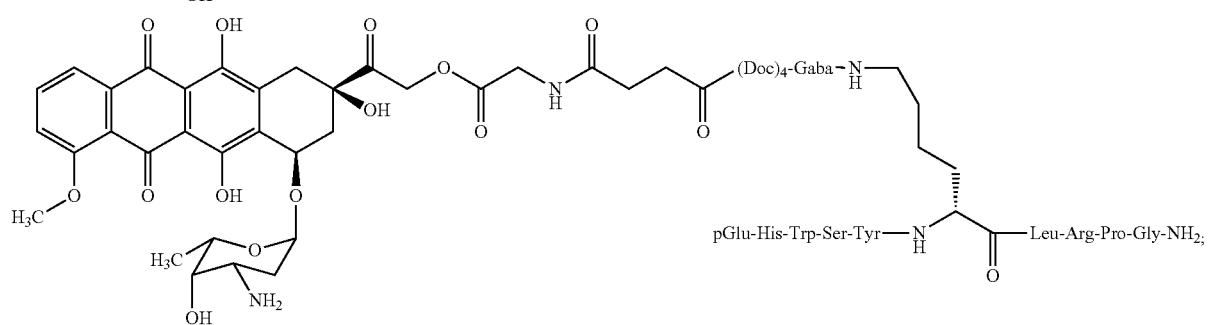

-continued
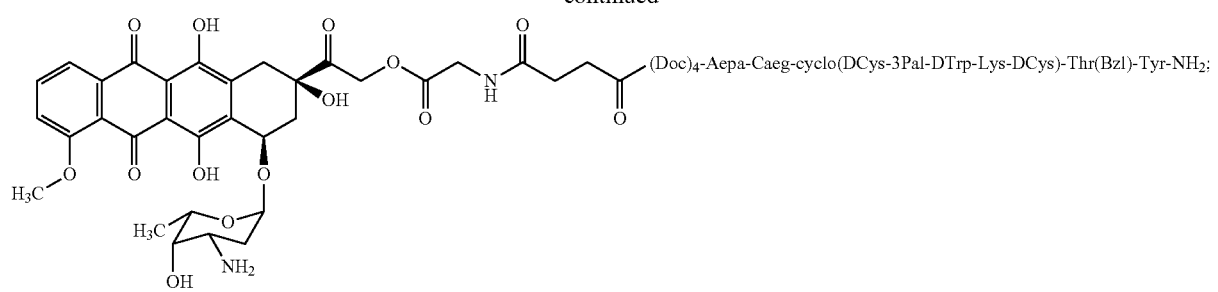
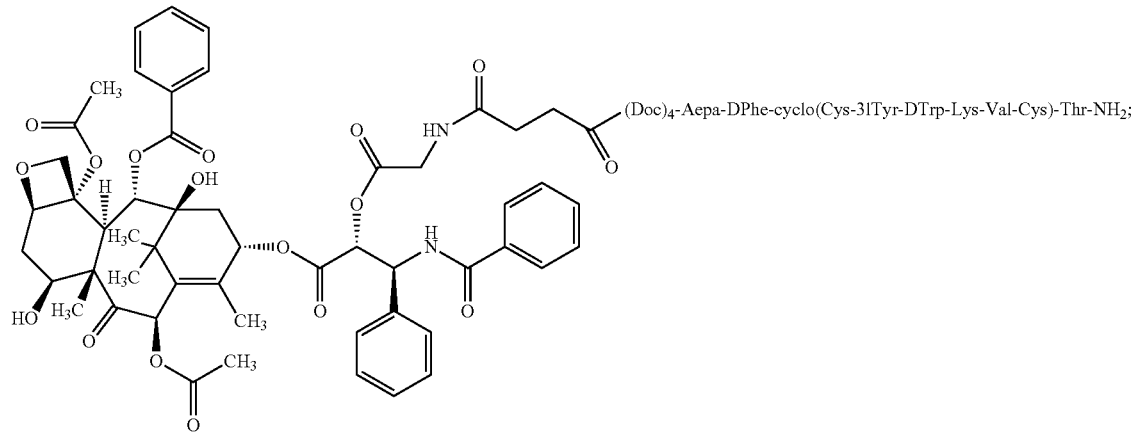
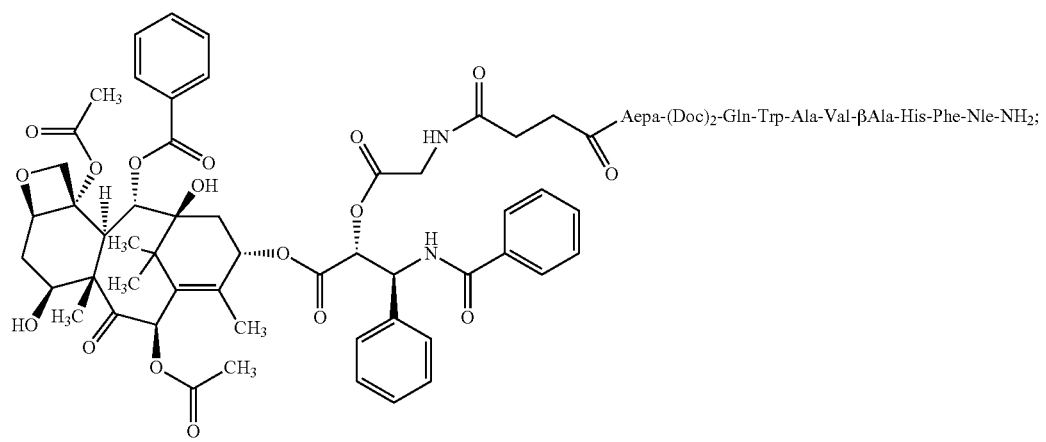
(SEQ ID NO: 18)
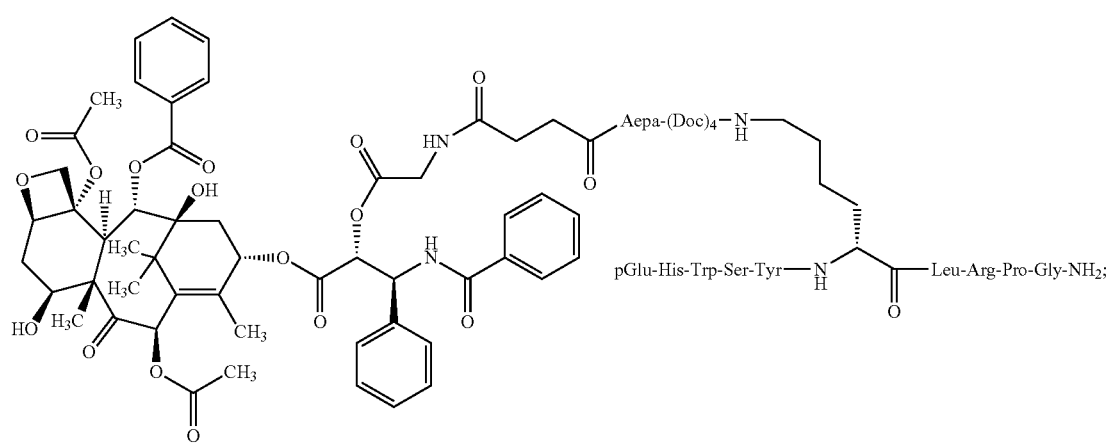

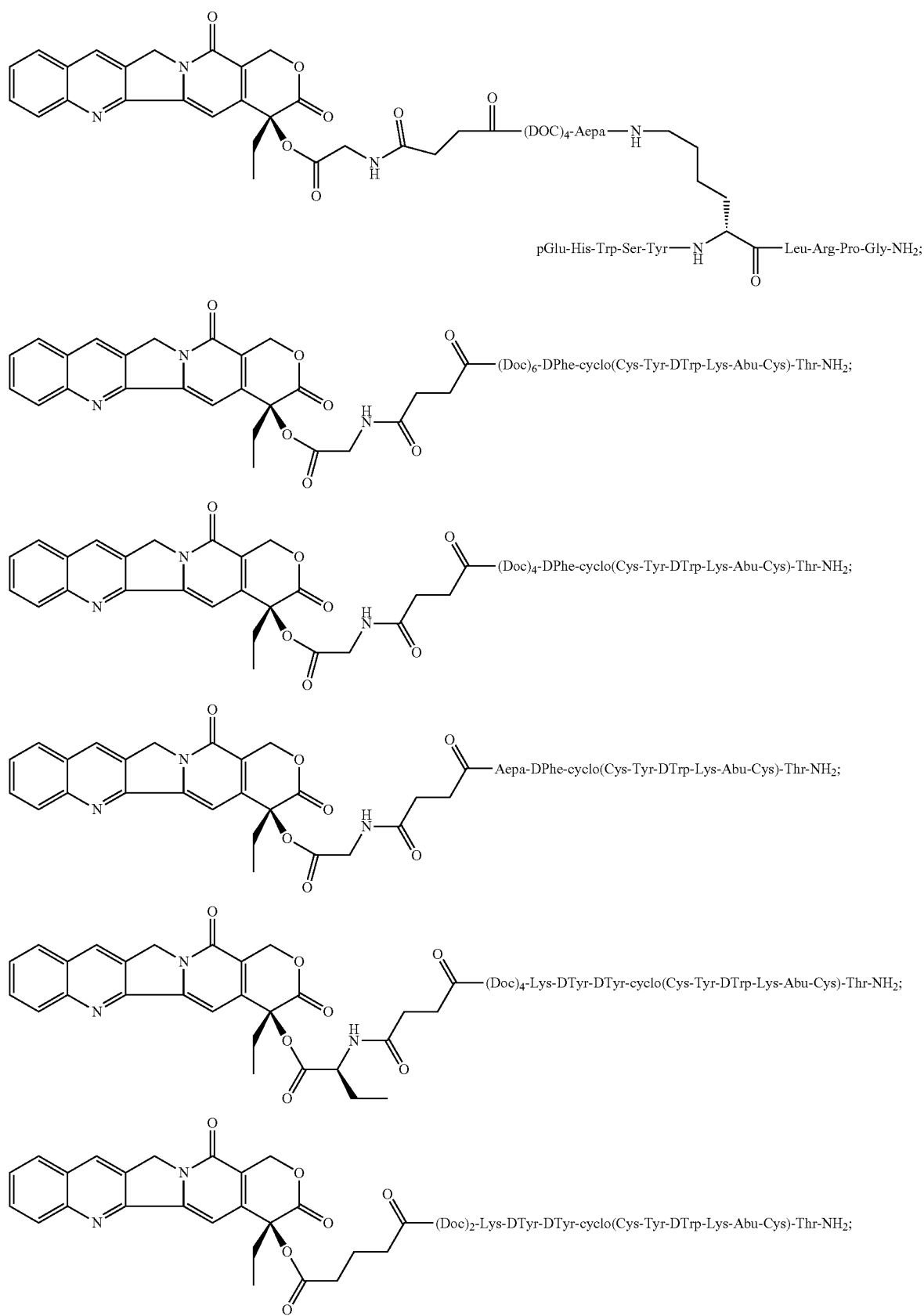

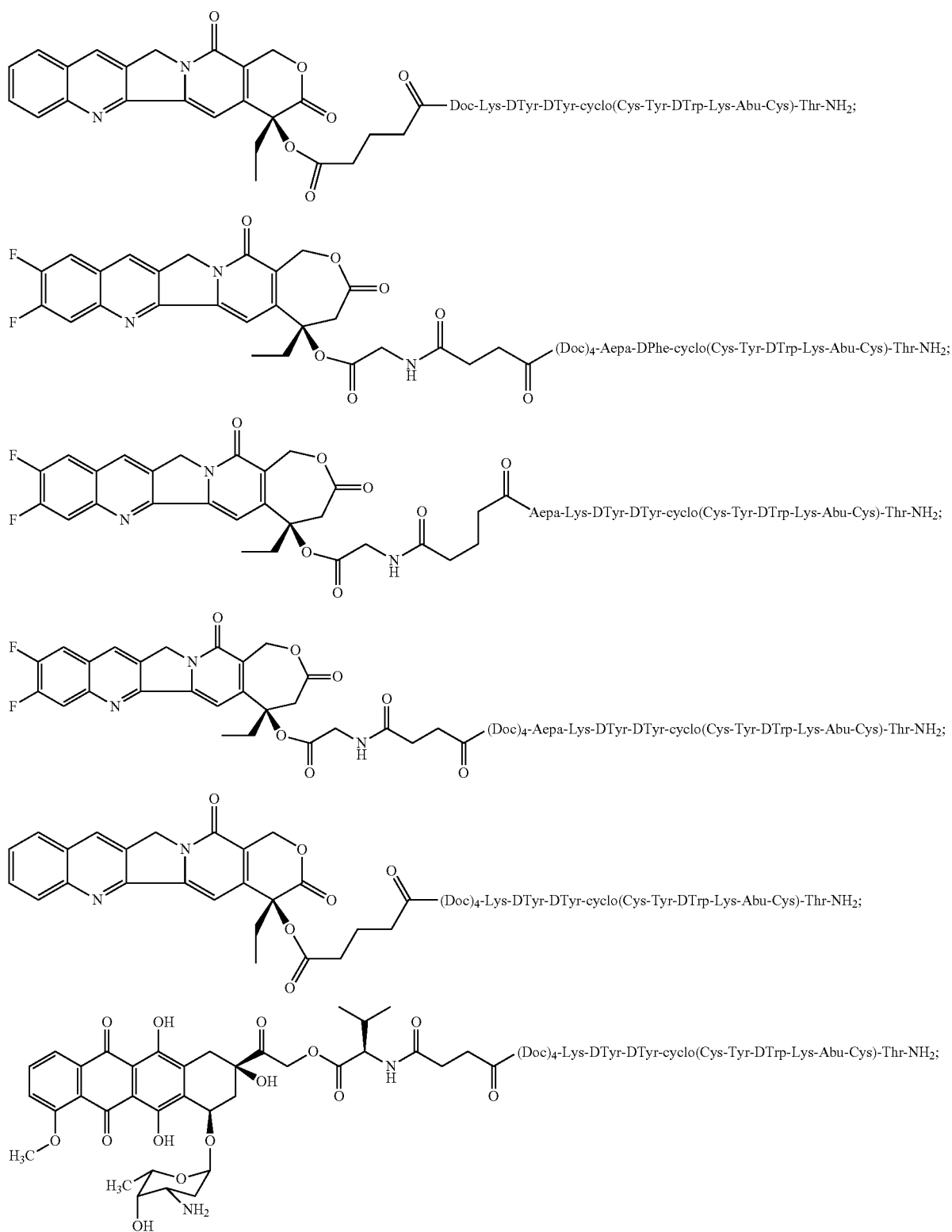

-continued
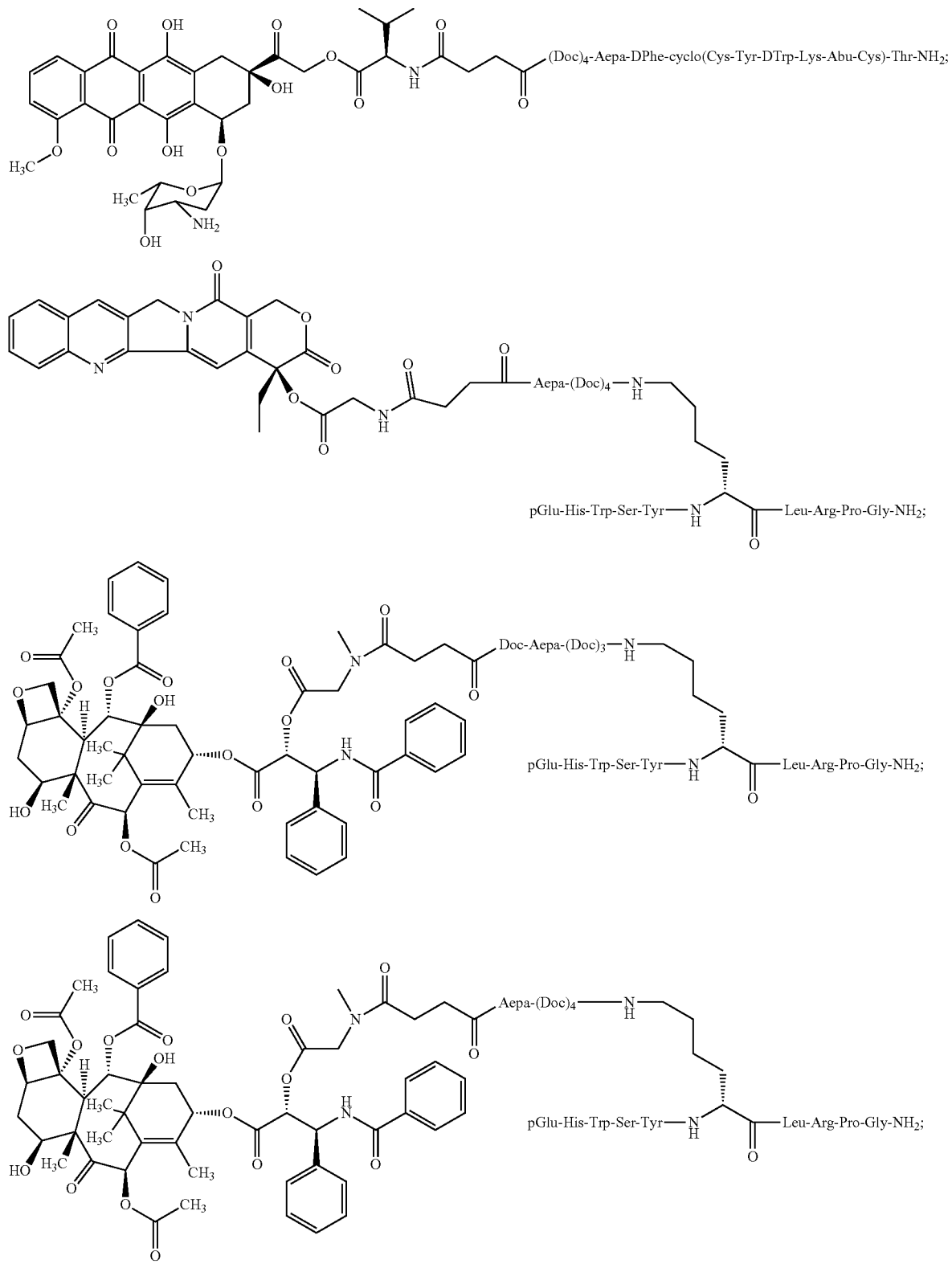

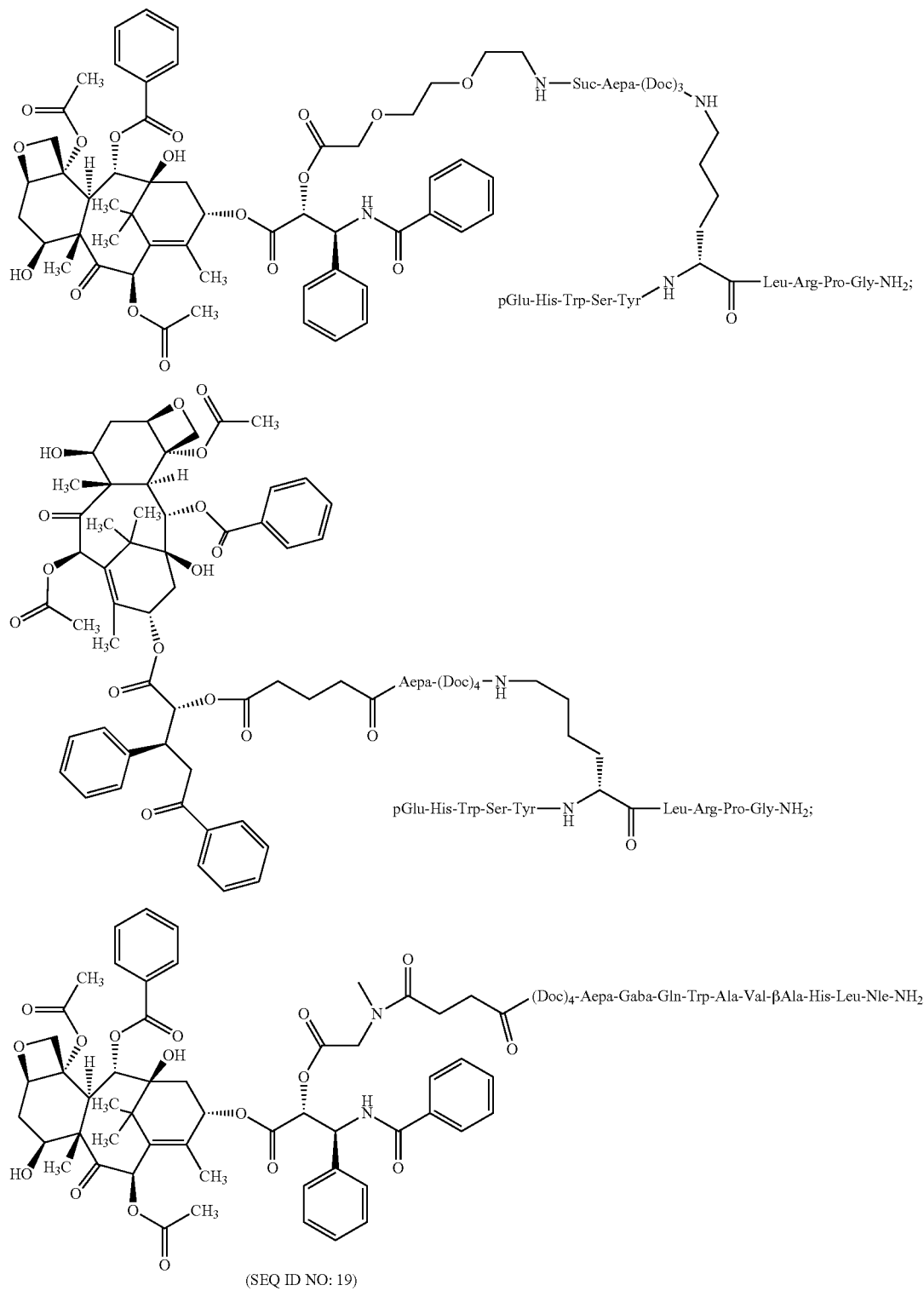
(SEQ ID NO: 19)

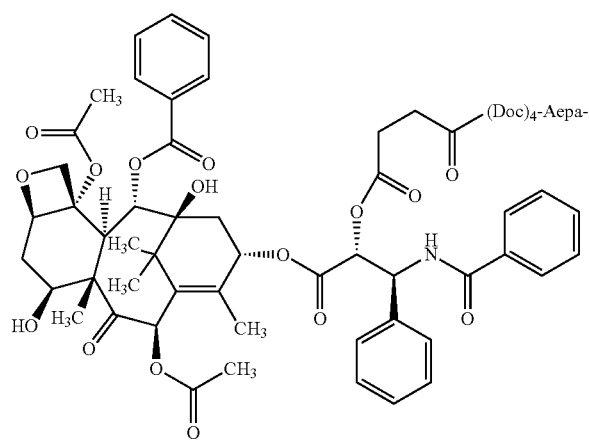
(Doc)$_4$-Aepa-DPhe-Gln-Trp-Ala-Val-βAla-His-Leu-Nle-NH$_2$;
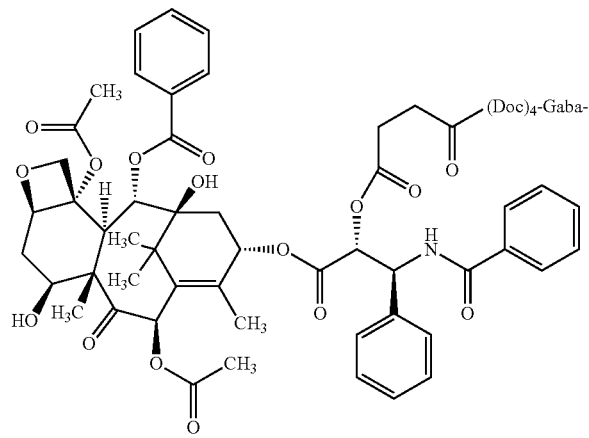
(Doc)$_4$-Gaba-Gln-Trp-Ala-Val-βAla-His-Leu-Nle-NH$_2$;
(SEQ ID NO: 19)
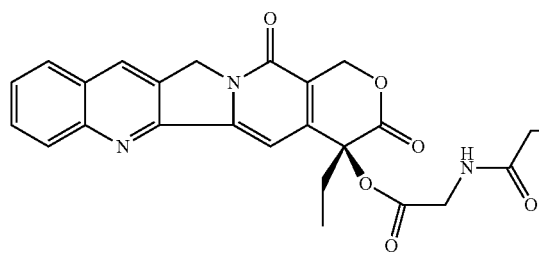
(Doc)$_4$-Aepa-Gaba-Gln-Trp-Ala-Val-βAla-His-Leu-Nle-NH$_2$;
(SEQ ID NO: 19)
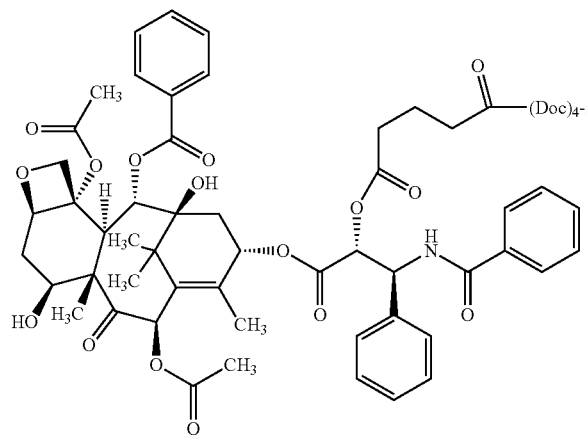
(Doc)$_4$-Aepa-Gaba-Gln-Trp-Ala-Val-βAla-His-Leu-Nle-NH$_2$;
(SEQ ID NO: 19)

-continued
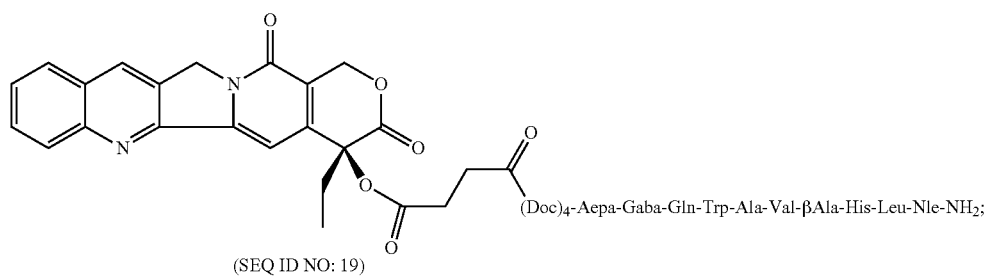
(SEQ ID NO: 19)
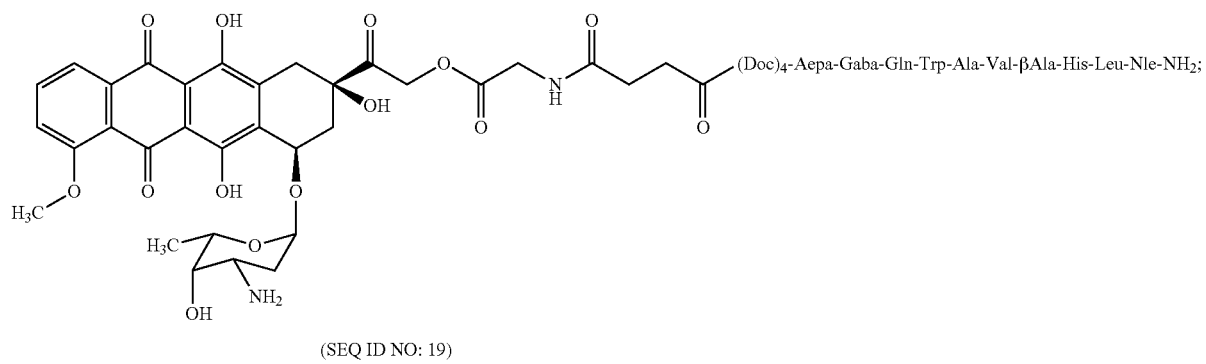
(SEQ ID NO: 19)
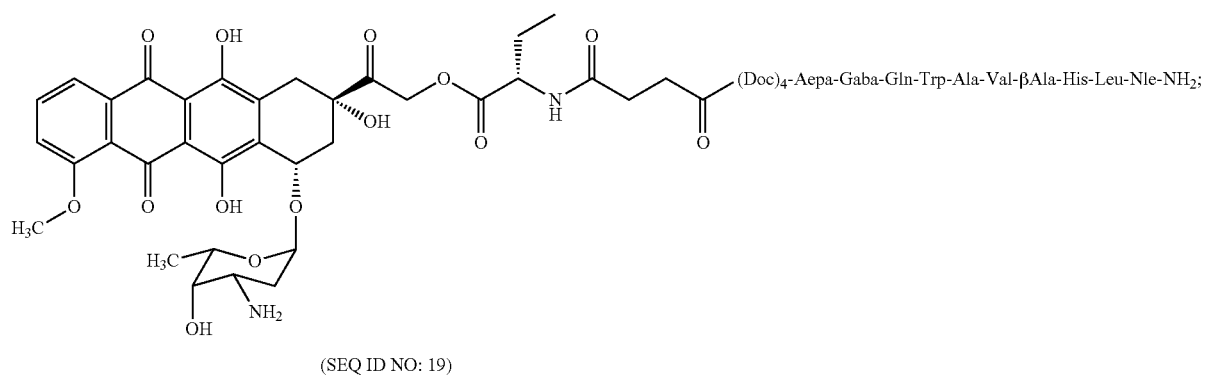
(SEQ ID NO: 19)
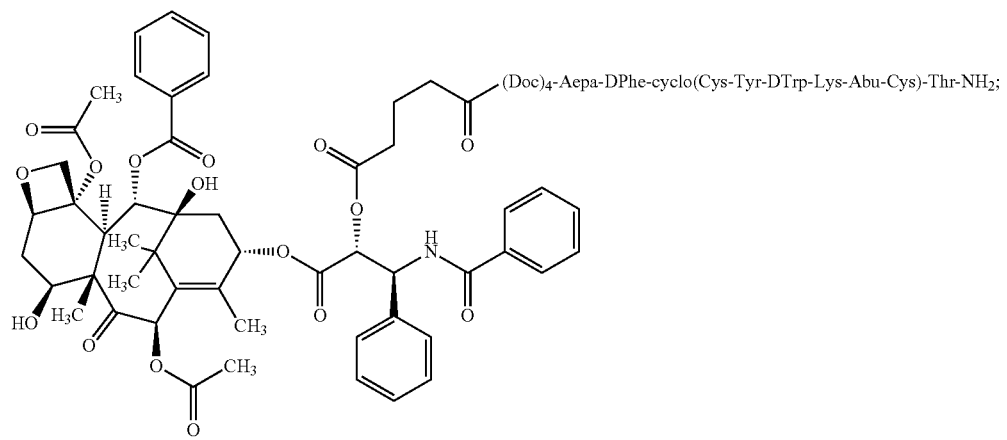

-continued
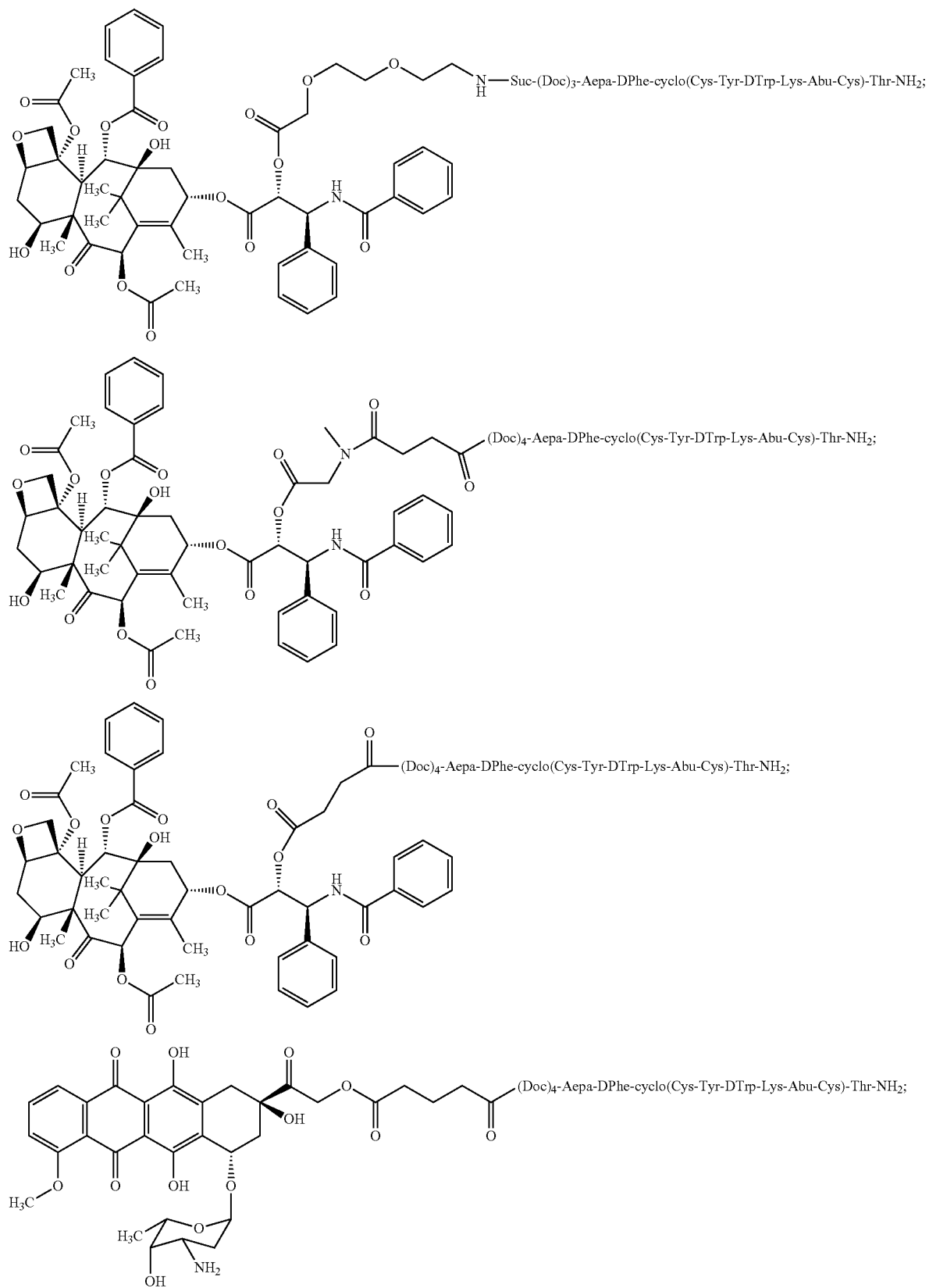

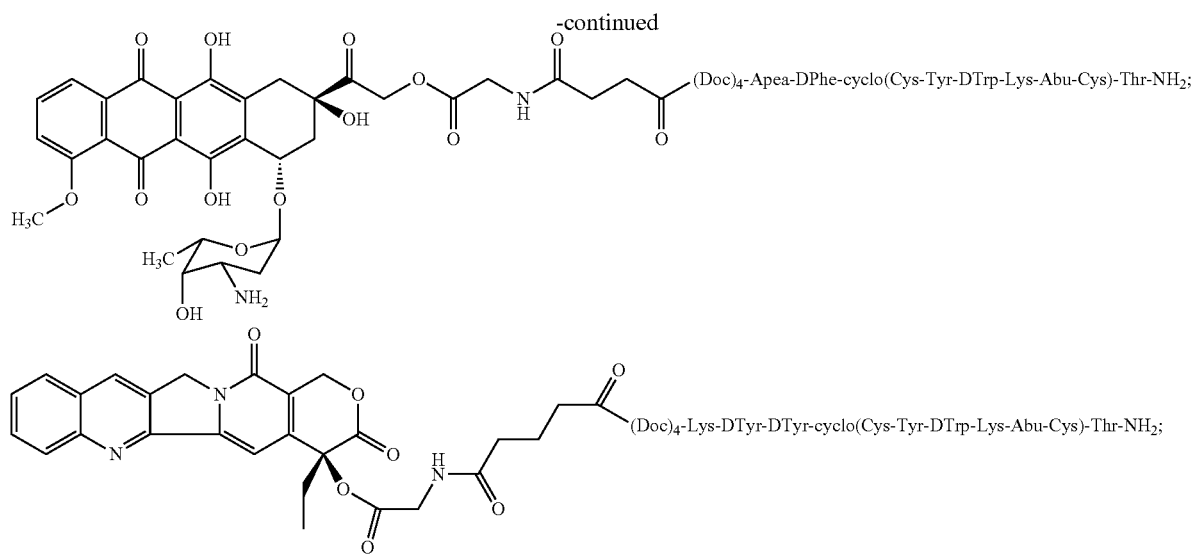
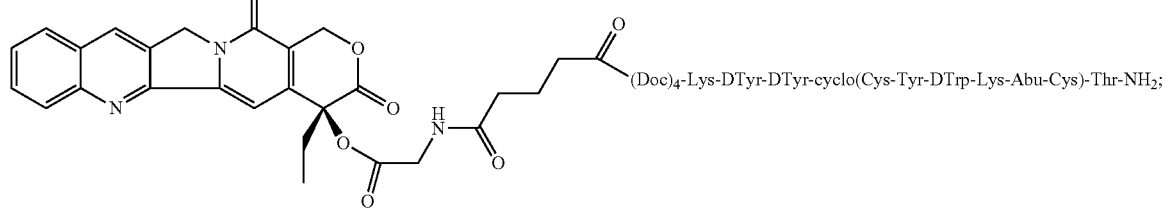
Or a pharmaceutically acceptable salt thereof.
13. The compound according to claim 1, wherein said compound is:
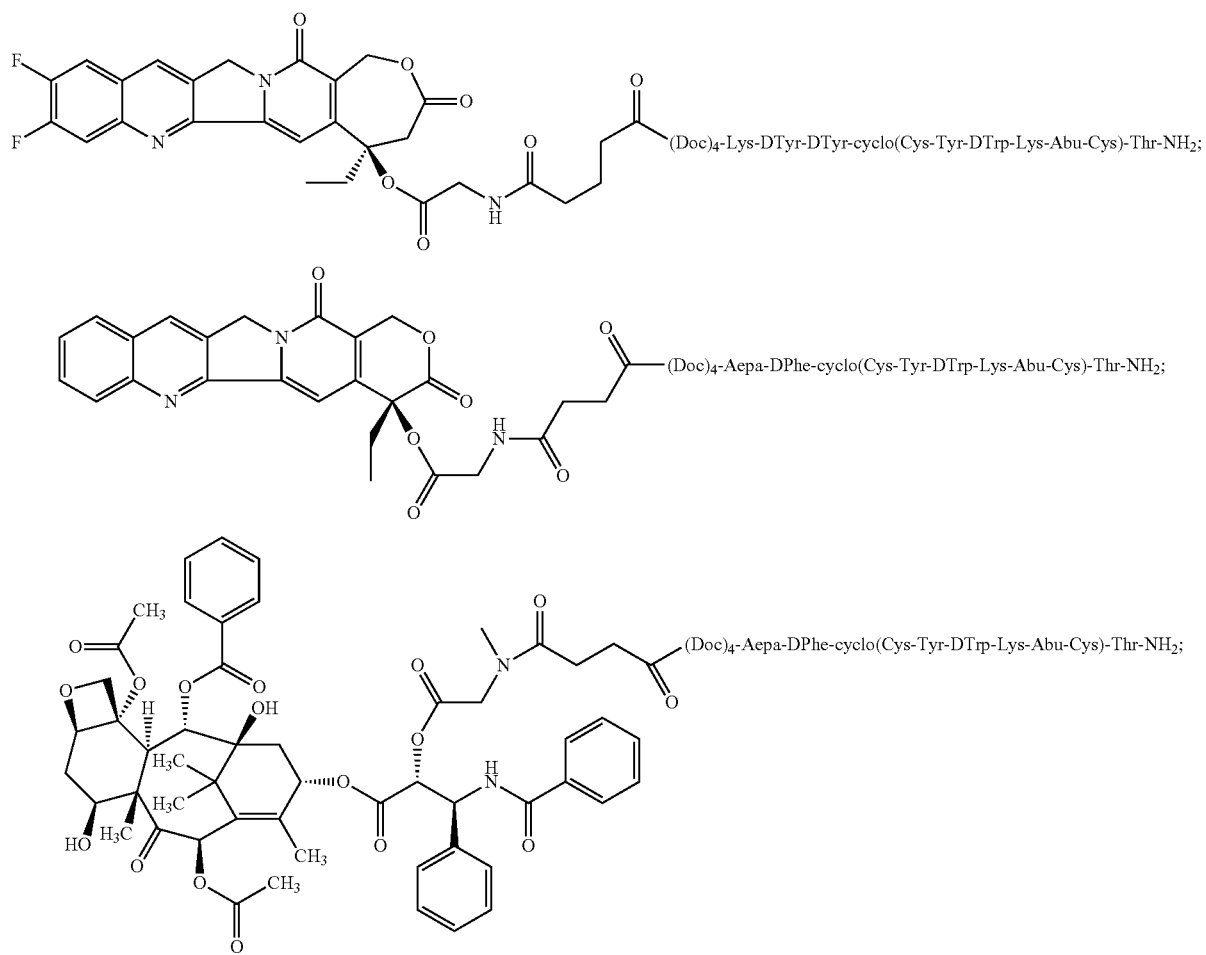

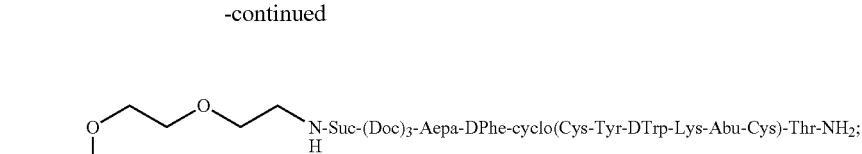
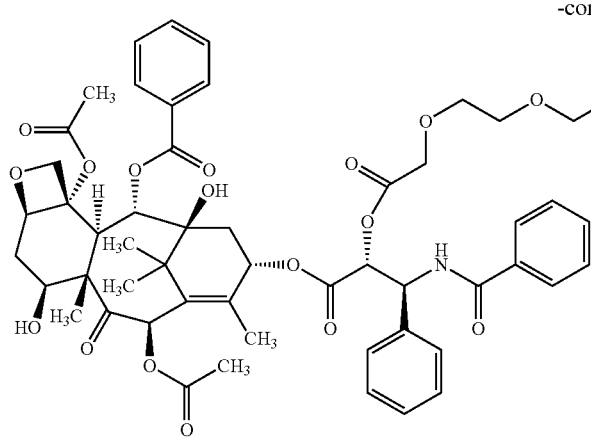
(SEQ ID NO: 19)
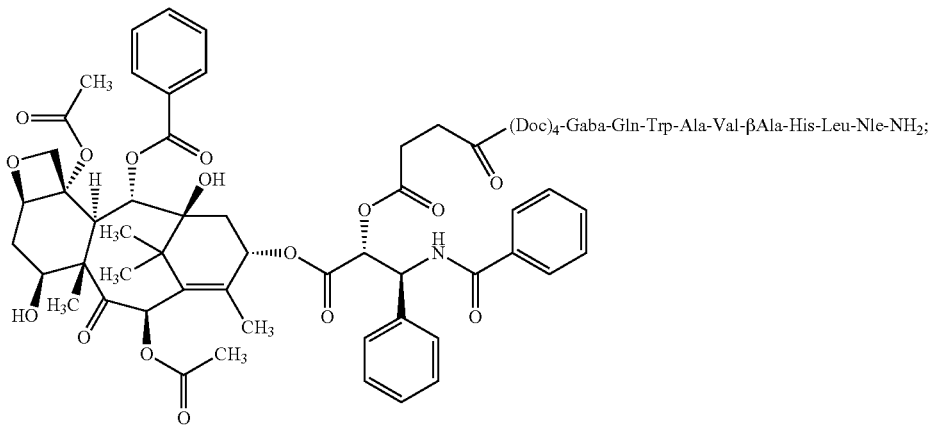
(SEQ ID NO: 19)
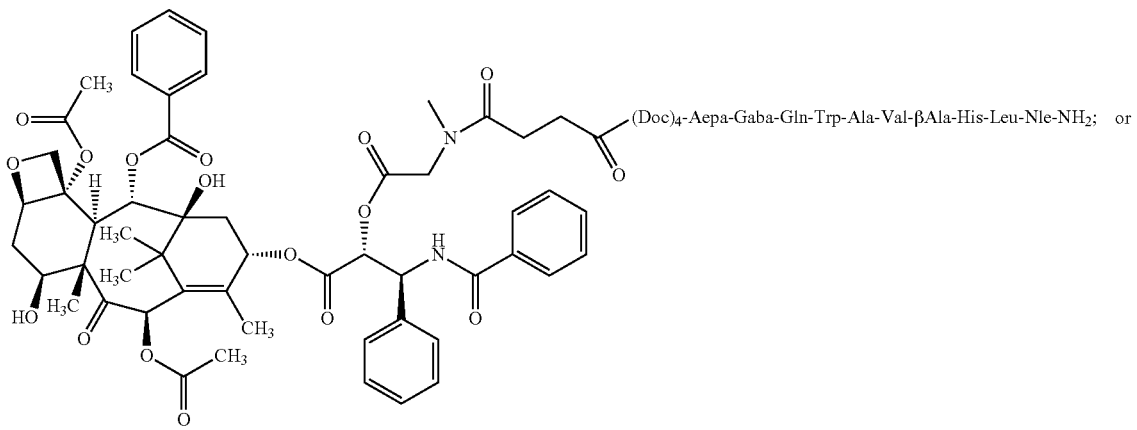
(SEQ ID NO: 19)
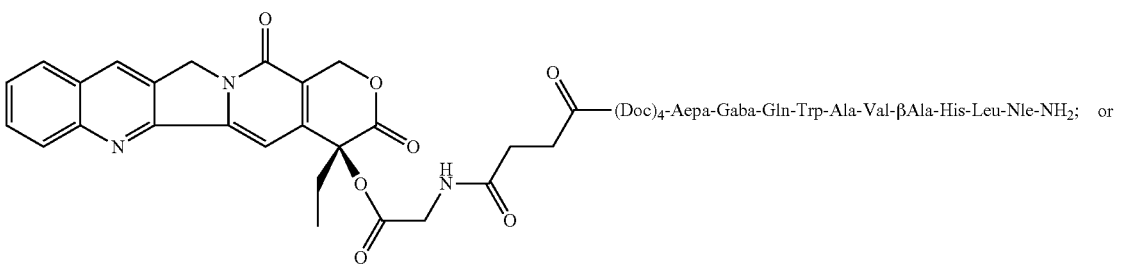
a pharmaceutically acceptable salt thereof.

14. The compound according to claim 12, wherein said compound is

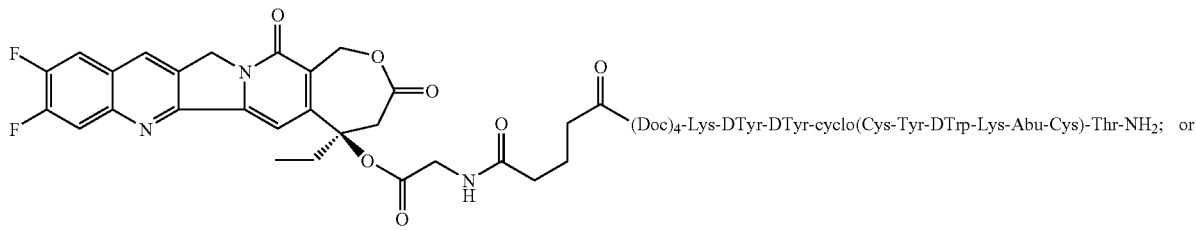

(Doc)₄-Lys-DTyr-DTyr-cyclo(Cys-Tyr-DTrp-Lys-Abu-Cys)-Thr-NH₂; or a pharmaceutically acceptable salt thereof.

15. The compound according to claim 12, wherein said compound is

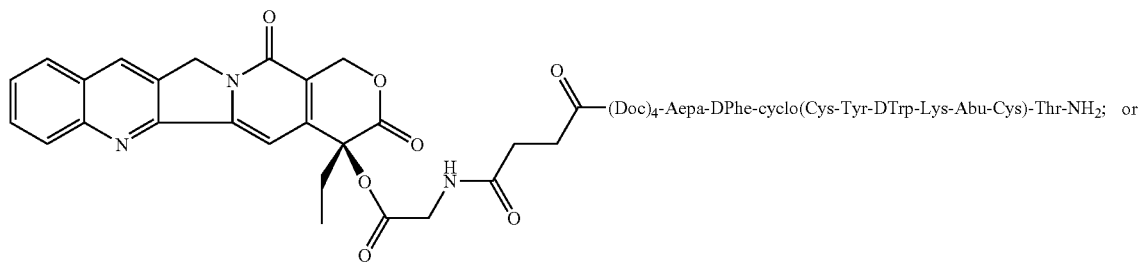

(Doc)₄-Aepa-DPhe-cyclo(Cys-Tyr-DTrp-Lys-Abu-Cys)-Thr-NH₂; or a pharmaceutically acceptable salt thereof.

16. A pharmaceutical composition comprising an effective amount of a compound according to claim 1 or a pharmaceutically acceptable salt thereof and a pharmaceutically acceptable carrier.

17. A method of treating a disease in a subject in need thereof, said method comprising administering to said subject a therapeutically effective amount of a compound according to claim 1, or a pharmaceutically acceptable salt thereof, wherein said disease is selected from the group consisting of fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, and hematopoietic cancer.

18. A method of treating a disease in a subject in need thereof, said method comprising administering to said subject a therapeutically effective amount of a compound according to claim 1, or a pharmaceutically acceptable salt thereof, wherein said disease is selected from the group consisting of benign prostatic hyperplasia, restenosis, breast cancer, colon cancer, pancreas cancer, prostate cancer, lung cancer, small cell lung carcinoma, ovarian cancer, epidermal cancer, and hematopoietic cancer.

19. A method of treating a disease in a subject in need thereof, said method comprising administering to said subject a therapeutically effective amount of a compound of claim 1, or a pharmaceutically acceptable salt thereof, wherein said disease is characterized by undesired proliferation of cells that express one or more somatostatin-type receptors.

20. A method of treating a disease in a subject in need thereof, said method comprising administering to said subject a therapeutically effective amount of a compound of claim 1, or a pharmaceutically acceptable salt thereof, wherein said disease is characterized by undesired proliferation of cells that express one or more of bombesin-type receptors.

21. A method of treating a disease in a subject in need thereof, said method comprising administering to said subject a therapeutically effective amount of a compound of claim 1, or a pharmaceutically acceptable salt thereof, wherein said disease is characterized by undesired proliferation of cells that express one or more LHRH-type receptors.

* * * * *

UNITED STATES PATENT AND TRADEMARK OFFICE
CERTIFICATE OF CORRECTION

PATENT NO. : 8,709,998 B2
APPLICATION NO. : 10/554240
DATED : April 29, 2014
INVENTOR(S) : Zheng Xin Dong et al.

It is certified that error appears in the above-identified patent and that said Letters Patent is hereby corrected as shown below:

In the claims
Claim 12, Column 244, Line 12 through Claim 15, Column 269, Line 33 are replaced with the following:

12. The compound according to claim 1, wherein said compound is:

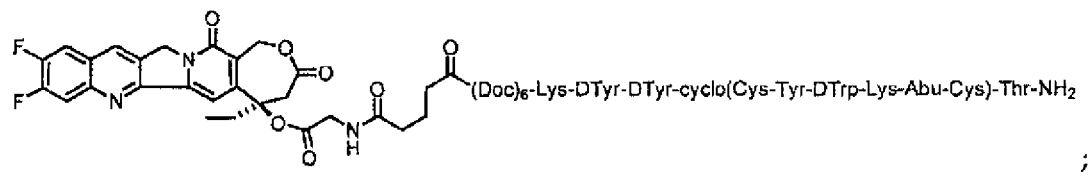

;

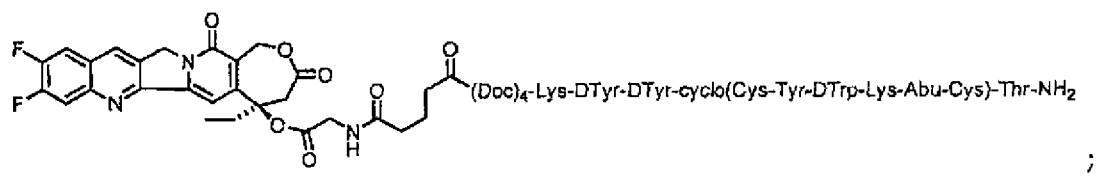

;

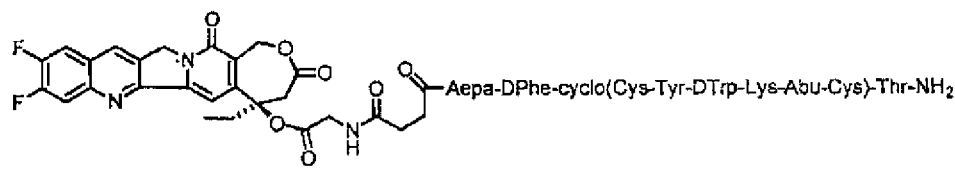

;

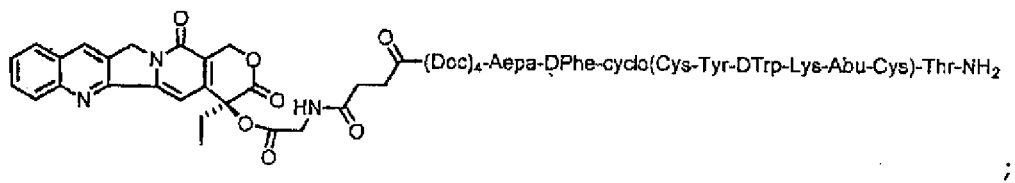

;

Signed and Sealed this
Eleventh Day of November, 2014

Michelle K. Lee
*Deputy Director of the United States Patent and Trademark Office*

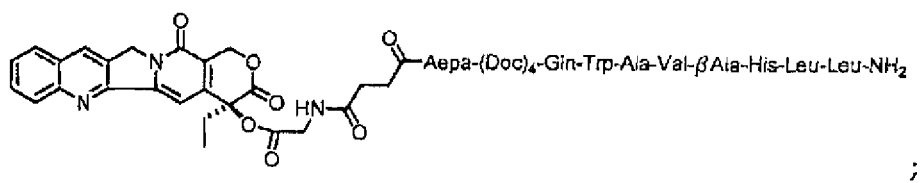
(SEQ ID NO: 16)
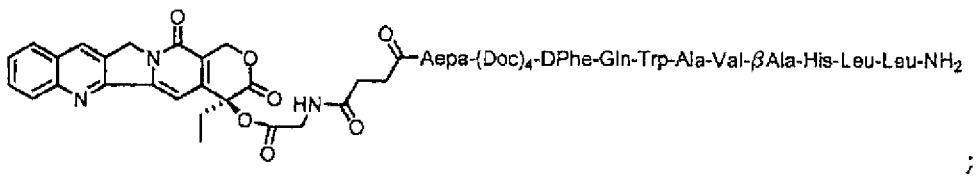
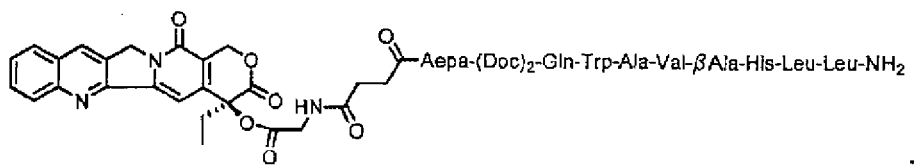
(SEQ ID NO: 16)
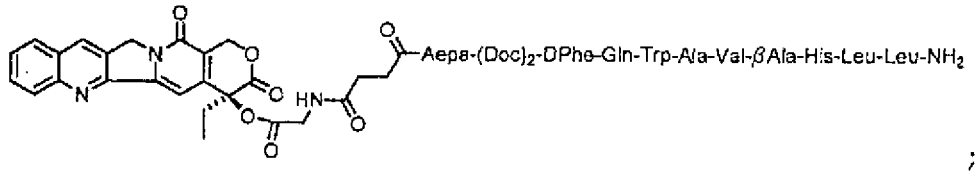
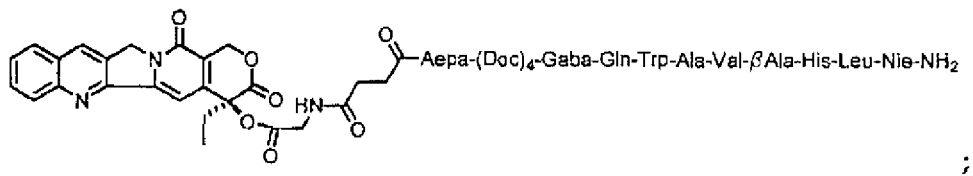
(SEQ ID NO: 17)
(SEQ ID NO: 18)
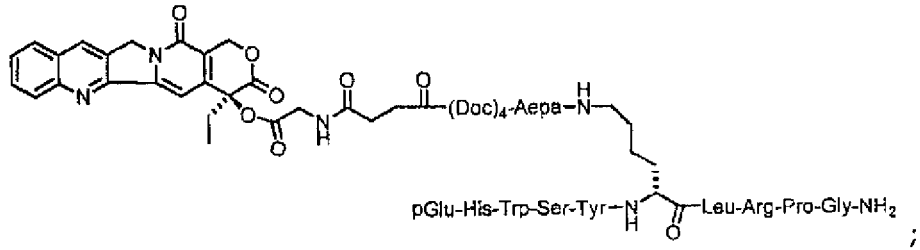

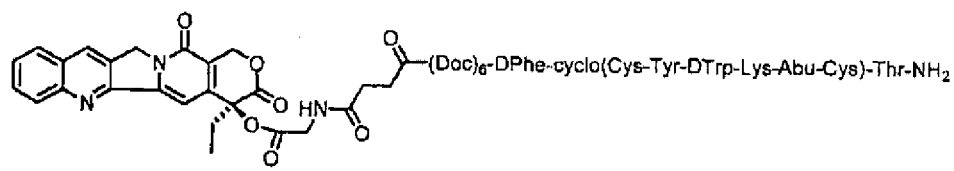
;
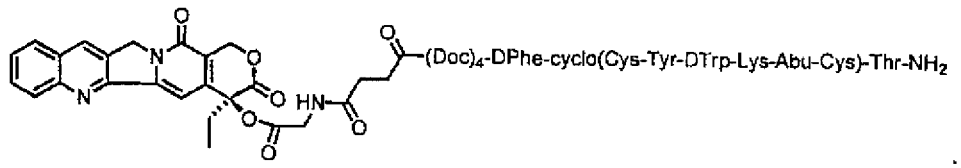
;
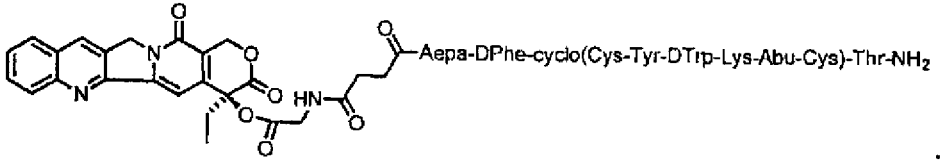
;
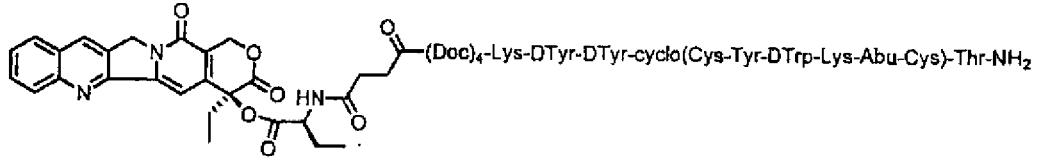
;
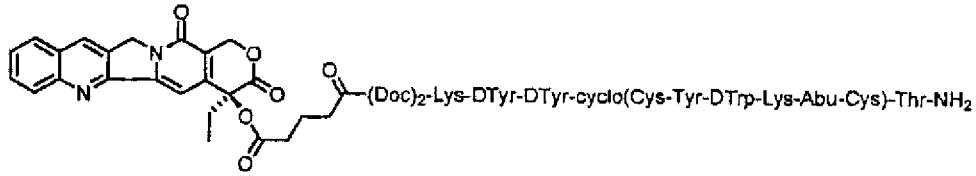
;
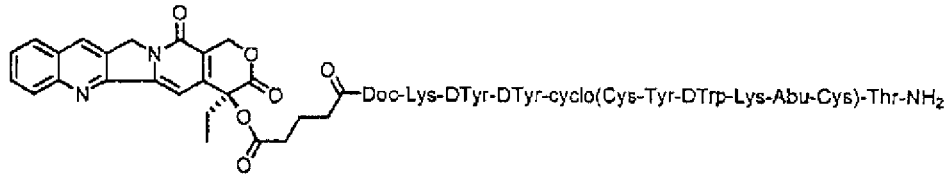
;
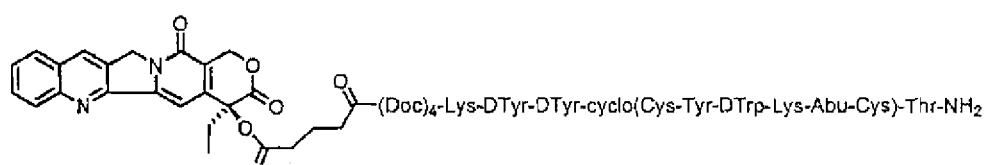
;
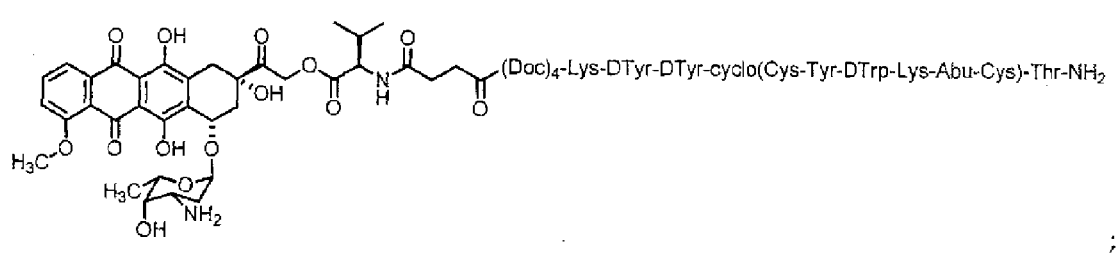
;

CERTIFICATE OF CORRECTION (continued)
U.S. Pat. No. 8,709,998 B2

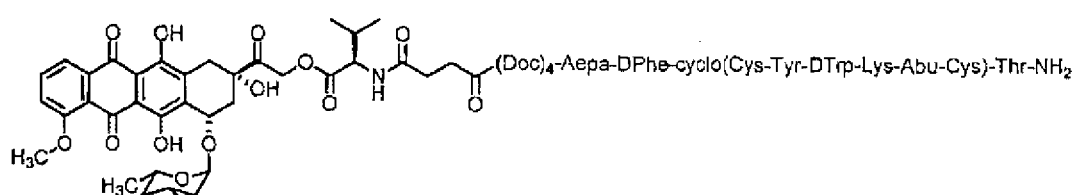

;

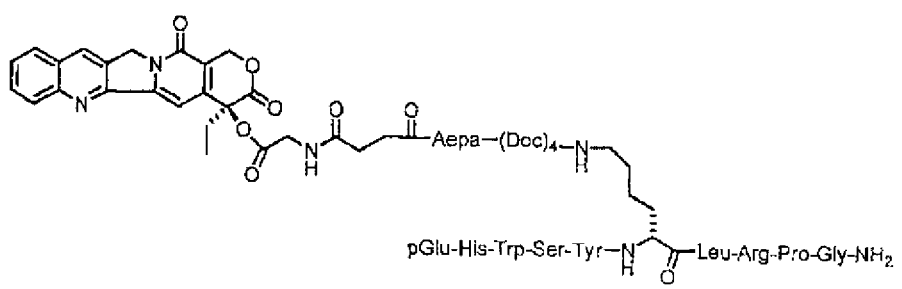

;

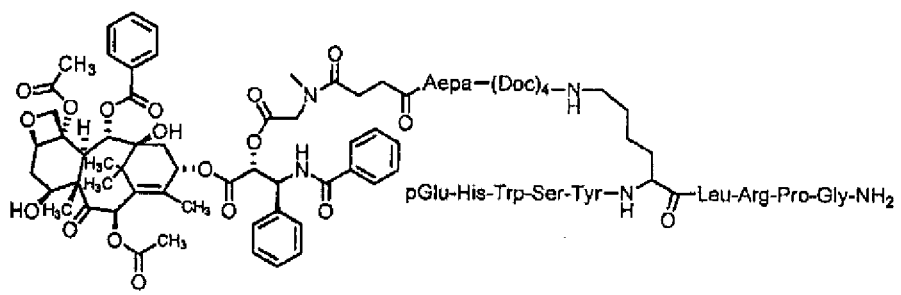

;

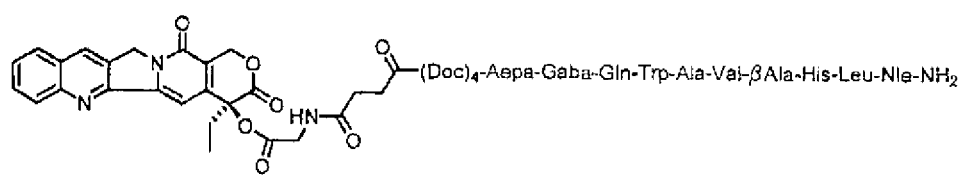

(SEQ ID NO: 19)   ;

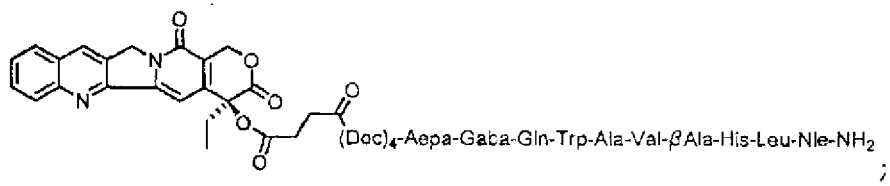

(SEQ ID NO: 19)   ;

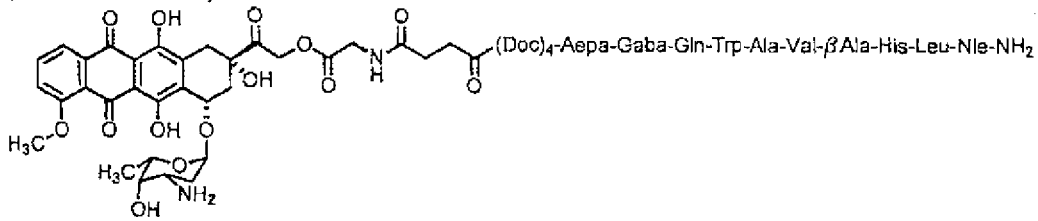

(SEQ ID NO: 19)   ;

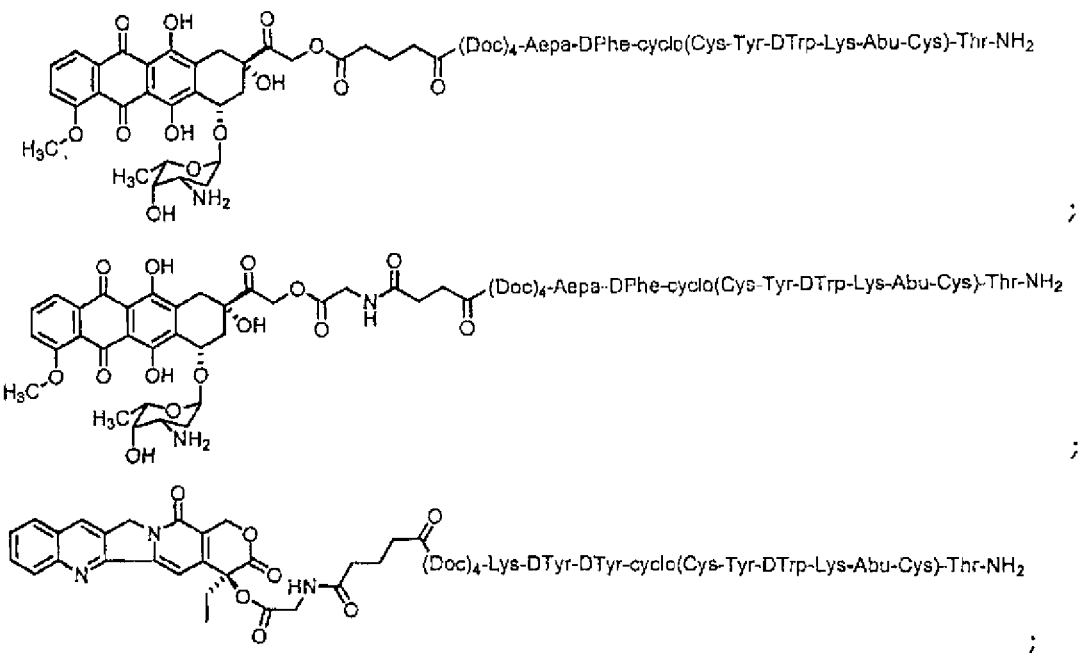
Or a pharmaceutically acceptable salt thereof.
13. The compound according to claim 1, wherein said compound is:
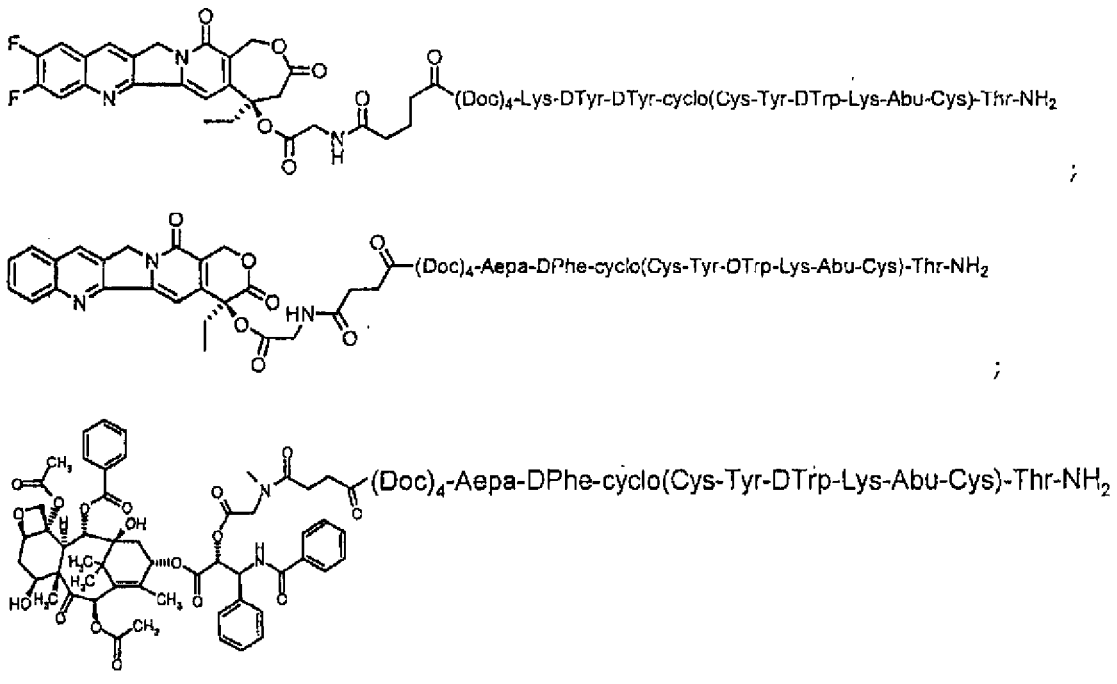

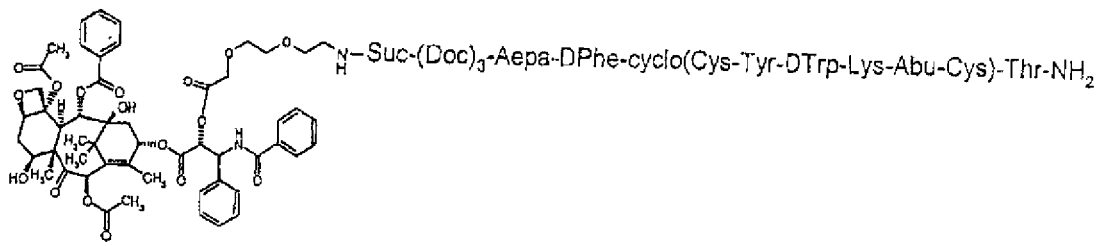
;
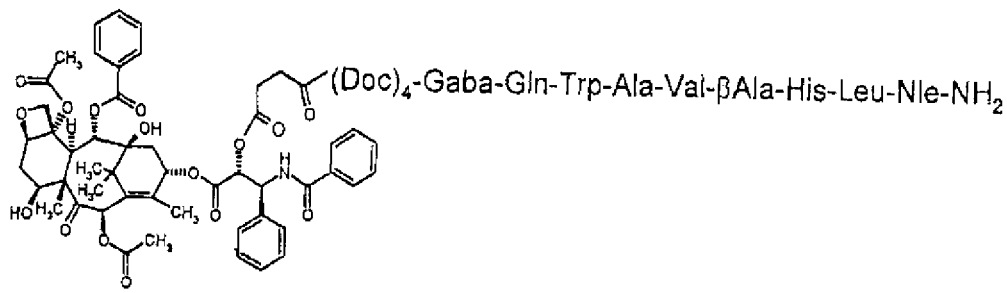
;
(SEQ ID NO: 19)
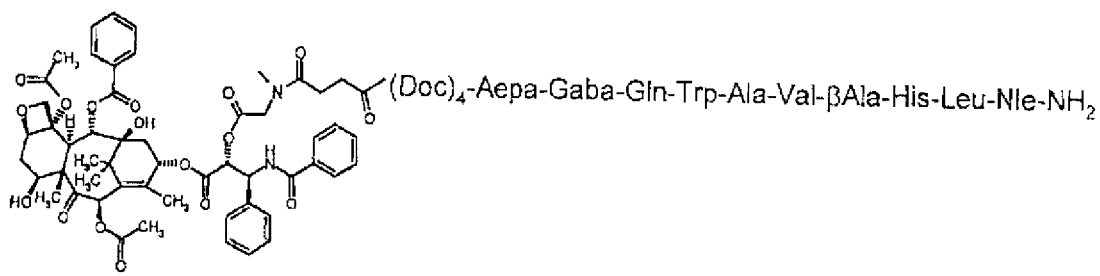
;
(SEQ ID NO: 19)   or
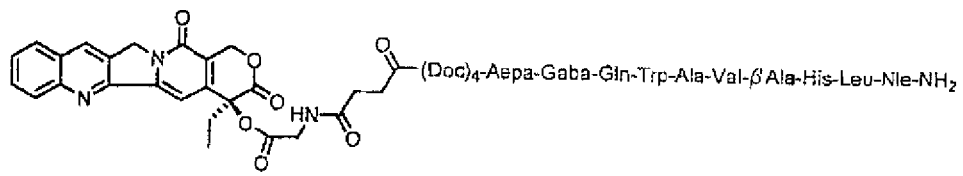
;
(SEQ ID NO: 19)   or
a pharmaceutically acceptable salt thereof.

SEQUENCE LISTING

```
<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 1

Gln Trp Ala Val Gly His Leu Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 2

Gln Trp Ala Val Gly His Leu Met
1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 3

Gln Trp Ala Val Gly His Phe Met
1               5

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 4

His Ser Asp Ala Val Phe Thr Asp Asn Tyr Thr Arg Leu Arg Lys Gln
1               5                   10                  15

Met Ala Val Lys Lys Leu Leu Asn Ser Ile Leu Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 5

His Ser Asp Ala Val Phe Thr Asp Asn Tyr Thr Arg Leu Arg Lys Gln
1               5                   10                  15

Met Ala Val Lys Lys Ala Leu Asn Ser Ile Leu Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 6

His Ser Asp Ala Val Phe Thr Asp Asn Tyr Thr Arg Leu Arg Lys Gln
1               5                   10                  15

Met Ala Val Lys Lys Phe Leu Asn Ser Ile Leu Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 7

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 8

Gln Trp Ala Ala Xaa His Phe Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (7)..(8)
<223> OTHER INFORMATION: Psi(CH2-NH) linker between residues 7-8

<400> SEQUENCE: 9

Gln Trp Ala Val Gly His Leu Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (7)..(8)
<223> OTHER INFORMATION: Psi(CH2-NH) linker between residues 7-8

<400> SEQUENCE: 10

Gln Trp Ala Val Gly His Leu Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)

<400> SEQUENCE: 11

Gln Trp Ala Val Xaa His Leu Leu
1               5

<210> SEQ ID NO 12
<211> LENGTH: 8
<212> TYPE: PRT
<213> ORGANISM: Artificial Sequence
```

```
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 12

Gln Trp Ala Val Xaa His Leu Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 13

Gln Trp Ala Val Xaa His Phe Xaa
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 14

Gln Trp Ala Val Xaa His Ala Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 15
```

```
Gln Trp Ala Val Xaa Ala Phe Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)

<400> SEQUENCE: 16

Gln Trp Ala Val Xaa His Leu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (1)..(1)
<223> OTHER INFORMATION: Xaa = 4-aminobutyric acid (Abu)
<220> FEATURE:
<221> NAME/KEY: MISC_FEATURE
<222> LOCATION: (6)..(6)
<223> OTHER INFORMATION: Xaa = beta-alanine (B-Ala)

<400> SEQUENCE: 17

Xaa Gln Trp Ala Val Xaa His Leu Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)

<400> SEQUENCE: 18

Gln Trp Ala Val Xaa His Phe Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MISC_FEATURE
<222> LOCATION: (1)..(1)
<223> OTHER INFORMATION: Xaa = 4-Aminobutyric acid (Abu)
<220> FEATURE:
<221> NAME/KEY: MISC_FEATURE
<222> LOCATION: (6)..(6)
```

<223> OTHER INFORMATION: Xaa = beta-alanine (B-Ala)
<220> FEATURE:
<221> NAME/KEY: MISC_FEATURE
<222> LOCATION: (9)..(9)
<223> OTHER INFORMATION: Xaa = norleucine (Nle)

<400> SEQUENCE: 19

Xaa Gln Trp Ala Val Xaa His Leu Xaa
1               5